US 8,088,801 B2

(12) United States Patent
Soll et al.

(10) Patent No.: US 8,088,801 B2
(45) Date of Patent: Jan. 3, 2012

(54) ARYLOAZOL-2-YL CYANOETHYLAMINO COMPOUNDS, METHOD OF MAKING AND METHOD OF USING THEREOF

(75) Inventors: Mark David Soll, Alpharetta, GA (US); Loïc Patrick Le Hir de Fallois, Chapel Hill, NC (US); Scot Kevin Huber, Raleigh, NC (US); Hyoung Ik Lee, Cary, NC (US); Douglas Edward Wilkinson, Wake Forest, NC (US); Robert Toms Jacobs, Wake Forest, NC (US)

(73) Assignees: Merial Limited, Duluth, GA (US); Aventis Agiziculture, Paris (FR)

( * ) Notice: Subject to any disclaimer, the term of this patent is extended or adjusted under 35 U.S.C. 154(b) by 0 days.

(21) Appl. No.: 12/119,150

(22) Filed: May 12, 2008

(65) Prior Publication Data

US 2008/0312272 A1    Dec. 18, 2008

Related U.S. Application Data

(60) Provisional application No. 60/930,485, filed on May 15, 2007.

(51) Int. Cl.
*A61K 31/41*    (2006.01)
*C07D 249/16*    (2006.01)

(52) U.S. Cl. ........................ 514/359; 548/261
(58) Field of Classification Search .............. 548/361.5, 548/362.5, 362.1, 261, 359; 514/300, 299, 514/359; 546/113
See application file for complete search history.

(56) References Cited

U.S. PATENT DOCUMENTS

| | | | |
|---|---|---|---|
| 6,239,077 B1 | 5/2001 | Andoh | |
| 7,052,707 B2 | 5/2006 | Ducray et al. | 424/405 |
| 7,084,280 B2 | 8/2006 | Ducray | |
| 7,446,219 B2 | 11/2008 | Ducray et al. | 558/391 |
| 2004/0044074 A1 | 3/2004 | Ducray et al. | 514/521 |
| 2004/0082624 A1 | 4/2004 | Ducray et al. | 514/357 |
| 2004/0209950 A1 | 10/2004 | Ducray et al. | 514/521 |
| 2004/0220055 A1 | 11/2004 | Ducray et al. | 504/244 |
| 2004/0236137 A1 | 11/2004 | Goebel et al. | 558/250 |
| 2004/0242913 A1 | 12/2004 | Ducray et al. | 558/250 |
| 2005/0026972 A1 | 2/2005 | Ducray et al. | 514/367 |
| 2005/0033081 A1 | 2/2005 | Ducray et al. | 558/392 |
| 2005/0059736 A1 | 3/2005 | Ducray et al. | 514/521 |
| 2005/0101614 A1 | 5/2005 | Xiao-Fa | 514/262.1 |
| 2005/0203148 A1 | 9/2005 | Ducray et al. | 514/342 |
| 2005/0203178 A1 | 9/2005 | Ducray et al. | 514/521 |
| 2005/0222448 A1 | 10/2005 | Steiger et al. | 558/390 |
| 2006/0128801 A1 | 6/2006 | Ducray et al. | 514/521 |
| 2007/0037881 A1 | 2/2007 | Goebel et al. | 514/521 |
| 2008/0045601 A1 | 2/2008 | Ducray et al. | 514/262 |
| 2008/0227863 A1 | 9/2008 | Ducray et al. | 614/617 |

FOREIGN PATENT DOCUMENTS

| | | |
|---|---|---|
| EP | 0953565 B1 | 8/2004 |
| EP | 1445251 B1 | 12/2006 |
| WO | WO 02/50052 A1 | 6/2002 |
| WO | WO 03/080577 A2 | 10/2003 |
| WO | WO 03/097036 A1 | 11/2003 |
| WO | WO 03/104202 A1 | 12/2003 |
| WO | WO 03104202 A1 * | 12/2003 |
| WO | WO 2004/024704 A1 | 3/2004 |
| WO | WO 2004024704 A1 * | 3/2004 |
| WO | WO 2005/044784 A1 | 5/2005 |
| WO | WO05/058802 A1 | 6/2005 |
| WO | WO 2005/121075 A1 | 12/2005 |
| WO | WO 2006/043654 A1 | 4/2006 |
| WO | WO06/050887 A1 | 5/2006 |
| WO | WO07/017088 A1 | 2/2007 |

OTHER PUBLICATIONS

Patani, G. Chem. Revs., 1996, vol. 96, pp. 3147-3176.*
Silverman, R., "The ORganic Chemistry of Drug Design and Drug Action," 2d ed., 2004, Elsevier, pp. 29-32.*
"A Novel and Efficient Synthesis of 2-Aryl-2H-indazoles via SnC12-Mediated Cyclization of 2-Nitrobenzylamines", Synthesis of 2-Aryl-2H-indazoles Da-Qing Shi et al., Synlett, 2007, 16, 2509-2512.
"Efficient and Regioselective Synthesis of 2-Alkyl-2H-indazoles", M. Cheung et al., J. Org. Chem., 2003, 68, 4093-4095.
"Claimed 2,1-Benzisoxazoles Are Indazalones", M. J. Kurth et al., J. Org. Chem., 2005, 70, 1060-1062.
"N,N-Bond-Forming Heterocyclization: Synthesis of 3-Alkoxy-2H-indazoles", A. D. Mills et al., J. Org. Chem., 2006, 71, 2687-2689.
"Synthesis of a Library of 2-Alkyl-3-alkyloxy-2H-indazole-6-carboxamides", A. D. Mills et al., J. Comb. Chem., 2007, 9, 171-177.
"Synthesis and activity of 1H-benzimidazole and 1H-benzotriazole derivatives as inhibitors of Acanthamoeba castellanii", K. Kopaska et al., Bioorganic & Medicinal Chemistry, 2004, 12, 2617-2624.
"Indazole N-oxide derivatives as antiprotozoal agents: Synthesis, biological evaluation and mechanism of action studies", A. Gerpe et al., Bioorganic & Medicinal Chemistry, 2006, 14, 3467-3480.

(Continued)

*Primary Examiner* — Janet Andres
*Assistant Examiner* — Heidi Reese
(74) *Attorney, Agent, or Firm* — Judy Jarecki-Black; John Ezcurra; Merial Limited

(57) ABSTRACT

The present invention relates to novel aryloazol-2-yl-cyanoethylamino derivatives of formula (I):

wherein $R_3$, $R_4$, $R_5$, $R_6$, $R_7$, P, Q, V, W, X, Y, Z and a are as defined in the description, compositions thereof, processes for their preparation and their uses as pesticides.

30 Claims, No Drawings

OTHER PUBLICATIONS

"Inhibition of Neuronal Nitric Oxide Synthase by 7-Methoxyindazole and Related Substituted Indazoles", P. Schumann et al., *Bioorganic& Medicinal Chemistry Letters*, 2001, 11, 1153-1156.

"4-Substituted indazoles as new inhibitors of neuronal nitric oxide synthase", M. Boulouard et al., *Bioorganic& Medicinal Chemistry Letters*, 2007, 17, 3177-3180.

"2-Substituted Indazoles From Electrogenerated Orho-nitrosobenzylamines", B. A. Frontana-Uribe et al., *Tetrahedron*, 1998, 54, 3197-3206.

"A Mild Method for the Conversion of Activated Aryl Methyl group to Carboxaldehydes via the Catalyzed Periodate Cleavage of Enamines," M.G. Vetelino et al., *Tetrahedron Letters*, 1994, 35, 219222.

"Preparation of Various Enantiomerically Pure (Benzotriazol-1-yl) and (benzotriazol-2-yl)-alkan-2- ols," B.K. Pcheika et al., *Tetrahedron: Asymmetry*, 2006, 17, 2516-2530.

\* cited by examiner

ARYLOAZOL-2-YL CYANOETHYLAMINO COMPOUNDS, METHOD OF MAKING AND METHOD OF USING THEREOF

INCORPORATION BY REFERENCE

This application claims priority to U.S. Provisional Application Ser. Nos. 60/930,485, filed May 15, 2007.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

FIELD OF THE INVENTION

The present invention relates to novel aryloazol-2-yl-cyanoethylamino derivatives of formula (I):

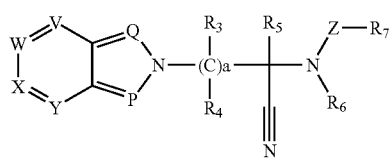

wherein, $R_3$, $R_4$, $R_5$, $R_6$, $R_7$, P, Q, V, W, X, Y, Z, and a are as defined in the description, compositions thereof, processes for their preparation and their uses as pesticides.

BACKGROUND OF THE INVENTION

The control of parasites, particularly endoparasites which parasitize animals, by means of active material having a cyanoethylamino group has been described by many patents or patent application such as International Patent Publications No. WO 2004/024704 (U.S. Pat. No. 7,084,280), WO 2005/044784, WO 2005/121075 and WO 2006/043654 as well as in EP 953565 (U.S. Pat. No. 6,239,077) and EP 1445251.

However none of the foregoing publications describe that compounds of formula (I) possess activity as pesticides, particularly for controlling endoparasitic pests in or on animals and ectoparasitic pests on animals.

OBJECTS AND SUMMARY OF THE INVENTION

This invention provides novel arylo-azol-2-yl-cyanoethylamino derivatives of the formula (I):

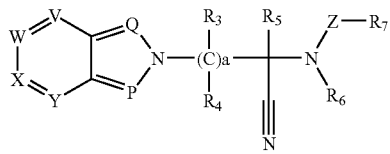

P is C—$R_1$ or N;
Q is C—$R_2$ or N;
V is C—$R_8$ or N;
W is C—$R_9$ or N;
X is C—$R_{10}$ or N;
Y is C—$R_{11}$ or N;

$R_1$, $R_2$, $R_8$, $R_9$, $R_{10}$ and $R_{11}$ either together or independently of one another, are hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkylsulfinyl, haloalkylsulfinyl, alkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, $HO_2C$—, alkyl-$O_2C$—, unsubstituted or substituted aryl or unsubstituted or substituted phenoxy, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl;

$R_3$, $R_4$ and $R_5$ either together or independently of one another, are hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independent of one another and are selected from the group consisting of halogen and alkyl; unsubstituted or substituted phenyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino, di(alkyl)amino; or $R_4$ and $R_5$ together with the carbon to which they are attached form a cycloalkyl ring;

$R_6$ is hydrogen, alkyl, alkoxyalkyl, alkylcarbonyl, alkylthiocarbonyl or unsubstituted or substituted benzyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino, di(alkyl)amino;

$R_7$ is hydrogen, alkyl, alkoxyalkyl, alkylcarbonyl, alkylthiocarbonyl or unsubstituted or substituted phenyl wherein the substituents may each be independent of one another and are selected from the group consisting of cyano, nitro, halogen, alkyl, haloalkyl, phenyl, phenoxy, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl alkylamino, di(alkyl)amino; unsubstituted or substituted hetaryl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino, di(alkyl)amino; or unsubstituted or substituted naphthyl or quinolyl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino, di(alkyl)amino;

Z is a direct bond, C(O), C(S) or S(O)$_p$;

a is 1, 2 or 3;

p is 0, 1 or 2.

It is an object of the present invention to provide new pesticidal compounds of the aryloazol-2-yl-cyanoethylamino family together with processes for their preparation.

A second object of the present invention is to provide pesticidal compositions and pesticidal methods of use of the pesticidal aryloazol-2-yl-cyanoethylamino in the field of pest control which are well tolerated by warm-blooded species, fish and plants, including in particular for controlling endo- and ectoparasites which parasitize mammals, fish and birds.

Another object of the present invention is to provide compounds with high activity and improved safety to the user and the environment, which are obtained by optimization of chemical, physical and biological properties such as solubility, melting point, stability, electronic and steric parameters, and the like.

For the purposes of this application, unless otherwise stated in the specification, the following terms have the definitions cited below:

(1) Alkyl refers to both straight and branched carbon chains; references to individual alkyl groups are specific for the straight chain (e.g. butyl=n-butyl). In one embodiment of alkyl, the number of carbons atoms is 1-20, in another embodiment of alkyl, the number of carbon atoms is 1-8 carbon atoms and in yet another embodiment of alkyl, the number of carbon atoms is 1-4 carbon atoms. Other ranges of carbon numbers are also contemplated depending on the location of the alkyl moiety on the molecule;

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in another embodiment of alkenyl, the number of carbon atoms is 2-8 and in yet another embodiment of alkenyl, the number of carbon atoms is 2-4. Other ranges of carbon-carbon double bonds and carbon numbers are also contemplated depending on the location of the alkenyl moiety on the molecule;

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in another embodiment of alkynyl, the number of carbon atoms is 2-8 and in yet another embodiment of alkynyl, the number of carbon atoms is 2-4. Other ranges of carbon-carbon double bonds and carbon numbers are also contemplated depending on the location of the alkenyl moiety on the molecule;

(4) Aryl refers to a $C_6$-$C_{10}$ aromatic ring structure. In one embodiment of aryl, the moiety is phenyl, naphthyl, tetrahydronapthyl, phenylcyclopropyl and indanyl; in another embodiment of aryl, the moiety is phenyl. Arylo refers to an aryl substituted at two adjacent sites.

(5) Alkoxy refers to —O-alkyl, wherein alkyl is as defined in (1);

(6) Alkanoyl refers to formyl (—C(=O)H) and —C(=O)-alkyl, wherein alkyl is as defined in (1);

(7) Alkanoyloxy refers to —O—C(=O)-alkyl, wherein alkanoyl is as defined in (6);

(8) Alkanoylamino refers to —NH$_2$—C(=O)-alkyl, wherein alkanoyl is as defined in (6) and the amino (NH$_2$) moiety can be substituted by alkyl as defined in (1);

(9) Aminocarbonyl refers to —NH$_2$—C(=O), wherein the amino (NH$_2$) moiety can be substituted by alkyl as defined in (1);

(10) Alkoxycarbonyl refers to —C(=O)—O-alkyl, wherein alkoxy is as defined in (5);

(11) Alkenoyl refers to —C(=O)-alkenyl, wherein alkenyl is as defined in (2);

(12) Alkynoyl refers to —C(=O)-alkynyl, wherein alkynyl is as defined in (3);

(13) Aroyl refers to —C(=O)-aryl, wherein aryl is as defined above;

(14) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(15) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$));

(16) Heterocycle, heterocyclic or heterocyclo refer to fully saturated or unsaturated, including aromatic (i.e. "hetaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]

pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means an arylo-azol-2-yl-cyanoethylamino compound of the invention.

The compounds of the invention are intended to encompass racemic mixtures, specific stereoisomers and tautomeric forms of the compound. Another aspect of the invention is a salt form of the compound of the invention.

Another aspect of the invention are solid state forms of the compounds of the invention which consists of crystalline forms selected from the group consisting of single crystals, nanocrystals, co-crystals, molecular complexes, hydrates, anhydrates, solvates, desolvates, clathrates and inclusion complexes and non-crystalline forms selected from the group consisting of non-crystalline glass and non-crystalline amorphous forms.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

DETAILED DESCRIPTION OF THE INVENTION

A first aspect of the invention provides novel aryloazol-2-yl-cyanoethylamino derivatives of the formula (I):

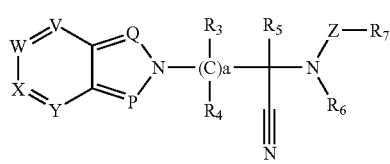

wherein:
P is C—$R_1$ or N;
Q is C—$R_2$ or N;
V is C—$R_8$ or N;
W is C—$R_9$ or N;
X is C—$R_{10}$ or N;
Y is C—$R_{11}$ or N;

$R_1$, $R_2$, $R_8$, $R_9$, $R_{10}$ and $R_{11}$ either together or independently of one another, are hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkylsulfinyl, haloalkylsulfinyl, alkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, $HO_2C$—, alkyl-$O_2C$—, unsubstituted or substituted aryl or unsubstituted or substituted phenoxy, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl;

$R_3$, $R_4$ and $R_5$ either together or independently of one another, are hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independent of one another and are selected from the group consisting of halogen and alkyl; unsubstituted or substituted phenyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino, di(alkyl)amino; or $R_4$ and $R_5$ together with the carbon to which they are attached form a cycloalkyl ring;

$R_6$ is hydrogen, alkyl, alkoxyalkyl, alkylcarbonyl, alkylthiocarbonyl or unsubstituted or substituted benzyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino, di(alkyl)amino;

$R_7$ is hydrogen, alkyl, alkoxyalkyl, alkylcarbonyl, alkylthiocarbonyl or unsubstituted or substituted phenyl wherein the substituents may each be independent of one another and are selected from the group consisting of cyano, nitro, halogen, alkyl, haloalkyl, phenyl, phenoxy, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl alkylamino, di(alkyl)amino; unsubstituted or substituted hetaryl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino, di(alkyl)amino; or unsubstituted or substituted naphthyl or quinolyl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino, di(alkyl)amino;

Z is a direct bond, C(O), C(S) or $S(O)_p$;
a is 1, 2 or 3; and
p is 0, 1 or 2.

In one embodiment of the first aspect of the invention provides a novel aryloazol-2-yl-cyanoethylamino derivatives of the formula (I), wherein P is C—$R_1$ or N;
Q is C—$R_2$ or N;
V is C—$R_8$ or N;
W is C—$R_9$ or N;
X is C—$R_{10}$ or N;
Y is C—$R_{11}$ or N;
$R_1$, $R_2$, $R_8$, $R_9$, $R_{10}$ and $R_{11}$ either together or independently of one another, are hydrogen, amino, amido, cyano, nitro, halogen, $C_1$-$C_6$-alkyl, $C_2$-$C_6$-alkenyl, $C_2$-$C_6$-alkynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio arylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$ alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, $HO_2C$—, $C_1$-$C_6$-alkyl-$O_2C$—, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$ alkylsulfonyl, halo-$C_1$-$C_6$-alkylsulfonyl;

$R_3$, $R_4$ and $R_5$ either together or independently of one another, are hydrogen, halogen, $C_1$-$C_6$-alkyl, hydroxy-$C_1$-$C_6$-alkyl, $C_1$-$C_6$-alkylthio-$C_1$-$C_6$-alkyl, halo-$C_1$-$C_6$-alkyl, $C_1$-$C_6$-alkoxy-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylsulfonyloxy-$C_1$-$C_6$-alkyl; unsubstituted or substituted $C_3$-$C_7$-cycloalkyl, wherein the substituents may each be independent of one another and are selected from the group consisting of halogen and $C_1$-$C_6$-alkyl; unsubstituted or substituted phenyl, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino; or $R_4$ and $R_5$ together with the carbon to which they are attached form a cycloalkyl ring;

$R_6$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or unsubstituted or substituted benzyl, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, di($C_1$-$C_6$-alkyl)amino;

$R_7$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or unsubstituted or substituted phenyl wherein the substituents may each be independent of one another and are selected from the group consisting of cyano, nitro, halogen, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl $C_1$-$C_6$-alkylamino, di($C_1$-$C_6$-alkyl)amino; unsubstituted or substituted hetaryl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino; or unsubstituted or substituted naphthyl or quinolyl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino;

Z is a direct bond, C(O), C(S) or $S(O)_p$;
a is 1, 2 or 3; and
p is 0, 1 or 2.

In another embodiment of the first aspect of the invention, compounds of formula (I) above are compounds wherein:

P and Q are N;
V is C—$R_8$;
W is C—$R_9$;
X is C—$R_{10}$;
Y is C—$R_{11}$;
$R_3$, $R_4$ and $R_6$ are H;
$R_8$, $R_9$, $R_{10}$ and $R_{11}$ either together or independently of one another, are hydrogen, amino, amido, cyano, nitro, halogen, $C_1$-$C_6$-alkyl, $C_2$-$C_6$-alkenyl, $C_2$-$C_6$-alkynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio arylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, $HO_2C$—, $C_1$-$C_6$-alkyl-$O_2C$—, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl;

$R_5$ is methyl or $C_1$-$C_3$-alkyl;
$R_7$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or unsubstituted or substituted phenyl wherein the substituents may each be independent of one another and are selected from the group consisting of cyano, nitro, halogen, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl $C_1$-$C_6$-alkylamino, di($C_1$-$C_6$-alkyl)amino; unsubstituted or substituted hetaryl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino; or unsubstituted or substituted naphthyl or quinolyl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino;

Z is a direct bond, C(O), C(S) or S(O)$_p$;
a is 1;
p is 0 or 1.

In yet another embodiment of the first aspect of the invention, compounds of formula (I) above are compounds wherein:
P and Q is N;
V is C—$R_8$;
W is C—$R_9$;
X is C—$R_{10}$;
Y is C—$R_{11}$;
$R_8$, $R_9$, $R_{10}$ and $R_{11}$ either together or independently of one another, are hydrogen, amino, amido, cyano, nitro, halogen, $C_1$-$C_6$-alkyl, $C_2$-$C_6$-alkenyl, $C_2$-$C_6$-alkynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio arylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, $HO_2C$—, $C_1$-$C_6$-alkyl-$O_2C$—, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl;

$R_3$, $R_4$ and $R_6$ are H;
$R_5$ is methyl or $C_1$-$C_3$-alkyl;
$R_7$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or unsubstituted or substituted phenyl wherein the substituents may each be independent of one another and are selected from the group consisting of cyano, nitro, halogen, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl $C_1$-$C_6$-alkylamino, di($C_1$-$C_6$-alkyl)amino; unsubstituted or substituted hetaryl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino;

Z is C(O); and
a is 1.

In still another embodiment of the first aspect of the invention, compounds of formula (I) above are compounds wherein:
P and Q are N;
V is C—$R_8$;
W is C—$R_9$;
X is C—$R_{10}$;
Y is C—$R_{11}$;
$R_8$, $R_9$, $R_{10}$ and $R_{11}$ either together or independently of one another, are hydrogen, amino, amido, cyano, nitro, halogen, $C_1$-$C_6$-alkyl, $C_2$-$C_6$-alkenyl, $C_2$-$C_6$-alkynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio arylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, $HO_2C$—, $C_1$-$C_6$-alkyl-$O_2C$—, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl;

$R_3$, $R_4$ and $R_6$ are H;
$R_5$ is methyl
$R_7$ is unsubstituted or substituted phenyl wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino; unsubstituted or substituted hetaryl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino;

Z is C(O); and
a is 1.

In still another embodiment of the first aspect of the invention, compounds of formula (I) above are compounds wherein:
P and Q are N;
V is C—$R_8$;
W is C—$R_9$;
X is C—$R_{10}$;
Y is C—$R_{11}$;
$R_3$, $R_4$ and $R_6$ are hydrogen;

$R_5$ is hydrogen, alkyl, haloalkyl, hydroxyalkyl, alkylthioalkyl, alkyloxyalkyl, or alkylsulfonyloxyalkyl;

$R_7$ is unsubstituted phenyl or phenyl substituted by one or more substituents selected from the group consisting of alkyl, haloalkyl, phenyl, phenyloxy, alkoxy, haloalkoxy, alkylthio, haloalkylthio, haloalkylsulfinyl and haloalkylsulfonyl;

$R_8$, $R_9$, $R_{10}$ and $R_{11}$ either together or independently of one another, are hydrogen, halogen, alkyl, haloalkyl, cyano, alkoxy, haloalkoxy, alkenyl, alkylamino, hydroxyalkyl, formyl, alkylaminoalkyl, dialkylaminoalkyl, aminoalkyl, $HO_2C—$, alkyl-$O_2C—$, formyl or unsubstituted or substituted phenyl wherein the substituents are alkyl or haloalkyl;

Z is C(O); and a is 1.

In still another embodiment of the first aspect of the invention, compounds of formula (I) above are compounds wherein:

P and Q is N;

V is C—$R_8$;

W is C—$R_9$;

X is C—$R_{10}$;

Y is C—$R_{11}$;

$R_3$, $R_4$ and $R_6$ are hydrogen;

$R_5$ is hydrogen, $C_1$-$C_6$-alkyl, halo-$C_1$-$C_6$-alkyl, hydroxy-$C_1$-$C_6$-alkyl, $C_1$-$C_6$-alkylthio-$C_1$-$C_6$-alkyl, $C_1$-$C_6$-alkyloxy-$C_1$-$C_6$-alkyl, or $C_1$-$C_6$-alkylsulfonyloxy-$C_1$-$C_6$-alkyl;

$R_7$ is unsubstituted phenyl or phenyl substituted by one or more substituents selected from the group consisting of $C_1$-$C_6$-alkyl, halo-$C_1$-$C_6$-alkyl, phenyl, phenyloxy, $C_1$-$C_6$-alkoxy, halo-$C_1$-$C_6$-alkoxy, $C_1$-$C_6$-alkylthio, halo-$C_1$-$C_6$-alkylthio, halo-$C_1$-$C_6$-alkylsulfinyl and halo-$C_1$-$C_6$-alkylsulfonyl;

$R_8$, $R_9$, $R_{10}$ and $R_{11}$ either, independently of one another, is hydrogen, halogen, $C_1$-$C_6$-alkyl, halo-$C_1$-$C_6$-alkyl, cyano, $C_1$-$C_6$-alkoxy, halo-$C_1$-$C_6$-alkoxy, $C_2$-$C_6$-alkenyl, $C_1$-$C_6$-alkylamino, hydroxy-$C_1$-$C_6$-alkyl, formyl, $C_1$-$C_6$-alkylamino-$C_1$-$C_6$-alkyl, $HO_2C—$, $C_1$-$C_6$-alkyl-$O_2C—$ or unsubstituted or substituted phenyl wherein the substituents are $C_1$-$C_6$-alkyl or halo-$C_1$-$C_6$-alkyl;

Z is C(O); and a is 1.

In still another embodiment of the first aspect of the invention, compounds of formula (I) above are compounds wherein:

P and Q is N;

V is C—$R_8$;

W is C—$R_9$;

X is C—$R_{10}$;

y is C—$R_{11}$;

$R_3$, $R_4$ and $R_6$ are hydrogen;

$R_5$ is methyl, ethyl, butyl, $CH_2OH$, $CH_2OCH_3$, $CH_2SCH_3$, $CH_2OSO_2CH_3$;

$R_7$ is a phenyl substituted with butyl, $CF_3$, phenyl, phenoxy, $OCF_3$, $SCF_3$, $SOCF_3$, $SO_2CF_3$;

$R_8$, $R_9$, $R_{10}$ and $R_{11}$ either, independently of one another, is hydrogen, methyl, $CH_2NH_2$, $CH_2N(CH_3)_2$, vinyl, $CH_2OH$, $CH(OH)CH_2OH$, $CO_2H$, $CO_2CH_3$, Ph-$CF_3$, F, Cl, Br, $CF_3$, $OCF_3$ or CN;

Z is C(O); and a is 1.

In a second aspect of the invention, compounds of formula (I) above are compounds wherein:

P is N;

Q is C—$R_2$;

V is C—$R_8$;

W is C—$R_9$;

X is C—$R_{10}$;

Y is C—$R_{11}$;

$R_2$ is hydrogen, halogen, alkyl, haloalkyl, alkoxy, haloalkoxy, alkoxyalkoxy, or alkylaminoalkoxy, dialkylaminoalkoxy;

$R_3$, $R_4$ and $R_6$ are hydrogen;

$R_5$ is hydrogen, alkyl, or haloalkyl;

$R_7$ is unsubstituted phenyl or phenyl substituted by one or more substituents selected from the group consisting of alkyl, haloalkyl, alkoxy, haloalkoxy, alkylthio, haloalkylthio, haloalkylsulfinyl and haloalkylsulfonyl;

$R_8$, $R_9$, $R_{10}$ and $R_{11}$ either together or independently of one another, are hydrogen, halogen, alkyl, haloalkyl, nitro, amino, amido, alkyl-$O_2C—$ or alkylcarbonylamino;

Z is C(O); and a is 1.

In another embodiment of the second aspect of the invention, compounds of formula (I) above are compounds wherein:

P is N;

Q is C—$R_2$;

V is C—$R_8$;

W is C—$R_9$;

X is C—$R_{10}$;

Y is C—$R_{11}$;

$R_2$ is hydrogen, halogen, $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkoxy-$C_1$-$C_6$-alkoxy, or $C_1$-$C_6$-alkylamino-$C_1$-$C_6$-alkoxy;

$R_3$, $R_4$ and $R_6$ are hydrogen;

$R_5$ is hydrogen, $C_1$-$C_6$-alkyl, or halo-$C_1$-$C_6$-alkyl;

$R_7$ is unsubstituted phenyl or phenyl substituted by one or more substituents selected from the group consisting of $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, halo-$C_1$-$C_6$-alkylsulfinyl and halo-$C_1$-$C_6$-alkylsulfonyl;

$R_8$, $R_9$, $R_{10}$ and $R_{11}$ either, independently of one another, is hydrogen, halogen, $C_1$-$C_6$-alkyl, halo-$C_1$-$C_6$-alkyl, nitro, amino, amido, $C_1$-$C_6$-alkyl-$O_2C—$ or $C_1$-$C_6$-alkylcarbonylamino;

Z is C(O); and a is 1.

In still another embodiment of the second aspect of the invention, compounds of formula (I) above are compounds wherein:

P is N;

Q is C—$R_2$;

V is C—$R_8$;

w is C—$R_9$;

X is C—$R_{10}$;

y is C—$R_{11}$;

$R_2$ is hydrogen, Cl, methyl, methoxy, ethoxy, propoxy, butoxy, $O(CH_2)_2OCH_3$, or $O(CH_2)_2N(CH_3)_2$;

$R_3$, $R_4$ and $R_6$ are hydrogen;

$R_5$ is methyl;

$R_7$ is phenyl substituted by $OCF_3$, phenoxy, or $SCF_3$;

$R_8$, $R_9$, $R_{10}$ and $R_{11}$ either, independently of one another, is hydrogen, Cl, Br, $C_1$-$C_6$-alkyl, $CF_3$, nitro, amino, amido, $CO_2CH_3$, or $NHCOCH_3$;

Z is C(O); and a is 1.

In a third aspect of the invention, compounds of formula (I) above are compounds wherein:

P is N;

Q is C—$R_2$ or N;

V is N;

W is C—$R_9$;

X is C—$R_{10}$;

Y is C—$R_{11}$;
$R_2$ is hydrogen, halogen, alkyl, alkoxy, or haloalkoxy;
$R_3$, $R_4$ and $R_6$ are hydrogen;
$R_5$ is hydrogen, alkyl, or haloalkyl;
$R_7$ is unsubstituted phenyl or phenyl substituted by one or more substituents selected from the group consisting of alkyl, haloalkyl, alkoxy, haloalkoxy, alkylthio, haloalkylthio, haloalkylsulfinyl and haloalkylsulfonyl;
$R_9$, $R_{10}$ and $R_{11}$ either together or independently of one another, are hydrogen, halogen, alkyl, or haloalkyl;
Z is C(O); and
a is 1.

In another embodiment of the third aspect of the invention, compounds of formula (I) above are compounds wherein:
P is N;
Q is C—$R_2$ or N;
V is N;
W is C—$R_9$;
X is C—$R_{10}$;
Y is C—$R_{11}$;
$R_2$ is hydrogen, halogen, $C_1$-$C_6$-alkyl, $C_1$-$C_6$-alkoxy, or halo-$C_1$-$C_6$-alkoxy;
$R_3$, $R_4$ and $R_6$ are hydrogen;
$R_5$ is hydrogen, $C_1$-$C_6$-alkyl, or halo-$C_1$-$C_6$-alkyl;
$R_7$ is unsubstituted phenyl or phenyl substituted by one or more substituents selected from the group consisting of $C_1$-$C_6$-alkyl, halo-$C_1$-$C_6$-alkyl, $C_1$-$C_6$-alkoxy, halo-$C_1$-$C_6$-alkoxy, $C_1$-$C_6$-alkylthio, halo-$C_1$-$C_6$-alkylthio, halo-$C_1$-$C_6$-alkylsulfinyl and halo-$C_1$-$C_6$-alkylsulfonyl;
$R_9$, $R_{10}$ and $R_{11}$ either, independently of one another, is hydrogen, halogen, $C_1$-$C_6$-alkyl, or halo-$C_1$-$C_6$-alkyl;
Z is C(O); and
a is 1.

In still another embodiment of the third aspect of the invention, compounds of formula (I) above are compounds wherein:
P is N;
Q is C—$R_2$ or N;
V is N;
W is C—$R_9$;
X is C—$R_{10}$;
Y is C—$R_{11}$;
$R_2$ is hydrogen, Cl, Br, methoxy;
$R_3$, $R_4$ and $R_6$ are hydrogen;
$R_5$ is methyl;
$R_7$ is phenyl substituted by $OCF_3$ or $SCF_3$;
$R_9$, $R_{10}$ and $R_{11}$ either, independently of one another, is hydrogen, Cl, Br or methyl;
Z is C(O); and
a is 1.

In a fourth aspect of the invention, compounds of formula (I) above are compounds wherein:
P is N;
Q is C—$R_2$ or N;
V is C—$R_8$ or N;
W is C—$R_9$;
X is C—$R_{10}$;
y is C—$R_{11}$;
$R_2$ is hydrogen, Cl, Br, methyl or methoxy;
$R_3$, $R_4$ and $R_6$ is H;
$R_5$ is methyl;
$R_7$ is phenyl optionally substituted with $OCF_3$, $SCF_3$ or $CHFCF_3$;
$R_8$, $R_9$, $R_{10}$ and $R_{11}$, either, independently of one another is H, Cl, Br, methyl, $CF_3$ or CN;
Z is C(O); and
a is 1.

In another embodiment of the fourth aspect of the invention, compounds of formula (I) above are compounds wherein:
P is N;
Q is C—$R_2$ or N;
V is C—$R_8$ or N;
W is C—$R_9$;
X is C—$R_{10}$;
Y is C—$R_{11}$;
$R_2$ is hydrogen, Cl, Br, methyl or methoxy;
$R_3$, $R_4$ and $R_6$ is H;
$R_5$ is methyl;
$R_7$ is phenyl substituted with $OCF_3$, $SCF_3$ or $CHFCF_3$;
$R_8$ is H, Cl, Br, F or CN;
$R_9$ is H, Cl or Br;
$R_{10}$ is H, Cl, Br or $CF_3$;
$R_{11}$ is H, Cl, Br or methyl;
Z is C(O); and
a is 1.

In a fifth aspect of the invention, compounds of formula (I) above are compounds wherein:
P is N;
Q is C—$R_2$ or N;
V is N;
W is C—$R_9$;
X is C—$R_{10}$;
Y is C—$R_{11}$;
$R_2$ is hydrogen, Cl, Br or methoxy;
$R_3$, $R_4$ and $R_6$ is H;
$R_5$ is methyl;
$R_7$ is phenyl substituted with $OCF_3$ or $SCF_3$;
$R_9$ is H;
$R_{10}$ is Cl or Br;
$R_{11}$ is H;
Z is C(O); and
a is 1.

Formulations and Administration for Pharmaceutical/Veterinary Use

Another aspect of the invention is the formation of parasiticidal compositions which comprise the aryloazol-2-yl-cyanoethylamino compounds of the invention. The composition of the invention can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the aryloazol-2-yl cyanoethylamino compound of the invention, the paste can also contain fumed silica; a viscosity modifier; a carrier; optionally, an absorbent; and optionally, a colorant, stabilizer, surfactant, or preservative.

The process for preparing a paste formulation comprises the steps of:

(a) dissolving or dispersing the aryloazol-2-yl cyanoethylamino compound into the carrier by mixing;
(b) adding the fumed silica to the carrier containing the dissolved aryloazol-2-yl cyanoethylamino compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing aryloazol-2-yl cyanoethylamino compound, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (polysorbate 80 or Tween 80), and poloxamers (e.g., Pluronic L 81); an absorbent selected from the group consisting of magnesium carbonate, calcium carbonate, starch, and cellulose and its derivatives; and a colorant selected from the group consisting of titanium dioxide iron oxide, and FD&C Blue #1 Aluminum Lake.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, a spot-on or pour-on composition, can allow for the inventive compound to be absorbed through the skin to achieve systemic levels, distributed through the sebaceous glands or on the surface of the skin achieving levels throughout the haircoat. When the compound is distributed through the sebaceous glands, they can act as a reservoir, whereby there can be a long-lasting effect (up to several months) effect. Spot-on formulations are typically applied in a localized region which refers to an area other than the entire animal. In one embodiment of a localized region, the location is between the shoulders. In another embodiment of a localized region it is a stripe, e.g. a stripe from head to tail of the animal.

Pour-on formulations are described in U.S. Pat. No. 6,010,710, incorporated herein by reference. The pour-on formulations may be advantageously oily, and generally comprise a diluent or vehicle and also a solvent (e.g. an organic solvent) for the active ingredient if the latter is not soluble in the diluent.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. One embodiment of the emollient and/or spreading and/or film-forming agent are those agents selected from the group consisting of:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the aryloazol-2-yl cyanoethylamino compound and its solubility in this solvent. It will be sought to have the lowest possible volume. The vehicle makes up the difference to 100%.

In one embodiment of the amount of emollient, the emollient is used in a proportion selected from the group consisting of from 0.1 to 50% and 0.25 to 5%, by volume.

In another embodiment of the invention, the composition can be in ready-to-use solution form as is described in U.S. Pat. No. 6,395,765, incorporated herein by reference. In addition to the aryloazol-2-yl cyanoethylamino compound, the ready-to-use solution can contain a crystallization inhibitor, an organic solvent and an organic co-solvent.

In one embodiment of the amount of crystallization inhibitor, the crystallization inhibitor can be present in a proportion selected from the group consisting of about 1 to about 20% (w/v) and about 5 to about 15%. In another embodiment of the amount of crystallization inhibitor, the amount corresponds to the test in which 0.3 ml of a solution comprising 10% (w/v) of aryloazol-2-yl cyanoethylamino compound in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystal.

The organic solvent has a dielectric constant of a range selected from the group consisting of between about 10 and 35 and between about 20 and 30, the content of this organic solvent in the overall composition representing the complement to 100% of the composition; and the organic co-solvent having a boiling point selected from the ranges consisting of below 100° C., and below 80° C., and having a dielectric constant of a range selected from the group consisting of between about 10 and 40 and between about 20 and 30; this co-solvent may be present in the composition in a organic co-solvent/organic solvent weight/weight (W/W) ratio of between about 1/15 and 1/2. The solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:
(a) polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others;
(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);
(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;
(d) amine salts of formula $N^+HR'R''R'''$, in which the R radicals are identical or different optionally hydroxylated hydrocarbon radicals; octadecylamine hydrochloride is one of the cationic surfactants which can be used;
(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;
(f) amphoteric surfactants, such as substituted lauryl compounds of betaine; or
(g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied can be of the order of about 0.3 to about 1 ml. In one embodiment for the volume, the volume is on the order of about 0.5 ml, for cats and on the order of about 0.3 to about 3 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference), which in one embodiment of the spot-on formulation comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

The liquid carrier vehicle can optionally contain a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent is present in the formulation at a concentration of about 0.05 to 10% weight/volume. In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

Another embodiment of the invention is directed toward a method of treating an endoparasitic infection in a mammal in need thereof which comprises administering an effective amount of the compound of the invention.

In one embodiment for treating an endoparasitic infection, the endoparasite is a helminth selected from the group consisting of, but not limited to, *Anaplocephala (Anoplocephala), Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria*, and combinations thereof.

In another embodiment of the invention, the helminth is *Haemonchus contortus, Ostertagia circumcincta, Trichostrongylus axei, Trichostrongylus colubriformis, Cooperia curticei, Nematodirus battus* and combinations thereof.

Another embodiment of the invention is directed toward a method of treating an ectoparasitic infection in a mammal in need thereof which comprises administering an effective amount of the compound of the invention.

In one embodiment for treating ectoparasitic infection, the mammal is infected with an ectoparasite selected from the group consisting of but not limited to fleas, ticks, mites, mosquitoes, flies, lice, blowfly and combinations thereof.

Formulations and Administration for Agrochemical Use

The compounds of the formula (I) or their salts can be employed as such or in the form of their preparations (formulations) as combinations with other pesticidally active substances, such as, for example, insecticides, attractants, sterilants, acaricides, nematicides, herbicides, fungicides, and with safeners, fertilizers and/or growth regulators, for example as a premix/readymix.

The insecticides include, for example, phosphoric esters, carbamates, carboxylic esters, chlorinated hydrocarbons, phenylureas, substances prepared by microorganisms.

Examples of insecticides which may optionally be admixed include but are not limited to: phosphoric esters, such as azinphos-ethyl, azinphos-methyl, α-1(4-chlorophenyl)-4-(O-ethyl, S-propyl)phosphoryloxy-pyrazole, chlorpyrifos, coumaphos, demeton, demeton-5-methyl, diazinon, dichlorvos, dimethoate, ethoate, ethoprophos, etrimfos, fenitrothion, fenthion, heptenophas, parathion, parathion-methyl, phosalone, poxim, pirimiphos-ethyl, pirimiphos-methyl, profenofos, prothiofos, sulfprofos, triazophos and trichlorphon;

carbamates, such as aldicarb, bendiocarb, α–2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds (e.g. dimethyl(phenyl)silyl-methyl 3-phenoxybenzyl ethers, such as dimethyl-(4-ethoxyphenyl)-silylmethyl 3-phenoxybenzyl ether) or (dimethylphenyl)-silyl-methyl 2-phenoxy-6-pyridylmethyl ethers such as, for example, dimethyl-(9-ethoxy-phenyl)-silylmethyl 2-phenoxy-6-pyridylmethyl ether or [(phenyl)-3-(3-phenoxyphenyl)-propyl[(dimethyl)-silanes such as, for example, (4-ethoxyphen-yl)-[3-(4-fluoro-3-phenoxyphenyl-propyl]dimethyl-silane, silafluofen;

pyrethroids (which are also useful for their repellent properties, e.g. against mosquitoes), such as allethrin, alphamethrin, bioresmethrin, byfenthrin, cycloprothrin, cyfluthirin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropane-carboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridinyl)-methyl]-4,5-dihydro-N-nitro-1H-imidazole-2-amine (imidacloprid), N-[(6-chloro-3-pyridyl)-methyl]-N$^2$-cyano-N$^1$-methylacetamide (NI-25); abamectin, AC 303, 630 (chlorfenapyr), acephate, acrinathrin, alanycarb, aldoxycarb, aldrin, amitraz, azamethiphos, *Bacillus thuringiensis*, phos-met, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tert-butyl-pyrimidin-5-yl-o-isopropylphosphorothiate, thiocyclam, thiofanox, thiometon, tralomethrin, triflumuron, trimethacarb, vamidothion, *Verticillium Lacanii*, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alphacypermethrin, cyophenothrin, cyromazine, dazomet, DDT, demeton-S-methylsulphone, diafenthiuron, dialifos, dicrotophos, diflubenzuron, dinoseb, deoxabenzofos, diazacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous chloride, metam, metarthizium, anisopliae, methacrifos, methamidophos, methidathion, methiocarb, methoprene, methoxychlor, methyl isothiocyanate, metolcarb, mevinphos, monocrotophos, naled, Neodiprion sertifer NPV, nicotine, omethoate, oxydemeton-methyl, pentachlorophenol, petroleum oils, phenothrin, phenthoate, phorate.

Other insecticides that may optionally be admixed may also be from the class of the compounds described by U.S. Pat. No. 7,001,903.

Fungicides which may optionally be admixed are include but are not limited to:

(1) Triazoles which include but are not limited to:
azaconazole, propiconazole, tebuconazole, cyproconazole, metconazole, amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, paclobutrazol, (+)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.
(2) Imidazoles which include but are not limited to:
imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.
(3) "Methyl(E)-2-phenyl-3-methoxyacrylate" compounds which include but are not limited to: methyl(E)-2-[2-[6-(2-cyanophenoxy)pyrimidin-4-yloxy]phenyl]3-methoxyacrylate, methyl(E)-2-[2-[6-(2-thioamidophenoxy)pyrimidin-4-yloxy]phenyl]-3-methoxyacrylate, methyl(E)-2-[2-[6-(2-fluorophenoxy)pyrimidin-4-yloxy]phenyl]-3-methoxyacrylate, methyl(E)-2-[2-[6-(2,6-difluorophenoxy)pyrimidin-4-yloxy]phenyl]-3-methoxyacrylate, methyl(E)-2-[2-[3-(pyrimidin-2-yloxy)phenoxy]phenyl]-3-methoxyacrylate, methyl(E)-2-[2-[3-(5-methylpyrimidin-2-yloxy)phenoxy]phenyl]-3-methoxyacrylate, methyl(E)-2-[2-[3-(phenyl-sulphonyloxy)phenoxy]phenyl]-3-methoxyacrylate, methyl(E)-2-[2-[3-(4-nitrophenoxy)phenoxy]phenyl]-3-methoxyacrylate, methyl(E)-2-[2-phenoxyphenyl]-3-methoxyacrylate, methyl(E)-2-[2-(3,5-dimethyl-benzoyl)pyrrol-1-yl]-3-methoxyacrylate, methyl (E)-2-[2-(3-methoxyphenoxy)phenyl]-3-methoxyacrylate, methyl(E)-2-[2-(2-phenylethen-1-yl)-phenyl]-3-methoxyacrylate, methyl(E)-2-[2-(3,5-dichlorophenoxy)pyridin-3-yl]-3-methoxyacrylate, methyl(E)-2-(2-(3-(1,1,2,2-tetrafluoroethoxy)phenoxy)phenyl)-3-methoxyacrylate, methyl(E)-2-(2-[3-(alpha-hydroxybenzyl)phenoxy]phenyl)-3-methoxyacrylate, methyl(E)-2-(2-(4-phenoxypyridin-2-yloxy)phenyl)-3-methoxyacrylate, methyl(E)-2-[2-(3-n-propyloxyphenoxy)phenyl]3-methoxyacrylate, methyl(E)-2-[2-(3-isopropyloxyphenoxy)phenyl]-3-methoxyacrylate, methyl(E)-2-[2-[3-(2-fluorophenoxy)phenoxy]phenyl]-3-methoxyacrylate, methyl(E)-2-[2-(3-ethoxyphenoxy)phenyl]-3-methoxyacrylate, methyl(E)-2-[2-(4-tert-butyl-pyridin-2-yloxy)phenyl]-3-methoxyacrylate, methyl(E)-2-[2-[3-(3-cyanophenoxy)phenoxy]phenyl]-3-methoxyacrylate, methyl(E)-2-[2-[(3-methylpyridin-2-yloxymethyl)phenyl]-3-methoxyacrylate, methyl(E)-2-[2-[6-(2-methylphenoxy)pyrimidin-4-yloxy]phenyl]-3-methoxyacrylate, methyl(E)-2-[2-(5-bromo-pyridin-2-yloxymethyl)phenyl]-3-methoxyacrylate, methyl(E)-2-[2-(3-(3-iodopyridin-2-yloxy)phenoxy)phenyl]-3-methoxyacrylate, methyl(E)-2-[2-[6-(2-chloropyridin-3-yloxy)pyrimidin-4-yloxy]phenyl]-3-methoxyacrylate, methyl(E),(E)-2-[2-(5,6-dimethylpyrazin-2-ylmethyloximinomethyl)phenyl]-3-methoxyacrylate, methyl(E)-2-{2-[6-(6-methylpyridin-2-yloxy)pyrimidin-4-yloxy]phenyl}-3-methoxyacrylate, methyl(E),(E)-2-{2-(3-methoxyphenyl)methyloximinomethyl]-phenyl}-3-methoxyacrylate, methyl(E)-2-{2-(6-(2-azidophenoxy)-pyrimidin-4-yloxy]phenyl}-3-methoxyacrylate, methyl(E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl(E)-2-{2-[6-(2-n-propylphenoxy)-1,3,5-triazin-4-yloxy]phenyl}-3-methoxyacrylate, and methyl(E),(E)-2-{2-[(3-nitrophenyl)methyloximinomethyl]phenyl}-3-methoxyacrylate;

(4) Succinate Dehydrogenase Inhibitors which include but are not limited to:
  (a) fenfuram, furcarbanil, cyclafluramid, furmecyclox, seedvax, metsulfovax, pyrocarbolid, oxycarboxin, shirlan, mebenil (mepronil), benodanil, flutolanil (Moncut);
  (b) naphthalene derivatives such as terbinafine, naftifine, butenafine, 3-chloro-7-(2-aza-2,7,7-trimethyl-oct-3-en-5-ine);
  (c) sulphenamides such as dichlofluanid, tolylfluanid, folpet, fluorfolpet; captan, captofol;
  (d) benzimidazoles such as carbendazim, benomyl, furathiocarb, fuberidazole, thiophonatmethyl, thiabendazole or their salts;
  (e) morpholine derivatives such as fenpropimorph, falimorph, dimethomorph, dodemorph, aldimorph, fenpropidine and their arylsulphonates, such as, for example, p-toluenesulphonic acid and p-dodecylphenyl-sulphonic acid;
  (f) dithiocarbamates, cufraneb, ferbam, mancopper, mancozeb, maneb, metam, metiram, thiram zeneb, ziram;
  (g) benzothiazoles, such as 2-mercaptobenzothiazole;
  (h) benzamides, such as 2,6-dichloro-N-(4-trifluoromethylbenzyl)-benzamide;
  (i) boron compounds, such as boric acid, boric esters, borax;
  (j) formaldehyde and formaldehyde-releasing compounds, such as benzyl alcohol mono-(poly)-hemiformal, oxazolidine, hexa-hydro-5-triazines, N-methylolchloroacetamide, paraformaldehyde, nitropyrin, oxolinic acid, tecloftalam;
(k) tris-N-(cyclohexyldiazeniumdioxy)-aluminium, N-(cyclo-hexyldiazeniumdioxy)-tri-butyltin or K salts, bis-N-(cyclohexyldiazeniumdioxy)-copper, N-methylisothiazolin-3-one, 5-chloro-N-methylisothiazolin-3-one, 4,5-dichloro-N-octylisothiazolin-3-one, N-octylisothiazolin-3-one, 4,5-trimethylene-isothiazolinone, 4,5-benzoisothiazolinone, N-methylolchloroacetamide;
(l) aldehydes, such as cinnamaldehyde, formaldehyde, glutaraldehyde, β-bromo-cinnamaldehyde;
(m) thiocyanates, such as thiocyanatomethylthiobenzothiazole, methylenebisthiocyanate, and the like;
(n) quaternary ammonium compounds, such as benzyldimethyltetradecylammonium chloride, benzyldimethyldodecylanmuonium chloride, didecyldimethylammonium chloride;
(o) iodine derivatives, such as diiodomethyl p-tolyl sulphone, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;
(p) phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts;
(q) microbicides having an activated halogen group, such as chloroacetamide, bronopol, bronidox, tectamer, such as 2-bromo-2-nitro-1,3-propanediol, 2-bromo-4'-hydroxyacetophenone, 2,2-dibromo-3-nitrile-propionamide, 1,2-dibromo-2,4-dicyanobutane, β-bromo-β-nitrostyrene;
(r) pyridines, such as 1-hydroxy-2-pyridinethione (and their Na, Fe, Mn, Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridine;
(s) metal soaps, such as tin naphthenate, copper naphthenate, zinc naphthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;
(t) metal salts, such as copper hydroxycarbonate, sodium dichromate, potassium dichromate, potassium chromate, copper sulphate, copper chloride, copper borate, zinc fluorosilicate, copper fluorosilicate, and mixtures with fixatives;
(u) oxides, such as tributyltin oxide, $Cu_2O$, CuO, ZnO;
(v) dialkyldithiocarbamates, such as Na and Zn salts of dialkyldithiocarbamates, tetramethylthiuram disulphide, potassium N-methyl-dithiocarbamate;
(w) nitriles, such as 2,4,5,6-tetrachloroisophthalodinitrile, disodium cyano-dithioimido-carbamate;
(x) quinolines, such as 8-hydroxyquinoline, and their Cu salts;
(y) mucochloric acid, 5-hydroxy-2(5H)-furanone;
(z) 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxymethyl-N'-methyl-dithiocarbamate, 2-oxo-2-(4-hydroxy-phenyl)acetohydroximic acid chloride, phenyl-(2-chloro-cyano-vinyl) sulphone, phenyl-(1,2-dichloro-2-cyano-vinyl) sulphone; and
(aa) Ag-, Zn- or Cu-containing zeolites, alone or enclosed in polymeric active compounds, or
(bb) mixtures of more than one of the abovementioned fungicides.

Herbicides which are known from the literature and which can be mentioned, which can be combined with the compounds of the formula (I), are, for example, the following active substances (Note: the compounds are either designated by the common name according to the International Organization for Standardization (ISO) or using the chemical name, if appropriate together with a customary code number):
acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; amitrol; AMS, i.e. ammonium sulfamate; anilofos; asulam; atrazine; azafenidin; azimsulfuron (DPX-A8947); aziprotryn; barban; BAS 516H, i.e. 5-fluoro-2-phenyl-4H-3,1-benzoxazin-4-one; beflubutamid; benazolin(-ethyl); benfluralin; benfuresate; bensulfuron (-methyl); bensulide; bentazone(-sodium); benzobicyclone; benzofenap, benzofluor; benzoylprop(-ethyl); benzthiazuron; bialaphos (bilanafos); bifenox; bispyribac(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole (CH-900); carbetamide; carfentrazone(-ethyl); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorflurenol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon(-methyl or -ethyl), cinmethylin; cinosulfuron; clethodim; clefoxydim, clodinafop and its ester derivatives (for example clodinafop-propargyl); clomazone; clomeprop; cloproxydim; clopyralid; clopyrasulfuron (-methyl); cloransulam(-methyl); cumyluron (JC 940); cyanazine; cycloate; cyclosulfamuron (AC 104); cycloxydim; cycluron; cyhalofop and its ester derivatives (for example butyl-ester, DEH-112); cyperquat; cyprazine; cyprazole; daimuron; 2,4-D; 2,4-DB; dalapon; dazomet, desmedipham; desmetryn; di-allate; dicamba; dichlobenil; dichlorprop(-P); diclofop and its esters such as diclofop-methyl; diclosulam, diethatyl(-ethyl); difenoxuron; difenzoquat; diflufenican; diflufenzopyr; dimefuron; dimepiperate; dimethachlor; dimethametryn; dimethenamid (SAN-582H); dimethenamid-P); dimethazone, dimethipin; dimexyflam, dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example ethyl ester, HC-252), ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl] ethanesulfonamide; fenoprop; fenoxan, fenoxaprop and fenoxaprop-P and their esters, for example fenoxaprop-P-ethyl and fenoxaprop-ethyl; fenoxydim; fentrazamide; fenuron; flamprop(-methyl or -isopropyl or -isopropyl-L); flazasulfuron; florasulam; fluazifop and fluazifop-P and their esters, for example fluazifop-butyl and fluazifop-P-butyl; fluazolate, flucarbazone(-sodium); fluchloralin; flufenacet (FOE 5043), flufenpyr, flumetsulam; flumeturon; flumiclorac (-pentyl); flumioxazin (S-482); flumipropyn; fluometuron; fluorochloridone, fluorodifen; fluoroglycofen(-ethyl); flupoxam (KNW-739); flupropacil (UBIC-4243); fluproanate, flupyrsulfuron(-methyl, or -sodium); flurenol(-butyl); fluridone; fluorochloridone; fluoroxypyr(-meptyl); flurprimidol, flurtamone; fluthiacet(-methyl); fluthiamide (also known as flufenacet); fomesafen; foramsulfuron; fosamine; furilazole (MON 13900), furyloxyfen; glufosinate(-ammonium); glyphosate(-isopropylammonium); halosafen; halosulfuron (-methyl) and its esters (for example the methyl ester, NC-319); haloxyfop and its esters; haloxyfop-P (=R-haloxyfop) and its esters; HC-252 (diphenylether), hexazinone; imazamethabenz(-methyl); imazamethapyr; imazamox; imazapic, imazapyr; imazaquin and salts such as the ammonium salts; imazethamethapyr; imazethapyr, imazosulfuron; indanofan; iodosulfuron-(methyl)-(sodium), ioxynil; isocarbamid; isopropalin; isoproturon; isouron; isoxaben; isoxachlortole; isoxaflutole; isoxapyrifop; karbutilate; lactofen; lenacil; linuron; MCPA; MCPB; mecoprop; mefenacet; mefluidid; mesosulfuron(-methyl); mesotrione; metam, metamifop, metamitron; metazachlor; methabenzthiazuron; methazole; methoxyphenone; methyldymron; metobenzuron, metobromuron; (S-)metolachlor; metosulam (XRD 511); metoxuron; metribuzin; metsulfuron-methyl; MK-616; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron; oxaziclomefone; oxyfluorfen; paraquat; pebulate; pelargonic acid; pendimethalin; penoxulam; pentanochlor, pentoxazone; perfluidone; pethoxamid, phenisopham; phenmedipham; picloram; picolinafen; piperophos; piributicarb; pirifenop-butyl; pretilachlor; primisulfuron(-methyl); procarbazone(-sodium); procyazine; prodiamine; profluazole, profluralin; proglinazine(-ethyl); prometon; prometryn; propachlor; propanil; propaquizafop; propazine; propham; propisochlor; propoxycarbazone(-sodium), propyzamide; prosulfalin; prosulfocarb; prosulfuron (CGA-152005); prynachlor; pyraclonil, pyraflufen(-ethyl); pyrazolinate; pyrazon; pyrazosulfuron(-ethyl); pyrazoxyfen; pyribenzoxim; pyributicarb; pyridafol; pyridate; pyriftalid, pyrimidobac(-methyl); pyrithiobac(-sodium) (KIH-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazuron; sulfometuron(-methyl); sulfosate (ICI-A0224); sulfosulfuron; TCA; tebutam (GCP-5544); tebuthiuron; tepraloxydim; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide; thiazafluoron; thiazopyr (Mon-13200); thidiazimin (SN-24085); thifensulfuron(-methyl); thiobencarb; tiocarbazil; tralkoxydim; tri-allate; triasulfuron; triaziflam; triazofenamide; tribenuron(-methyl); 2,3,6-trichlorobenzoic acid (2,3,6-TBA), triclopyr; tridiphane; trietazine; trifloxysulfuron(-sodium), trifluralin; triflusulfuron and esters (e.g. methyl ester, DPX-66037); trimeturon; tritosulfuron; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127; KIH-2023 and KIH5996.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Components which may be employed for the active substances according to the invention in mixed formulations, for example, known active compounds which are based on an inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other compounds which can be employed, whose mechanism of action is to a degree unknown or different, are described, for example, in Weed Research 26, 441-445 (1986), or "The Pesticide Manual", 12th Edition 2000 (hereinbelow also abbreviated to "PM"), The British Crop Protection Council and the Royal Soc. of Chemistry (editors) and literature cited therein.

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (I) can be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell, Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq;. "Perry's Chemical Engineer's Handbook", 5th Ed., McGraw-Hill, New York 1973, p. 8-57.

In general, the agrochemical preparations comprise a range selected from the group consisting of about 0.1 to about 99% by weight and about 0.1 to about 95% by weight, of compounds of formula (I).

The concentration of compounds of formula (I) in wettable powders is, for example, about 10 to about 90% by weight, the remainder to 100% by weight being composed of customary formulation components. In the case of emulsifiable concentrates, the concentration of compounds of formula (I) can amount to ranges selected from the group consisting of about 1% to about 90% and about 5% to about 80% by weight. Formulations in the form of dusts usually comprise in the range selected from the group consisting of about 1% to about 30% by weight of compounds of formula (I) and about 5% to about 20% by weight of compounds of formula (I). For sprayable solutions comprise a range selected from the group consisting of about 0.05% to about 80% by weight of compounds of formula (I) and about 2% to about 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The mixtures according to the invention can be applied via the soil either pre-emergently or post-emergently. The mixtures according to the invention can also be applied via the leaf. The mixtures according to the invention can be employed for seed dressing. It is also possible to apply the mixtures according to the invention via an irrigation system, for example via the water for irrigation.

Other Active Agents for Pharmaceutical/Veterinary Use

Additional pharmaceutical, pesticidal or veterinarily active ingredients, which include, but are not limited to, parasiticidals including acaricides, anthelmintics, endectocides and insecticides, may also be added to the compositions of the invention. Anti-parasitic agents can include both ectoparasiticisal and endoparasiticidal agents. Veterinary pharmaceutical agents are well-known in the art (see e.g. *Plumb'Veterinary Drug Handbook,* 5$^{th}$ Edition, ed. Donald C. Plumb, Blackwell Publishing, (2005) or *The Merck Veterinary Manual,* 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil HCl, allopurinol, alprazolam, altrenogest, amantadine HCl, amikacin sulfate, aminocaproic acid, aminopentamide hydrogen sulfate, aminophylline/theophylline, amiodarone HCl, amitraz, amitriptyline HCl, amlodipine besylate, ammonium chloride, ammonium molybdenate, amoxicillin, amoxicillin, clavulanate potassium, amphotericin B desoxycholate, amphotericin B lipid-based, ampicillin, amprolium HCl, antacids (oral), antivenin, apomorphione HCl, apramycin sulfate, ascorbic acid, asparaginase, aspiring, atenolol, atipamezole HCl, atracurium besylate, atropine sulfate, aurnofin, aurothioglucose, azaperone, azathioprine, azithromycin, baclofen, barbituates, benazepril HCl, betamethasone, bethanechol chloride, bisacodyl, bismuth subsalicylate, bleomycin sulfate, boldenone undecylenate, bromides, bromocriptine mesylate, budenoside, buprenorphine HCl, buspirone HCl, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur HCl, ceftiaxone sodium, cephalexin, cephalosporins, cephapirin, charcoal (activated), chlorambucil, chloramphenicol, chlordiazepoxide, chlordiazepoxide +/−clidinium bromide, chlorothiazide, chlorpheniramine maleate, chlorpromazine HCl, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol HCl, clindamycin, clofazimine, clomipramine HCl, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine HCl, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine HCl, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin HCl, digoxin, dihydrotachysterol (DHT), diltiazem HCl, dimenhydrinate, dimercaprol/BAL, dimethyl sulfoxide, dinoprost tromethamine, diphenylhydramine HCl, disopyramide phosphate, dobutamine HCl, docusate/DSS, dolasetron mesylate, domperidone, dopamine HCl, doramectin, doxapram, doxepin HCl, doxorubicin HCl, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol HCl, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine HCL, gentamicin sulfate, glimepiride, glipizide, glucagon, glucocorticoid agents, glucosamine/chondroitin sulfate, glutamine, glyburide, glycerine (oral), glycopyrrolate, gonadorelin, griseofulvin, guaifenesin, halothane, hemoglobin glutamer-200 (Oxyglobin®), heparin, hetastarch, hyaluronate sodium, hydrazaline HCl, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol HCl, isotretinoin, isoxsuprine HCl, itraconazole, ivermectin, kaolin/pectin, ketamine HCl, ketoconazole, ketoprofen, ketorolac tromethamine, lactulose, leuprolide, levamisole, levetiracetam, levothyroxine sodium, lidocaine HCl, lincomycin HCl, liothyronine sodium, lisinopril, lomustine (CCNU), lufenuron, lysine, magnesium, mannitol, marbofloxacin, mechlorethamine HCl, meclizine HCl, meclofenamic acid, medetomidine HCl, medium chain triglycerides, medroxyprogesterone acetate, megestrol acetate, melarsomine, melatonin, meloxican, melphalan, meperidine HCl, mercaptopurine, meropenem, metformin HCl, methadone HCl, methazolamide, methenamine mandelate/hippurate, methimazole, methionine, methocarbamol, methohexital sodium, methotrexate, methoxyflurane, methylene blue, methylphenidate, methylprednisolone, metoclopramide HCl, metoprolol, metronidaxole, mexiletine HCl, mibolerlone, midazolam HCl milbemycin oxime, mineral oil, minocycline HCl, misoprostol, mitotane, mitoxantrone HCl, morantel tartrate, morphine sulfate, moxidectin, naloxone HCl, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone HCl, oxytretracycline, oxytocin, pamidronate disodium, pancreplipase, pancuronium bromide, paromomycin sulfate, parozetine HCl, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine HCl, pheylbutazone, phenylephrine HCL, phenypropanolamine HCl, phenyloin sodium, pheromones, parenteral phosphate, phytonadione/vitamin K-1, pimobendan, piperazine, pirlimycin HCL, piroxicam, polysulfated glycosaminoglycan, ponazuril, potassium chloride, pralidoxime chloride, praziquantel, prazosin HCl, prednisolone/prednisone, primidone, procainamide HCl, procarbazine HCl, prochlorperazine, propantheline bromide, *propionibacterium acnes* injection, propofol, propranolol HCl, protamine sulfate, pseudoephedrine HCl, psyllium hydrophilic mucilloid, pyrantel pamoate, pyridostigmine bromide, pyrilamine maleate, pyrimethamine, quinacrine HCl, quinidine, ranitidine HCl, rifampin, s-adenosyl-methionine (SAMe), saline/hyperosmotic laxative, selamectin, selegiline HCL/1-deprenyl, sertraline HCl, sevelamer HCl, sevoflurane, silymarin/milk thistle, sodium bicarbonate, sodium polystyrene sulfonate, sodium stibogluconate, sodium sulfate, sodium thiosulfate, somatotropin, sotalol HCl, spectinomycin HCl, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline HCl, terbutaline sulfate, testosterone, tetracycline HCl, thiabendazole, thiacetarsamide sodium, thiamine HCl, thioguanine, thiopental sodium, thiotepa, thyrotropin, tiamulin, ticarcilin disodium, tiletamine HCl/zolazepam HCl, tilmocsin, tiopronin, tobramycin sulfate, tocamide HCl, tolazoline HCl, telfenamic acid, topiramate, tramadol HCl, trimcinolone acetonide, trientine HCl, trilostane, trimepraxine tartrate w/prednisolone, tripelennamine HCl, tylosin, urdosiol, valproic acid, vanadium, vancomycin HCl, vasopressin, vecuronium bromide, verapamil HCl, vinblastine sulfate, vincristine sulfate, vitamin E/selenium, warfarin sodium, xylazine HCl, yohimbine HCl, zafirlukast, zidovudine (AZT), zinc acetate/zinc sulfate, zonisamide and mixtures thereof.

In one embodiment of the invention, other arylpyrazole compounds such as phenylpyrazoles, as described above in the Background (e.g. fipronil, pyriprole), are known in the art and are suitable for combination with the aryloazol-2-yl cyanoethylamino compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131—each assigned to Merial, Ltd., Duluth, Ga.).

In another embodiment of the invention, nodulisporic acid and its derivatives (a class of known acaricidal, anthelminitic, anti-parasitic and insecticidal agents) can be added to the compositions of the invention. These compounds are used to treat or prevent infections in humans and animals and are described, for example, in U.S. Pat. Nos. 5,399,582, 5,962,499, 6,221,894 and 6,399,786. The composition can include one or more of the known nodulisporic acid derivatives in the art, including all stereoisomers, such as those described in the literature cited above.

In another embodiment of the invention, one or more macrocyclic lactones, which act as an acaricide, anthelmintic agent and insecticide, can be added to the compositions of the invention.

The macrocyclic lactones also include, but are not limited to, avermectins, such as abamectin, dimadectin, doramectin, emamectin, eprinomectin, ivermectin, latidectin, lepimectin, selamectin and milbemycins, such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131—each assigned to Merial, Ltd., Duluth, Ga.

The macrocyclic lactone compounds are known in the art and can be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag, "Macrocyclic Lactones in Antiparasitic Therapy", 2002, by J Vercruysse and RS Rew published by CABI Publishing or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring; milbemycins lack the glycosidic moiety of the avermectins. The natural product avermectins are disclosed in U.S. Pat. No. 4,310,519 to Albers-Schonberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, U.S. Pat. No. 4,920,148 and EP 0 667 054.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. No. 3,748,356; U.S. Pat. No. 3,818,047; U.S. Pat. No. 4,225,598; U.S. Pat. No. 4,798,837; U.S. Pat. No. 4,751,225, EP 0 179 022 or U.K. 2 140 010 as well as U.S. Pat. Nos. 6,096,329 and 6,685,954 (both assigned to Merial Ltd., Duluth, Ga.). Examples of IGRs suitable for use include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An anthelmintic agent that can be combined with the compound of the invention to form a composition can be a benzenedisulfonamide compound, which includes but is not limited to clorsulon; or a cestodal agent, which includes but is not limited to praziquantel, pyrantel or morantel An parasiticidal agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside.

An insecticidal agent that can be combined with the compound of the invention to form a composition can be a spinosyn (e.g. spinosad) or a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular infection of an insect. For endoparasites, parasiticides which can be combined include but are not limited to pyrantel, morantel, the benzimidazoles (including albendazole, cambendazole, thiabendazole, fenbendazole, febantel, oxfendazole, oxibendazole, triclabendazole mebendazole and netobimin), levamisole, closantel, rafoxanide, nitroxynil, disophenol and paraherquamide. For ectoparasites, insecticides which can be combined also include but are not limited to pyrethoids, organophosphates and neonicotinoids such as imidacloprid, as well as compounds such as metaflumizone, amitraz and ryanodine receptor antagonists.

Where appropriate the anthelmintic, parasiticidal and insecticial agent may also be selected from the group of compounds described above as suitable for agrochemical use. In general, the additional pesticidal agent is included in a dose of between about 0.1 μg and about 10 mg. In one embodiment of the invention, the additional pesticidal agent is included in a dose of between about 1 μg and about 10 mg. In another embodiment of the invention, the additional pesticidal agent is included in a dose of about 5 to about 200 μg/kg of weight of animal. In yet another embodiment of the invention, the additional pesticidal agent is included in a dose between about 0.1 to about 10 mg/kg of weight of animal. In still another embodiment of the invention, the additional pesticidal agent is included in a dose between about 0.5 to 50 mg/kg.

The proportions, by weight, of the aryloazol-2-yl-cyanoethylamino compound and the additional pesticidal agent are for example between about 5/1 and about 10,000/1. However, one of ordinary skill in the art would be able to select the appropriate ratio of aryloazol-2-yl-cyanoethylamino compound and the additional pesticidal agent for the intended host and use thereof.

Another aspect of the invention is the process of making the aryloazol-2-yl-cyanoethylamino compounds of the invention.

EXAMPLES

All temperatures are given in degrees Centigrade; room temperature means 20 to 25° C. Reagents were purchased from commercial sources or prepared following literature procedures.

DCM=dichloromethane
THF=tetrahydrofuran
MeOH=methanol
EtOH=ethanol
EA=ethyl acetate
DMF=dimethylformamide
AcOH=acetic acid
TFA=trifluoroacetic acid
TEA=triethylamine
DIEA=diisopropylethylamine Proton and fluorine magnetic resonance (respectively 1H NMR and 19F NMR) spectra were recorded on a Varian INOVA NMR spectrometer [400 MHz (1H) or 500 MHz (1H) and 377 MHz (19F)]. All spectra were determined in the solvents indicated. Chemical shifts are reported in ppm downfield of tetramethylsilane (TMS), referenced to the residual proton peak of the respective solvent peak for 1H NMR. Interproton coupling constants are reported in Hertz (Hz).

LC-MS spectra were either obtained using a Thermofinnigan AQA MS ESI instrument, using a Phenomenex Aqua 5 micron C18 125A 50×4.60 mm column and a linear gradient from 55% methanol:1% acetonitrile in water to 100% methanol over 3 minutes. 100% methanol was maintained for 2 minutes. Alternatively, LCMS spectra were obtained using an Agilent 1200SL HPLC equipped with a 6130 mass spectrometer operating with electrospray ionization; chromatographic data were obtained using a Shimadzu Shim-pack XR-ODS, 3.0×30 mm, 2.2 micron particle size column and a water:methanol gradient from 15% methanol to 95% methanol in 2.2 minutes under a 1.5 mL/min flow; a hold at 95% methanol was applied at the end of the gradient for 0.8 minutes; and both water and methanol mobile phases contained 0.1% formic acid.

General Synthetic Procedures

The compounds of formula (I) may be prepared by the application or adaptation of known methods (i.e. methods heretofore used or described in the chemical literature).

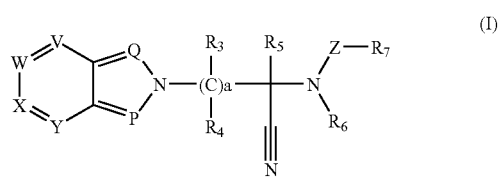

For example, compounds of formula (I) are obtainable by a process wherein compound (II) is reacted with compound (III) wherein $R_3$, $R_4$, $R_5$, $R_6$, $R_7$, P, Q, V, W, X, Y, Z, and a are as defined above for the compounds of formula (I) and T is a leaving group such as a halogen atom, methanesulfonyl, trifluoromethanesulfonyl, toluenesulfonyl and the like.

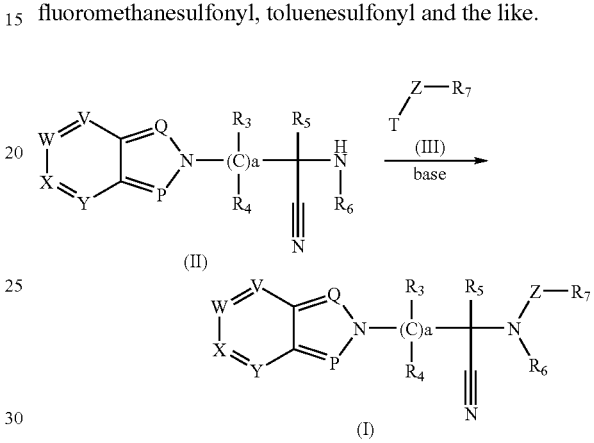

The reaction is generally carried out in the presence of a base in a solvent.

The base to be used in this reaction includes, for example but not limited to, inorganic bases such as sodium carbonate, potassium carbonate and the like, organic bases such as dimethylaminopyridine, triethylamine, diisopropylethylamine, 1,8-diazabicyclo[5.4.0]-7-undecene and the like.

The solvent to be used in the reaction includes, for example but not limited to, ethers such as diethylether, tetrahydrofuran and the like, halogenated hydrocarbon such as such as methylene chloride, chloroform, 1,2-dichloroethane and the like.

The reaction temperature is usually in the range of −78° C. to 150° C., preferably in the range of −20° C. to 80° C. and the reaction time is usually in the range of 1 to 72 hours.

After completion of the reaction, the compounds of formula (I) can be isolated by employing conventional methods such as adding the reaction mixture to water, extracting with an organic solvent, concentrating the extract and the like. The isolated compound of formula (I) can be purified by a technique such as chromatography, recrystallization and the like, if necessary.

The compounds of formula (Ia) may be prepared by the application or adaptation of known methods of amide formation (i.e. methods heretofore used or described in the chemical literature).

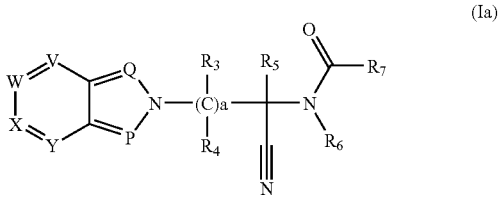

Many procedures are available for forming amide bonds between an amine derivative such as the α-amino nitrile derivatives of formula (II) and a carboxylic acid with the use of coupling agents. Procedures have been developed which use reagents such as carbodiimides as amide coupling agents. These carbodiimides include for example dicyclohexylcarbodiimide (DCC), diisopropylcarbodiimide (DIC), 1-(3-dimethylaminopropyl)-3-ethylcarbodiimide hydrochloride (EDC) and the like. Catalysts such as 1-hydroxybenzotriazole (HOBT) and derivatives thereof have also been used. A summary of such methods is found in "Comprehensive Organic Transformations", R. C. Larock, VCH Publishers (1989) pp. 972-972. An overview of such transformations is also available in "March's Advanced Organic Chemistry: Reactions, Mechanisms, and Structure (Sixth Edition)", Michael B. Smith and Jerry March, Wiley-Interscience Publishers, (2007), pp 1431-1434.

Another general reaction for the preparation of amides is the treatment of acyl halides with amine. Such a transformation is well known to those skilled in the art and an overview of such transformations is available in "March's Advanced Organic Chemistry: Reactions, Mechanisms, and Structure (Sixth Edition)", Michael B. Smith and Jerry March, Wiley-Interscience Publishers, (2007), pp 1427-1429.

The α-amino nitrile derivatives of formula (II) can be prepared in one step by the treatment of carbonyl compounds of general formula (IV) with a suitable cyanide source such as sodium cyanide, potassium cyanide, trimethylsilyl cyanide and the like, with amines of general formula $R_6$—$NH_2$ such as ammonia, methyl amine and the like and generally in presence of ammonium salt such as ammonium chloride and the like. Those skilled in the art will recognize this as the Strecker synthesis (see e.g. page 1391 in "March's Advanced Organic Chemistry: Reactions, Mechanisms, and Structure (Sixth Edition)", Michael B. Smith and Jerry March, Wiley-Interscience Publishers, (2007).

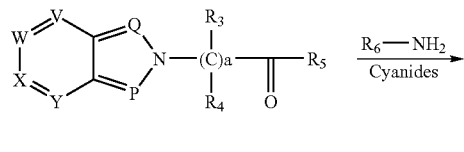

(IV)

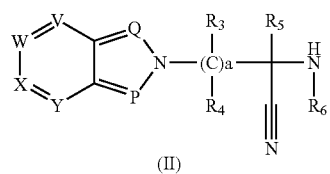

(II)

The carbonyl compounds of formula (IV) can be prepared by treatment of a NH-arylo-azole of general formula (V) with compound of general formula (VI) wherein, $R_1$, $R_2$, $R_3$, $R_4$, $R_5$, $R_7$, P, Q, V, W, X, Y, a, m and n are as defined above for the compounds of formula (I) and T is a leaving group such as a halogen atom, methanesulfonyl, trifluoromethanesulfonyl, toluenesulfonyl and the like.

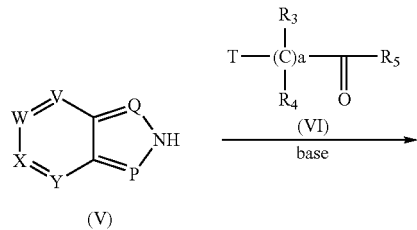

(V)

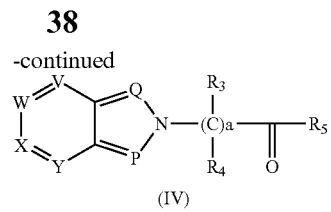

(IV)

The reaction is generally carried out in the presence of a base in a solvent.

The base to be used in this reaction includes, for example but not limited to, inorganic bases such as sodium carbonate, potassium carbonate and the like, organic bases such as dimethylaminopyridine, triethylamine, diisopropylethylamine, 1,8-diazabicyclo[5.4.0]-7-undecene and the like.

The solvent to be used in the reaction includes, for example but not limited to, acetone, ethers such as diethylether, tetrahydrofuran and the like, halogenated hydrocarbon such as such as methylene chloride, chloroform, 1,2-dichloroethane and the like.

The reaction temperature is usually in the range of −78° C. to 150° C., preferably in the range of −20° C. to 80° C. and the reaction time is usually in the range of 1 to 72 hours.

After completion of the reaction, the compounds of formula (IV) can be isolated by employing conventional methods such as adding the reaction mixture to water, extracting with an organic solvent, concentrating the extract and the like. The isolated compound of formula (IV) can be purified by a technique such as chromatography, recrystallization and the like, if necessary.

The 2H—NH-arylo-azole of formula (Va), (formula (V) with P=N), are generally represented as their tautomeric structure 1H—NH-arylo-azole (Vb). Specifically, 2H-benzotriazole of formula (Vc) and 2H-indazole of formula (Ve) are generally represented as their alternative tautomeric forms, respectively 1H-benzotriazole of formulas (Vd) or (Ve) and 1H-indazole of formula (Vg).

A discussion on tautomerism of heterocycles can be found in "The Tautomerism of Heterocycles, Advances in Heterocyclic Chemistry Supplement 1", eds. José Elguero, Claude Marzin, Alan R. Katritzky and Paolo Linda, Academic Press Publishers, (1976).

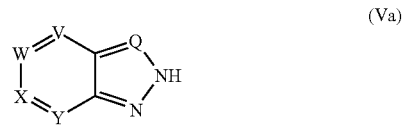

(Va)

(Vb)

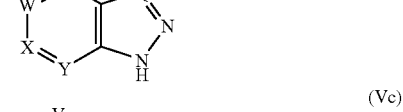

(Vc)

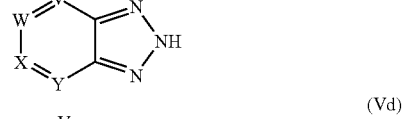

(Vd)

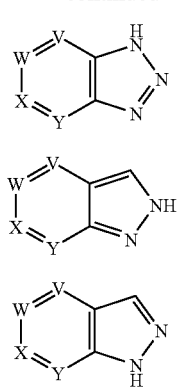

(Ve)

(Vf)

(Vg)

When carbonyl compounds of formula (IVa) were prepared by treatment of a 1H—NH-arylo-azole of general formula (Va) with compound of general formula (VI), regioisomer carbonyl compounds of formula (IVb) were also usually obtained. Those could be separated from desired carbonyl compounds of formula (IVa) by standard technique of purification known by persons skilled in the art such as, but not limited to, liquid chromatography using normal phase or reverse phase silica column and crystallization.

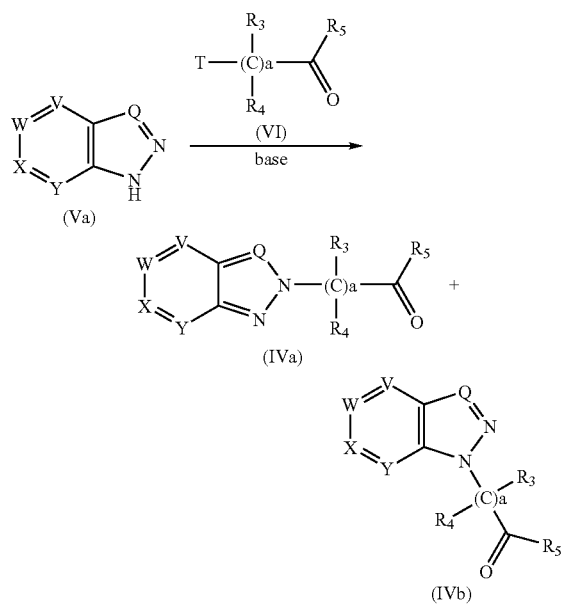

Those 1H—NH-arylo-azole compounds of general formula (Va) not commercially available can be prepared by the application or adaptation of known methods (i.e. methods heretofore used or described in the chemical literature).

For example, a general method of preparation of 1H-benzotriazole of formula (Vd) or (Ve) wherein, $R_1$, $R_2$, V, W, X, Y, m and n are as defined above for the compounds of formula (I) can be found in Organic Synthesis, Coll. Vol. 3, p. 106 (1955) and in *Journal of Heterocyclic Chemistry*, volume 22, (1985), pp. 1165-1167. Halogenation of 1H-benzotriazole of formula (Vd) or (Ve) can be achieved by adapting procedures described in the literature such as ones described by R. H. Wiley and K. F. Hussung in *Journal of the American Chemical Society*, (1957), pages 4395-4400 and by K. Koparńska et al. in *Bioorganic & Medicinal Chemistry*, volume 13 (2005) page 3601 and in *Bioorganic & Medicinal Chemistry*, volume 12 (2004), pages 2617-2624.

A general method of preparation of 1H-indazole of formula (Vg) wherein, $R_1$, $R_2$, V, W, X, Y, m and n are as defined above for the compounds of formula (I) was reported in the literature by R. A. Bartsch and Il-Woo Yang in *Journal of Heterocyclic Chemistry*, volume 21, (1984), pp. 1063-1164 and recently by the team of Valerie Collot and Sylvain Rault in *Bioorganic & Medicinal Chemistry Letters*, volume 11 (2001), pages 1153-1156 and volume 17 (2007), pages 3177-3180.

In one embodiment of the invention, carbonyl compounds of formula (IVa), wherein Q is alkoxymethylene (Q=C—$OR_{13}$) or methylene (Q=CH), are formed by oxidation of the alcohol compounds of formula (VIIa).

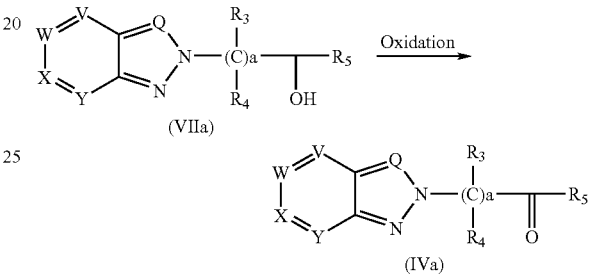

Such a transformation is well known to those skilled in the art, a summary of such methods is found in "Comprehensive Organic Transformations", VCH Publishers, (1989), R. C. Larock, pp. 604-614. For example, it can be realized with dimethylsufoxide-based reagents such as reacting oxalyl chloride with dimethylsufoxide at low temperature, those skilled in the art will recognize this as the Swern oxidation. It can also be realized by nitroxyl radical, 2,2,6,6-tetramethylpiperidine-1-oxyl free radical (TEMPO) and related reagents and with hypervalent iodine reagents such as the so called Dess-Martin Periodinane reagent (see e.g. page 1715-1728, "Oxidation or Dehydrogenation of Alcohols to Aldehydes and Ketones" in "March's Advanced Organic Chemistry: Reactions, Mechanisms, and Structure (Sixth Edition)", Michael B. Smith and Jerry March, Wiley-Interscience Publishers, (2007)). The solvent to be used in the reaction includes, for example but not limited to, ethers such as diethylether, tetrahydrofuran and the like, halogenated hydrocarbon such as such as methylene chloride, chloroform, 1,2-dichloroethane and the like. The reaction temperature is usually in the range of –78° C. to 150° C., preferably in the range of –78° C. to 50° C. and the reaction time is usually in the range of 1 to 72 hours.

In another embodiment of the invention, free alcohol compounds of formula (VIIa), wherein Q is alkoxymethylene (Q=C—$OR_{13}$) or methylene (Q=CH), are formed by cleavage of a protecting group on the corresponding protected alcohol compounds of formula (VIIIa) wherein $R_{12}$ is a hydroxyl protecting group. Hydroxyl protecting group to be used in the reaction includes, for example but not limited to, ethers, such as para-methoxybenzyl ether, and silyl ethers, such as tert-butyldimethylsilyl ether, (see e.g. "Protection for the hydroxyl group" pages 16-299 in "Protective Groups in Organic Synthesis (Fourth Edition)", eds. Peter G. M. Wuts and Theodora W. Greene, Wiley-Interscience Publishers, (2007)).

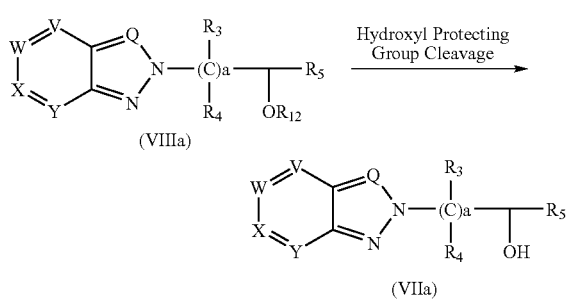

(VIIIa)

(VIIa)

In another embodiment of the invention, compounds of formula (VIIIb) are formed by treating compounds of formula (IXa) with alcohol of formula $R_{13}$—OH and a base such as, but not limited to, potassium hydroxide, sodium hydroxide and the like.

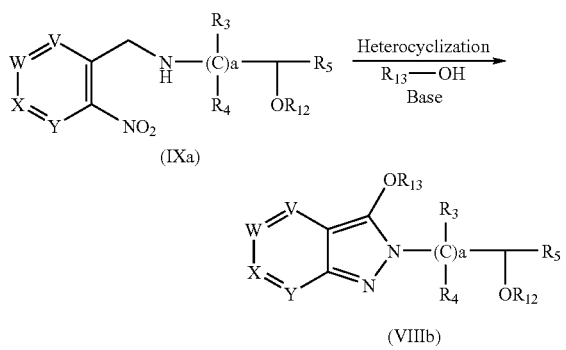

(IXa)

(VIIIb)

The synthesis of 3-alkoxy-2-substituted 2H-indazoles has been described in the chemical literature such as in *Journal of Organic Chemistry*, 2006, 71, 2687-2689 ("N,N-Bond-Forming Heterocyclization: Synthesis of 3-Alkoxy-2H-indazoles" by A. D. Mills, M. Z. Nazer, M. J. Haddadin and M. J. Kurth) and in *Journal of Combinatorial Chemistry*, 2007, 9, 171-177 ("Synthesis of a Library of 2-Alkyl-3-alkyloxy-2H-indazole-6-carboxamides" by A. D. Mills, P. Maloney, E. Hassanein, M. J. Haddadin and M. J. Kurth). However none of the foregoing publications describe the synthesis of compound of formula (VIIIb).

In another embodiment of the invention, compounds of formula (VIIIc) are formed by heterocyclization of compounds of formula (IXa) when treated with a reducing agent such as zinc.

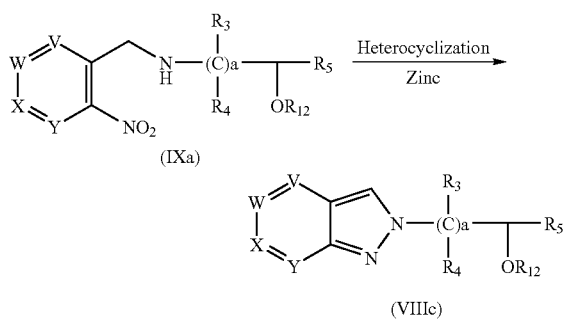

(IXa)

(VIIIc)

The synthesis of 2-substituted 2H-indazoles from 2-nitrobenzylamines derivatives has been described in the chemical literature such as in *Synlett*, 2007, 16, 2509-2512 ("A Novel and Efficient Synthesis of 2-Aryl-2H-indazoles via SnCl$_2$-Mediated Cyclization of 2-Nitrobenzylamines" by Da-Qing Shi et al), in *Journal of the Chemical Society, Perkin Transactions* 1, 1973, 3, 319-324 ("Pyrazolopyridines. Part II. Preparation of 3-Substituted 2-Aryl-2H-pyrazolo[4,3-b]pyridines. Acid-catalysed Cyclisation of 2-Arylamino-methyl-3-nitropyridines" by H. E. Foster and J. Hurst) and in *Tetrahedron*, 1998, 54, 3197-3206 ("2-Substituted Indazoles from Electrogenerated Ortho-nitrosobenzylamines" by B. A. Frontana-Uribe and C. Moinet). However none of the foregoing publications describe the synthesis of compound of formula (VIIIc).

In another embodiment of the invention, compounds of formula (VIIId) are formed by reacting aldehydes of formula (Xa) with compounds of formula (XI) in presence of a reducing agent such as, but not limited to, sodium cyanoborohydride, sodium borohydride, sodium triacetoxyborohydride, L-selectride® (lithium tri-sec-butyl(hydrido)borate), decaborane and the like.

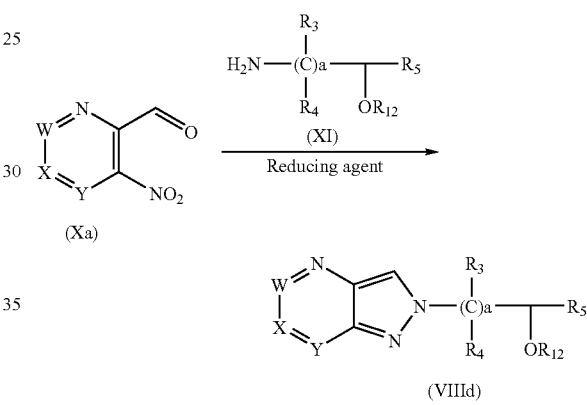

(Xa)

(VIIId)

The solvent to be used in the reaction includes, for example but not limited to, ethers such as diethylether, tetrahydrofuran and the like, halogenated hydrocarbon such as such as methylene chloride, chloroform, 1,2-dichloroethane and the like. The reaction temperature is usually in the range of −78° C. to 150° C., preferably in the range of 0° C. to 80° C. and the reaction time is usually in the range of 1 to 72 hours.

The compounds of formula (IXa) can be prepared by treating aldehydes of formula (X) with compounds of formula (XI) and a reducing agent such as, but not limited to, sodium cyanoborohydride, sodium borohydride, sodium triacetoxyborohydride, L-selectride® (lithium tri-sec-butyl(hydrido)borate), decaborane and the like.

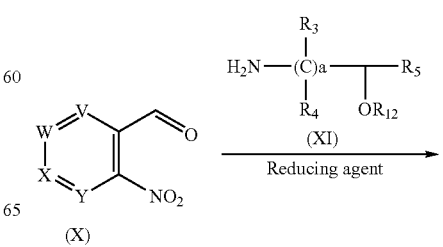

(X)

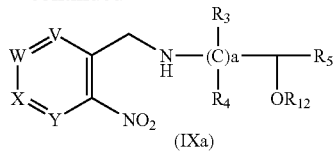

Such a transformation is well known to those skilled in the art and is known as reductive amination, a summary of such methods is found in "Comprehensive Organic Transformations", VCH Publishers, (1989), R. C. Larock, pp. 421-425. The solvent to be used in the reaction includes, for example but not limited to, ethers such as diethylether, tetrahydrofuran and the like, halogenated hydrocarbon such as such as methylene chloride, chloroform, 1,2-dichloroethane and the like. The reaction temperature is usually in the range of −78° C. to 150° C., preferably in the range of 0° C. to 80° C. and the reaction time is usually in the range of 1 to 72 hours.

Alternatively, the compounds of formula (IXa) can be prepared by treating compounds of formula (XI) with compounds of formula (XII) where T is a leaving group such as a halogen atom, methanesulfonyl, trifluoromethanesulfonyl, toluenesulfonyl and the like.

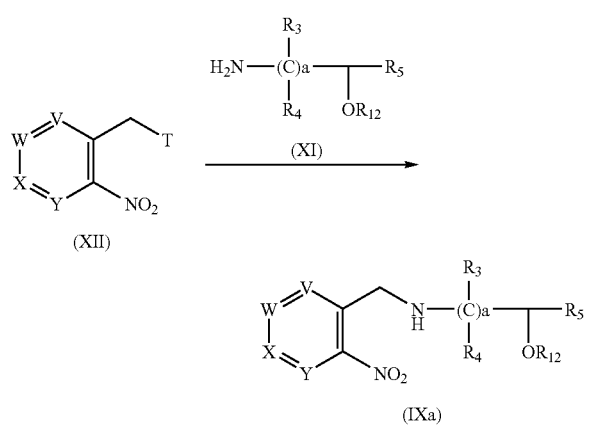

When not commercially available, the aldehydes of formula (IXa) can be prepared by oxidative cleavage of the alkene moiety of compound of formula (XIII) wherein $R_{14}$ and $R_{15}$ are independently selected from $C_1$-$C_4$ alkylcarbonyl and $C_1$-$C_4$ alkyl.

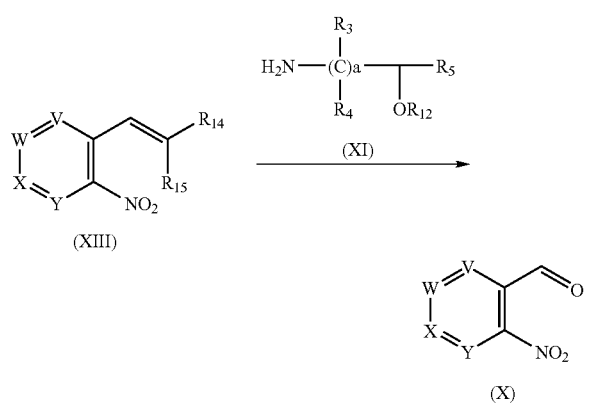

Such a transformation is well known to those skilled in the art and can be realized for example with ozone, potassium permanganate and sodium metaperiodate. The process may be carried out optionally in a solvent such as methylene chloride, diethylether, chloroform and generally at temperatures between about −100 and about 100° C. A summary of such methods is found in "Comprehensive Organic Transformations", VCH Publishers, (1989), R. C. Larock, pp. 595-596.

The alkene compounds of formula (XIII), wherein $R_{14}$ and $R_{15}$ are independently selected from C1-C4 alkylcarbonyl and C1-C4 alkyl, can be prepared from coupling reactions of compound of formula (XIV), wherein $R_{16}$ is halogen atom or trifluoromethanesulfonyl and the like, with compound of formula (XV), wherein M is trialkyltin, boronic acid or boronate ester, and a palladium catalyst.

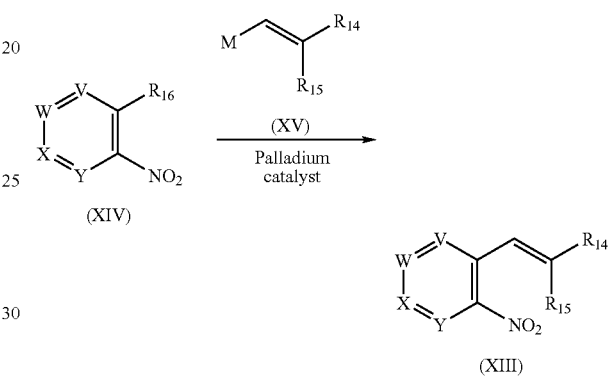

Such a transformation using compound of formula (XV), wherein M is trialkyltin, is known to those skilled in the art as the Stille coupling. A description of such methods is found in "March's Advanced Organic Chemistry Reactions, Mechanisms, and Structure (Sixth Edition)", Michael B. Smith and Jerry March, Wiley-Interscience Publishers, (2007) pp. 792-795.

The solvent to be used in the reaction includes, for example but not limited to, ethers such as tetrahydrofuran, dioxane and the like, halogenated hydrocarbon such as such as 1,2-dichloroethane and the like, aromatic solvent such as benzene, toluene, xylene and the like. The reaction temperature is usually in the range of 0° C. to 200° C., preferably in the range of 20° C. to 120° C. and the reaction time is usually in the range of 1 to 72 hours.

The compounds of formula (XIVa), wherein $R_{16}$ is halogen atom, can be prepared from compounds of formula (XV) via formation of diazonium salt from corresponding aniline and treatment with cuprous halides.

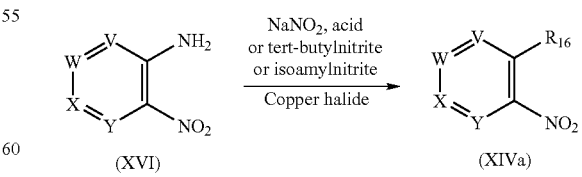

Such a transformation is known to those skilled in the art as the Sandmyer reaction (see e.g. "March's Advanced Organic Chemistry: Reactions, Mechanisms, and Structure (Sixth Edition)", Michael B. Smith and Jerry March, Wiley-Interscience Publishers, (2007) pp. 984-985).

The compounds of formula (II); wherein V is nitrogen or C—R$_8$, R$_{10}$ is halogen and R$_2$ and R$_{11}$ are either together or independently of each another, halogen or hydrogen; can be achieved by halogenation of the corresponding precursor compound of formula (Ig) using electrophilic halogenating agent known in the art such as, but not limited to, N-iodosuccinimide, N-bromosuccinimide, N-chlorosuccinimide, Selectfluor® [1-chloromethyl-4-fluoro-1,4-diazoniabicyclo[2.2.2]octane bis-(tetrafluoroborate)] and the like.

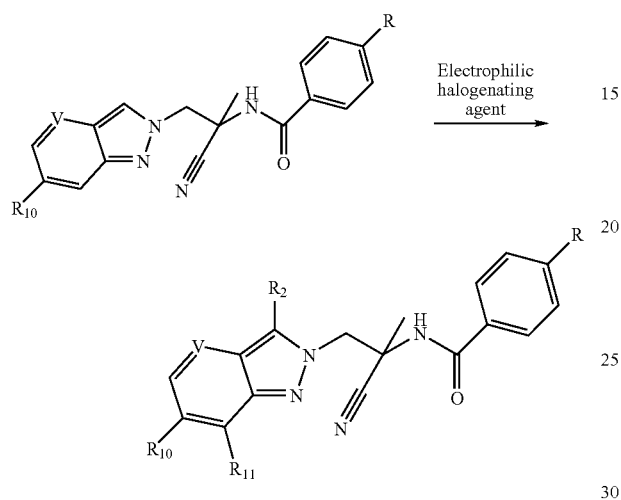

The compounds of formula (Ig) wherein p is 1 or 2 can be achieved by oxidation of the corresponding precursor compound of formula (If) using conventional oxidizers known in the art.

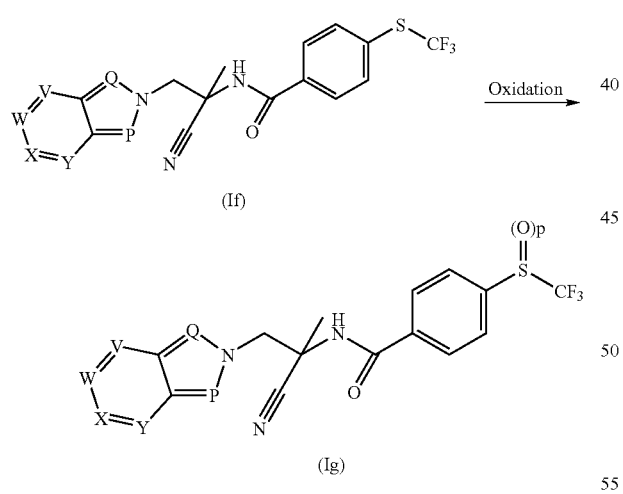

It will be appreciated by persons skilled in the art that, within aspect of the processes described above; the order of the synthetic steps employed may be varied and will depend inter alia on factors such as the nature of other functional groups present in a particular substrate, the availability of key intermediates, and the protecting group strategy (if any) to be adopted (see e.g. "Protective Groups in Organic Synthesis (Fourth Edition)", eds. Peter G. M. Wuts and Theodora W. Greene, Wiley-Interscience Publishers, (2007)). Clearly, such factors will also influence the choice of reagents for use in the said synthetic steps.

Compounds of Examples 1 to 10 and 52 to 58 were prepared according to the general reaction scheme:

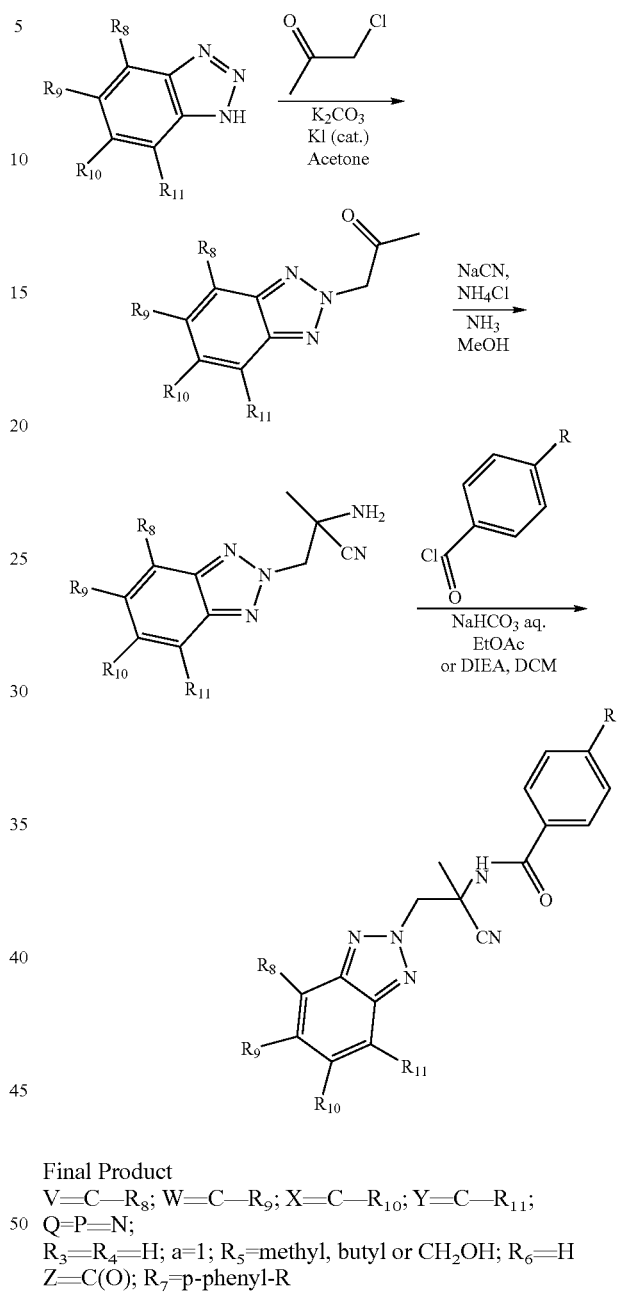

Final Product
V=C—R$_8$; W=C—R$_9$; X=C—R$_{10}$; Y=C—R$_{11}$;
Q=P=N;
R$_3$=R$_4$=H; a=1; R$_5$=methyl, butyl or CH$_2$OH; R$_6$=H
Z=C(O); R$_7$=p-phenyl-R Example 1

N-[2-(5-Chloro-2H-benzotriazol-2-yl)-1-cyano-1-methylethyl]-4-trifluoromethoxybenzamide (compound No 1.001)

4-trifluoromethoxybenzoyl chloride (0.34 g) was added to a solution of 2-amino-3-(5-chloro-2H-benzotriazol-2-yl)-2-methylpropionitrile (0.3 g) in dry DCM mixed with TEA (0.27 mL). The reaction mixture was stirred 48 hours at room temperature. Silica gel was added to the reaction mixture and solvent evaporated under reduced pressure. The resulting crude product loaded on silica gel was purified by chromatography (SiO$_2$, heptane/EA) to afford the title compound as a white solid (0.3 g, 54%). Rf=0.7 (1:1 EA/heptane). MS (ES): M/Z [M+H]=424. 1H NMR: (400 MHz, DMSO-$d_6$): 1.74 (s, 3H), 5.39-5.49 (m, 2H), 7.48 (dd, J=9.1, 1.9 Hz, 1H), 7.51 (br d, J=8.0 Hz, 2H), 7.93 (m, 2H), 8.01 (dd, J=9.1, 0.6 Hz, 1H), 8.13 (dd, J=1.9, 0.6 Hz, 1H) and 8.92 (s, 1H). 19F NMR (376 MHz, DMSO-$d_6$): −57.09 (s, 3F).

The starting material, 2-amino-3-(5-chloro-2H-benzotriazol-2-yl)-2-methylpropionitrile, was prepared as follows:

a. A mixture of 5-chloro-1H-benzotriazole (8 g), chloroacetone (6.5 mL), potassium carbonate (9.5 g) and potassium iodide (0.5 g) was stirred in acetone (90 mL) at room temperature for 48 hours. The reaction mixture was filtered and the filtrate concentrated under reduced pressure to give a residue that was purified by chromatography ($SiO_2$, heptane/EA) to afford 1-(5-chloro-2H-benzotriazol-2-yl)-propan-2-one as clear oil [1.8 g, 16%, Rf=0.6 (1:1 EA/heptane)]. The two other regioisomers were also isolated, 1-(6-chloro-1H-benzotriazol-1-yl)-propan-2-one [3.8 g, 35%, Rf=0.45 (1:1 EA/heptane)] and 1-(5-chloro-1H-benzotriazol-1-yl)-propan-2-one [3.2 g, 29%, Rf=0.35 (1:1 EA/heptane)].

b. Ammonia was charged into methanol (50 mL) at −78° C. for 5 min. The solution was allowed to warm to room temperature and was then treated with sodium cyanide (0.7 g), ammonium chloride (0.9 g) and 1-(5-chloro-2H-benzotriazol-2-yl)-propan-2-one (2.25 g). The reaction mixture was stirred for 6 days at room temperature before being concentrated under reduced pressure. The residue was taken into ethyl acetate, filtered and the filtrate concentrated under reduced pressure to give a residue that was purified by chromatography ($SiO_2$, heptane/EA) to afford 2-amino-3-(5-chloro-2H-benzotriazol-2-yl)-2-methylpropionitrile as a light yellow solid (2.0 g, 79%). Rf=0.25 (1:1 EA/heptane).

Example 2

N-[2-(5-Chloro-2H-benzotriazol-2-yl)-1-cyano-1-methylethyl]-4-trifluoromethylbenzamide (compound No 1.002)

Using a procedure similar to that described in Example 1, except using 4-trifluoromethylbenzoyl chloride, the title compound was isolated as a white solid (0.12 g, 71%). Rf=0.65 (1:1 EA/heptane). MS (ES): M/Z [M+H]=408. 1H NMR: (400 MHz, DMSO-$d_6$): 1.75 (s, 3H), 5.40-5.52 (m, 2H), 7.48 (dd, J=9.1, 1.9 Hz, 1H), 7.88-7.93 (m, 2H), 7.99 (br d, J=7.8 Hz, 1H), 8.03 (d, J=0.6 Hz, 1H), 8.13 (dd, J=1.9, 0.6 Hz, 1H) and 9.04 (s, 1H).

Example 3

N-[2-(5-Chloro-2H-benzotriazol-2-yl)-1-cyano-1-methylethyl]-4-trifluoromethylthiobenzamide (compound No 1.003)

Using a procedure similar to that described in Example 1, except using 4-trifluoromethylthiobenzoyl chloride, the title compound was isolated as a white solid (1.4 g, 75%). Rf=0.65 (1:1 EA/heptane). MS (ES): M/Z [M+H]=440. 1H NMR: (400 MHz, DMSO-$d_6$): 1.74 (s, 3H), 5.39-5.50 (m, 2H), 7.48 (dd, J=9.1, 1.9 Hz, 1H), 7.85-7.92 (m, 4H), 8.01 (dd, J=9.1, 0.7 Hz, 1H), 8.13 (dd, J=1.9, 0.6 Hz, 1H) and 9.01 (s, 1H). 19F NMR (376 MHz, DMSO-$d_6$): −41.93 (s, 3F).

Example 4

N-[2-(5-Chloro-2H-benzotriazol-2-yl)-1-cyano-1-methylethyl]-4-phenoxybenzamide (compound No 1.032)

Using a procedure similar to that described in Example 1, except using 4-phenoxybenzoyl chloride, the title compound was isolated as a white solid (57 mg, 65%). MS (ES): M/Z [M+H]=432. 1H NMR: (400 MHz, DMSO-$d_6$): 1.74 (s, 3H), 5.40-5.46 (m, 2H), 7.04-7.16 (m, 4H), 7.20-7.27 (m, 1H), 7.42-7.51 (m, 3H), 7.82-7.88 (m, 2H), 7.99-8.05 (m, 1H), 8.12-8.15 (m, 1H,) and 8.74 (s, 1H).

4-Phenoxybenzoyl chloride was prepared by reacting 4-phenoxybenzoic acid with oxalyl chloride.

Example 5

N-[2-(2H-Benzotriazol-2-yl)-1-cyano-1-methylethyl]-4-trifluoromethoxybenzamide (compound No 1.004)

Using a procedure similar to that described in Example 1, except using 2-amino-3-(2H-benzotriazol-2-yl)-2-methylpropionitrile, the title compound was isolated as a white solid (0.1 g, 51%). Rf=0.55 (1:1 EA/heptane). MS (ES): M/Z [M+H]=390. 1H NMR: (400 MHz, DMSO-$d_6$): 1.75 (s, 3H), 5.39-5.49 (m, 2H), 7.45 (br s, 2H), 7.51 (d, J=8.0 Hz, 2H), 7.94 (br d, J=7.5 Hz, 4H) and 8.93 (s, 1H).

2-Amino-3-(2H-benzotriazol-2-yl)-2-methylpropionitrile [1.9 g, 97%, Rf=0.2 (1:1 EA/heptane)] was prepared using a procedure similar to that described in Example 1, part a and b, except starting from 1H-benzotriazole.

Example 6

N-[2-(2H-Benzotriazol-2-yl)-1-cyano-1-methylethyl]-4-trifluoromethylthiobenzamide (compound No 1.005)

Using a procedure similar to that described in Example 1, except using 2-amino-3-(2H-benzotriazol-2-yl)-2-methylpropionitrile, described in Example 5, and 4-trifluoromethylthiobenzoyl chloride, the title compound was isolated as a white solid (0.12 g, 59%). Rf=0.6 (1:1 EA/heptane). MS (ES): M/Z [M+H]=406. 1H NMR: (400 MHz, DMSO-$d_6$): 1.75 (s, 3H), 5.39-5.50 (m, 2H), 7.46 (dd, J=6.6, 3.1 Hz, 2H), 7.85-7.95 (m, 6H) and 9.01 (s, 1H).

Example 7

N-[1-Cyano-1-methyl-2-(5-methyl-2H-benzotriazol-2-yl)ethyl]-4-trifluoromethoxybenzamide (compound No 1.006)

Using a procedure similar to that described in Example 1, except using 2-amino-2-methyl-3-(5-methyl-2H-benzotriazol-2-yl)propionitrile, the title compound was isolated as a white solid (0.09 g, 45%). Rf=0.6 (1:1 EA/heptane). MS (ES): M/Z [M+H]=404. 1H NMR: (400 MHz, DMSO-$d_6$): 1.73 (s, 3H), 2.45 (s, 3H), 5.34-5.43 (m, 2H), 7.30 (dd, J=8.8, 1.4 Hz, 1H), 7.52 (d, J=8.0 Hz, 2H), 7.68 (d, J=1.0 Hz, 1H), 7.82 (d, J=8.8 Hz, 1H), 7.90-7.97 (m, 2H) and 8.91 (s, 1H). 19F NMR (376 MHz, DMSO-$d_6$): −57.08 (s, 3F).

2-Amino-2-methyl-3-(5-methyl-2H-benzotriazol-2-yl)propionitrile [2.1 g, 92%, Rf=0.2 (1:1 EA/heptane)] was prepared using a procedure similar to that described in Example 1, part a and b, except starting from 5-methyl-1H-benzotriazole.

Example 8

N-[1-Cyano-1-methyl-2-(5-methyl-2H-benzotriazol-2-yl)ethyl]-4-trifluoromethylthiobenzamide (compound No 1.007)

Using a procedure similar to that described in Example 1, except using 2-amino-2-methyl-3-(5-methyl-2H-benzotriazol-2-yl)propionitrile, described in Example 7, and 4-trifluoromethylthiobenzoyl chloride, the title compound was isolated as a white solid (0.12 g, 57%). Rf=0.65 (1:1 EA/heptane). MS (ES): M/Z [M+H]=420. 1H NMR: (400 MHz, DMSO-$d_6$): 1.73 (s, 3H), 2.45 (s, 3H), 5.34-5.44 (m, 2H), 7.30 (dd, J=8.8, 1.4 Hz, 1H), 7.68 (d, J=1.0 Hz, 1H), 7.82 (d, J=8.8 Hz, 1H), 7.84-7.94 (m, 4H) and 8.91 (s, 1H). 19F NMR (376 MHz, DMSO-$d_6$): −41.94 (s, 3F).

Example 9

N-[2-(5-Chloro-6-methyl-2H-benzotriazol-2-yl)-1-cyano-1-methylethyl]-4-trifluoromethoxybenzamide (compound No 1.040)

Using a procedure similar to that described in Example 1, except using 2-amino-3-(5-chloro-6-methyl-2H-benzotriazol-2-yl)-2-methylpropionitrile (90 mg), the title compound was isolated as a white solid (125 mg, 79%). Rf=0.65 (1:1 EA/heptane). MS (ES): M/Z [M+H]=438. 1H NMR: (400 MHz, DMSO-$d_6$): 1.73 (s, 3H), 2.46 (s, 3H), 5.38 (d, J=13.4 Hz, 1H), 5.44 (d, J=13.3 Hz, 1H), 7.52 (d, J=8.0 Hz, 2H), 7.93 (d, J=8.8 Hz, 2H), 7.96 (s, 1H), 8.13 (s, 1H) and 8.92 (s, 1H). 19F NMR (376 MHz, DMSO-$d_6$): −57.08 (s, 3F).

2-Amino-3-(5-chloro-6-methyl-2H-benzotriazol-2-yl)-2-methylpropionitrile [2.1 g, 92%, Rf=0.2 (1:1 EA/heptane)] was prepared using a procedure similar to that described in Example 1, part a and b, except starting from 6-chloro-5-methyl-1H-benzotriazole.

Example 10

N-[2-(5-Chloro-6-methyl-2H-benzotriazol-2-yl)-1-cyano-1-methylethyl]-4-trifluoromethylthiobenzamide (compound No 1.041)

Using a procedure similar to that described in Example 1, except using 2-amino-3-(5-chloro-6-methyl-2H-benzotriazol-2-yl)-2-methylpropionitrile (90 mg, described in Example 9) and 4-trifluoromethylthiobenzoyl chloride (0.1 mL), the title compound was isolated as a white solid (152 mg, 93%). Rf=0.6 (1:1 EA/heptane). MS (ES): M/Z [M+H]= 454. 1H NMR: (400 MHz, DMSO-$d_6$): 1.73 (s, 3H), 2.46 (s, 3H), 5.38 (d, J=13.4 Hz, 1H), 5.45 (d, J=13.4 Hz, 1H), 7.87 (d, J=8.5 Hz, 2H), 7.91 (d, J=8.6 Hz, 2H), 7.96 (s, 1H), 8.13 (s, 1H) and 9.00 (s, 1H). 19F NMR (376 MHz, DMSO-$d_6$): −41.93 (s, 3F).

Compounds of Examples 11 to 51 were prepared according to the general reaction scheme:

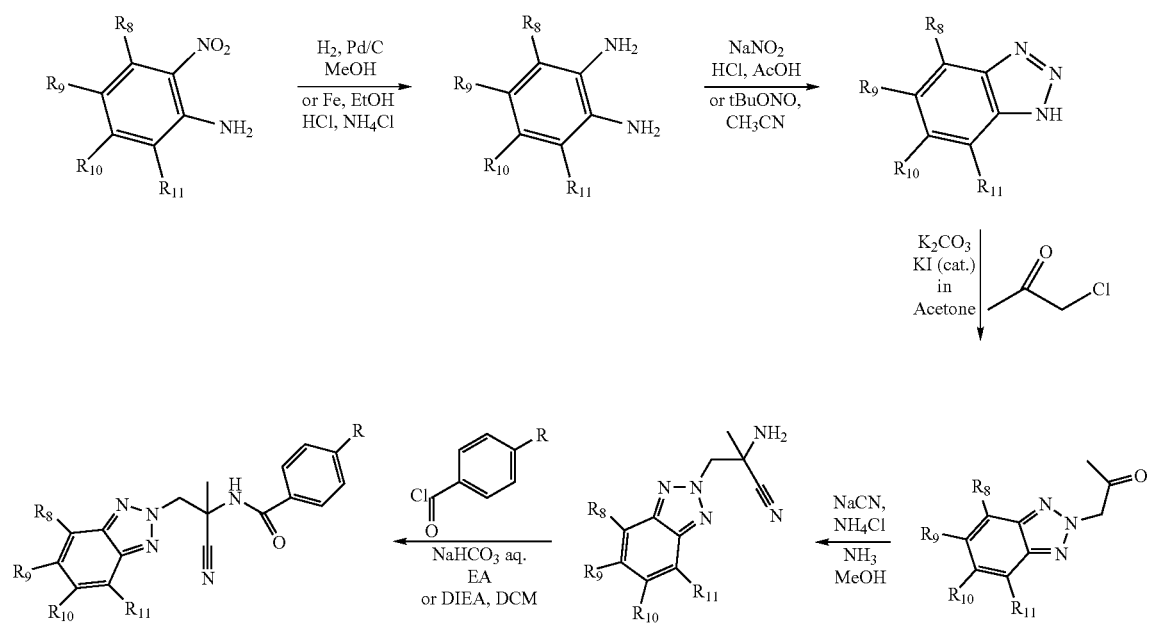

Final Product
V=C—$R_8$; W=C—$R_9$; X=C—$R_{10}$; Y=C—$R_{11}$;
Q=P=N;
$R_3$=$R_4$=H; a=1; $R_5$=$CH_3$; $R_6$=H;
Z=C(O); $R_7$=p-phenyl-R

Example 11

N-[1-Cyano-1-methyl-2-(5-trifluoromethyl-2H-benzotriazol-2-yl)ethyl]-4-trifluoromethoxybenzamide (compound No 1.008)

Using a procedure similar to that described in Example 1, except using 2-amino-2-methyl-3-(5-trifluoromethyl-2H-benzotriazol-2-yl)propionitrile, the title compound was isolated as a white solid (65 mg, 26%). Rf=0.6 (1:1 EA/heptane). MS (ES): M/Z [M+H]=458. 1H NMR: (400 MHz, DMSO-$d_6$): 1.76 (s, 3H), 5.47-5.57 (m, 2H), 7.50 (d, J=8.0 Hz, 2H), 7.71 (dd, J=9.0, 1.6 Hz, 1H), 7.93 (m, 2H), 8.20 (d, J=9.0 Hz, 1H), 8.50 (br s, 1H) and 8.91 (s, 1H). 19F NMR (376 MHz, DMSO-$d_6$): −61.17 (s, 3F) and −57.09 (s, 3F).

2-Amino-2-methyl-3-(5-trifluoromethyl-2H-benzotriazol-2-yl)propionitrile [1.2 g, 69%, Rf=0.35 (1:1 EA/heptane)] was prepared using a procedure similar to that described in Example 1, part a and b, except starting from 5-trifluoromethyl-1H-benzotriazole, that was prepared as follows:
  a. A mixture of 2-nitro-4-trifluoromethylaniline (12 g) and activated palladium on charcoal (0.6 g) in methanol was hydrogenated with one atmosphere of hydrogen under stirring at room temperature for one hour. The reaction mixture was filtered through a pad of diatomaceous earth and the filtrate concentrated under reduced pressure to give a residue. This residue was then dissolved in acetic acid (100 mL) and water (15 mL) and cooled to 0° C. prior to adding hydrochloric acid (4 mL) and a solution of sodium nitrite (4.4 g) in water (10 mL). The mixture was stirred at room temperature for two hours and then diluted with water. The resulting solid was filtered, washed with water and dried to obtain an off-white solid (8.0 g, 73%).

Example 12

N-[1-Cyano-1-methyl-2-(5-trifluoromethyl-2H-benzotriazol-2-yl)ethyl]-4-trifluoromethylthiobenzamide (compound No 1.009)

Using a procedure similar to that described in Example 1, except using 2-amino-2-methyl-3-(5-trifluoromethyl-2H-benzotriazol-2-yl)-propionitrile, described in Example 11, and 4-trifluoromethylthiobenzoyl chloride, the title compound was isolated as a white solid (0.16 g, 61%). Rf=0.65 (1:1 EA/heptane). MS (ES): M/Z [M+H]=474. 1H NMR: (400 MHz, CHLOROFORM-d): 1.88 (s, 3H), 5.39 (dd, J=112.8, 13.7 Hz, 2H), 7.38 (br s, 1H), 7.65 (d, J=9.1 Hz, 1H), 7.75-7.88 (m, 4H), 8.02 (d, J=9.0 Hz, 1H) and 8.25 (br s, 1H). 19F NMR (376 MHz, CHLOROFORM-d): −63.01 (s, 3F) and −42.23 (s, 3F).

Example 13

N-[1-Cyano-2-(5,6-dichloro-2H-benzotriazol-2-yl)-1-methylethyl]-4-trifluoromethoxybenzamide (compound No 1.010)

Using a procedure similar to that described in Example 1, except using 2-amino-3-(5,6-dichloro-2H-benzotriazol-2-yl)-2-methylpropionitrile, the title compound was isolated as a white solid (72 mg, 28%). Rf=0.6 (1:1 EA/heptane). MS (ES): M/Z [M+H]=458. 1H NMR: (400 MHz, DMSO-$d_6$): 1.74 (s, 3H), 5.41-5.51 (m, 2H), 7.51 (d, J=8.1 Hz, 2H), 7.93 (d, J=8.8 Hz, 2H), 8.43 (br s, 2H) and 8.92 (s, 1H). 19F NMR (376 MHz, DMSO-$d_6$): −57.10 (s, 3F).

2-Amino-3-(5,6-dichloro-2H-benzotriazol-2-yl)-2-methylpropionitrile [0.35 g, 79%, Rf=0.25 (1:1 EA/heptane)] was prepared using a procedure similar to that described in Example 1, part a and b, except starting from 5,6-dichloro-1H-benzotriazole, that was prepared as follows:
  a. 4,5-Dichlorobenzene-1,2-diamine (4.8 g) was dissolved in acetic acid (45 mL) and water (15 mL) and cooled to 0° C. prior to adding hydrochloric acid (2 mL) and a solution of sodium nitrite (2.8 g) in water (15 mL). The mixture was stirred at room temperature for 30 minutes and then diluted with water. The resulting solid was filtered, washed with water and dried. The resulting crude product was dissolved in hot ethanol. Any residual solid was filtered off and the filtrate let cooled down. Addition of water formed a solid that was filtered, washed with water and dried to give a tan solid (2.8 g, 55%).

Example 14

N-[1-Cyano-2-(5,6-dichloro-2H-benzotriazol-2-yl)-1-methylethyl]-4-trifluoromethylthiobenzamide (compound No 1.011)

Using a procedure similar to that described in Example 1, except using 2-amino-3-(5,6-dichloro-2H-benzotriazol-2-yl)-2-methylpropionitrile, described in Example 13, and 4-trifluoromethylthiobenzoyl chloride, the title compound was isolated as a white solid (90 mg, 34%). MS (ES): M/Z [M+H]=474. 1H NMR: (400 MHz, DMSO-$d_6$): 1.74 (s, 3H), 5.41-5.51 (m, 2H), 7.82-7.91 (m, 4H), 8.41 (br s, 2H) and 9.00 (s, 1H). 19F NMR (376 MHz, DMSO-$d_6$): −41.94 (s, 3F).

Example 15

N-[1-Cyano-2-(4,6-dichloro-2H-benzotriazol-2-yl)-1-methylethyl]-4-trifluoromethoxybenzamide (compound No 1.012)

Using a procedure similar to that described in Example 1, except using 2-amino-3-(4,6-dichloro-2H-benzotriazol-2-yl)-2-methylpropionitrile, the title compound was isolated as a white solid (83 mg, 33%). Rf=0.65 (1:1 EA/heptane). MS (ES): M/Z [M+H]=458. 1H NMR: (400 MHz, DMSO-$d_6$): 1.75 (s, 3H), 5.40-5.55 (m, 2H), 7.47 (d, J=8.25 Hz, 2H), 7.69 (dd, J=1.5, 0.8 Hz, 1H), 7.92 (d, J=8.8 Hz, 2H), 8.13 (d, J=1.6 Hz, 1H) and 8.87 (s, 1H). 19F NMR (376 MHz, DMSO-$d_6$): −57.19 (s, 3F).

2-Amino-3-(4,6-dichloro-2H-benzotriazol-2-yl)-2-methylpropionitrile [0.35 g, 63%, Rf=0.35 (1:1 EA/heptane)] was prepared using a procedure similar to that described in Example 1, part a and b, except starting from 5,7-dichloro-1H-benzotriazole. 5,7-Dichloro-1H-benzotriazole (11 g, 99%) was prepared using a procedure similar to that described in Example 11, part a, except starting from 2,4-dichloro-6-nitroaniline (12 g).

Example 16

N-[1-Cyano-2-(4,6-dichloro-2H-benzotriazol-2-yl)-1-methylethyl]-4-trifluoromethylthiobenzamide (compound No 1.013)

Using a procedure similar to that described in Example 1, except using 2-amino-3-(4,6-dichloro-2H-benzotriazol-2- yl)-2-methylpropionitrile, described in Example 15, and 4-trifluoromethylthiobenzoyl chloride, the title compound was isolated as a white solid (50 mg, 20%). Rf=0.7 (1:1 EA/heptane). MS (ES): M/Z [M+H]=475. NMR: (400 MHz, DMSO-$d_6$): 1.75 (s, 3H), 5.40-5.56 (m, 2H), 7.65 (m, 1H), 7.79-7.95 (m, 4H), 8.10 (m, 1H) and 8.95 (s, 1H). 19F NMR (376 MHz, DMSO-$d_6$): −42.05 (s, 3F).

Example 17

N-[1-Cyano-2-(4,6-dichloro-2H-benzotriazol-2-yl)-1-methylethyl]biphenyl-4-carboxamide (compound No 1.046)

Using a procedure similar to that described in Example 1, except using 2-amino-3-(4,6-dichloro-2H-benzotriazol-2-yl)-2-methylpropionitrile, described in Example 15, and 4-biphenyl carbonyl chloride, the title compound was isolated as a white solid (32 mg). MS (ES): M/Z [M+H]=450. NMR: (400 MHz, DMSO-$d_6$): 1.78 (s, 3H), 5.45 (d, J=13.3 Hz, 1H), 5.55 (d, J=13.3 Hz, 1H), 7.43 (m, 1H), 7.51 (t, J=7.5 Hz, 1H), 7.70-7.78 (m, 3H), 7.81 (d, J=8.4 Hz, 2H), 7.90 (d, J=8.5 Hz, 2H), 8.18 (d, J=1.6 Hz, 1H) and 8.83 (s, 1H).

Example 18

N-[1-Cyano-2-(4,6-dichloro-2H-benzotriazol-2-yl)-1-methylethyl]-4-tert-butylbenzamide (compound No 1.053)

Using a procedure similar to that described in Example 1, except using 2-amino-3-(4,6-dichloro-2H-benzotriazol-2-yl)-2-methylpropionitrile, described in Example 15, and 4-tert-butylbenzoyl chloride, the title compound was isolated as a white solid (80 mg). MS (ES): M/Z [M+H]=430. NMR: (400 MHz, DMSO-$d_6$): 1.30 (s, 9H), 1.75 (s, 3H), 5.47 (q, J=17.8 Hz, 2H), 5.51 (d, J=8.3 Hz, 2H), 7.70-7.76 (m, 3H), 8.18 (d, J=1.5 Hz, 1H) and 8.70 (br s, 1H).

Example 19

N-[2-(4-Chloro-6-trifluoromethyl-2H-benzotriazol-2-yl)-1-cyano-1-methylethyl]-4-trifluoromethoxybenzamide (compound No 1.014)

Using a procedure similar to that described in Example 1, except using 2-amino-3-(4-chloro-6-trifluoromethyl-2H-benzotriazol-2-yl)-2-methylpropionitrile, the title compound was isolated as a white solid (0.66 g, 82%). Rf=0.7 (1:1 EA/heptane). MS (ES): M/Z [M+H]=492. 1H NMR: (400 MHz, DMSO-$d_6$): 1.77 (s, 3H), 5.46-5.67 (m, 2H), 7.50 (d, J=8.1 Hz, 2H), 7.89-7.96 (m, 2H), 8.56 (br s, 1H) and 8.87 (s, 1H). 19F NMR (376 MHz, DMSO-$d_6$): −61.07 (s, 3F) and −57.15 (s, 3F).

2-Amino-3-(4-chloro-6-trifluoromethyl-2H-benzotriazol-2-yl)-2-methylpropionitrile [1.7 g, 89%, Rf=0.35 (1:1 EA/heptane)] was prepared using a procedure similar to that described in Example 1, part a and b, except starting from 7-chloro-5-trifluoromethyl-1H-benzotriazole. 7-Chloro-5-trifluoromethyl-1H-benzotriazole (4.6 g, 99%) was prepared using a procedure similar to that described in Example 11, part a, except starting from 4-amino-3-chloro-5-nitrobenzotrifluoride (5 g).

Example 20

N-[2-(4-Chloro-6-trifluoromethyl-2H-benzotriazol-2-yl)-1-cyano-1-methylethyl]-4-trifluoromethylthiobenzamide (compound No 1.015)

Using a procedure similar to that described in Example 1, except using 2-amino-3-(4-chloro-6-trifluoromethyl-2H-benzotriazol-2-yl)-2-methylpropionitrile, described in Example 19, and 4-trifluoromethylthiobenzoyl chloride, the title compound was isolated as a white solid (0.45 g, 90%). Rf=0.6 (1:1 EA/heptane). MS (ES): M/Z [M+H]=508. 1H NMR: (400 MHz, DMSO-$d_6$): 1.77 (s, 3H), 5.49-5.65 (m, 2H), 7.84-7.93 (m, 5H), 8.56 (d, J=1.1 Hz, 1H) and 8.95 (s, 1H). 19F NMR (376 MHz, DMSO-$d_6$): −61.09 (s, 3F) and −42.03 (s, 3F).

Example 21

N-[1-Cyano-2-(5-cyano-2H-benzotriazol-2-yl)-1-methylethyl]-4-trifluoromethoxybenzamide (compound No 1.016)

Using a procedure similar to that described in Example 1, except using 2-amino-3-(5-cyano-2H-benzotriazol-2-yl)-2-methylpropionitrile, the title compound was isolated as a white solid (0.25 g, 45%). Rf=0.45 (1:1 EA/heptane). MS (ES): M/Z [M+H]=415. 1H NMR: (400 MHz, DMSO-$d_6$): 1.76 (s, 3H), 5.46-5.59 (m, 2H), 7.51 (d, J=8.0 Hz, 2H), 7.76 (dd, J=8.8, 1.4 Hz, 1H), 7.89-7.96 (m, 2H), 8.17 (dd, J=8.9, 0.9 Hz, 1H), 8.77 (m, 1H) and 8.93 (s, 1H). 19F NMR (376 MHz, DMSO-$d_6$): −57.11 (s, 3F).

2-Amino-3-(5-cyano-2H-benzotriazol-2-yl)-2-methylpropionitrile [0.85 g, 75%, Rf=0.15 (1:1 EA/heptane)] was prepared using a procedure similar to that described in Example 1, part a and b, except starting from 5-cyano-1H-benzotriazole. 5-Cyano-1H-benzotriazole (5.7 g, 65%) was prepared using a procedure similar to that described in Example 11, part a, except starting from 4-amino-3-nitrobenzonitrile (10 g).

Example 22

N-[1-Cyano-2-(5-cyano-2H-benzotriazol-2-yl)-1-methylethyl]-4-trifluoromethylthiobenzamide (compound No 1.017)

Using a procedure similar to that described in Example 1, except using 2-amino-3-(5-cyano-2H-benzotriazol-2-yl)-2-methylpropionitrile, described in Example 21, and 4-trifluoromethylthiobenzoyl chloride, the title compound was isolated as a white solid (0.46 g, 81%). Rf=0.45 (1:1 EA/heptane). MS (ES): M/Z [M+H]=431. 1H NMR: (400 MHz, DMSO-$d_6$): 1.76 (s, 3H), 5.46-5.59 (m, 2H), 7.76 (dd, J=8.9, 1.3 Hz, 1H), 7.84-7.93 (m, 4H), 8.18 (d, J=8.9 Hz, 1H), 8.78 (br s, 1H) and 9.01 (br s, 1H). 19F NMR (376 MHz, DMSO-$d_6$): −41.93 (s, 3F).

Example 23

N-[2-(4,6-Bis(trifluoromethyl)-2H-benzotriazol-2-yl)-1-cyano-1-methylethyl]-4-trifluoromethoxybenzamide (compound No 1.018)

Using a procedure similar to that described in Example 1, except using 2-amino-3-(4,6-bis(trifluoromethyl)-2H-benzotriazol-2-yl)-2-methylpropionitrile, the title compound was isolated as a white solid (0.41 g, 88%). Rf=0.6 (1:1 EA/heptane). MS (ES): M/Z [M+H]=526. 1H NMR: (400 MHz, DMSO-$d_6$): 1.79 (s, 3H), 5.61 (dd, J=55.9, 13.3 Hz, 2H), 7.48 (d, J=8.0 Hz, 2H), 7.88-7.91 (m, 2H), 8.13 (s, 1H), 8.83 (s, 1H) and 8.98 (s, 1H). 19F NMR (376 MHz, DMSO-$d_6$): −57.18 (s, 3F), −61.00 (s, 3F) and −61.59 (s, 3F).

2-Amino-3-(4,6-bis(trifluoromethyl)-2H-benzotriazol-2-yl)-2-methylpropionitrile [1.5 g, 77%, Rf=0.3 (1:1 EA/heptane)] was prepared using a procedure similar to that described in Example 1, part a and b, except starting from 5,7-bis(trifluoromethyl)-2H-benzotriazole. 5,7-Bis(trifluoromethyl)-1H-benzotriazole (5.2 g, 99%) was prepared using a procedure similar to that described in Example 13, part a, except starting from 3,5-bis(trifluoromethyl)-1,2-phenylenediamine (5 g).

Example 24

N-[2-(4,6-Bis(trifluoromethyl)-2H-benzotriazol-2-yl)-1-cyano-1-methylethyl]-4-trifluoromethylthiobenzamide (compound No 1.019)

Using a procedure similar to that described in Example 1, except using 2-amino-3-(4,6-bis(trifluoromethyl)-2H-benzotriazol-2-yl)-2-methylpropionitrile, described in Example 23, and 4-trifluoromethylthiobenzoyl chloride, the title compound was isolated as a white solid (0.40 g, 83%). Rf=0.7 (1:1 EA/heptane). MS (ES): M/Z [M+H]=542. 1H NMR: (400 MHz, DMSO-$d_6$): 1.79 (s, 3H), 5.62 (dd, J=60.6, 13.3 Hz, 2H), 7.76-7.97 (m, 4H), 8.13 (s, 1H), 8.92 (s, 1H) and 8.97 (s, 1H). 19F NMR (376 MHz, DMSO-$d_6$): −61.62 (s, 3F), −61.04 (s, 3F) and −42.10 (s, 3F).

Example 25

N-[2-(5-Bromo-2H-benzotriazol-2-yl)-1-cyano-1-methylethyl]-4-trifluoromethoxybenzamide (compound No 1.020)

Using a procedure similar to that described in Example 1, except using 2-amino-3-(5-bromo-2H-benzotriazol-2-yl)-2-methylpropionitrile, the title compound was isolated as a white solid (0.36 g, 72%). Rf=0.65 (1:1 EA/heptane). MS (ES): M/Z [M+H]=468. 1H NMR: (400 MHz, DMSO-$d_6$): 1.74 (s, 3H), 5.44 (dd, J=26.8, 13.3 Hz, 2H), 7.51 (d, J=8.0 Hz, 2H), 7.58 (dd, J=9.1, 1.8 Hz, 1H), 7.91-7.96 (m, 2H), 7.96 (dd, J=9.1, 0.5 Hz, 1H), 8.29 (dd, J=1.7, 0.5 Hz, 1H) and 8.92 (s, 1H). 19F NMR (376 MHz, DMSO-$d_6$): −57.09 (s, 3F).

2-Amino-3-(5-bromo-2H-benzotriazol-2-yl)-2-methylpropionitrile [1.7 g, 93%, Rf=0.35 (1:1 EA/heptane)] was prepared using a procedure similar to that described in Example 1, part a and b, except starting from 5-bromo-1H-benzotriazole. 5-bromo-1H-benzotriazole was prepared using a procedure similar to that described in Example 13, part a, except starting from 4-bromo-1,2-diamino benzene.

Example 26

N-[2-(5-Bromo-2H-benzotriazol-2-yl)-1-cyano-1-methylethyl]-4-trifluoromethylthiobenzamide (compound No 1.021)

Using a procedure similar to that described in Example 1, except using 2-amino-3-(5-bromo-2H-benzotriazol-2-yl)-2-methylpropionitrile, described in Example 25, and 4-trifluoromethylthiobenzoyl chloride, the title compound was isolated as a white solid (0.45 g, 87%). Rf=0.65 (1:1 EA/heptane). MS (ES): M/Z [M+H]=484. 1H NMR: (400 MHz, DMSO-$d_6$): 1.74 (s, 3H), 5.36-5.53 (m, 2H), 7.58 (dd, J=9.1, 1.8 Hz, 1H), 7.84-7.92 (m, 4H), 7.95 (dd, J=9.1, 0.5 Hz, 1H), 8.29 (dd, J=1.7, 0.6 Hz, 1H) and 9.00 (s, 1H). 19F NMR (376 MHz, DMSO-$d_6$): −41.93 (s, 3F).

Example 27

N-[−2-(6-Chloro-4-methyl-2H-benzotriazol-2-yl)-1-cyano-1-methylethyl]-4-trifluoromethoxybenzamide (compound No 1.033)

Using a procedure similar to that described in Example 1, except using 2-amino-3-(6-chloro-4-methyl-2H-benzotriazol-2-yl)-2-methylpropionitrile, the title compound was isolated as a white solid (192 mg, 55%). MS (ES): M/Z [M+H]= 438. 1H NMR: (400 MHz, DMSO-$d_6$): 1.74 (s, 3H), 2.47 (s, 3H), 5.35-5.51 (m, 2H), 7.27 (s, 1H), 7.52 (d, J=8.0 Hz, 2H), 7.88-7.95 (m, 3H) and 8.84 (s, 1H). 19F NMR (376 MHz, DMSO-$d_6$): −57.12 (s, 3F).

2-Amino-3-(6-chloro-4-methyl-2H-benzotriazol-2-yl)-2-methylpropionitrile (0.4 g, 67%) was prepared using a procedure similar to that described in Example 1, part a and b, except starting from 5-chloro-7-methyl-1H-benzotriazole. 5-Chloro-7-methyl-1H-benzotriazole (4.35 g, 97%) was prepared using a procedure similar to that described in Example 11, part a, except starting from 4-chloro-2-methyl-6-nitroaniline (5 g).

Example 28

N-[2-(6-Chloro-4-methyl-2H-benzotriazol-2-yl)-1-cyano-1-methylethyl]-4-trifluoromethylthiobenzamide (compound No 1.034)

Using a procedure similar to that described in Example 1, except using 2-amino-3-(6-chloro-4-methyl-2H-benzotriazol-2-yl)-2-methylpropionitrile, described in Example 27, and 4-trifluoromethylthiobenzoyl chloride, the title compound was isolated as a white solid (233 mg, 64%). MS (ES): M/Z [M+H]=454. NMR: (400 MHz, DMSO-$d_6$): 1.74 (s, 3H), 2.47 (s, 3H), 5.44 (dd, J=57.5, 13.3 Hz, 2H), 7.27 (s, 1H), 7.79-7.99 (m, 5H) and 8.92 (s, 1H). 19F NMR (376 MHz, DMSO-$d_6$): −42.01 (s, 3F).

Example 29

N-[2-(6-Chloro-4-methyl-2H-benzotriazol-2-yl)-1-cyano-1-methylethyl]-4-phenoxybenzamide (compound No 1.039)

Using a procedure similar to that described in Example 1, except using 2-amino-3-(6-chloro-4-methyl-2H-benzotriazol-2-yl)-2-methylpropionitrile (60 mg, described in Example 27) and 4-phenoxybenzoyl chloride (0.067 mL), the title compound was isolated as a white solid (90 mg, 84%). MS (ES): M/Z [M+H]=446. NMR: (400 MHz, DMSO-$d_6$): 1.73 (s, 3H), 2.47 (s, 3H), 5.38 (d, J=13.3 Hz, 1H), 5.45 (d, J=13.3 Hz, 1H), 7.08 (t, J=8.25 Hz, 4H), 7.23 (t, 1H), 7.28 (s, 1H), 7.45 (t, 2H), 7.84 (d, J=8.79 Hz, 2H), 7.91 (m, 1H) and 8.68 (s, 1H).

4-Phenoxybenzoyl chloride was prepared by reacting 4-phenoxybenzoic acid with oxalyl chloride.

Example 30

N-[1-Cyano-1-methyl-2-(5-trifluoromethoxy-2H-benzotriazol-2-yl)ethyl]-4-trifluoromethoxybenzamide (compound No 1.035)

Using a procedure similar to that described in Example 1, except using 2-amino-3-(5-trifluoromethoxy-2H-benzotriazol-2-yl)-2-methylpropionitrile (100 mg), the title compound was isolated as a white solid (140 mg, 85%). MS (ES): M/Z [M+H]=474. 1H NMR: (400 MHz, DMSO-$d_6$): 1.75 (s, 3H), 5.44 (d, J=13.3 Hz, 1H), 5.51 (d, J=13.4 Hz, 1H), 7.45-7.52 (m, 3H), 7.93 (d, J=8.8 Hz, 2H), 8.06 (br s, 1H), 8.12 (d, 1H, J=9.9 Hz) and 8.89 (s, 1H). 19F NMR (376 MHz, DMSO-$d_6$): −57.42 (s, 3F) and −57.11 (s, 3F).

2-Amino-3-(5-trifluoromethoxy-2H-benzotriazol-2-yl)-2-methylpropionitrile (0.24 g) was prepared using a procedure similar to that described in Example 1, part a and b, except starting from 5-trifluoromethoxy-1H-benzotriazole (3.2 g). 5-Trifluoromethoxy-1H-benzotriazole (3.4 g, 74%) was prepared using a procedure similar to that described in Example 11, part a, except starting from 2-nitro-4-trifluoromethoxyaniline (5 g).

Example 31

N-[1-Cyano-1-methyl-2-(5-trifluoromethoxy-2H-benzotriazol-2-yl)ethyl]-4-trifluoromethylthiobenzamide (compound No 1.036)

Using a procedure similar to that described in Example 1, except using 2-amino-3-(5-trifluoromethoxy-2H-benzotriazol-2-yl)-2-methylpropionitrile (100 mg, described in Example 30) and 4-trifluoromethylthiobenzoyl chloride (0.12 mL), the title compound was isolated as a white solid (142 mg, 83%). MS (ES): M/Z [M+H]=490. 1H NMR: (400 MHz, CHLOROFORM-d): 1.75 (s, 3H), 5.48 (d, J=13.4 Hz, 1H), 5.52 (d, J=13.3 Hz, 1H), 7.47 (d, J=10.6 Hz, 1H), 7.85-7.91 (m, 4H), 8.05 (br s, 1H), 8.12 (d, 1H, J=9.3 Hz) and 8.98 (br s, 1H). 19F NMR (376 MHz, CHLOROFORM-d): −57.43 (s, 3F) and −41.96 (s, 3F).

Example 32

N-[2-(6-Chloro-4-trifluoromethyl-2H-benzotriazol-2-yl)-1-cyano-1-methylethyl]-4-trifluoromethoxybenzamide (compound No 1.037)

Using a procedure similar to that described in Example 1, except using 2-amino-3-(6-chloro-4-trifluoromethyl-2H-benzotriazol-2-yl)-2-methylpropionitrile (100 mg), the title compound was isolated as a white solid (148 mg, 91%). MS (ES): M/Z [M+H]=492. 1H NMR: (400 MHz, DMSO-$d_6$): 1.77 (s, 3H), 2.47 (s, 3H), 5.46 (d, J=13.2 Hz, 1H), 5.60 (d, J=13.4 Hz, 1H), 7.49 (d, J=8.0 Hz, 2H), 7.89 (d, J=8.8 Hz, 2H), 7.96 (s, 1H), 8.56 (s, 1H) and 8.85 (s, 1H). 19F NMR (376 MHz, DMSO-$d_6$): −61.51 (s, 3F) and −57.16 (s, 3F).

2-Amino-3-(6-chloro-4-trifluoromethyl-2H-benzotriazol-2-yl)-2-methylpropionitrile (0.82 g) was prepared using a procedure similar to that described in Example 1, part a and b, except starting from 5-chloro-7-trifluoromethyl-1H-benzotriazole (2.5 g). 5-Chloro-7-trifluoromethyl-1H-benzotriazole (2.5 g, 55%) was prepared using a procedure similar to that described in Example 11, part a, except starting from 2-amino-5-chloro-3-nitrobenzotrifluoride (5 g).

Example 33

N-[2-(6-Chloro-4-trifluoromethyl-2H-benzotriazol-2-yl)-1-cyano-1-methylethyl]-4-trifluoromethylthiobenzamide (compound No 1.038)

Using a procedure similar to that described in Example 1, except using 2-amino-3-(6-chloro-4-trifluoromethyl-2H-benzotriazol-2-yl)-2-methylpropionitrile (100 mg, described in Example 32) and 4-trifluoromethylthiobenzoyl chloride (0.12 mL), the title compound was isolated as a white solid (142 mg, 85%). MS (ES): M/Z [M+H]=508. NMR: (400 MHz, DMSO-$d_6$): 1.77 (s, 3H), 2.47 (s, 3H), 5.46 (d, J=13.3 Hz, 1H), 5.62 (d, J=13.3 Hz, 1H), 7.82-7.88 (m, 4H), 7.96 (s, 1H), 8.57 (s, 1H) and 8.93 (s, 1H). 19F NMR (376 MHz, DMSO-$d_6$): −42.05 (s, 3F) and −61.51 (s, 3F).

Example 34

N-[2-(6-Chloro-4-trifluoromethyl-2H-benzotriazol-2-yl)-1-cyano-1-methylethyl]-4-phenoxybenzamide (compound No 1.042)

Using a procedure similar to that described in Example 1, except using 2-amino-3-(6-chloro-4-trifluoromethyl-2H-benzotriazol-2-yl)-2-methylpropionitrile (100 mg, described in Example 32) and 4-phenoxybenzoyl chloride (0.10 mL), the title compound was isolated as a white solid (95 mg, 58%). Rf=0.75 (1:1 EA/heptane). MS (ES): M/Z [M+H]=500. NMR: (400 MHz, DMSO-$d_6$): 1.76 (s, 3H), 2.47 (s, 3H), 5.47 (d, J=13.3 Hz, 1H), 5.57 (d, J=13.3 Hz, 1H), 7.04-7.12 (m, 4H), 7.22 (t, J=7.4 Hz, 1H), 7.97 (s, 1H), 8.57 (s, 1H) and 8.69 (s, 1H). 19F NMR (376 MHz, DMSO-$d_6$): −61.41 (s, 3F).

4-Phenoxybenzoyl chloride was prepared by reacting 4-phenoxybenzoic acid with oxalyl chloride.

Example 35

N-[2-(4-Chloro-2H-benzotriazol-2-yl)-1-cyano-1-methylethyl]-4-trifluoromethoxybenzamide (compound No 1.043)

Using a procedure similar to that described in Example 1, except using 2-amino-3-(4-chloro-2H-benzotriazol-2-yl)-2-methylpropionitrile (100 mg), the title compound was isolated as a white solid (142 mg, 80%). Rf=0.65 (1:1 EA/heptane). MS (ES): M/Z [M+H]=424. 1H NMR: (400 MHz, DMSO-$d_6$): 1.77 (s, 3H), 5.43 (d, J=13.4 Hz, 1H), 5.54 (d, J=13.4 Hz, 1H), 7.46 (t, 1H), 7.50 (d, J=7.9 Hz, 2H), 7.59 (d, J=6.8 Hz, 1H), 7.91-7.97 (m, 3H) and 8.90 (s, 1H). 19F NMR (376 MHz, DMSO-$d_6$): −57.12 (s, 3F).

2-Amino-3-(4-chloro-2H-benzotriazol-2-yl)-2-methylpropionitrile (0.3 g) was prepared using a procedure similar to that described in Example 1, part a and b, except starting from 7-chloro-1H-benzotriazole (1.0 g). 7-chloro-1H-benzotriazole (1.0 g, 23%) was prepared using a procedure similar to that described in Example 11, part a, except starting from 3-chloro-2-nitroaniline (5 g).

Example 36

N-[2-(4-Chloro-2H-benzotriazol-2-yl)-1-cyano-1-methylethyl]-4-trifluoromethylthiobenzamide (compound No 1.044)

Using a procedure similar to that described in Example 1, except using 2-amino-3-(4-chloro-2H-benzotriazol-2-yl)-2- methylpropionitrile (100 mg, described in Example 35) and 4-trifluoromethylthiobenzoyl chloride (0.1 mL), the title compound was isolated as a white solid (130 mg, 70%). Rf=0.6 (1:1 EA/heptane). MS (ES): M/Z [M+H]=440. NMR: (400 MHz, DMSO-$d_6$): 1.75 (s, 3H), 5.43 (d, J=13.3 Hz, 1H), 5.55 (d, J=13.4 Hz, 1H), 7.46 (t, J=8.0 Hz, 1H), 7.59 (d, J=6.7 Hz, 1H), 7.75-7.95 (m, 5H) and 8.97 (s, 1H). 19F NMR (376 MHz, DMSO-$d_6$): −41.98 (s, 3F).

Example 37

N-[2-(4-Chloro-2H-benzotriazol-2-yl)-1-cyano-1-methylethyl]-4-phenoxybenzamide (compound No 1.045)

Using a procedure similar to that described in Example 1, except using 2-amino-3-(4-chloro-2H-benzotriazol-2-yl)-2-methylpropionitrile (100 mg, described in Example 35) and 4-phenoxybenzoyl chloride (0.10 mL), the title compound was isolated as a white solid (70 mg, 38%). Rf=0.7 (1:1 EA/heptane). MS (ES): M/Z [M+H]=432. NMR: (400 MHz, DMSO-$d_6$): 1.75 (s, 3H), 5.43 (d, J=13.3 Hz, 1H), 5.50 (d, J=13.3 Hz, 1H), 7.04-7.10 (m, 4H), 7.22 (t, J=7.4 Hz, 1H), 7.43-7.48 (m, 3H), 7.59 (d, J=6.6 Hz, 1H), 7.84 (d, J=8.9 Hz, 2H), 7.94 (d, J=8.0 Hz, 1H) and 8.73 (s, 1H).

4-Phenoxybenzoyl chloride was prepared by reacting 4-phenoxybenzoic acid with oxalyl chloride.

Example 38

N-[2-(4-Bromo-6-chloro-2H-benzotriazol-2-yl)-1-cyano-1-methylethyl]-4-trifluoromethoxybenzamide (compound No 1.060)

Using a procedure similar to that described in Example 1, except using 2-amino-3-(4-bromo-6-chloro-2H-benzotriazol-2-yl)-2-methylpropionitrile (1.0 g), the title compound was isolated as a white solid (1.5 g, 90%). Rf=0.6 (1:1 EA/heptane). MS (ES): M/Z [M+H]=502. 1H NMR: (400 MHz, DMSO-$d_6$): 1.75 (s, 3H), 5.42 (d, 1H), 5.53 (d, 1H), 7.51 (d, J=8.0 Hz, 2H), 7.86 (d, J=1.6 Hz, 1H), 7.92 (d, J=8.8 Hz, 2H), 8.20 (d, J=1.6 Hz, 1H) and 8.88 (s, 1H). 19F NMR (376 MHz, DMSO-$d_6$): −57.1 (s, 3F).

2-Amino-3-(4-bromo-6-chloro-2H-benzotriazol-2-yl)-2-methylpropionitrile was prepared using a procedure similar to that described in Example 1, part a and b, except starting from 7-bromo-5-chloro-1H-benzotriazole. 7-Bromo-5-chloro-1H-benzotriazole (7.6 g, 99%) was prepared using a procedure similar to that described in Example 13, part a, except starting from 3-bromo-5-chloro-1,2-diaminobenzene that was prepared as follows:

a. A mixture of 4-chloro-2-nitroaniline (10 g) and N-bromosuccinimide (11.3 g) in acetonitrile (200 mL) was heated at 70° C. overnight. The mixture was concentrated under reduced pressure and then poured into water and let stirred at room temperature for one hour. The resulting solid was filtered, washed with water and dried. The resulting crude product loaded on silica gel was purified by chromatography (SiO$_2$, heptane/EA) to afford 2-bromo-4-chloro-6-nitroaniline as a yellow solid (11.5 g, 79%). Rf=0.6 (3:7 EA/heptane).

b. To a rapidly stirred suspension of iron powder (1.1 g) in ethanol (10 mL) was added concentrated hydrochloric acid (2.5 ml) and the mixture heated at 65° C. After 4 hours, a 25% aqueous solution of ammonium chloride was added (4 mL) followed by slow addition of a solution of 2-bromo-4-chloro-6-nitroaniline (1 g) in ethanol.

After 3 hours, the mixture was allowed to cool down to room temperature and Celite® filter agent was added directly to the mixture. The suspension was filtered through a plug of Celite® filter agent. The filtrate was concentrated under reduced pressure, dissolved in ethyl acetate and filtered through a plug of Celite® filter agent. The filtered solution was treated with a saturated solution of sodium bicarbonate, washed with brine, dried over anhydrous sodium sulfate, filtered and concentrated under reduced pressure to give 3-bromo-5-chloro-1,2-diaminobenzene as an off-white solid (0.86 g, 98%). Rf=0.25 (3:7 EA/heptane).

Example 39

N-[1-Cyano-1-methyl-2-(4,5,7-trichloro-2H-benzotriazol-2-yl)-ethyl]-4-trifluoromethoxybenzamide (compound No 1.064)

Using a procedure similar to that described in Example 1, except using 2-amino-2-methyl-3-(4,5,7-trichloro-2H-benzotriazol-2-yl)-propionitrile (150 mg), the title compound was isolated as a white solid (210 mg, 87%). Rf=0.6 (1:1 EA/heptane). MS (ES): M/Z [M+H]=492. 1H NMR: (400 MHz, DMSO-$d_6$): 1.76 (s, 3H), 5.45 (d, 1H), 5.59 (d, 1H), 7.47 (d, J=8.25 Hz, 2H), 7.69 (dd, J=1.5, 0.8 Hz, 1H), 7.81-8.04 (m, 3H) and 8.83 (s, 1H). 19F NMR (376 MHz, DMSO-$d_6$): −57.1 (s, 3F).

2-Amino-2-methyl-3-(4,5,7-trichloro-2H-benzotriazol-2-yl)-propionitrile [1.3 g, Rf=0.2 (1:1 EA/heptane)] was prepared using a procedure similar to that described in Example 1, part a and b, except starting from 4,5,7-trichloro-1H-benzotriazole. 4,5,7-Trichloro-1H-benzotriazole (4 g, 85%) was prepared using a procedure similar to that described in Example 11, part a, except starting from 2-nitro-3,4,6-trichloroaniline (6.1 g) that was prepared as follows:

a. 2,4,5-trichloroaniline (10 g) was dissolved in acetic anhydride (50 mL) and stirred overnight at room temperature. The resulting solid was filtered and air dried to give N-(2,4,5-trichlorophenyl)acetamide as an off white solid (12 g, 99%). Rf=0.5 (1:1 EA/heptane).

b. To a solution of N-(2,4,5-trichlorophenyl)acetamide (12 g) in concentrated sulfuric acid (50 mL) at 0° C., was added dropwise, concentrated nitric acid (8 mL). After addition was complete, the mixture was allowed to warm slowly to room temperature. After 5 hours, the mixture was poured into ice water (200 mL). The resulting solid was filtered, washed with water and crystallized from a mixture of water and ethanol. The resulting solid was filtered and dried to give N-(2-nitro-3,4,6-trichlorophenyl)-acetamide as a grey solid (12 g, 99%).

c. A solution of N-(2-nitro-3,4,6-trichlorophenyl)acetamide (7 g) in dioxane and concentrated hydrochloric acid (70 mL) was heated at reflux overnight. The mixture was concentrated under reduced pressure to remove dioxane, diluted with water (150 mL), neutralized with a saturated solution of sodium bicarbonate and extracted with ethyl acetate. The organic phase was washed with brine, dried over anhydrous sodium sulfate, filtered and concentrated under reduced pressure to give 2-nitro-3,4,6-trichloroaniline as a grey solid (6.1 g, quantitative). Rf=0.6 (3:7 EA/heptane).

Example 40

N-[1-Cyano-1-methyl-2-(4,5,7-trichloro-2H-benzotriazol-2-yl)-ethyl]-4-trifluoromethylthiobenzamide (compound No 1.065)

Using a procedure similar to that described in Example 1, except using 2-amino-2-methyl-3-(4,5,7-trichloro-2H-benzotriazol-2-yl)-propionitrile (150 mg, described in Example 39) and 4-trifluoromethylthiobenzoyl chloride (0.1 mL), the title compound was isolated as a white solid (200 mg, 80%). Rf=0.55 (1:1 EA/heptane). MS (ES): M/Z [M+H]=508. NMR: (400 MHz, DMSO-$d_6$): 1.76 (s, 3H), 5.45 (d, J=13.3 Hz, 1H), 5.61 (d, J=13.3 Hz, 1H), 7.83-7.92 (m, 4H), 7.94 (s, 1H) and 8.91 (s, 1H). 19F NMR (376 MHz, DMSO-$d_6$): −42.0 (s, 3F).

Example 41

N-[1-Cyano-1-methyl-2-(4,5,7-trichloro-2H-benzotriazol-2-yl)-ethyl]-4-(1,2,2,2-tetrafluoroethyl)benzamide (compound No 1.069)

Using a procedure similar to that described in Example 1, except using 2-amino-2-methyl-3-(4,5,7-trichloro-2H-benzotriazol-2-yl)-propionitrile (35 mg, described in Example 39) and 4-(1,2,2,2-tetrafluoroethyl)benzoyl chloride, the title compound was isolated as a solid (6.2 mg, 11%). MS (ES): M/Z [M+H]=508. NMR: (400 MHz, CHLOROFORM-d): 1.90 (s, 3H), 5.20 (d, J=13.8 Hz, 1H), 5.53 (d, J=13.8 Hz, 1H), 5.69 (dq, J=44.3 Hz, 5.9 Hz, 1H), 7.54 (br.s, 1H), 7.58 (s, 1H), 7.60 (d, J=8.1 Hz, 2H) and 7.98 (d, J=8.2 Hz, 2H). 19F NMR (376 MHz, CHLOROFORM-d): −197.6−−197.1 (m, 1F), −79.0 (q, J=5.9 Hz, 3F).

4-(1,2,2,2-Tetrafluoroethyl)benzoyl chloride was prepared as follows:

a. To a solution of 4-formylbenzoic acid methyl ester (4 g) in THF (40 mL), was added a solution of tetrabutylammonium fluoride (1 molar in THF, 2.4 mL), followed by a solution of (trifluoromethyl)trimethylsilane (2 molar THF, 13.4 mL). Water was added to quench the reaction and the mixture was extracted with ethyl acetate. The organic phase was dried over anhydrous sodium sulfate, filtered and the filtrate concentrated under reduced pressure to give a residue that was purified by chromatography ($SiO_2$, heptane/EA) to afford methyl 4-(2,2,2-trifluoro-1-hydroxyethyl)benzoate (4.5 g, 78%). 1H NMR: (400 MHz, DMSO-$d_6$): 3.86 (s, 3H), 5.30 (m, 1H), 7.01 (d, J=5.7 Hz, 1H), 7.65 (d, J=8.2 Hz, 2H), 8.00 (d, J=8.4 Hz, 2H). 19F NMR (376 MHz, DMSO-$d_6$): −77.0 (d, J=7.3 Hz, 3F).

b. To a cooled solution of methyl 4-(2,2,2-trifluoro-1-hydroxyethyl)benzoate (0.94 g) in DCM (9 mL) was added of (diethylamino)sulfur trifluoride (1.2 mL). The mixture was allowed to warm slowly to room temperature overnight. Water was added and the mixture was extracted with more DCM. The organic phase was washed with water and brine, dried over anhydrous sodium sulfate, filtered and the filtrate concentrated under reduced pressure to afford methyl 4-(1,2,2,2-tetrafluoroethyl)benzoate (0.94 g, 99%). 1H NMR: (400 MHz, DMSO-$d_6$): 3.88 (s, 3H), 6.52 (m, 1H), 7.69 (d, J=8.2 Hz, 2H), 8.09 (d, J=8.1 Hz, 2H). 19F NMR (376 MHz, DMSO-$d_6$): −197.9 (m, 1F), −78.0 (m, 3F)

c. A mixture of methyl 4-(1,2,2,2-tetrafluoroethyl)benzoate (190 mg) and lithium hydroxide (19 mg) in methanol and water was stirred at room temperature overnight. The mixture was made slightly acidic with a solution of 6 normal hydrochloric acid and then extracted with ethyl acetate. The organic phase was dried over anhydrous sodium sulfate, filtered and the filtrate concentrated under reduced pressure to afford 4-(1,2,2,2-tetrafluoroethyl)benzoic acid (86 mg, 48%). 1H NMR: (400 MHz, DMSO-$d_6$): 6.50 (m, 1H), 7.65 (d, J=8.2 Hz, 2H), 8.07 (d, J=8.0 Hz, 2H), 13.43 (br. s, 1H). 19F NMR (376 MHz, DMSO-$d_6$): −199.0−−196.4 (m, 1F), −78.0 (m, 3F)

d. Oxalyl chloride (0.13 mL) was added to 4-(1,2,2,2-tetrafluoroethyl)benzoic acid (96 mg) in DCM (5 mL) and dimethyl formamide (0.2 mL). After 4 hours at room temperature, the mixture was concentrated under reduced pressure to afford 4-(1,2,2,2-tetrafluoroethyl)benzoyl chloride.

Example 42

N-[2-(4-Chloro-6-methoxy-2H-benzotriazol-2-yl)-1-cyano-1-methylethyl]-4-trifluoromethoxybenzamide (compound No 1.070)

Using a procedure similar to that described in Example 1, except using 2-amino-3-(4-chloro-6-methoxy-2H-benzotriazol-2-yl)-2-methylpropionitrile (50 mg), the title compound was isolated as a white solid (87 mg, 88%). MS (ES): M/Z [M+H]=454. 1H NMR: (400 MHz, DICHLOROMETHANE-$d_2$): 1.86 (s, 3H), 3.88 (s, 3H), 5.11 (d, J=13.9 Hz, 1H), 5.35 (d, J=13.9 Hz, 1H), 7.05 (d, J=2.1 Hz, 1H), 7.20 (d, J=2.0 Hz, 1H), 7.34 (d, J=8.1 Hz, 2H), 7.67 (s, 1H) and 7.93 (d, J=8.8 Hz, 2H). 19F NMR (376 MHz, DICHLOROMETHANE-$d_2$): −58.5 (s, 3F).

2-amino-3-(4-chloro-6-methoxy-2H-benzotriazol-2-yl)-2-methylpropionitrile was prepared using a procedure similar to that described in Example 1, part a and b, except starting from 7-chloro-5-methoxy-1H-benzotriazole. 7-Chloro-5-methoxy-1H-benzotriazole (0.8 g) was prepared using a procedure similar to that described in Example 13, part a, except starting from 3-chloro-1,2-diamino-5-methoxybenzene. 3-Chloro-1,2-diamino-5-methoxybenzene (1.88 g, 75%) was prepared using a procedure similar to that described in Example 38, part a and b, except starting from 4-methoxy-2-nitroaniline (16.8 g) and N-chlorosuccinimide (15 g) in part a to yield 6-chloro-4-methoxy-2-nitroaniline (2.9 g, 14%) used in part b.

Example 43

N-[2-(4-Chloro-6-methoxy-2H-benzotriazol-2-yl)-1-cyano-1-methylethyl]-4-trifluoromethylthiobenzamide (compound No 1.071)

Using a procedure similar to that described in Example 1, except using 2-amino-3-(4-chloro-6-methoxy-2H-benzotriazol-2-yl)-2-methylpropionitrile (50 mg, described in Example 42) and 4-trifluoromethylthiobenzoyl chloride (0.04 mL), the title compound was isolated as a white solid (45 mg, 51%). MS (ES): M/Z [M+H]=470. 1H NMR: (400 MHz, DICHLOROMETHANE-$d_2$): 1.86 (s, 3H), 3.88 (s, 3H), 5.11 (d, J=13.9 Hz, 1H), 5.36 (d, J=13.9 Hz, 1H), 7.05 (d, J=2.1 Hz, 1H), 7.20 (d, J=2.0 Hz, 1H), 7.72 (s, 1H), 7.79 (d, J=8.2 Hz, 2H) and 7.92 (d, J=8.6 Hz, 2H). 19F NMR (376 MHz, DICHLOROMETHANE-$d_2$): −42.8 (s, 3F).

Example 44

N-[1-cyano-2-(5-methoxy-2H-benzotriazol-2-yl)-1-methylethyl]-4-trifluoromethoxybenzamide (compound No 1.072)

Using a procedure similar to that described in Example 1, except using 2-amino-3-(5-methoxy-2H-benzotriazol-2-yl)-2-methylpropionitrile (150 mg), the title compound was isolated as a white solid (190 mg, 70%). Rf=0.35 (1:1 EA/heptane). MS (ES): M/Z [M+H]=420. 1H NMR: (400 MHz, DMSO-$d_6$): 1.73 (s, 3H), 3.84 (s, 3H), 5.32 (d, J=13.4 Hz, 1H), 5.37 (d, J=13.4 Hz, 1H), 7.10 (dd, J=9.3, 2.1 Hz, 1H), 7.24 (d, J=2.1 Hz, 1H), 7.52 (d, J=8.1 Hz, 2H), 7.82 (dd, J=9.3, 0.4 Hz, 1H), 7.95 (d, J=8.9 Hz, 2H) and 8.92 (s, 1H). 19F NMR (376 MHz, DMSO-$d_6$): −57.1 (s, 3F).

2-amino-3-(5-methoxy-2H-benzotriazol-2-yl)-2-methylpropionitrile was prepared using a procedure similar to that described in Example 1, part a and b, except starting from 5-methoxy-1H-benzotriazole that was prepared as follows:

a. To a solution of 1,2-diamino-4-methoxybenzene hydrochloride (2 g) in acetonitrile (20 mL) was added dropwise tert-butylnitrite (1.35 mL) at 0° C. After 4 hours at room temperature, the mixture was concentrated under reduced pressure to a solid residue, which was then dissolved in water. The aqueous solution was neutralized with a saturated solution of sodium bicarbonate and extracted with ethyl acetate. The organic phase was washed with brine, dried over anhydrous sodium sulfate, filtered and the filtrate concentrated under reduced pressure to afford 5-methoxy-1H-benzotriazole as an off-white solid (1.2 g, 85%). MS (ES): M/Z [M+H]=150.

Example 45

N-[1-cyano-2-(5-methoxy-2H-benzotriazol-2-yl)-1-methylethyl]-4-trifluoromethylthiobenzamide (compound No 1.073)

Using a procedure similar to that described in Example 1, except using 2-amino-3-(5-methoxy-2H-benzotriazol-2-yl)-2-methylpropionitrile (120 mg, described in Example 44) and 4-trifluoromethylthiobenzoyl chloride (0.16 mL), the title compound was isolated as a white solid (150 mg, 66%). Rf=0.3 (1:1 EA/heptane). MS (ES): M/Z [M+H]=436. 1H NMR: (400 MHz, DMSO-$d_6$): 1.73 (s, 3H), 3.84 (s, 3H), 5.32 (d, J=13.4 Hz, 1H), 5.38 (d, J=13.4 Hz, 1H), 7.10 (dd, J=9.3, 2.3 Hz, 1H), 7.24 (d, J=2.1 Hz, 1H), 7.82 (dd, J=9.2, 0.4 Hz, 1H), 7.87 (d, J=8.6 Hz, 2H), 7.92 (d, J=8.6 Hz, 2H) and 9.00 (s, 1H). 19F NMR (376 MHz, DMSO-$d_6$): −41.9 (s, 3F).

Example 46

N-[1-Cyano-2-(5,7-dichloro-4-fluoro-2H-benzotriazol-2-yl)-1-methylethyl]-4-trifluoromethoxybenzamide (compound No 1.090)

Using a procedure similar to that described in Example 1, except using 2-amino-3-(5,7-dichloro-4-fluoro-2H-benzotriazol-2-yl)-2-methylpropionitrile (90 mg), the title compound was isolated as a white solid (65 mg, 44%). Rf=0.6 (1:1 EA/heptane). MS (ES): M/Z [M+H]=476. 1H NMR: (400 MHz, DMSO-$d_6$): 1.76 (s, 3H), 5.47 (d, J=13.3 Hz, 1H), 5.58 (d, J=13.4 Hz, 1H), 7.50 (d, J=8.1 Hz, 2H), 7.70-8.10 (m, 3H) and 8.86 (s, 1H). 19F NMR (376 MHz, DMSO-$d_6$): −127.6 (d, J=5.9 Hz, 1F) and −57.1 (s, 3F).

2-Amino-3-(5,7-dichloro-4-fluoro-2H-benzotriazol-2-yl)-2-methylpropionitrile [1.3 g, Rf=0.2 (1:1 EA/heptane)] was prepared using a procedure similar to that described in Example 1, part a and b, except starting from 5,7-dichloro-4-fluoro-1H-benzotriazole. 5,7-Dichloro-4-fluoro-1H-benzotriazole (4 g, 85%) was prepared using a procedure similar to that described in Example 11, part a, except starting from 4,6-dichloro-3-fluoro-2-nitroaniline. 4,6-Dichloro-3-fluoro-2-nitroaniline (6.1 g) was prepared using a procedure similar to that described in Example 39, part a, b and c, except starting from 2,4-dichloro-5-fluoroaniline (10 g).

Example 47

N-[1-Cyano-2-(5,7-dichloro-4-fluoro-2H-benzotriazol-2-yl)-1-methylethyl]-4-trifluoromethylthiobenzamide (compound No 1.091)

Using a procedure similar to that described in Example 1, except using 2-amino-3-(5,7-dichloro-4-fluoro-2H-benzotriazol-2-yl)-2-methylpropionitrile (90 mg, described in Example 46) and 4-trifluoromethylthiobenzoyl chloride (0.06 mL), the title compound was isolated as a white solid (95 mg, 62%). Rf=0.55 (1:1 EA/heptane). MS (ES): M/Z [M+H]=492. NMR: (400 MHz, DMSO-$d_6$): 1.76 (s, 3H), 5.47 (d, J=13.3 Hz, 1H), 5.60 (d, J=13.3 Hz, 1H), 7.58-8.22 (m, 5H) and 8.94 (s, 1H). 19F NMR (376 MHz, DMSO-$d_6$): −127.6 (d, J=5.3 Hz, 1F) and −42.0 (s, 3F).

Example 48

N-[2-(5-Chloro-4,7-dimethyl-2H-benzotriazol-2-yl)-1-cyano-1-methylethyl]-4-trifluoromethoxybenzamide (compound No 1.092)

Using a procedure similar to that described in Example 1, except using 2-amino-3-(5-chloro-4,7-dimethyl-2H-benzotriazol-2-yl)-2-methylpropionitrile (120 mg), the title compound was isolated as a white solid (85 mg, 41%). Rf=0.7 (1:1 EA/heptane). MS (ES): M/Z [M+H]=452. 1H NMR: (400 MHz, DMSO-$d_6$): 1.74 (s, 3H), 2.43 (s, 3H), 2.45 (s, 3H), 5.35 (d, J=13.3 Hz, 1H), 5.52 (d, J=13.3 Hz, 1H), 7.25 (d, J=0.6 Hz, 1H), 7.51 (d, J=8.1 Hz, 2H), 7.91 (d, J=8.8 Hz, 2H) and 8.78 (s, 1H). 19F NMR (376 MHz, DMSO-$d_6$): −57.2 (s, 3F).

2-Amino-3-(5-chloro-4,7-dimethyl-2H-benzotriazol-2-yl)-2-methylpropionitrile [1.3 g, Rf=0.2 (1:1 EA/heptane)] was prepared using a procedure similar to that described in Example 1, part a and b, except starting from 5-chloro-4,7-dimethyl-1H-benzotriazole. 5-Chloro-4,7-dimethyl-1H-benzotriazole (4 g, 85%) was prepared using a procedure similar to that described in Example 11, part a, except starting from 4-chloro-3,6-dimethyl-2-nitroaniline. 4-Chloro-3,6-dimethyl-2-nitroaniline (6.1 g) was prepared using a procedure similar to that described in Example 39, part a, b and c, except starting from 4-chloro-2,5-dimethylaniline (10 g).

Example 49

N-[2-(5-Chloro-4,7-dimethyl-2H-benzotriazol-2-yl)-1-cyano-1-methylethyl]-4-trifluoromethylthiobenzamide (compound No 1.093)

Using a procedure similar to that described in Example 1, except using 2-amino-3-(5-chloro-4,7-dimethyl-2H-benzotriazol-2-yl)-2-methylpropionitrile (120 mg, described in Example 48) and 4-trifluoromethylthiobenzoyl chloride (0.09 mL), the title compound was isolated as a white solid (180 mg, 85%). Rf=0.7 (1:1 EA/heptane). MS (ES): M/Z [M+H]=468. NMR: (400 MHz, DMSO-$d_6$): 1.74 (s, 3H), 2.43 (s, 3H), 2.44 (s, 3H), 5.34 (d, J=13.3 Hz, 1H), 5.54 (d, J=13.3 Hz, 1H), 7.24 (d, J=0.7 Hz, 1H), 7.81-7.93 (m, 4H) and 8.86 (s, 1H). 19F NMR (376 MHz, DMSO-$d_6$): −42.1 (s, 3F).

Example 50

N-[2-(5-bromo-4-fluoro-7-methyl-2H-benzotriazol-2-yl)-1-cyano-1-methylethyl]-4-trifluoromethoxybenzamide (compound No 1.094)

Using a procedure similar to that described in Example 1, except using 2-amino-3-(5-bromo-4-fluoro-7-methyl-2H-benzotriazol-2-yl)-2-methylpropionitrile (120 mg), the title compound was isolated as a white solid (130 mg, 68%). Rf=0.65 (1:1 EA/heptane). MS (ES): M/Z [M+H]=500. 1H NMR: (400 MHz, DMSO-$d_6$): 1.75 (s, 3H), 2.42 (s, 3H), 5.40 (d, J=13.3 Hz, 1H), 5.54 (d, J=13.4 Hz, 1H), 7.45 (d, J=5.7 Hz, 1H), 7.51 (d, J=8.3 Hz, 2H), 7.91 (d, J=8.7 Hz, 2H) and 8.82 (s, 1H). 19F NMR (376 MHz, DMSO-$d_6$): −122.4 (d, J=5.3 Hz, 1F) and −57.1 (s, 3F).

2-Amino-3-(5-bromo-4-fluoro-7-methyl-2H-benzotriazol-2-yl)-2-methylpropionitrile [1.3 g, Rf=0.2 (1:1 EA/heptane)] was prepared using a procedure similar to that described in Example 1, part a and b, except starting from 5-bromo-4-fluoro-7-methyl-1H-benzotriazole. 5-Bromo-4-fluoro-7-methyl-1H-benzotriazole (4 g, 85%) was prepared using a procedure similar to that described in Example 11, part a, except starting from 4-bromo-3-fluoro-6-methyl-2-nitroaniline. 4-Bromo-3-fluoro-6-methyl-2-nitroaniline (6.1 g) was prepared using a procedure similar to that described in Example 39, part a, b and c, except starting from 4-bromo-5-fluoro-2-methylaniline (10 g).

Example 51

N-[2-(5-bromo-4-fluoro-7-methyl-2H-benzotriazol-2-yl)-1-cyano-1-methylethyl]-4-trifluoromethylthiobenzamide (compound No 1.095)

Using a procedure similar to that described in Example 1, except using 2-amino-3-(5-bromo-4-fluoro-7-methyl-2H-benzotriazol-2-yl)-2-methylpropionitrile (120 mg, described in Example 50) and 4-trifluoromethylthiobenzoyl chloride (0.09 mL), the title compound was isolated as a white solid (175 mg, 88%). Rf=0.65 (1:1 EA/heptane). MS (ES): M/Z [M+H]=516. NMR: (400 MHz, DMSO-$d_6$): 1.75 (s, 3H), 2.41 (s, 3H), 5.41 (d, J=13.3 Hz, 1H), 5.56 (d, J=13.3 Hz, 1H), 7.45 (dd, J=5.9, 1.1 Hz, 1H), 7.85-7.90 (m, 4H), 8.90 (s, 1H). 19F NMR (376 MHz, DMSO-$d_6$): −122.4 (d, J=5.3 Hz, 1F), −42.0 (s, 3F).

Example 52

N-[2-(4-Bromo-5-chloro-2H-benzotriazol-2-yl)-1-cyano-1-methylethyl]-4-trifluoromethoxybenzamide (compound No 1.057)

Using a procedure similar to that described in Example 1, except using 2-amino-3-(4-bromo-5-chloro-2H-benzotriazol-2-yl)-2-methylpropionitrile (48 mg), the title compound was isolated as a white solid (43 mg, 56%). MS (ES): M/Z [M+H]=502. 1H NMR: (400 MHz, DMSO-$d_6$): 1.75 (s, 3H), 5.42 (d, J=13.4 Hz, 1H), 5.54 (d, J=13.4 Hz, 1H), 7.51 (d, J=8.1 Hz, 2H), 7.63 (d, J=9.0 Hz, 1H), 7.93 (d, J=8.8 Hz, 2H), 8.02 (d, J=9.0 Hz, 1H) and 8.88 (s, 1H). 19F NMR (376 MHz, DMSO-$d_6$): −57.1 (s, 3F).

2-amino-3-(4-bromo-5-chloro-2H-benzotriazol-2-yl)-2-methylpropionitrile (48 mg) was prepared using a procedure similar to that described in Example 1, part a and b, except starting from 4-bromo-5-chloro-1H-benzotriazole (213 mg) that was prepared as follows:

a. To a solution of 5-chloro-1H-benzotriazole (1 g) and sodium acetate (1 g) in acetic acid was added bromine (2 g). After 10 days at room temperature, the mixture was treated with a saturated solution sodium thiosulfate, neutralized with a saturated solution of sodium bicarbonate and extracted with ethyl acetate. The organic phase was washed with brine, dried over anhydrous sodium sulfate, filtered and the filtrate concentrated under reduced pressure to afford a residue that was purified by semi-preparative liquid chromatography to afford 4-bromo-5-chloro-1H-benzotriazole as an off-white solid (213 mg, 14%). MS (ES): M/Z [M+H]=232. 1H NMR: (400 MHz, DMSO-$d_6$): 7.58 (d, J=8.7 Hz, 2H) and 7.91 (d, J=8.7 Hz, 1H).

Example 53

N-[2-(5-Chloro-4,7-dibromo-2H-benzotriazol-2-yl)-1-cyano-1-methylethyl]-4-trifluoromethoxybenzamide (compound No 1.083)

Using a procedure similar to that described in Example 1, except using 2-amino-3-(5-chloro-4,7-dibromo-2H-benzotriazol-2-yl)-2-methylpropionitrile (390 mg), the title compound was isolated as a white solid (530 mg, 90%). MS (ES): M/Z [M+H]=580. 1H NMR: (400 MHz, DMSO-$d_6$): 1.75 (s, 3H), 5.43 (d, J=13.3 Hz, 1H), 5.59 (d, J=13.4 Hz, 1H), 7.51 (d, J=8.0 Hz, 2H), 7.84-7.96 (m, 2H), 8.04 (s, 1H) and 8.83 (s, 1H). 19F NMR (376 MHz, DMSO-$d_6$): −57.1 (s, 3F).

2-Amino-3-(5-chloro-4,7-dibromo-2H-benzotriazol-2-yl)-2-methylpropionitrile (440 mg) was prepared using a procedure similar to that described in Example 1, part a and b, except starting from 5-chloro-4,7-dibromo-1H-benzotriazole (4.2 g) that was prepared as follows by adapting a procedure described in the literature by K. Kopańska et al. in Bioorganic & Medicinal Chemistry, volume 13 (2005) page 3601 and in Bioorganic & Medicinal Chemistry, volume 12 (2004), pages 2617-2624:

a. To a solution of 5-chloro-1H-benzotriazole (7.7 g) and silver sulfate (19 g) in sulfuric acid (100 mL) was slowly added bromine (15 mL). After 2 days at room temperature, water was slowly added to the chilled mixture and the mixture stirred at room temperature for 3 days. The resulting solid was filtered, washed with water and triturated with ethyl acetate. The organic filtrate was collected and treated with a saturated solution of sodium bisulfite, a saturated solution of sodium bicarbonate, then water, dried over anhydrous sodium sulfate and filtered through a pad of Celite®. The filtrate was concentrated under reduced pressure to afford 5-chloro-4,7-dibromo-1H-benzotriazole as a solid (11.2 g, 71%). MS (ES): M/Z [M+H]=310. 1H NMR: (400 MHz, DMSO-d6): 8.0 (s, 1H).

Example 54

N-[2-(5-Chloro-4,7-dibromo-2H-benzotriazol-2-yl)-1-cyano-1-methylethyl]-4-trifluoromethylthiobenzamide (compound No 1.085)

Using a procedure similar to that described in Example 1, except using 2-amino-3-(5-chloro-4,7-dibromo-2H-benzotriazol-2-yl)-2-methylpropionitrile (44 mg, described in Example 53) and 4-trifluoromethylthiobenzoyl chloride, the title compound was isolated as a white solid (15 mg, 22%). MS (ES): M/Z [M−H]=594. NMR: (400 MHz, DMSO-$d_6$): 1.75 (s, 3H), 5.43 (d, J=13.4 Hz, 1H), 5.61 (d, J=13.3 Hz, 1H), 7.88 (q, J=8.5 Hz, 4H), 8.04 (s, 1H) and 8.91 (s, 1H). 19F NMR (376 MHz, DMSO-d$_6$): −42.0 (s, 3F).

Example 55

N-[2-(4-Bromo-5,7-dichloro-2H-benzotriazol-2-yl)-1-cyano-1-methylethyl]-4-trifluoromethoxybenzamide (compound No 1.086)

Using a procedure similar to that described in Example 1, except using 2-amino-3-(4-bromo-5,7-dichloro-2H-benzotriazol-2-yl)-2-methylpropionitrile, the title compound was isolated as a white solid (260 mg). MS (ES): M/Z [M+H]= 536. 1H NMR: (400 MHz, DMSO-d$_6$): 1.76 (s, 3H), 5.44 (d, J=13.2 Hz, 1H), 5.59 (d, J=13.4 Hz, 1H), 7.51 (d, J=8.1 Hz, 2H), 7.84-7.99 (m, 3H) and 8.83 (s, 1H). 19F NMR (376 MHz, DMSO-d$_6$): −57.1 (s, 3F).

2-Amino-3-(4-bromo-5,7-dichloro-2H-benzotriazol-2-yl)-2-methylpropionitrile was prepared using a procedure similar to that described in Example 1, part a and b, except starting from 4-bromo-5,7-dichloro-1H-benzotriazole that was prepared along with 4,6-dibromo-5,7-dichloro-1H-benzotriazole using a procedure similar to that described in Example 53 except using 5,7-dichloro-1H-benzotriazole described in Example 15.

Example 56

N-[2-(4-Bromo-5,7-dichloro-2H-benzotriazol-2-yl)-1-cyano-1-methylethyl]-4-trifluoromethylthiobenzamide (compound No 1.087)

Using a procedure similar to that described in Example 1, except using 2-amino-3-(4-bromo-5,7-dichloro-2H-benzotriazol-2-yl)-2-methylpropionitrile and 4-trifluoromethylthiobenzoyl chloride, the title compound was isolated as a white solid (110 mg, described in Example 55). MS (ES): M/Z [M+H]=552. NMR: (400 MHz, DMSO-d$_6$): 1.75 (s, 3H), 5.44 (d, J=13.3 Hz, 1H), 5.60 (d, J=13.7 Hz, 1H), 7.75-8.04 (m, 5H) and 8.91 (s, 1H). 19F NMR (376 MHz, DMSO-d$_6$): −42.0 (s, 3F).

Example 57

N-[1-Cyano-2-(4,6-dibromo-5,7-dichloro-2H-benzotriazol-2-yl)-1-methylethyl]-4-trifluoromethoxybenzamide (compound No 1.088)

Using a procedure similar to that described in Example 1, except using 2-amino-3-(4,6-dibromo-5,7-dichloro-2H-benzotriazol-2-yl)-2-methylpropionitrile, the title compound was isolated as a white solid (130 mg). MS (ES): M/Z [M+H]= 614. 1H NMR: (400 MHz, DMSO-d$_6$): 1.75 (s, 3H), 5.45 (d, J=13.3 Hz, 1H), 5.59 (d, J=13.4 Hz, 1H), 7.51 (d, J=8.0 Hz, 2H), 7.91 (d, J=8.8 Hz, 2H) and 8.82 (s, 1H). 19F NMR (376 MHz, DMSO-d$_6$): −57.1 (s, 3F).

2-Amino-3-(4,6-dibromo-5,7-dichloro-2H-benzotriazol-2-yl)-2-methylpropionitrile was prepared using a procedure similar to that described in Example 1, part a and b, except starting from 4,6-dibromo-5,7-dichloro-1H-benzotriazole that was prepared along with 4-bromo-5,7-dichloro-1H-benzotriazole described in Example 55 using a procedure similar to that described in Example 53 except using 5,7-dichloro-1H-benzotriazole described in Example 15.

Example 58

N-[1-Cyano-2-(4,6-dibromo-5,7-dichloro-2H-benzotriazol-2-yl)-1-methylethyl]-4-trifluoromethylthiobenzamide (compound No 1.089)

Using a procedure similar to that described in Example 1, except using 2-amino-3-(4,6-dibromo-5,7-dichloro-2H-benzotriazol-2-yl)-2-methylpropionitrile, described in Example 57, and 4-trifluoromethylthiobenzoyl chloride, the title compound was isolated as a white solid (100 mg). MS (ES): M/Z [M+H]=630. NMR: (400 MHz, DMSO-d$_6$): 1.75 (s, 3H), 5.45 (d, J=13.3 Hz, 1H), 5.60 (d, J=13.0 Hz, 1H), 7.82-7.92 (m, 4H) and 8.90 (s, 1H). 19F NMR (376 MHz, DMSO-d$_6$): −42.0 (s, 3F).

Compounds of Examples 59 and 60 were prepared according to the following general reaction scheme:

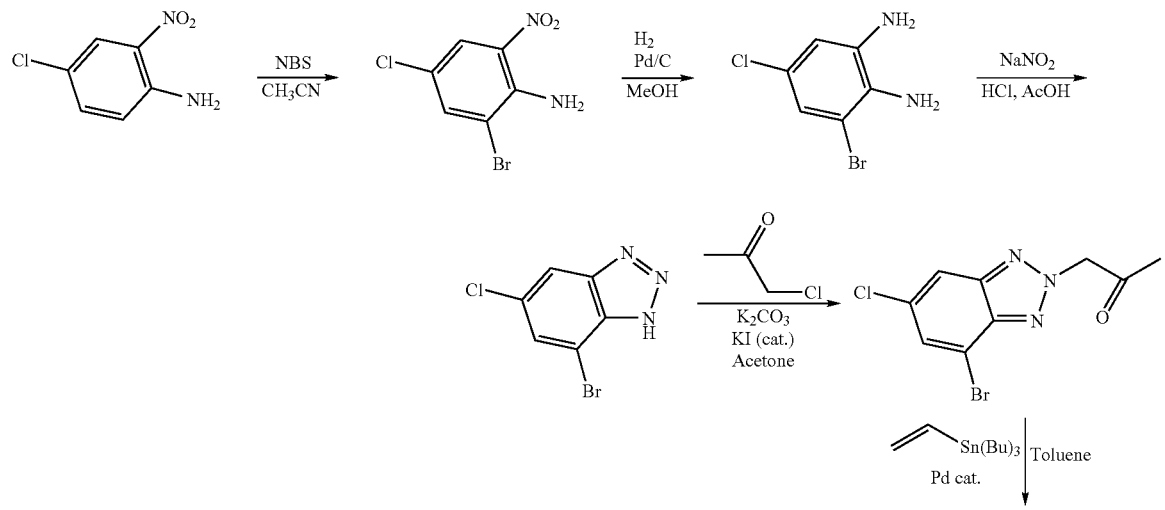

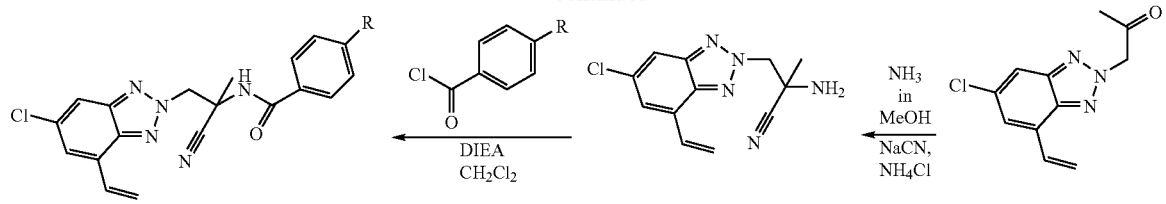

Final Product
V=C—H; W=C—Cl; X=C—H; Y=C—CH=CH₂;
Q=P=N;
R₃=R₄=H; a=1; R₅=CH₃; R₆=H;
Z=C(O); R₇=p-phenyl-R Example 59

N-[2-(6-Chloro-4-vinyl-2H-benzotriazol-2-yl)-1-cyano-1-methylethyl]-4-trifluoromethoxybenzamide (compound No 1.075)

Using a procedure similar to that described in Example 1, except using 2-amino-3-(6-chloro-4-vinyl-2H-benzotriazol-2-yl)-2-methylpropionitrile (2.3 g), the title compound was isolated as a white solid (3.2 g, 80%). Rf=0.45 (1:1 EA/heptane). MS (ES): M/Z [M+H]=450. 1H NMR: (400 MHz, DMSO-d₆): 1.75 (s, 3H), 5.41 (d, J=13.3 Hz, 1H), 5.51 (dd, J=11.2, 1.2 Hz, 1H), 5.55 (d, J=13.4 Hz, 1H), 6.45 (dd, J=17.7, 1.2 Hz, 1H), 6.91 (dd, J=17.6, 11.3 Hz, 1H), 7.48-7.52 (m, 3H), 7.93 (d, J=8.8 Hz, 2H), 8.03 (d, J=1.8 Hz, 1H), and 8.87 (s, 1H). 19F NMR (376 MHz, DMSO-d₆): −57.1 (s, 3F).

2-Amino-3-(6-chloro-4-vinyl-2H-benzotriazol-2-yl)-2-methylpropionitrile [2.3 g, 97%, Rf=0.3 (1:1 EA/heptane)] was prepared using a procedure similar to that described in Example 1, part b, except starting from 1-(6-chloro-4-vinyl-2H-benzotriazol-2-yl)-propan-2-one. 1-(6-Chloro-4-vinyl-2H-benzotriazol-2-yl)-propan-2-one (4 g, 85%) was prepared as follows:

a. 1-(4-Bromo-6-chloro-2H-benzotriazol-2-yl)-propan-2-one (3 g), tributylvinyltin (3.5 g) and bis(tri-t-butylphosphine)palladium (0.5 g) were heated in toluene (20 mL) at 50° C. overnight. The mixture was concentrated under reduced pressure, taken up in ethyl acetate and filtered through a plug of Celite®. Filtrate was concentrated under reduced pressure to give a residue that was purified by chromatography (SiO₂, heptane/EA) to afford 1-(6-chloro-4-vinyl-2H-benzotriazol-2-yl)-propan-2-one as a white solid (2.2 g, 90%). Rf=0.5 (1:1 EA/heptane). 1-(4-Bromo-6-chloro-2H-benzotriazol-2-yl)-propan-2-one was prepared using a procedure similar to that described in Example 1, part a, except starting from 7-bromo-5-chloro-1H-benzotriazole described in Example 38, part a and b.

Example 60

N-[2-(6-Chloro-4-vinyl-2H-benzotriazol-2-yl)-1-cyano-1-methylethyl]-4-trifluoromethylthiobenzamide (compound No 1.076)

Using a procedure similar to that described in Example 1, except using 2-amino-3-(6-chloro-4-vinyl-2H-benzotriazol-2-yl)-2-methylpropionitrile (50 mg) described in Example 59 above and 4-trifluoromethylthiobenzoyl chloride (0.05 mL), the title compound was isolated as a white solid (65 mg, 73%). Rf=0.5 (1:1 EA/heptane). MS (ES): M/Z [M+H]=466. NMR: (400 MHz, DMSO-d₆): 1.75 (s, 3H), 5.41 (d, J=13.4 Hz, 1H), 5.50 (d, J=11.5 Hz, 1H), 5.57 (d, J=13.4 Hz, 1H), 6.45 (d, J=17.6 Hz, 1H), 6.91 (dd, J=17.6, 11.3 Hz, 1H), 7.51 (s, 1H), 7.84 (d, J=8.2 Hz, 2H), 7.91 (d, J=8.3 Hz, 2H), 8.03 (s, 1H) and 8.96 (s, 1H). 19F NMR (376 MHz, DMSO-d₆): −42.0 (s, 3F).

Compounds of Examples 61 to 67 were prepared according to the following general reaction scheme:

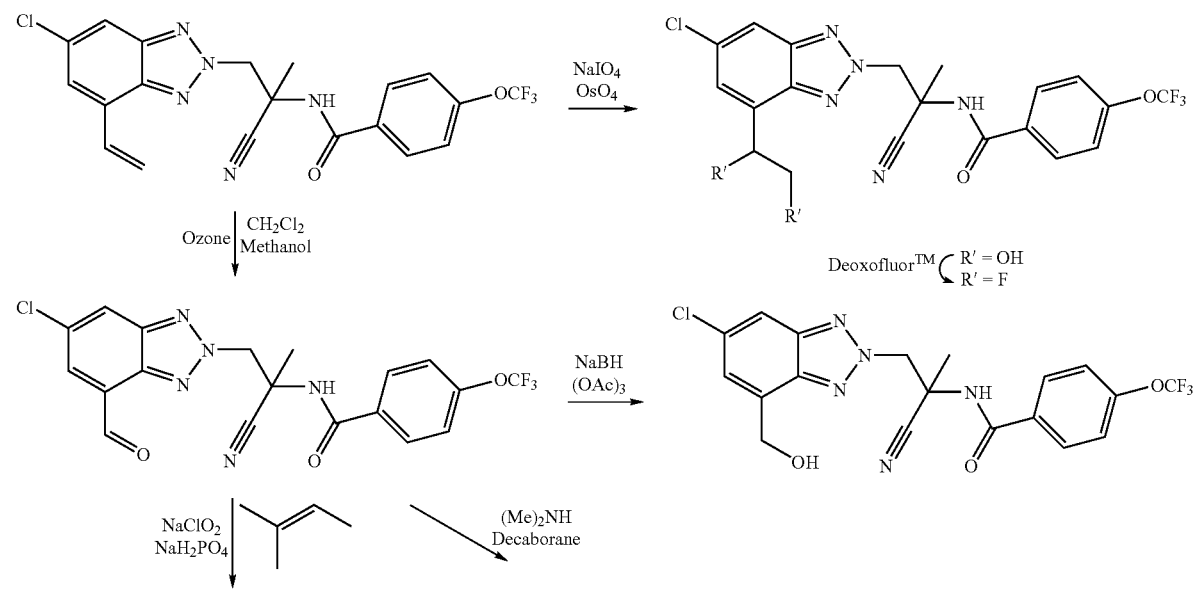

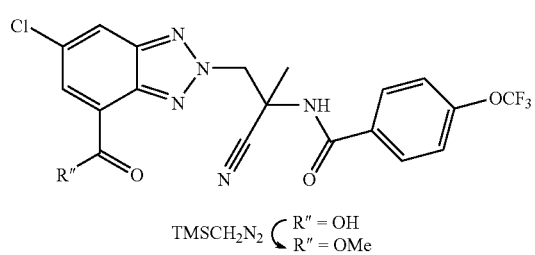 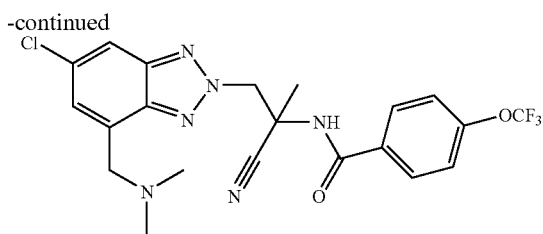

TMSCH₂N₂, R″ = OH / R″ = OMe

Final Product
V=C—H; W=C—Cl; X=C—H; Y=C—R₁₁;
R₁₁=CO₂H, CO₂Me, CH₂N(CH₃)₂, CH₂OH, CH(OH)CH₂OH, CHFCH₂F
Q=P=N;
R₃=R₄=H; a=1; R₅=CH₃; R₆=H;
Z=C(O); R₇=p-phenyl-OCF₃

Example 61

N-{2-[6-Chloro-4-(1,2-dihydroxyethyl)-2H-benzotriazol-2-yl]-1-cyano-1-methyl-ethyl}-4-trifluoromethoxybenzamide (compound No 1.077)

To a solution of N-[2-(6-Chloro-4-vinyl-2H-benzotriazol-2-yl)-1-cyano-1-methylethyl]-4-trifluoromethoxybenzamide (0.25 g) in 5 mL of a mixture of THF and water (10 to 1), was added sodium periodate (0.24 g, 2.1 equivalent) and a 4% osmium tetroxide solution in water (17 mL, 5 mole %). After 2 hours at room temperature, the mixture was quenched with a 10% solution of sodium thiosulfate, extracted with ethylacetate and washed with water. The organic layer was dried over sodium sulfate, filtered and concentrated under reduced pressure to give a residue that was purified by chromatography (SiO₂, heptane/EA) to afford the title compound as a white solid mixture of diastereoisomers (110 mg, 40%). Rf=0.35 (1:1 EA/heptane). MS (ES): M/Z [M+H]=484. 1H NMR: (400 MHz, DMSO-d₆): 1.74-1.75 (d, 3H), 3.40-3.56 (m, 1H), 3.67-3.82 (m, 1H), 4.78 (dt, J=17.3, 6.0 Hz, 1H), 5.01-5.12 (m, 1H), 5.35-5.43 (m, 1H), 5.43-5.51 (m, 1H), 5.61 (d, J=4.8 Hz, 1H), 7.42 (s, 1H), 7.51 (d, J=7.9 Hz, 2H), 7.93 (dd, J=8.7, 3.8 Hz, 2H), 7.98 (t, J=2.1 Hz, 1H) and 8.92 (d, 1H). 19F NMR (376 MHz, DMSO-d₆): −57.1 (s, 3F).

Example 62

N-{2-[6-Chloro-4-(1,2-difluoroethyl)-2H-benzotriazol-2-yl]-1-cyano-1-methyl-ethyl}-4-trifluoromethoxybenzamide (compound No 1.078)

To a solution of N-{2-[6-Chloro-4-(1,2-dihydroxyethyl)-2H-benzotriazol-2-yl]-1-cyano-1-methyl-ethyl}-4-trifluoromethoxybenzamide (50 mg) in DCM (3 mL), was added Deoxofluor™ [Bis(2-methoxyethyl)aminosulfur Trifluoride] (0.07 mL). After stirring overnight at room temperature, the mixture was concentrated under reduced pressure to give a residue that was purified by chromatography (SiO₂, heptane/EA) to afford the title compound as a white solid mixture of diastereoisomers (35 mg, 69%). Rf=0.7 (1:1 EA/heptane). MS (ES): M/Z [M+H]=488. 1H NMR: (400 MHz, CHLOROFORM-d): 1.88-1.89 (d, 3H), 4.71-5.00 (m, 2H), 5.19 (dd, J=13.7, 4.5 Hz, 1H), 5.47 (t, J=13.9 Hz, 1H), 5.99-6.25 (m, 1H), 7.20 (d, J=18.7 Hz, 1H), 7.33 (d, J=8.1 Hz, 2H), 7.53 (s, 1H), 7.86 (d, J=8.7 Hz, 2H) and 7.90 (s, 1H). 19F NMR (376 MHz, CHLOROFORM-d): −192.2 (s, 1F), −58.1 (s, 3F) and 3.1 (br. s, 1F).

Example 63

N-[2-(6-Chloro-4-formyl-2H-benzotriazol-2-yl)-1-cyano-1-methylethyl]-4-trifluoromethoxybenzamide (compound No 1.079)

A solution of N-[2-(6-Chloro-4-vinyl-2H-benzotriazol-2-yl)-1-cyano-1-methylethyl]-4-trifluoromethoxybenzamide (0.29 g) in 35 mL of a 3 to 1 mixture of DCM and methanol was treated with ozone gas for 15 minutes. After stirring one hour at −78° C., the mixture was purged 10 minutes with oxygen and then quenched with dimethyl sulfide followed by a 10% solution of sodium thiosulfate, then diluted with DCM (100 mL). The mixture was separated, and the organic layer was dried over sodium sulfate, filtered and concentrated under reduced pressure to give a residue that was purified by chromatography (SiO₂, heptane/EA) to afford the title compound as a white solid (0.23 g, 79%). Rf=0.6 (1:1 EA/heptane). MS (ES): M/Z [M+H]=452. 1H NMR: (400 MHz, CHLOROFORM-d): 1.58 (s, 3H), 5.24 (d, J=13.8 Hz, 1H), 5.47 (d, J=13.8 Hz, 1H), 7.37 (d, J=8.1 Hz, 2H), 7.94 (br. s, 1H), 8.00 (d, J=1.8 Hz, 1H), 8.05 (m, 2H), 8.22 (d, J=1.9 Hz, 1H) and 10.34 (s, 1H). 19F NMR (376 MHz, CHLOROFORM-d): −58.1 (s, 3F).

Example 64

N-[2-(6-Chloro-4-dimethylaminomethyl-2H-benzotriazol-2-yl)-1-cyano-1-methylethyl]-4-trifluoromethoxybenzamide (compound No 1.080)

To a solution of N-[2-(6-Chloro-4-formyl-2H-benzotriazol-2-yl)-1-cyano-1-methylethyl]-4-trifluoromethoxybenzamide (0.18 g) in methanol (3 mL) was added a 2 molar methanolic solution of dimethylamine (0.24 mL). After one hour stirring at room temperature, decaborane was added (15 mg) and the mixture stirred one more hour before being concentrated under reduced pressure. The residue was purified by chromatography (SiO₂, heptane/EA) to afford the title compound as a white solid (100 mg, 52%). Rf=0.2 (3:1 EA/heptane). MS (ES): M/Z [M+H]=481. 1H NMR: (400

MHz, CHLOROFORM-d): 1.81 (s, 3H), 2.31 (s, 6H), 3.75 (d, J=13.5 Hz, 1H), 3.92 (d, J=13.5 Hz, 1H), 5.12 (d, J=13.8 Hz, 1H), 5.52 (d, J=13.7 Hz, 1H), 7.32 (d, J=8.1 Hz, 2H), 7.36 (s, 1H), 7.81 (d, J=1.7 Hz, 1H) and 7.95 (br. d, J=8.7 Hz, 3H). 19F NMR (376 MHz, CHLOROFORM-d): −58.1 (s, 3F).

Example 65

N-[2-(6-Chloro-4-hydroxymethyl-2H-benzotriazol-2-yl)-1-cyano-1-methylethyl]-4-trifluoromethoxybenzamide (compound No 1.081)

To a solution of N-[2-(6-Chloro-4-formyl-2H-benzotriazol-2-yl)-1-cyano-1-methylethyl]-4-trifluoromethoxybenzamide (150 mg) in ethanol (2 mL) cooled in an ice bath was added sodium triacetoxyborohydride (0.22 g). After 6 hour at room temperature, more sodium triacetoxyborohydride (0.29 g) was added and the mixture stirred overnight at room temperature. The mixture was quenched with water, extracted with ethyl acetate. The organic layer was dried over sodium sulfate, filtered and concentrated under reduced pressure to give a residue that was purified by chromatography ($SiO_2$, heptane/EA) to afford the title compound as a white solid (100 mg, 67%). Rf=0.4 (3:1 EA/heptane). MS (ES): M/Z [M+H]=454. 1H NMR: (400 MHz, CHLOROFORM-d): 1.87 (s, 3H), 5.06 (s, 2H), 5.15 (d, J=13.8 Hz, 1H), 5.43 (d, J=13.8 Hz, 1H), 7.33 (d, J=8.8 Hz, 2H), 7.43 (dt, J=1.8, 1.0 Hz, 1H), 7.47 (s, 1H), 7.80 (d, J=1.8 Hz, 1H) and 7.88 (d, J=8.8 Hz, 2H). 19F NMR (376 MHz, CHLOROFORM-d): −58.1 (s, 3F).

Example 66

6-Chloro-2-[2-cyano-2-({[4-(trifluoromethoxy)phenyl]carbonyl}-amino)-propyl]-2H-benzotriazole-4-carboxylic acid (compound No 1.082)

To a solution of N-[2-(6-Chloro-4-formyl-2H-benzotriazol-2-yl)-1-cyano-1-methylethyl]-4-trifluoromethoxybenzamide (1.5 g) in a mixture of THF (25 mL), t-butanol (10 mL) and 2-methyl-2-butene was added dropwise the solution of sodium hypochlorite (0.9 g) and sodium dihydrogen phosphate (1.15 g) in water (20 mL). After 4 hour at room temperature, the mixture was concentrated under reduced pressure, diluted with water (50 mL) and acidified to pH 2 with normal HCl. The white solid was filtered and washed with water and dried under vacuum to give the title compound (1.35 g, 87%). MS (ES): M/Z [M+H]=468. 1H NMR: (400 MHz, DMSO-$d_6$): 1.72 (s, 3H), 5.48-5.64 (m, 2H), 7.43 (d, J=8.2 Hz, 2H), 7.83 (d, J=2.0 Hz, 1H), 7.99 (d, J=8.8 Hz, 2H), 8.23 (d, J=1.8 Hz, 0H) and 9.41 (br. s, 1H). 19F NMR (376 MHz, DMSO-$d_6$): −57.1 (s, 3F).

Example 67

Methyl 6-chloro-2-[2-cyano-2-({[4-(trifluoromethoxy)phenyl]carbonyl}-amino)propyl]-2H-benzotriazole-4-carboxylate (compound No 1.084)

A 2 molar ether solution of trimethylsilyldiazomethane was added to 6-chloro-2-[2-cyano-2-({[4-(trifluoromethoxy)phenyl]carbonyl}amino)-propyl]-2H-benzotriazole-4-carboxylic acid (100 mg) dissolved in a ten to 1 one mixture of THF and methanol (2 mL). After overnight at room temperature, the mixture was concentrated under reduced pressure to give a residue that was purified by chromatography ($SiO_2$, heptane/EA) to afford the title compound as a white solid (42 mg, 40%). MS (ES): M/Z [M+H]=482. 1H NMR: (400 MHz, DMSO-$d_6$): 1.75 (s, 3H), 3.78 (s, 3H), 5.44 (d, J=13.3 Hz, 1H), 5.58 (d, J=13.3 Hz, 1H), 7.50 (d, J=8.1 Hz, 2H), 7.92 (d, J=8.8 Hz, 2H), 8.02 (d, J=1.9 Hz, 1H), 8.52 (d, J=1.9 Hz, 1H) and 8.87 (s, 1H). 19F NMR (376 MHz, DMSO-$d_6$): −57.1 (s, 3F).

The preparation of 6-chloro-2-[2-cyano-2-({[4-(trifluoromethoxy)phenyl]carbonyl}amino)-propyl]-2H-benzotriazole-4-carboxylic acid is described in Example 66 above.

Compound of Example 68 was prepared according to the following reaction scheme:

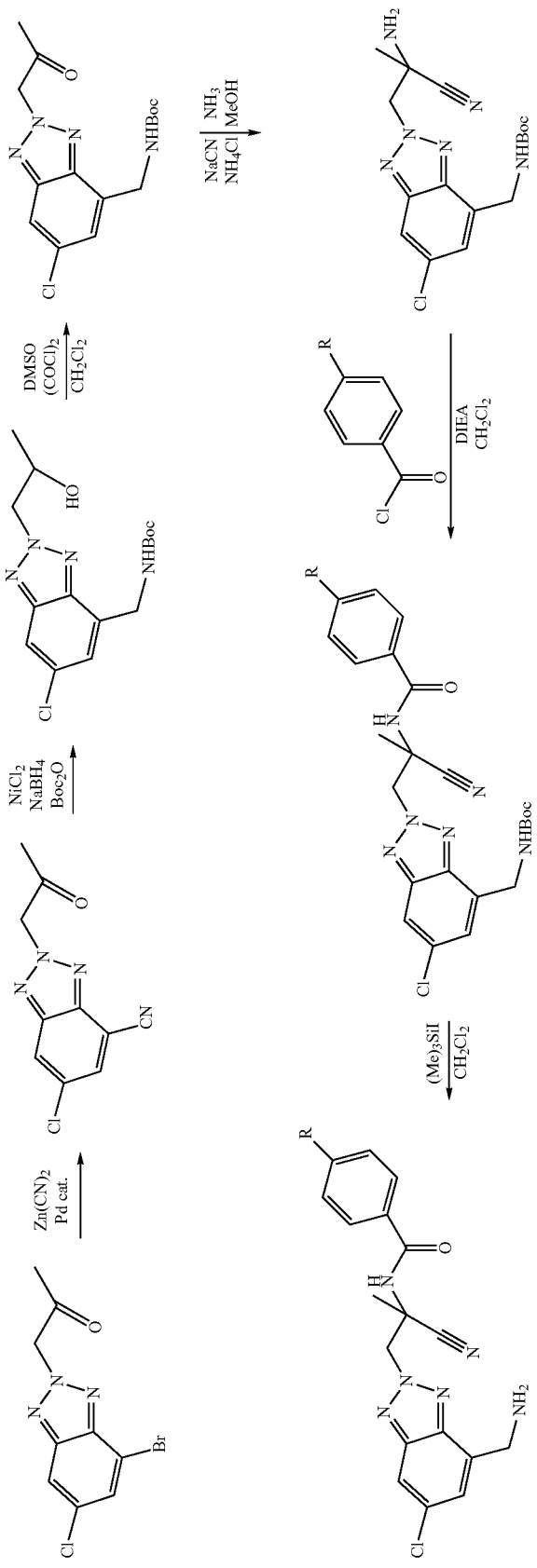

Final Product
V=C—H; W=C—Cl; X=C—H; Y=C—CH$_2$NH$_2$;
Q=P=N;
R$_3$=R$_4$=H; a=1; R$_5$=CH$_3$; R$_6$=H;
Z=C(O); R$_7$=p-phenyl-R Example 68

N-[2-(4-Aminomethyl-6-chloro-2H-benzotriazol-2-yl)-1-cyano-1-methylethyl]-4-trifluoromethoxybenzamide (compound No 1.074)

To a solution of {6-chloro-2-[2-cyano-2-methyl-2-(4-trifluoromethoxy-benzoylamino)-ethyl]-2H-benzotriazol-4-ylmethyl}-carbamic acid tert-butyl ester (100 mg) in DCM (2 mL) was added trimethylsilyl iodide (0.05 mL). After 20 minutes, the mixture was quenched with methanol and concentrated under reduced pressure. The residue was taken up in ethyl acetate, washed with a saturated solution of sodium bicarbonate, dried over sodium sulfate, filtered and concentrated under reduced pressure to give the title compound as a white solid (70 mg, 87%). Rf=0.2 (1:1 EA/heptane). MS (ES): M/Z [M+H]=453. 1H NMR: (500 MHz, CHLOROFORM-d): 1.86 (s, 3H), 4.21 (d, J=3.4 Hz, 2H), 5.16 (d, J=13.7 Hz, 1H), 5.43 (d, J=13.8 Hz, 1H), 7.30 (d, J=8.4 Hz, 2H), 7.33 (d, J=0.7 Hz, 1H), 7.60 (s, 1H), 7.75 (d, J=1.5 Hz, 1H) and 7.88 (d, J=8.7 Hz, 2H). 19F NMR (376 MHz, DMSO-d$_6$): −57.1 (s, 3F).

The starting material {6-chloro-2-[2-cyano-2-methyl-2-(4-trifluoromethoxy-benzoylamino)-ethyl]-2H-benzotriazol-4-ylmethyl}-carbamic acid tert-butyl ester [0.25 g, 60%, MS (ES): M/Z [M+H]=553)] was prepared using a procedure similar to that described in Example 1 except starting from [2-(2-amino-2-cyano-2-methylethyl)-6-chloro-2H-benzotriazol-4-ylmethyl]-carbamic acid tert-butyl ester (0.28 g) that was prepared using a procedure similar to that described in Example 1, part b, except starting from [6-chloro-2-(2-oxopropyl)-2H-benzotriazol-4-ylmethyl]-carbamic acid tert-butyl ester (0.4 g) that was prepared as follows:

a. 1-(4-Bromo-6-chloro-2H-benzotriazol-2-yl)-propan-2-one (3.5 g), zinc cyanide (2.8 g), zinc powder (0.4 g) and bis(tri-t-butylphosphine)palladium (0.62 g) were heated in degassed dimethylacetamide (60 mL) at 60° C. After stirring two hours, the mixture was diluted with water. A solid residue formed and was filtered, washed with water and taken up in ethyl acetate. Organic layer was filtered and concentrated under reduced pressure to give a residue that was purified by chromatography (SiO$_2$, heptane/EA) to afford 6-chloro-2-(2-oxopropyl)-2H-benzotriazole-4-carbonitrile as a white solid (2 g, 70%). Rf=0.55 (1:1 EA/heptane). 1-(4-Bromo-6-chloro-2H-benzotriazol-2-yl)-propan-2-one was prepared using a procedure similar to that described in Example 1, part a, except starting from 7-bromo-5-chloro-1H-benzotriazole described in Example 38, part a and b.

b. To a solution of 6-chloro-2-(2-oxopropyl)-2H-benzotriazole-4-carbonitrile in methanol (160 mL) at 0° C. was added di-tert-butyl dicarbonate (7.6 g) and nickel chloride hexahydrate (0.4 g) followed by slow addition over 1.5 hours of sodium borohydride (5.2). After stirring one additional hour, the mixture was treated with diethylenetriamine (1.8 mL), concentrated under reduced pressure, taken up in ethyl acetate and washed with a saturated solution of sodium bicarbonate. The organic layer was dried over sodium sulfate, filtered and concentrated under reduced pressure to give a brown residue (5.6 g) that contained [6-chloro-2-(2-hydroxypropyl)-2H-benzotriazol-4-ylmethyl]-carbamic acid tert-butyl ester and the des-halogeno analog [2-(2-hydroxypropyl)-2H-benzotriazol-4-ylmethyl]-carbamic acid tert-butyl ester. This residue was taken directly to the next step without further purification.

c. To a solution of oxalyl chloride (0.8 mL) in DCM (20 mL) was added dropwise at −78° C. under nitrogen a solution of DMSO (1.2 mL) in DCM (10 mL). After stirring 10 minutes, a solution of the crude residue containing 6-chloro-2-(2-hydroxypropyl)-2H-benzotriazol-4-ylmethyl]-carbamic acid tert-butyl ester (1.45 g) in DCM (5 mL) was added dropwise under nitrogen. After stirring 30 minutes, TEA (5 mL) was added under nitrogen and the mixture allowed warming to room temperature. The mixture was concentrated under reduced pressure to give a residue that was purified by chromatography (SiO$_2$, heptane/EA) to afford [6-chloro-2-(2-oxopropyl)-2H-benzotriazol-4-ylmethyl]-carbamic acid tert-butyl ester as a yellow solid (0.4 g, 30%). Rf=0.45 (1:1 EA/heptane). 1H NMR: (400 MHz, CHLOROFORM-d): 1.47 (s, 9H), 2.19 (s, 3H), 4.71 (d, J=5.3 Hz, 2H), 5.21 (br. s, 1H), 5.50 (s, 2H), 7.30 (d, J=0.8 Hz, 1H) and 7.78 (d, J=1.3 Hz, 1H).

Compounds of Examples 69 to 74 were prepared according to the following general reaction scheme:

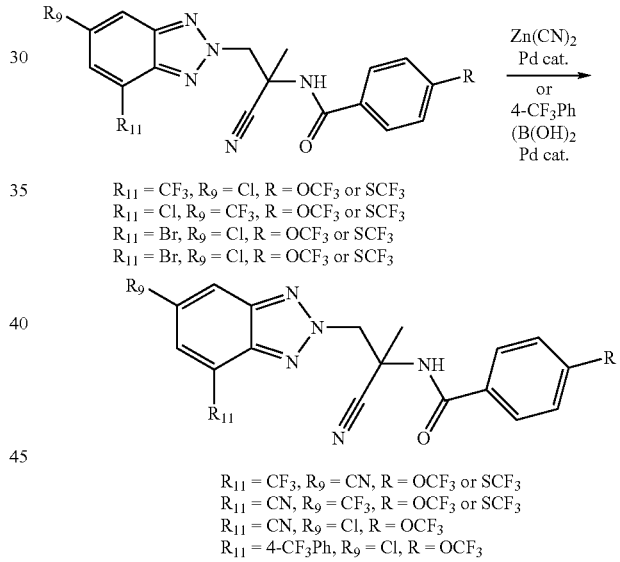

R$_{11}$ = CF$_3$, R$_9$ = Cl, R = OCF$_3$ or SCF$_3$
R$_{11}$ = Cl, R$_9$ = CF$_3$, R = OCF$_3$ or SCF$_3$
R$_{11}$ = Br, R$_9$ = Cl, R = OCF$_3$ or SCF$_3$
R$_{11}$ = Br, R$_9$ = Cl, R = OCF$_3$ or SCF$_3$

R$_{11}$ = CF$_3$, R$_9$ = CN, R = OCF$_3$ or SCF$_3$
R$_{11}$ = CN, R$_9$ = CF$_3$, R = OCF$_3$ or SCF$_3$
R$_{11}$ = CN, R$_9$ = Cl, R = OCF$_3$
R$_{11}$ = 4-CF$_3$Ph, R$_9$ = Cl, R = OCF$_3$

Final Product
V=C—H; W=C—R$_9$; X=C—H; Y=C—R$_{11}$;
Q=P=N;
R$_3$=R$_4$=H; a=1; R$_5$=CH$_3$; R$_6$=H;
Z=C(O); R$_7$=p-phenyl-R Example 69

N-[1-Cyano-2-(4-cyano-6-trifluoromethyl-2H-benzotriazol-2-yl)-1-methylethyl]-4-trifluoromethoxybenzamide (compound No 1.054)

N-[2-(4-Chloro-6-trifluoromethyl-2H-benzotriazol-2-yl)-1-cyano-1-methylethyl]-4-trifluoromethoxybenzamide (100 mg, described in Example 19), zinc cyanide (50 mg), zinc powder (10 mg), 2-di-t-butylphosphino-1,1'-binaphthyl (40 mg) and palladium trifluoroacetate (34 mg) were heated under nitrogen in degassed dimethylacetamide (1 mL) at 100° C. overnight. The mixture was concentrated under reduced pressure to give a residue that was purified by chromatography (SiO$_2$, heptane/EA) to afford the title compound as a white solid (62 mg, 63%). Rf=0.6 (1:1 EA/heptane). MS (ES): M/Z [M+H]=483. NMR: (400 MHz, DMSO-d$_6$): 1.77 (s, 3H), 5.56 (d, J=13.3 Hz, 1H), 5.66 (d, J=13.3 Hz, 1H), 7.49 (d, J=8.2 Hz, 2H), 7.92 (d, J=8.6 Hz, 2H), 8.59 (s, 1H), 8.90 (s, 1H) and 9.02 (s, 1H). 19F NMR (376 MHz, DMSO-d$_6$): −61.0 (s, 3F) and −57.1 (s, 3F).

Example 70

N-[1-Cyano-2-(4-cyano-6-trifluoromethyl-2H-benzotriazol-2-yl)-1-methylethyl]-4-trifluoromethylthiobenzamide (compound No 1.055)

Using a procedure similar to that described in Example 69, except using N-[2-(4-chloro-6-trifluoromethyl-2H-benzotriazol-2-yl)-1-cyano-1-methylethyl]-4-trifluoromethylthiobenzamide (100 mg, described in Example 20), the title compound was isolated as a white solid (52 mg, 53%). Rf=0.5 (1:1 EA/heptane). MS (ES): M/Z [M+H]=499. NMR: (400 MHz, DMSO-d$_6$): 1.77 (s, 3H), 5.57 (d, J=13.2 Hz, 1H), 5.67 (d, J=13.3 Hz, 1H), 7.84 (d, J=8.3 Hz, 2H), 7.90 (d, J=8.4 Hz, 2H), 8.60 (d, J=1.1 Hz, 1H), 8.99 (s, 1H) and 9.01 (s, 1H). 19F NMR (376 MHz, DMSO-d$_6$): −42.0 (s, 3F) and −61.0 (s, 3F).

Example 71

N-[1-Cyano-2-(6-cyano-4-trifluoromethyl-2H-benzotriazol-2-yl)-1-methylethyl]-4-trifluoromethoxybenzamide (compound No 1.056)

Using a procedure similar to that described in Example 69, except using N-[2-(6-chloro-4-trifluoromethyl-2H-benzotriazol-2-yl)-1-cyano-1-methylethyl]-4-trifluoromethoxybenzamide (100 mg, described in Example 32), the title compound was isolated as a white solid (44 mg, 45%). Rf=0.55 (1:1 EA/heptane). MS (ES): M/Z [M+H]=483. NMR: (400 MHz, DMSO-d$_6$): 1.78 (s, 3H), 5.53 (d, J=13.2 Hz, 1H), 5.68 (d, J=13.3 Hz, 1H), 7.48 (d, J=8.1 Hz, 2H), 7.89 (d, J=8.8 Hz, 2H), 8.32 (s, 1H), 8.85 (s, 1H) and 9.18 (s, 1H). 19F NMR (376 MHz, DMSO-d$_6$): −61.7 (s, 3F) and −57.2 (s, 3F).

Example 72

N-[1-Cyano-2-(6-cyano-4-trifluoromethyl-2H-benzotriazol-2-yl)-1-methylethyl]-4-trifluoromethylthiobenzamide (compound No 1.066)

Using a procedure similar to that described in Example 69, except using N-[2-(6-chloro-4-trifluoromethyl-2H-benzotriazol-2-yl)-1-cyano-1-methylethyl]-4-trifluoromethylthiobenzamide (590 mg, described in Example 33), the title compound was isolated as a white solid (320 mg, 55%). Rf=0.5 (1:1 EA/heptane). MS (ES): M/Z [M+H]=499. NMR: (400 MHz, DMSO-d$_6$): 1.78 (s, 3H), 5.53 (d, J=13.2 Hz, 1H), 5.69 (d, J=13.3 Hz, 1H), 7.79-7.91 (m, 4H), 8.31 (s, 1H), 8.94 (s, 1H) and 9.18 (s, 1H). 19F NMR (376 MHz, DMSO-d$_6$): −42.1 (s, 3F) and −61.7 (s, 3F).

Example 73

N-[2-(6-Chloro-4-cyano-2H-benzotriazol-2-yl)-1-cyano-1-methylethyl]-4-trifluoromethoxybenzamide (compound No 1.067)

Using a procedure similar to that described in Example 69, except using N-[2-(4-bromo-6-chloro-2H-benzotriazol-2-yl)-1-cyano-1-methylethyl]-4-trifluoromethoxybenzamide (100 mg) described in Example 38 and bis(tri-t-butylphosphine)palladium (20 mg) as palladium catalyst with no additional phosphine ligand and heating the reaction mixture at 60° C. for one hour; the title compound was isolated as a white solid (70 mg, 79%). Rf=0.6 (1:1 EA/heptane). MS (ES): M/Z [M+H]=449. NMR: (400 MHz, DICHLOROMETHANE-d$_2$): 1.87 (s, 3H), 5.28 (d, J=13.7 Hz, 1H), 5.52 (d, J=13.7 Hz, 1H), 7.29-7.43 (m, 3H), 7.85 (d, J=1.8 Hz, 1H), 7.87-7.95 (m, 2H) and 8.20 (d, J=1.7 Hz, 1H). 19F NMR (376 MHz, DICHLOROMETHANE-d$_2$): −58.5 (s, 3F).

Example 74

N-{2-[6-Chloro-4-(4-trifluoromethylphenyl)-2H-benzotriazol-2-yl]-1-cyano-1-methylethyl}-4-trifluoromethoxybenzamide (compound No 1.068)

N-[2-(4-Bromo-6-chloro-2H-benzotriazol-2-yl)-1-cyano-1-methylethyl]-4-trifluoromethoxybenzamide (120 mg) described in Example 38, bis(tri-t-butylphosphine)palladium (20 mg), bis(dibenzylideneacetone)palladium (20 mg), potassium fluoride (42 mg) and 4-trifluoromethylphenyl boronic acid (45 mg) in THF were stirred at room temperature for 3 days. The mixture was concentrated under reduced pressure to give a residue that was purified by chromatography (SiO$_2$, heptane/EA) to afford a one to one mixture of title compound and starting material [110 mg, Rf=0.3 (3:7 EA/heptane)]. This mixture was further purified by semi-preparative liquid chromatography (methanol/water) to afford the title compound as pure solid (35 mg, 26%). MS (ES): M/Z [M+H]=568. NMR: (400 MHz, DMSO-d$_6$): 1.74 (s, 3H), 1.84 (s, 1H), 5.39 (d, J=13.3 Hz, 1H), 5.64 (d, J=13.3 Hz, 1H), 7.41 (d, J=8.0 Hz, 2H), 7.60 (d, J=8.3 Hz, 2H), 7.84 (d, J=1.8 Hz, 1H), 7.93 (d, J=8.9 Hz, 2H), 8.12 (d, J=8.1 Hz, 2H) and 8.23 (d, J=1.8 Hz, 1H). 19F NMR (376 MHz, DMSO-d$_6$): −61.8 (s, 3F) and −57.3 (s, 3F).

Compounds of Examples 75 to 84 were prepared according to the following general reaction scheme:

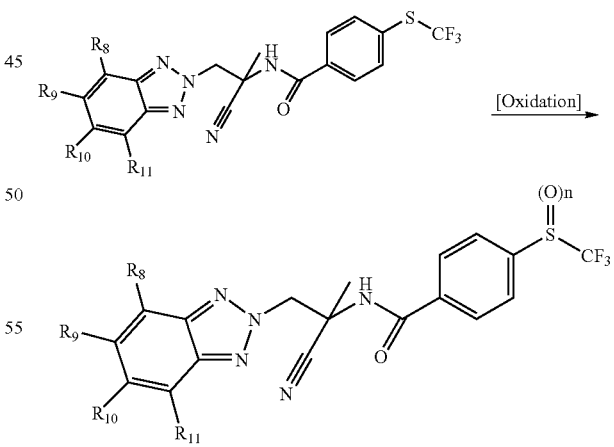

Final Product

V=C—R$_8$; W=C—R$_9$; X=C—R$_{10}$; Y=C—R$_{11}$;

Q=P=N;

R$_3$=R$_4$=H; a=1; R$_5$=CH$_3$; R$_6$=H;

Z=C(O); R$_7$=p-phenyl-R; R=S(O)$_n$CF$_3$; n=0, 1, or 2

Example 75

N-[1-Cyano-2-(5-cyano-2H-benzotriazol-2-yl)-1-methylethyl]-4-trifluoromethylsulfinylbenzamide (compound No 1.022)

3-Chloroperbenzoic acid (77% pure, 0.13 g) was added at 0° C. to a DCM solution of N-[1-cyano-2-(5-cyano-2H-benzotriazol-2-yl)-1-methylethyl]-4-trifluoromethylthiobenzamide (0.11 g, described in Example 22). The reaction mixture was stirred 72 hours at room temperature. The reaction mixture was diluted with DCM then washed with saturated aqueous sodium bicarbonate solution. The organic phase was dried over anhydrous sodium sulfate, filtered and concentrated under reduced pressure to give a residue that was purified by chromatography ($SiO_2$, heptane/EA) to afford the title compound as a white solid (60 mg, 53%). MS (ES): M/Z [M+H]=447. 1H NMR: (400 MHz, DMSO-$d_6$): 1.77 (s, 3H), 5.44-5.65 (m, 2H), 7.76 (d, J=8.8 Hz, 1H), 8.02-8.07 (m, 4H), 7.94 (d, J=8.9 Hz, 1H), 8.78 (s, 1H) and 9.10 (s, 1H). 19F NMR (376 MHz, DMSO-$d_6$): −74.20 (s, 3F).

Example 76

N-[2-(4-Chloro-6-trifluoromethyl-2H-benzotriazol-2-yl)-1-cyano-1-methylethyl]-4-trifluoromethylsulfinylbenzamide (compound No 1.023)

Using a procedure similar to that described in Example 75, except using N-[1-cyano-1-methyl-2-(4-chloro-6-trifluoromethyl benzotriazol-2-yl)-ethyl]-4-trifluoromethylthiobenzamide described in Example 20, the title compound was isolated as a white solid (60 mg, 53%). MS (ES): M/Z [M+H]=524. 1H NMR: (400 MHz, DMSO-$d_6$): 1.78 (s, 3H), 5.46-5.56 (m, 2H), 7.94 (d, 1H, J=0.7 Hz), 8.01-8.07 (m, 4H), 8.56 (d, J=0.8 Hz, 1H) and 9.02 (s, 1H). 19F NMR (376 MHz, DMSO-$d_6$): −74.27 (s, 3F) and −61.08 (s, 3F).

Example 77

N-[1-Cyano-2-(4,6-dichloro-2H-benzotriazol-2-yl)-1-methylethyl]-4-trifluoromethylsulfinylbenzamide (compound No 1.024)

3-Chloroperbenzoic acid (77% pure, 0.57 g) was added at 0° C. to a DCM solution of N-[1-cyano-2-(4,6-dichloro-2H-benzotriazol-2-yl)-1-methylethyl]-4-trifluoromethylthiobenzamide (0.3 g, described in Example 16). The reaction mixture was stirred over night at room temperature. The reaction mixture was diluted with DCM, washed with saturated aqueous sodium bicarbonate solution. The organic phase was dried over anhydrous sodium sulfate, filtered and concentrated under reduced pressure to give a residue that was purified by chromatography ($SiO_2$, heptane/EA) to afford the title compound as a white solid (100 mg, 32%). Rf=0.6 (1:1 EA/heptane). MS (ES): M/Z [M+H]=490. NMR: (400 MHz, DMSO-$d_6$): 1.76 (s, 3H), 5.39-5.60 (m, 2H), 7.74 (d, J=1.6 Hz, 1H), 7.99-8.08 (m, 4H), 8.18 (dd, J=1.5, 0.9 Hz, 1H), and 9.04 (s, 1H). 19F NMR (376 MHz, DMSO-$d_6$): −74.24 (s, 3F).

Example 78

N-[1-Cyano-2-(4,6-dichloro-2H-benzotriazol-2-yl)-1-methylethyl]-4-trifluoromethylsulfonylbenzamide (compound No 1.025)

The crude residue described in Experimental 77 that was purified by chromatography ($SiO_2$, heptane/EA) also provided the sulfone title compound as a white solid (100 mg, 31%). Rf=0.65 (1:1 EA/heptane). MS (ES): M/Z [M+H]= 506. NMR: (400 MHz, DMSO-$d_6$): 1.76 (s, 3H), 5.51 (dd, J=60.1, 13.4 Hz, 1H), 7.73 (d, J=1.6 Hz, 1H), 8.12-8.17 (m, 2H), 8.19 (d, J=1.6 Hz, 1H), 8.31 (d, J=8.4 Hz, 2H) and 9.19 (s, 1H). 19F NMR (376 MHz, DMSO-$d_6$): −78.70 (s, 3F).

Example 79

N-[1-Cyano-1-methyl-2-(5-trifluoromethyl-2H-benzotriazol-2-yl)ethyl]-4-trifluoromethylsulfonylbenzamide (compound No 1.026)

3-Chloroperbenzoic acid (60 mg) was added at 0° C. to a DCM solution of N-[1-cyano-1-methyl-2-(5-trifluoromethyl-2H-benzotriazol-2-yl)ethyl]-4-trifluoromethylthiobenzamide (50 mg, described in Example 11). The reaction mixture was stirred 48 hours at room temperature then more 3-chloroperbenzoic acid (60 mg) was added and the reaction mixture was stirred 48 additional hours at room temperature. The reaction mixture was diluted with DCM, washed with saturated aqueous sodium bicarbonate solution. The organic phase was dried over anhydrous sodium sulfate, filtered and concentrated under reduced pressure to give a residue that was purified by chromatography ($SiO_2$, heptane/EA) to afford the title compound as a white solid (42 mg, 79%). Rf=0.5 (1:1 EA/heptane). MS (ES): M/Z [M+H]=506. 1H NMR: (400 MHz, CHLOROFORM-d): 1.90 (s, 3H), 5.40 (dd, J=120.3, 13.8 Hz, 2H), 7.38 (br s, 1H), 7.66 (dd, J=9.1, 1.5 Hz, 1H), 8.07-8.14 (m, 2H), 8.16-8.23 (m, 2H) and 8.26 (br s, 1H). 19F NMR (376 MHz, CHLOROFORM-d): −78.33 (s, 3F) and −63.04 (s, 3F).

Example 80

N-[1-Cyano-1-methyl-2-(5-cyano-2H-benzotriazol-2-yl)-ethyl]-4-trifluoromethylsulfonylbenzamide (compound No 1.027)

Using a procedure similar to that described in Example 79, except using N-[1-cyano-2-(5-cyano-2H-benzotriazol-2-yl)-1-methylethyl]-4-trifluoromethylthiobenzamide (50 mg, described in Example 22), the title compound was isolated as a white solid (35 mg, 65%). Rf=0.4 (1:1 EA/heptane). MS (ES): M/Z [M+H]=463. 1H NMR: (400 MHz, DMSO-$d_6$): 1.76 (s, 3H), 5.44-5.65 (m, 2H), 7.77 (d, J=8.8 Hz, 1H), 8.15 (d, J=8.6 Hz, 2H), 8.19 (d, J=8.8 Hz, 1H), 8.32 (d, J=8.4 Hz, 2H), 8.79 (s, 1H) and 9.26 (s, 1H). 19F NMR (376 MHz, DMSO-$d_6$): −78.67 (s, 3F).

Example 81

N-[2-(4-Chloro-6-trifluoromethyl-2H-benzotriazol-2-yl)-1-cyano-1-methylethyl]-4-trifluoromethylsulfonylbenzamide (compound No 1.028)

Using a procedure similar to that described in Example 77, except using N-[2-(4-chloro-6-trifluoromethyl-2H-benzotriazol-2-yl)-1-cyano-1-methylethyl]-4-trifluoromethylthiobenzamide (50 mg, described in Example 20) and a 6 fold excess of 3-chloroperbenzoic acid (77% pure, 130 mg), the title compound was isolated as a white solid (35 mg, 66%). Rf=0.65 (1:1 EA/heptane). MS (ES): M/Z [M+H]=540. 1H NMR: (400 MHz, DMSO-$d_6$): 1.78 (s, 3H), 5.59 (dd, J=58.3, 13.3 Hz, 2H), 7.93 (s, 1H), 8.16 (d, J=8.58 Hz, 2H), 8.57 (s, 1H) and 9.17 (s, 1H). 19F NMR (376 MHz, DMSO-$d_6$): −78.73 (s, 3F) and −61.08 (s, 3F).

Example 82

N-[2-(2H-Benzotriazol-2-yl)-1-cyano-1-methyl-ethyl]-4-trifluoromethylsulfonylbenzamide (compound No 1.029)

Sodium periodate (200 mg) and ruthenium chloride (10 mg) were added to a solution of N-[2-(2H-benzotriazol-2-yl)-1-cyano-1-methylethyl]-4-trifluoromethylthiobenzamide (100 mg, described in Example 6), in a mixture of acetonitrile-water (2:1). The reaction mixture was stirred 48 hours whereupon the mixture was diluted with ethyl acetate and washed with saturated aqueous sodium bicarbonate solution. The organic filtrate was dried over anhydrous magnesium sulfate, filtered and concentrated under reduced pressure to give to give a residue that was purified by chromatography ($SiO_2$, heptane/EA) to afford the title compound as a white solid (50 mg, 46%). Rf=0.6 (1:1 EA/heptane). MS (ES): M/Z [M+H]=438. 1H NMR: (400 MHz, DMSO-$d_6$): 1.75 (s, 3H), 5.39-5.53 (m, 2H), 7.47 (dd, J=6.6, 3.1 Hz, 2H), 7.95 (dd, J=6.6, 3.1 Hz, 2H), 8.17 (d, J=8.6 Hz, 2H), 8.31 (d, J=8.4 Hz, 2H) and 9.25 (s, 1H). 19F NMR (376 MHz, DMSO-$d_6$): −78.66 (s, 3F).

Example 83

N-[1-Cyano-1-methyl-2-(5-methyl-2H-benzotriazol-2-yl)ethyl]-4-trifluoromethylsulfonylbenzamide (compound No 1.030)

Using a procedure similar to that described in Example 79, except using N-[1-cyano-1-methyl-2-(5-methyl-2H-benzotriazol-2-yl)ethyl]-4-trifluoromethylthiobenzamide (50 mg, described in Example 8), the title compound was isolated as a white solid (40 mg, 37%). Rf=0.6 (1:1 EA/heptane). MS (ES): M/Z [M+H]=452. 1H NMR: (400 MHz, DMSO-$d_6$): 1.73 (s, 3H), 5.34-5.47 (m, 2H), 7.30 (dd, J=8.8, 1.4 Hz, 1H), 7.69 (s, 1H), 7.83 (d, J=8.8 Hz, 1H), 8.17 (d, J=8.5 Hz, 2H), 8.32 (d, J=8.4 Hz, 2H) and 9.24 (s, 1H). 19F NMR (376 MHz, DMSO-$d_6$): −78.67 (s, 3F).

Example 84

N-[2-(5-Chloro-2H-benzotriazol-2-yl)-1-cyano-1-methylethyl]-4-trifluoromethylsulfonylbenzamide (compound No 1.031)

Using a procedure similar to that described in Example 79, except using N-[2-(5-chloro-2H-benzotriazol-2-yl)-1-cyano-1-methylethyl]-4-trifluoromethylthiobenzamide (50 mg, described in Example 3), the title compound was isolated as a white solid (120 mg, 45%). Rf=0.6 (1:1 EA/heptane). MS (ES): M/Z [M+H]=472. 1H NMR: (400 MHz, DMSO-$d_6$): 1.75 (s, 3H), 5.41-5.52 (m, 2H), 7.49 (m, 1H), 8.02 (m, 1H), 8.14-8.32 (m, 4H) and 9.25 (s, 1H). 19F NMR (376 MHz, DMSO-$d_6$): −78.67 (s, 3F).

Compounds of Examples 85 to 88 were prepared according to the following general reaction scheme:

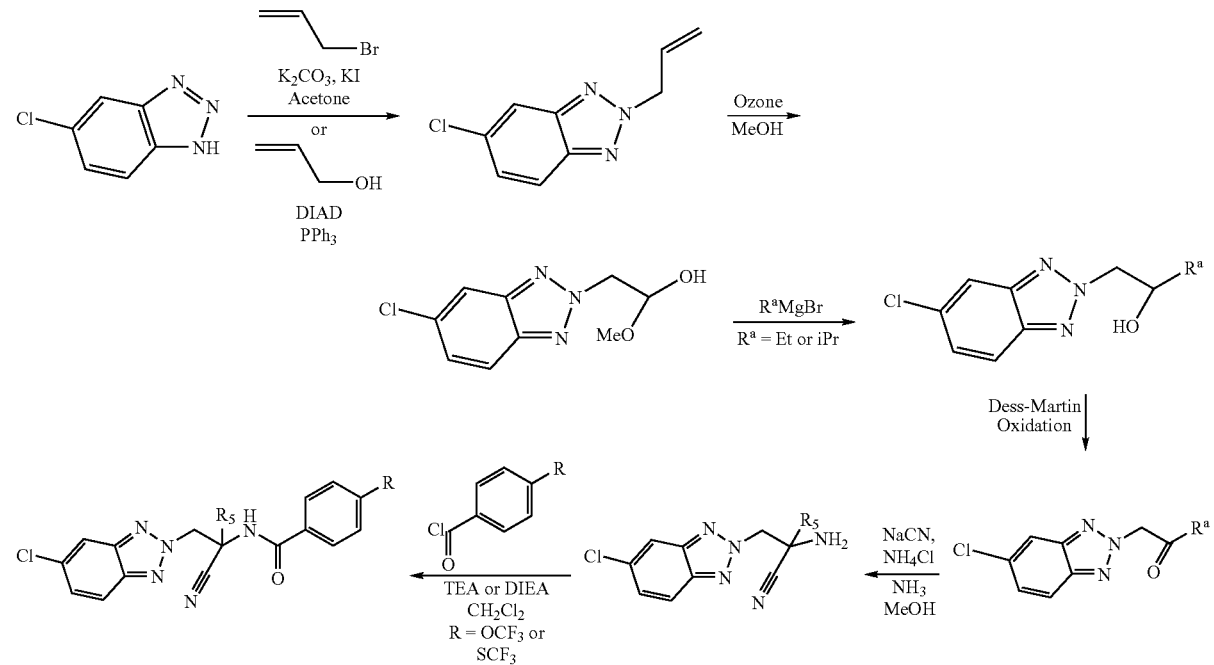

Final Product
V=C—H; W=C—Cl; X=C—H; Y=C—H;
Q=P=N;
$R_3$=$R_4$=H; a=1; $R_6$H;
Z=C(O); $R_7$=p-phenyl-R; R=$OCF_3$ or $SCF_3$

Example 85

N-{1-[(5-Chloro-2H-benzotriazol-2-yl)methyl]-1-cyanopropyl}-4-trifluoromethoxybenzamide (compound No 1.047)

Using a procedure similar to that described in Example 1, except using 2-amino-2-[(5-chloro-2H-benzotriazol-2-yl)

methyl]butyronitrile, the title compound was isolated as a solid. MS (ES): M/Z [M+H]=438. 1H NMR: (400 MHz, CHLOROFORM-d): 1.29 (t, J=7.4 Hz, 3H), 1.72-1.94 (m, J=14.4, 7.4 Hz, 1H), 2.29 (m, J=14.3, 7.4 Hz, 1H), 5.23 (d, J=13.9 Hz, 1H), 5.47 (d, J=13.8 Hz, 1H), 7.15 (s, 1H), 7.33 (d, J=8.2 Hz, 2H), 7.40 (dd, J=9.1, 1.8 Hz, 1H), 7.82 (d, J=9.1 Hz, 1H), 7.85 (d, J=8.7 Hz, 2H) and 7.87 (d, J=1.2 Hz, 1H). 19F NMR (376 MHz, CHLOROFORM-d): −58.1 (s, 3F).

2-Amino-2-[(5-chloro-2H-benzotriazol-2-yl)methyl]butyronitrile was prepared using a procedure similar to that described in Example 1, part b, except starting from 1-(5-chloro-2H-benzotriazol-2-yl)butan-2-one that was prepared as follows:

a. A solution of 5-chloro-1H-benzotriazole (1.53 g) in THF was added at 0° C. to a mixture of diisopropylic azodicarboxylate (2 mL), triphenyl phosphine (2.9 g) and allyl alcohol (1.4 mL) in THF. After stirring one hour at 0° C., the mixture was concentrated under reduced pressure to give a residue that was purified by chromatography (SiO$_2$, heptane/EA) to afford 2-allyl-5-chloro-2H-benzotriazole (1.02 g, 53%). A mixture of 1-allyl-5-chloro-1H-benzotriazole and 1-allyl-6-chloro-1H-benzotriazole was also recovered (0.9 g, 47%). Alternatively, 2-allyl-5-chloro-2H-benzotriazole [4.87 g, 25%, Rf=0.4 (1:3 EA/heptane)] was obtained using a procedure similar to that described in Example 1, part a, except using 3-bromopropene. Similarly, a mixture of 1-allyl-5-chloro-1H-benzotriazole and 1-alkyl-6-chloro-1H-benzotriazole was also recovered [10.81 g, 56%, Rf=0.2 (1:3 EA/heptane)].

b. 2-Allyl-5-chloro-2H-benzotriazole dissolved in a mixture of DCM and methanol was treated with ozone gas for 30 minutes. After stirring one hour at −78° C., the mixture was purged 10 minutes with oxygen and then quenched with dimethyl sulfide followed by a 10% solution of sodium thiosulfate and diluted with DCM (100 mL). The organic layer was dried over sodium sulfate, filtered and concentrated under reduced pressure to give quantitatively 2-(5-chloro-2H-benzotriazol-2-yl)-1-methoxyethanol c. To a solution of 2-(5-chloro-2H-benzotriazol-2-yl)-1-methoxyethanol (300 mg) in THF was added a 2 molar solution of ethyl magnesium bromide Grignard reagent (1.6 mL) at −78° C. under nitrogen and the mixture let warm slowly to room temperature. The mixture was quenched with a saturated solution of ammonium chloride, followed by magnesium sulfate. The resulted solids were filtered off and the organic layer concentrated under reduced pressure to give a residue that was purified by chromatography (SiO$_2$, heptane/EA) to afford 1-(5-chloro-2H-benzotriazol-2-yl)butan-2-ol (107 mg). Rf=0.7 (2:1 EA/heptane).

d. 1-(5-Chloro-2H-benzotriazol-2-yl)butan-2-ol in DCM was reacted with Dess-Martin periodinane. After stirring at room temperature, the mixture was concentrated under reduced pressure and purified by chromatography (SiO$_2$, heptane/EA) to afford 1-(5-chloro-2H-benzotriazol-2-yl)butan-2-one.

Example 86

N-{1-[(5-Chloro-2H-benzotriazol-2-yl)methyl]-1-cyanopropyl}-4-trifluoromethylthiobenzamide (compound No 1.048)

Using a procedure similar to that described in Example 1, except using 2-amino-2-[(5-chloro-2H-benzotriazol-2-yl)methyl]butyronitrile described in Example 85 and 4-trifluoromethylbenzoyl chloride, the title compound was isolated as a solid. MS (ES): M/Z [M+H]=454. 1H NMR: (400 MHz, CHLOROFORM-d): 1.29 (t, J=7.4 Hz, 3H), 1.77-1.94 (m, J=14.4, 7.4, 7.4, 7.3 Hz, 1H), 2.16-2.36 (m, J=14.4, 7.4, 7.4, 7.3 Hz, 1H), 5.23 (d, J=13.9 Hz, 1H), 5.47 (d, J=13.8 Hz, 1H), 7.21 (s, 1H), 7.39 (dd, J=9.1, 1.9 Hz, 1H), 7.73-7.79 (m, 2H), 7.79-7.85 (m, 3H) and 7.87 (dd, J=1.8, 0.7 Hz, 1H). 19F NMR (376 MHz, CHLOROFORM-d): −42.3 (s, 3F).

Example 87

N-{1-[(5-Chloro-2H-benzotriazol-2-yl)methyl]-1-cyano-3-methylbutyl}-4-trifluoromethoxybenzamide (compound No 1.049)

Using a procedure similar to that described in Example 1, except using 2-amino-2-[(5-chloro-2H-benzotriazol-2-yl)methyl]-4-methylpentanenitrile, the title compound was isolated as a solid. MS (ES): M/Z [M+H]=466. 1H NMR: (400 MHz, CHLOROFORM-d): 1.11 (d, J=6.4 Hz, 3H), 1.14 (d, J=6.3 Hz, 3H), 1.79-1.90 (m, 1H), 2.05-2.21 (m, 2H), 5.27 (d, J=13.8 Hz, 1H), 5.48 (d, J=13.8 Hz, 1H), 7.27 (s, 1H), 7.32 (d, J=8.5 Hz, 2H), 7.39 (dd, J=9.1, 1.7 Hz, 1H), 7.78-7.86 (m, 3H) and 7.87 (d, J=1.8 Hz, 1H). 19F NMR (376 MHz, CHLOROFORM-d): −58.1 (s, 3F).

2-Amino-2-[(5-chloro-2H-benzotriazol-2-yl)methyl]-4-methylpentanenitrile was prepared using a procedure similar to that described in Example 1, part b, except starting from 1-(5-chloro-2H-benzotriazol-2-yl)-4-methylpentan-2-one. 1-(5-Chloro-2H-benzotriazol-2-yl)-4-methylpentan-2-one was prepared using a procedure similar to that described in Example 85, part a to d, except using isopropyl magnesium bromide Grignard reagent in part c.

Example 88

N-{1-[(5-Chloro-2H-benzotriazol-2-yl)methyl]-1-cyano-3-methylbutyl}-4-trifluoromethylthiobenzamide (compound No 1.050)

Using a procedure similar to that described in Example 1, except using 2-amino-2-[(5-chloro-2H-benzotriazol-2-yl)methyl]-4-methylpentanenitrile described in Example 87 and 4-trifluoromethylbenzoyl chloride, the title compound was isolated as a solid. 1H NMR: (400 MHz, CHLOROFORM-d): 1.11 (d, J=6.5 Hz, 3H), 1.15 (d, J=6.4 Hz, 3H), 1.78-1.91 (m, 1H), 2.06-2.21 (m, 2H), 5.27 (d, J=13.8 Hz, 1H), 5.49 (d, J=13.8 Hz, 1H), 7.16 (s, 1H), 7.40 (dd, J=9.1, 1.8 Hz, 1H), 7.75-7.80 (m, 2H), 7.80-7.86 (m, 3H) and 7.87 (dd, J=1.8, 0.5 Hz, 1H). 19F NMR (376 MHz, CHLOROFORM-d): −42.2 (s, 3F).

Compounds of Examples 89 and 90 were prepared according to the following reaction scheme:

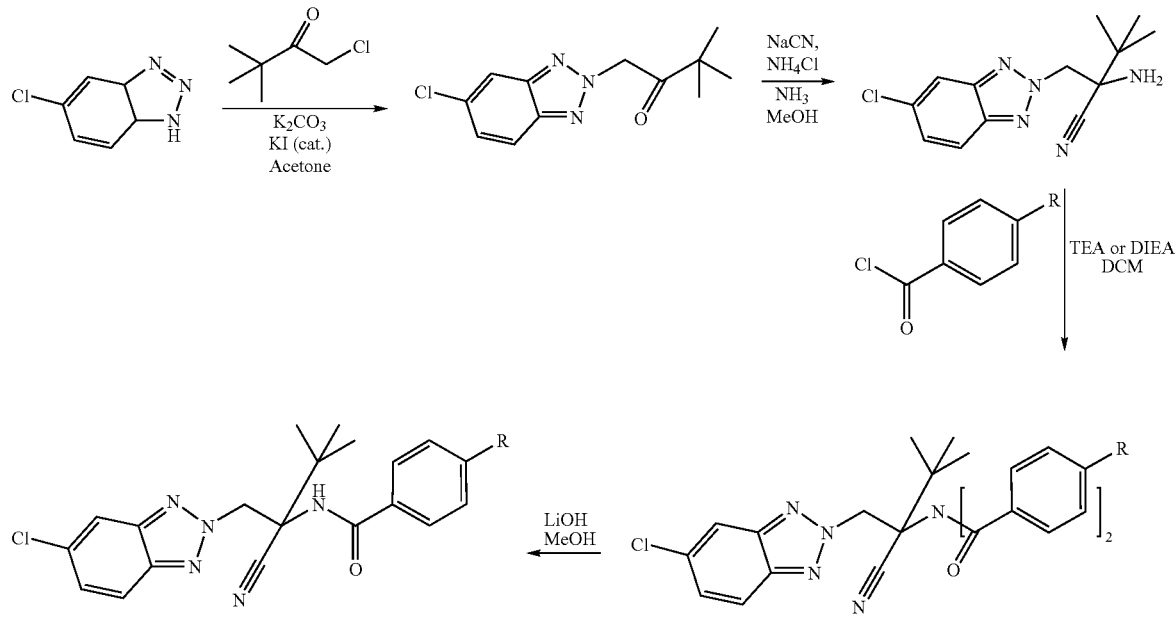

Final Product
V=C—H; W=C—Cl; X=C—H; Y=C—H;
Q=P=N;
$R_3=R_4=H$; a=1; $R_5$=t-butyl; $R_6$=H;
Z=C(O); $R_7$=p-phenyl-R Example 89

N-{1-[(5-Chloro-2H-benzotriazol-2-yl)methyl]-1-cyano-2,2-dimethylpropyl}-4-trifluoromethoxybenzamide (compound No 1.051)

Using a procedure similar to that described in Example 1, except using 2-amino-2-[(5-chloro-2H-benzotriazol-2-yl)methyl]-3,3-dimethylbutyronitrile, the bis-amide derivative N-{1-[(5-chloro-2H-benzotriazol-2-yl)methyl]-1-cyano-2,2-dimethylpropyl}-4-trifluoromethoxy-N-(4-trifluoromethoxybenzoyl)-benzamide was isolated instead of the title compound. MS (ES): M/Z [M+H]=654. Subsequent treatment with lithium hydroxide in methanol and purification by chromatography (SiO$_2$, heptane/EA) afforded the title compound as a solid. MS (ES): M/Z [M+H]=466. 1H NMR: (400 MHz, CHLOROFORM-d): 0.17 (s, 9H), 5.34 (d, J=14.1 Hz, 1H), 5.51 (d, J=14.1 Hz, 1H), 7.02 (s, 1H), 7.35 (d, J=8.0 Hz, 2H), 7.38 (dd, J=9.1, 1.9 Hz, 1H), 7.79 (dd, J=9.1, 0.6 Hz, 1H), 7.84 (dd, J=1.8, 0.6 Hz, 1H) and 7.89 (d, J=8.8 Hz, 2H). 19F NMR (376 MHz, CHLOROFORM-d): −58.1 (s, 3F).

2-Amino-2-[(5-chloro-2H-benzotriazol-2-yl)methyl]-3,3-dimethylbutyronitrile was prepared using a procedure similar to that described in Example 1, part a and b, except using 1-chloro-3,3-dimethylbutan-2-one instead of chloroacetone in part a.

Example 90

N-{1-[(5-Chloro-2H-benzotriazol-2-yl)methyl]-1-cyano-2,2-dimethylpropyl}-4-trifluoromethylthiobenzamide (compound No 1.052)

Using a procedure similar to that described in Example 1, except using 2-amino-2-[(5-chloro-2H-benzotriazol-2-yl)methyl]-3,3-dimethylbutyronitrile described in Example 89 and 4-trifluoromethylbenzoyl chloride, the bis-amide derivative N-{1-[(5-chloro-2H-benzotriazol-2-yl)methyl]-1-cyano-2,2-dimethylpropyl}-4-trifluoromethylthio-N-(4-trifluoromethylthiobenzoyl)-benzamide was isolated instead of the title compound. MS (ES): M/Z [M+H]=686. Subsequent treatment with lithium hydroxide in methanol and purification by chromatography (SiO$_2$, heptane/EA) afforded the title compound as a solid. MS (ES): M/Z [M+H]=482. 1H NMR: (400 MHz, CHLOROFORM-d): 1.17 (s, 9H), 5.35 (d, J=14.1 Hz, 1H), 5.51 (d, J=14.1 Hz, 1H), 7.06 (s, 1H), 7.38 (dd, J=9.1, 1.9 Hz, 1H), 7.75-7.82 (m, 3H), 7.84 (dd, J=1.8, 0.6 Hz, 1H) and 7.85-7.91 (m, 2H). 19F NMR (376 MHz, CHLOROFORM-d): −42.3 (s, 3F).

Compounds of Examples 91 and 92 were prepared according to the following general reaction scheme:

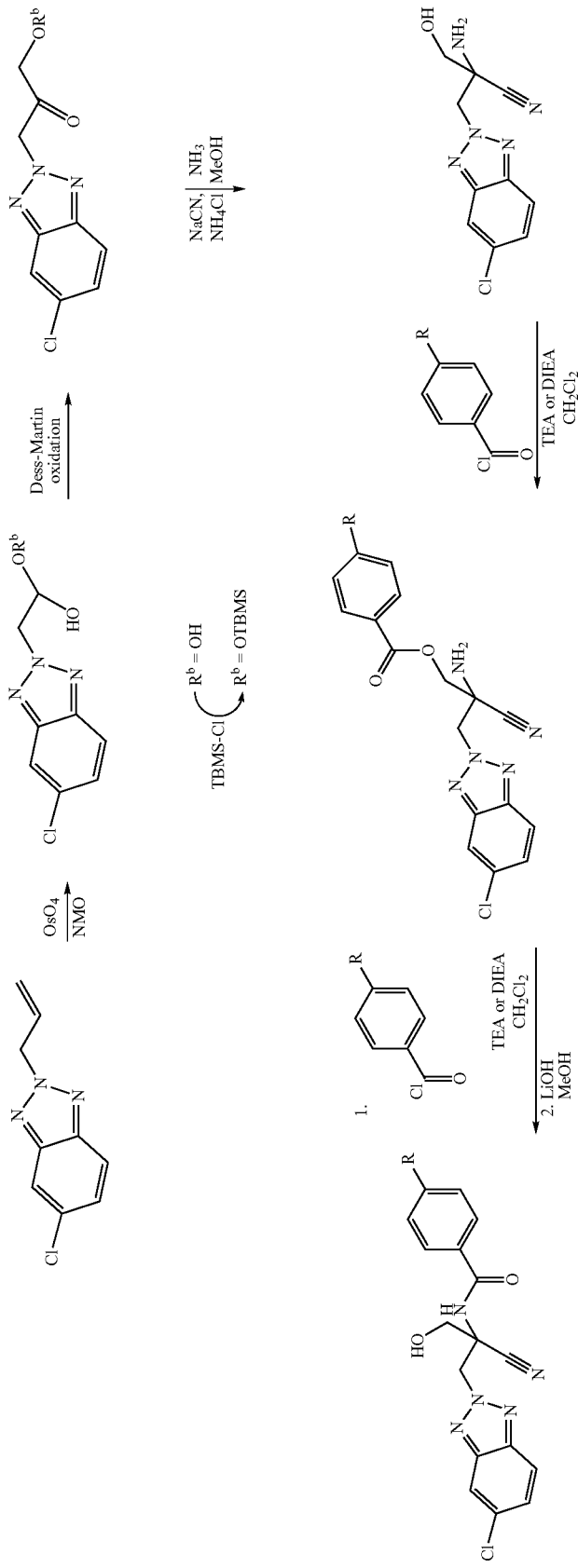

Final Product
V=C—H; W=C—Cl; X=C—H; Y=C—H;
Q=P=N;
$R_3$=$R_4$=H; a=1; $R_5$=$CH_2OH$; $R_6$=H;
Z=C(O); $R_7$=p-phenyl-R Example 91

N-[2-(5-Chloro-2H-benzotriazol-2-yl)-1-cyano-1-(hydroxymethyl)ethyl]-4-trifluoromethoxybenzamide (compound No 1.058)

Using a procedure similar to that described in Example 1, except using 2-amino-3-(5-chloro-2H-benzotriazol-2-yl)-2-(hydroxymethyl)propionitrile, the ester derivative 4-trifluoromethoxybenzoic acid 2-amino-3-(5-chloro-2H-benzotriazol-2-yl)-2-cyanopropyl ester was isolated instead of the title compound. This ester was reacted with more 4-trifluoromethoxybenzoyl chloride, subsequently treated with lithium hydroxide in methanol and purified by chromatography ($SiO_2$, heptane/EA) to afford the title compound as a solid. MS (ES): M/Z [M+H]=440. 1H NMR: (400 MHz, CHLOROFORM-d): 3.27 (t, J=7.3 Hz, 1H), 3.94 (dd, J=11.9, 7.3 Hz, 1H), 4.30 (dd, J=11.9, 5.9 Hz, 1H), 5.43 (d, J=13.9 Hz, 1H), 5.48 (, J=14.0 Hz, 1H), 7.33 (d, J=8.1 Hz, 2H), 7.43 (dd, J=9.1, 1.9 Hz, 1H), 7.45 (s, 1H), 7.82-7.89 (m, 3H) and 7.90 (dd, J=1.8, 0.6 Hz, 1H). 19F NMR (376 MHz, CHLOROFORM-d): −58.1 (s, 3F).

2-Amino-3-(5-chloro-2H-benzotriazol-2-yl)-2-(hydroxymethyl)propionitrile was prepared using a procedure similar to that described in Example 1, part b, except starting from 1-(tert-butyldimethylsilyloxy)-3-(5-chloro-2H-benzotriazol-2-yl)-propan-2-one that was prepared as follows (the tert-butyldimethylsilyl protecting group was removed under the Strecker reaction conditions):

a. To a solution of 2-allyl-5-chloro-2H-benzotriazole (5.2 g), described in Example 85 part a, in a 10 to 1 mixture of THF and water (45 mL), was added a 50% solution of 4-methylmorpholine-N-oxide in water (7 mL) followed by a 4% solution of osmium tetroxide in water (2 mL). After stirring overnight at room temperature, the mixture was quenched with a 10% solution of sodium thiosulfate, extracted with ethyl acetate. The organic layer was dried over magnesium sulfate, filtered and concentrated under reduced pressure to give 3-(5-chloro-2H-benzotriazol-2-yl)-propane-1,2-diol (4.8 g, 79%) that was used directly into the next step without further purification.

b. To a solution of 3-(5-chloro-2H-benzotriazol-2-yl)-propane-1,2-diol (1.09 g) in DCM at 0° C. was added imidazole (0.65 g) and tert-butyldimethylsilyl chloride (0.8 g). After stirring overnight at room temperature, the mixture was diluted with DCM, washed with water, dried over magnesium sulfate, filtered and concentrated under reduced pressure to give a residue that was purified by chromatography ($SiO_2$, heptane/EA) to afford 1-(tert-butyldimethylsilyloxy)-3-(5-chloro-2H-benzotriazol-2-yl)-propan-2-ol (1.5 g, 85%). Rf=0.55 (1:1 EA/heptane).

c. 1-(tert-Butyldimethylsilyloxy)-3-(5-chloro-2H-benzotriazol-2-yl)-propan-2-ol (1.5 g) in DCM (20 mL) was reacted with Dess-Martin periodinane (2.1 g). After stirring overnight at room temperature, the mixture was concentrated under reduced pressure and purified by chromatography ($SiO_2$, heptane/EA) to afford 1-(tert-butyldimethylsilyloxy)-3-(5-chloro-2H-benzotriazol-2-yl)-propan-2-one (1.2 g).

Example 92

N-[2-(5-Chloro-2H-benzotriazol-2-yl)-1-cyano-1-(hydroxymethyl)ethyl]-4-trifluoromethylthiobenzamide (compound No 1.059)

Using a procedure similar to that described in Example 1, except using 2-amino-3-(5-chloro-2H-benzotriazol-2-yl)-2-(hydroxymethyl)propionitrile, described in Example 91, and 4-trifluoromethylbenzoyl chloride, the ester derivative 4-trifluoromethylbenzoic acid 2-amino-3-(5-chloro-2H-benzotriazol-2-yl)-2-cyanopropyl ester was isolated instead of the title compound. This ester was reacted with more 4-trifluoromethylbenzoyl chloride, subsequently treated with lithium hydroxide in methanol and purified by chromatography ($SiO_2$, heptane/EA) to afford the title compound as a solid. MS (ES): M/Z [M+H]=456. 1H NMR: (400 MHz, CHLOROFORM-d): 3.31 (br. s, 1H), 3.94 (d, J=11.8 Hz, 1H), 4.31 (d, J=11.7 Hz, 1H), 5.43 (d, J=14.0 Hz, 1H), 5.49 (d, J=13.9 Hz, 1H), 7.43 (dd, J=9.1, 1.9 Hz, 1H), 7.51 (s, 1H), 7.78 (d, J=8.3 Hz, 2H), 7.84-7.87 (m, 3H) and 7.90 (dd, J=1.8, 0.6 Hz, 1H). 19F NMR (376 MHz, CHLOROFORM-d): −42.2 (s, 3F).

Compounds of Examples 93 to 95 were prepared according to the following general reaction scheme:

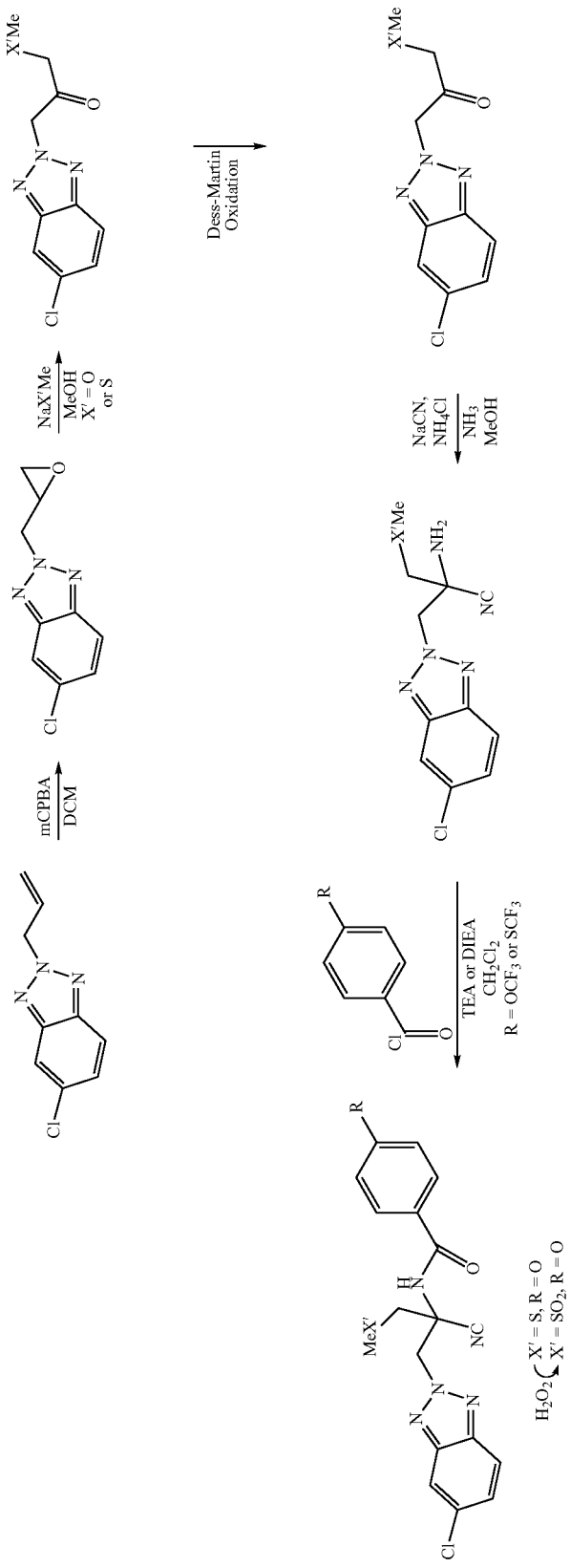

Final Product
V=C—H; W=C—Cl; X=C—H; Y=C—H;
Q=P=N;
$R_3=R_4=H$; a=1; $R_5=CH_2X'Me$; $R_6=H$;
Z=C(O); $R_7$=p-phenyl-R; R=$OCF_3$ or $SCF_3$

Example 93

N-[2-(5-Chloro-2H-benzotriazol-2-yl)-1-cyano-1-(methylthiomethyl)ethyl]-4-trifluoromethoxybenzamide (compound No 1.061)

Using a procedure similar to that described in Example 1, except using 2-amino-3-(5-chloro-2H-benzotriazol-2-yl)-2-(methylthiomethyl)propionitrile, the title compound was isolated as a solid. MS (ES): M/Z [M+H]=470. 1H NMR: (400 MHz, CHLOROFORM-d): 2.41 (s, 3H), 3.07 (d, J=14.7 Hz, 1H), 3.52 (d, J=14.6 Hz, 1H), 5.47 (dd, 2H), 7.34 (d, J=8.5 Hz, 2H), 7.41 (dd, J=9.1, 1.8 Hz, 2H) and 7.79-7.94 (m, 5H). 19F NMR (376 MHz, CHLOROFORM-d): −58.1 (s, 3F).

2-Amino-3-(5-chloro-2H-benzotriazol-2-yl)-2-(methylthiomethyl)propionitrile was prepared using a procedure similar to that described in Example 1, part b, except starting from 1-(5-chloro-2H-benzotriazol-2-yl)-3-(methylthio)propan-2-one that was prepared as follows:

a. To a solution of 2-allyl-5-chloro-2H-benzotriazole (5.0 g), described in Example 85 part a, in DCM (50 mL), was added meta-chloroperbenzoic acid (8.5 g, 55% pure). After stirring at room temperature for 24 hours, the mixture was filtered through a plug of basic alumina. The filtrate was concentrated under reduced pressure to give a residue that was purified by chromatography ($SiO_2$, heptane/EA) to afford 5-chloro-2-oxiranylmethyl-2H-benzotriazole (0.7 g). Rf=0.55 (2:1 EA/heptane).

b. To a solution of 5-chloro-2-oxiranylmethyl-2H-benzotriazole (306 mg) in methanol (5 mL) was added sodium thiomethoxide (307 mg). After stirring overnight at room temperature, the mixture was extracted with ethyl acetate. The organic layer was washed with water, dried over magnesium sulfate, filtered and concentrated under reduced pressure to give 1-(5-chloro-2H-benzotriazol-2-yl)-3-(methylthio)propan-2-ol that was used directly into the next oxidation step.

c. 1-(5-Chloro-2H-benzotriazol-2-yl)-3-(methylthio)propan-2-ol in DCM (5 mL) was reacted with Dess-Martin periodinane (720 mg). After stirring overnight at room temperature, the mixture was concentrated under reduced pressure and purified by chromatography ($SiO_2$, heptane/EA) to afford 1-(5-chloro-2H-benzotriazol-2-yl)-3-(methylthio)propan-2-one (149 mg, 40% in two steps).

Example 94

N-[2-(5-Chloro-2H-benzotriazol-2-yl)-1-cyano-1-(methoxymethyl)ethyl]-4-trifluoromethoxybenzamide (compound No 1.062)

Using a procedure similar to that described in Example 1, except using 2-amino-3-(5-chloro-2H-benzotriazol-2-yl)-2-(methoxymethyl)propionitrile, the title compound was isolated as a solid. MS (ES): M/Z [M+H]=454. 1H NMR: (400 MHz, CHLOROFORM-d): 3.52 (s, 3H), 3.71 (d, J=9.8 Hz, 1H), 4.12 (d, J=9.7 Hz, 1H), 5.37-5.47 (m, 2H), 7.33 (d, 2H), 7.40 (dd, J=9.1, 1.9 Hz, 1H), 7.48 (s, 1H) and 7.81-7.90 (m, 4H). 19F NMR (376 MHz, CHLOROFORM-d): −58.1 (s, 3F).

2-Amino-3-(5-chloro-2H-benzotriazol-2-yl)-2-(methoxymethyl)propionitrile was prepared using a procedure similar to that described in Example 1, part b, except starting from 1-(5-chloro-2H-benzotriazol-2-yl)-3-methoxypropan-2-one. 1-(5-Chloro-2H-benzotriazol-2-yl)-3-methoxypropan-2-one was prepared using a procedure similar to that described in Example 93, part a to c, except using sodium methoxide in part b.

Example 95

N-[2-(5-Chloro-2H-benzotriazol-2-yl)-1-cyano-1-(methanesulfonylmethyl)ethyl]-4-trifluoromethoxybenzamide (compound No 1.063)

To a solution of N-[2-(5-Chloro-2H-benzotriazol-2-yl)-1-cyano-1-(methylthiomethyl)ethyl]-4-trifluoromethoxybenzamide (36 mg) in a mixture of DCM and TFA was added 3 drops of hydrogen peroxide (30% weight in water). After stirring overnight at room temperature, the mixture was concentrated under reduced pressure to give the title compound as a solid. MS (ES): M/Z [M+H]=502. 1H NMR: (400 MHz, DMSO-$d_6$): 3.03 (s, 3H), 4.13 (d, J=5.0 Hz, 1H), 4.20 (d, J=5.1 Hz, 1H), 5.54 (s, 2H), 7.43 (dd, J=9.1, 1.9 Hz, H), 7.50 (d, J=8.7, 0.8 Hz, 2H), 7.68 (s, 1H), 7.81-7.90 (m, 2H), 7.91-8.00 (m, 2H), 8.05 (dd, J=1.9, 0.6 Hz, 1H) and 8.29 (s, 1H). 19F NMR (376 MHz, DMSO-$d_6$): −57.1 (s, 3F).

Compounds of Examples 96 to 104 were prepared according to the following general reaction scheme:

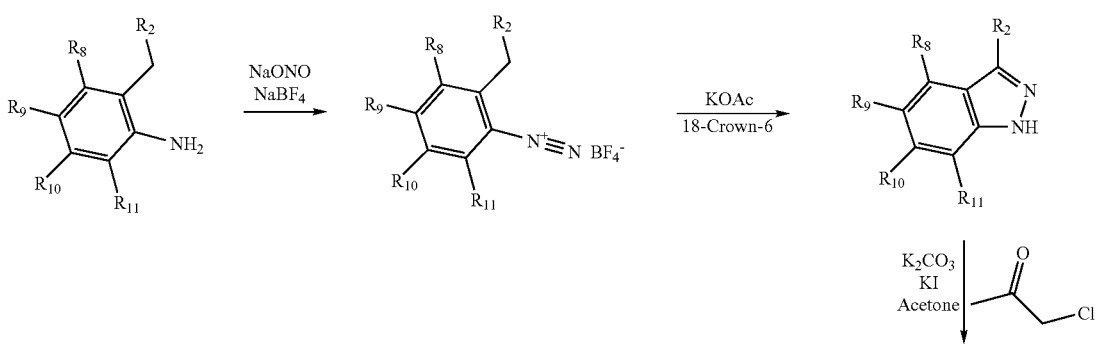

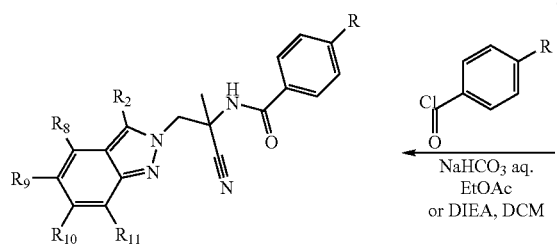 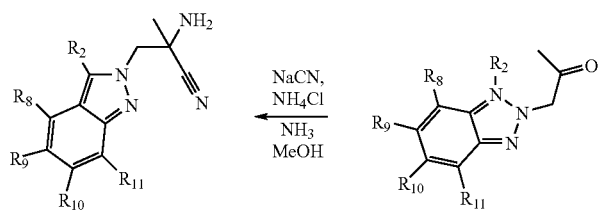

Final Product
V=C—R$_8$; W=C—R$_9$; X=C—R$_{10}$; Y=C—R$_{11}$;
Q=C—R$_2$; P=N;
R$_3$=R$_4$=H; a=1; R$_5$=CH$_3$; R$_6$=H;
Z=C(O); R$_7$=p-phenyl-R

Example 96

N-[1-Cyano-1-methyl-2-(5-nitro-2H-indazol-2-yl)ethyl]-4-trifluoromethoxybenzamide (compound No 2.001)

Using a procedure similar to that described in Example 1, except using 2-amino-2-methyl-3-(5-nitro-2H-indazol-2-yl)propionitrile (62 mg), the title compound was isolated as a white solid (100 mg, 91%). MS (ES): M/Z [M+H]=434. 1H NMR: (400 MHz, DMSO-d$_6$): 1.72 (s, 3H), 5.21 (q, J=13.7 Hz, 2H), 7.53 (d, J=8.2 Hz, 2H), 7.81 (d, J=9.5 Hz, 1H), 7.97 (d, J=8.8 Hz, 2H), 8.01 (dd, J=2.2 Hz, 1H), 8.82 (s, 1H), 8.94 (d, J=2.0 Hz, 1H) and 8.99 (s, 1H). 19F NMR (376 MHz, DMSO-d$_6$): −57.1 (s, 3F).

2-Amino-2-methyl-3-(5-nitro-2H-indazol-2-yl)propionitrile (444 mg) was prepared using a procedure similar to that described in Example 1, part a and b, except starting from commercially available 5-nitro-1H-indazole (7 g), one-half molar equivalent of potassium carbonate (3.1 g), one equivalent of potassium iodide (9.2 g) and heating the reaction mixture to reflux in acetone to isolate desired 1-(5-nitro-2H-indazol-2-yl)propan-2-one (890 mg, 9.5%) along with 1-(5-nitro-1H-indazol-1-yl)propan-2-one in part a.

Example 97

N-[1-Cyano-1-methyl-2-(5-nitro-2H-indazol-2-yl)ethyl]-4-trifluoromethylthiobenzamide (compound No 2.002)

Using a procedure similar to that described in Example 1, except using 2-amino-2-methyl-3-(5-nitro-2H-indazol-2-yl)propionitrile (62 mg, described in Example 96) and 4-trifluoromethylthiobenzoyl chloride, the title compound was isolated as a white solid (96 mg, 84%). MS (ES): M/Z [M+H] = 450. 1H NMR: (400 MHz, DMSO-d$_6$): 1.72 (s, 3H), 5.22 (q, 2H), 7.81 (d, J=9.5 Hz, 1H), 7.86-7.90 (m, 2H), 7.92-7.97 (m, 2H), 8.00-8.05 (m, 1H), 8.83 (s, 1H), 8.95 (d, J=1.9 Hz, 1H) and 9.07 (s, 1H). 19F NMR (376 MHz, DMSO-d$_6$): −41.9 (s, 3F).

Example 98

N-[1-Cyano-2-(5,7-dichloro-2H-indazol-2-yl)-1-methylethyl]-4-trifluoromethoxybenzamide (compound No 2.003)

Using a procedure similar to that described in Example 1, except using 2-amino-3-(5,7-dichloro-2H-indazol-2-yl)-2-methylpropionitrile (60 mg), the title compound was isolated as a white solid (80 mg, 78%). MS (ES): M/Z [M+H]=457. 1H NMR: (400 MHz, DMSO-d$_6$): 1.70 (s, 3H), 5.11 (d, 1H), 5.23 (d, 1H), 7.51 (d, J=8.3 Hz, 2H), 7.89 (d, J=1.6 Hz, 1H), 7.97 (d, J=8.8 Hz, 2H), 8.53 (s, 1H), 8.94 (d, J=2.0 Hz, 1H) and 8.95 (s, 1H). 19F NMR (376 MHz, DMSO-d$_6$): −57.1 (s, 3F).

2-Amino-3-(5,7-dichloro-2H-indazol-2-yl)-2-methylpropionitrile was prepared using a procedure similar to that described in Example 1, part a and b, except starting from 5,7-dichloro-1H-indazole (3 g) and heating the reaction mixture to reflux in acetone to isolate desired 1-(5,7-dichloro-2H-indazol-2-yl)propan-2-one (1.7 g, 44%) along with 1-(5,7-dichloro-1H-indazol-1-yl)propan-2-one (1.2 g, 30%) in part a.

5,7-Dichloro-1H-indazole was prepared as follows by adapting procedures described in the literature for the preparation of indazoles substituted on the six-membered ring. See for example, R. A. Bartsch, et al. *J. Heterocycl. Chem.* 1984, 21, 1063 and P. Schumann et al, *Bioorganic & Medicinal Chemistry Letters,* 2001, 11, 1153.

a. To a suspension of 2,4-dichloro-6-methylaniline (5 g) in a mixture of hydrochloric acid (7.5 mL) and water (7.5 mL), was slowly added at 0° C. a solution of sodium nitrite (2 g) in a minimal amount of water. After all solid starting materials disappeared to yield a yellow mixture; a solution of sodium tetrafluoroborate (4.4 g) in water (10 mL) was added. After stirring 45 minutes at 0° C., the solids that formed were filtered, washed with chilled methanol, washed with diethyl ether and dried under vacuum to yield 2,4-dichloro-6-methylbenzenediazonium tetrafluoroborate (5.7 g).

b. A mixture of 2,4-dichloro-6-methylbenzenediazonium tetrafluoroborate (5.5 g), 18-crown-6 (271 mg) and potassium acetate (4 g) were stirred in chloroform (60 mL) for 1.5 hours at room temperature. The resulting crude mixture was extracted with ethyl acetate, washed with brine, dried over anhydrous sodium sulfate, filtered and concentrated under reduced pressure to give 5,7-dichloro-1H-indazole as a pale brown solid (3 g).

Example 99

N-[1-Cyano-2-(5,7-dichloro-2H-indazol-2-yl)-1-methylethyl]-4-trifluoromethylthiobenzamide (compound No 2.005)

Using a procedure similar to that described in Example 1, except using 2-amino-2-methyl-3-(5,7-dichloro-2H-indazol-2-yl)propionitrile (60 mg, described in Example 98) and 4-trifluoromethylthiobenzoyl chloride, the title compound was isolated as a white solid (80 mg, 76%). MS (ES): M/Z [M+H]=473. 1H NMR: (400 MHz, DMSO-$d_6$): 1.70 (s, 3H), 5.11 (d, 1H), 5.25 (d, 1H), 7.48 (s, 1H), 7.84-7.91 (m, 3H), 7.95 (d, 2H), 8.54 (s, 1H) and 9.03 (s, 1H). 19F NMR (376 MHz, DMSO-$d_6$): −42.0 (s, 3F).

Example 100

N-[1-Cyano-2-(5,7-dichloro-2H-indazol-2-yl)-1-methylethyl]-4-phenoxybenzamide (compound No 2.004)

Using a procedure similar to that described in Example 1, except using 2-amino-2-methyl-3-(5,7-dichloro-2H-indazol-2-yl)propionitrile (60 mg, described in Example 98) and 4-phenoxybenzoyl chloride, the title compound was isolated as a white solid (90 mg, 87%). MS (ES): M/Z [M+H]=465. 1H NMR: (400 MHz, DMSO-$d_6$): 1.71 (s, 3H), 5.12 (d, 1H), 5.21 (d, 1H), 7.04-7.13 (m, 4H), 7.23 (t, J=7.4 Hz, 1H), 7.41-7.51 (m, 3H), 7.85-7.92 (m, 3H), 8.52 (s, 1H) and 8.80 (s, 1H).

Example 101

N-[2-(5-Chloro-7-methyl-2H-indazol-2-yl)-1-cyano-1-methylethyl]-4-trifluoromethoxybenzamide (compound No 2.006)

Using a procedure similar to that described in Example 1, except using 2-amino-3-(5-chloro-7-methyl-2H-indazol-2-yl)-2-methylpropionitrile (58 mg), the title compound was isolated as a white solid (73 mg, 72%). MS (ES): M/Z [M+H]=437. 1H NMR: (400 MHz, DMSO-$d_6$): 1.69 (s, 3H), 2.39 (s, 3H), 5.05 (d, 1H), 5.19 (d, J=13.7 Hz, 1H), 7.03 (s, 1H), 7.52 (d, J=8.2 Hz, 2H), 7.65 (d, J=0.8 Hz, 1H), 7.97 (d, J=8.7 Hz, 2H), 8.36 (s, 1H) and 8.89 (s, 1H). 19F NMR (376 MHz, DMSO-$d_6$): −57.1 (s, 3F).

2-Amino-3-(5-chloro-7-methyl-2H-indazol-2-yl)-2-methylpropionitrile was prepared using a procedure similar to that described in Example 1, part a and b, except starting from 5-chloro-7-methyl-1H-indazole (6.9 g) and heating the reaction mixture to reflux in acetone for 1.5 days to afford 1-(5-chloro-7-methyl-2H-indazol-2-yl)propan-2-one (1.9 g) in part a.

5-Chloro-7-methyl-1H-indazole was prepared using a procedure similar to that described in Example 98, part a and b, except starting from 4-chloro-2,6-dimethylaniline (5 g).

Example 102

N-[2-(5-Chloro-7-methyl-2H-indazol-2-yl)-1-cyano-1-methylethyl]-4-trifluoromethylthiobenzamide (compound No 2.007)

Using a procedure similar to that described in Example 1, except using 2-amino-2-methyl-3-(5-chloro-7-methyl-2H-indazol-2-yl)propionitrile (58 mg, described in Example 101) and 4-trifluoromethylthiobenzoyl chloride, the title compound was isolated as a white solid (77 mg, 73%). MS (ES): M/Z [M+H]=453. 1H NMR: (400 MHz, DMSO-$d_6$): 1.69 (s, 3H), 2.38 (s, 3H), 5.05 (d, 1H), 5.21 (d, 1H), 7.03 (s, 1H), 7.66 (s, 1H), 7.87 (d, 2H), 7.94 (d, 2H), 8.37 (s, 1H) and 8.97 (s, 1H). 19F NMR (376 MHz, DMSO-$d_6$): −42.0 (s, 3F).

Example 103

N-[1-Cyano-2-(5,7-dichloro-3-methyl-2H-indazol-2-yl)-1-methylethyl]-4-trifluoromethoxybenzamide (compound No 2.010)

Using a procedure similar to that described in Example 1, except using 2-amino-3-(5,7-dichloro-3-methyl-2H-indazol-2-yl)-2-methylpropionitrile (40 mg), the title compound was isolated as a white solid (60 mg, 90%). MS (ES): M/Z [M+H]=471. 1H NMR: (400 MHz, DMSO-$d_6$): 1.82 (s, 3H), 2.73 (s, 3H), 4.98 (d, 1H), 5.08 (d, J=13.7 Hz, 1H), 7.45 (dd, 1H), 7.52 (d, 2H), 7.91 (d, 1H), 8.00-8.04 (m, 2H) and 9.09 (s, 1H). 19F NMR (376 MHz, DMSO-$d_6$): −57.1 (s, 3F).

2-Amino-3-(5,7-dichloro-3-methyl-2H-indazol-2-yl)-2-methylpropionitrile was prepared using a procedure similar to that described in Example 1, part a and b, except starting from 5,7-dichloro-3-methyl-1H-indazole (400 mg) and heating the reaction mixture to reflux in acetone to afford 1-(5,7-dichloro-3-methyl-2H-indazol-2-yl)propan-2-one (140 mg) in part a.

5,7-Dichloro-3-methyl-1H-indazole was prepared using a procedure similar to that described in Example 98, part a and b, except starting from 2,4-dichloro-6-ethylaniline (2.9 g) that was prepared by chlorination of 6-ethylaniline (10 g) with N-chlorosuccinimide (22 g) in acetonitrile (80 mL).

Example 104

N-[2-(5,7-Dichloro-3-methyl-2H-indazol-2-yl)-1-cyano-1-methylethyl]-4-trifluoromethylthiobenzamide (compound No 2.011)

Using a procedure similar to that described in Example 1, except using 2-amino-2-methyl-3-(5,7-dichloro-3-methyl-2H-indazol-2-yl)propionitrile (40 mg, described in Example 103) and 4-trifluoromethylthiobenzoyl chloride, the title compound was isolated as a white solid (64 mg, 92%). MS (ES): M/Z [M+H]=487. 1H NMR: (400 MHz, DMSO-$d_6$): 1.83 (s, 3H), 2.73 (s, 3H), 5.00 (d, 1H), 5.06 (d, 1H), 7.45 (dd, J=1.6 Hz, 1H), 7.87 (d, J=8.2 Hz, 2H), 7.91 (dd, J=1.6 Hz, 1H), 8.00 (d, J=8.4 Hz, 2H) and 9.16 (s, 1H). 19F NMR (376 MHz, DMSO-$d_6$): −42.0 (s, 3F).

Compounds of Examples 105 to 131 were prepared according to the following general reaction scheme:

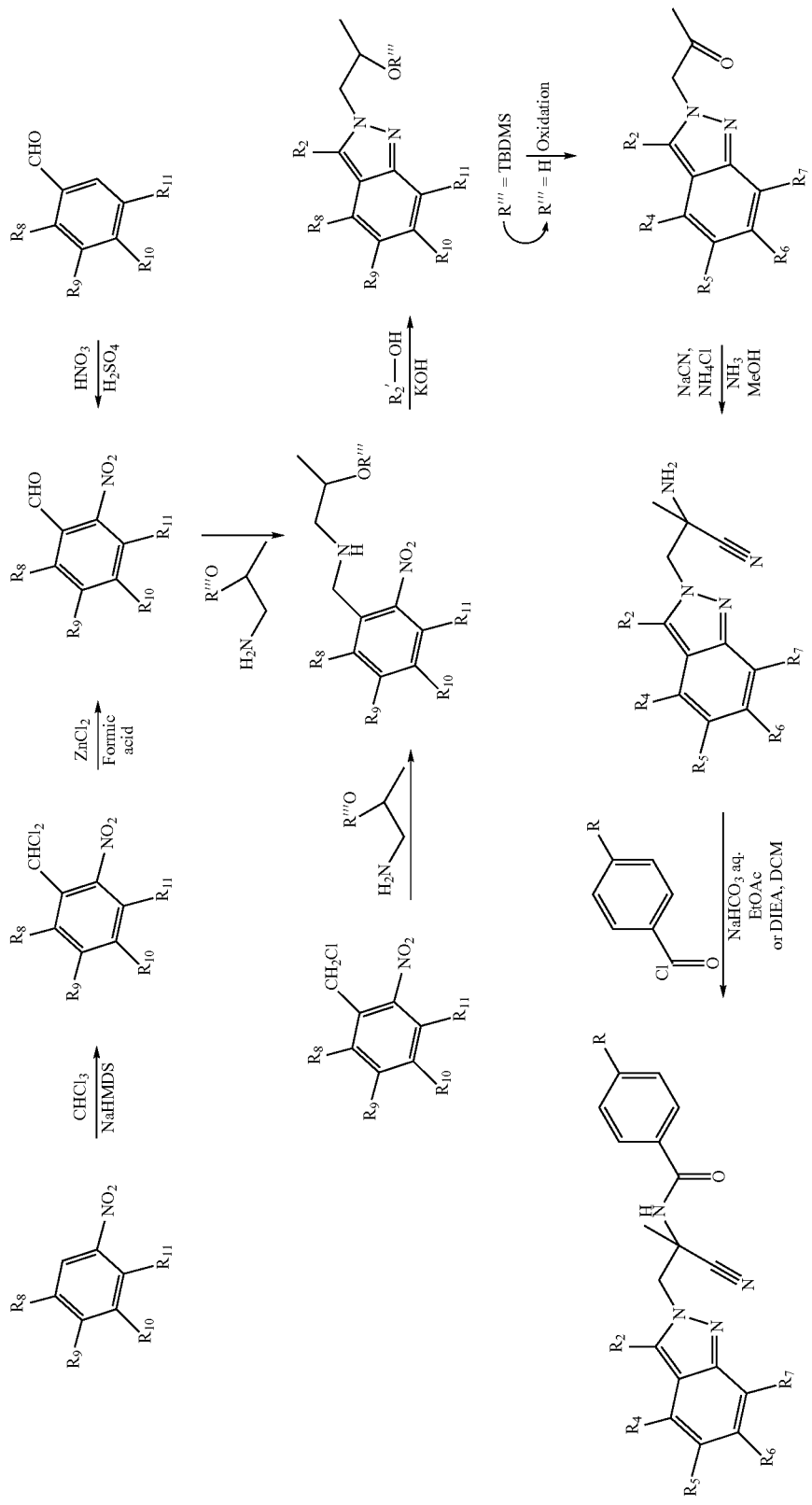

Final Product
V=C—R$_8$; W=C—R$_9$; X=C—R$_{10}$; Y=C—R$_{11}$;
Q=C—R$_2$; P=N;
R$_2$=O—C$_1$-C$_4$-alkyl, O—C$_1$-C$_4$-alkyl-O—C$_1$-C$_4$-alkyl, O—C$_1$-C$_4$—NH—C$_1$-C$_4$-alkyl, O—C$_1$-C$_4$—N(C$_1$-C$_4$-alkyl)$_2$;
R$_3$=R$_4$=H; a=1; R$_5$=CH$_3$; R$_6$=H;
Z=C(O); R$_7$=p-phenyl-R

Example 105

N-[2-(6-Chloro-3-methoxy-2H-indazol-2-yl)-1-cyano-1-methylethyl]-4-trifluoromethoxybenzamide (compound No 2.008)

Using a procedure similar to that described in Example 1, except using 2-amino-3-(6-chloro-3-methoxy-2H-indazol-2-yl)-2-methylpropionitrile (40 mg), the title compound was isolated as a white solid (60 mg, 88%). MS (ES): M/Z [M+H]=453. 1H NMR: (400 MHz, DMSO-d$_6$): 1.71 (s, 3H), 4.19 (s, 3H), 4.76 (d, 1H), 4.88 (d, 1H), 6.87 (dd, J=9.0, 1.7 Hz, 1H), 7.50-7.55 (m, 3H), 7.89 (d, J=9.1 Hz, 1H), 7.97 (d, J=8.8 Hz, 2H) and 8.92 (s, 1H). 19F NMR (376 MHz, DMSO-d$_6$): −57.1 (s, 3F).

2-Amino-3-(6-chloro-3-methoxy-2H-indazol-2-yl)-2-methylpropionitrile (475 mg, 93%) was prepared using a procedure similar to that described in Example 1, part b, except starting from 1-(6-chloro-3-methoxy-2H-indazol-2-yl)propan-2-one (462 mg) that was prepared as follows:

a. To a solution of 4-chloro-2-nitrobenzaldehyde (4 g) in dioxane (35 mL), was added 2-(tert-butyldimethylsilanyloxy)propylamine (6.1 g, 1.5 equivalent) in methanol (15 mL) followed by acid acetic (1.9 mL) in methanol (15 mL). After overnight stirring at room temperature, a molar solution of sodium cyanoborohydride in THF (22 mL) was added. After 30 minutes, the reaction mixture was quenched with water and extracted with ethyl acetate. The organic phase was dried over anhydrous magnesium sulfate, filtered and concentrated under reduced pressure to yield a residue that was purified by chromatography (SiO$_2$, heptane/EA) to afford [2-(tert-butyldimethylsilanyloxy)propyl]-(4-chloro-2-nitrobenzyl)amine (5.9 g, 77%). 2-(tert-Butyldimethylsilanyloxy)propylamine was obtained by reacting 1-aminopropan-2-ol with 2-tert-butyldimethylsilyl chloride and imidazole in DCM for two hours at room temperature followed by an aqueous work-up.

b. Potassium hydroxide (0.72 g) was added to a stirred solution of [2-(tert-butyldimethylsilanyloxy)propyl]-(4-chloro-2-nitrobenzyl)amine (3 g) in methanol (30 mL). After overnight stirring at 60° C., the reaction mixture was quenched with water and extracted with ethyl acetate. The organic phase was dried over anhydrous magnesium sulfate, filtered and concentrated under reduced pressure to yield a residue that was purified by chromatography (SiO$_2$, heptane/EA) to afford 2-[2-(tert-butyldimethylsilanyloxy)propyl]-6-chloro-3-methoxy-2H-indazole (2.2 g, 87%).

c. To a solution of 2-[2-(tert-butyldimethylsilanyloxy)propyl]-6-chloro-3-methoxy-2H-indazole (1 g) in THF (35 mL), was added a solution of tert-butylammonium fluoride (1M in THF, 3 mL). After stirring at room temperature for 1.5 hours, the reaction mixture was quenched with water and extracted with ethyl acetate. The organic phase was dried over anhydrous magnesium sulfate, filtered and concentrated under reduced pressure to afford quantitatively 1-(6-chloro-3-methoxy-2H-indazol-2-yl)-propan-2-ol as a solid (0.85 g).

d. A solution of dimethyl sulfoxide (1 mL) in DCM was added at −78° C. to a solution of oxalyl chloride (0.6 mL) in DCM. After stirring for 30 minutes at −78° C., a solution of 1-(6-chloro-3-methoxy-2H-indazol-2-yl)-propan-2-ol (0.85 g) in DCM was added. After stirring for 30 minutes at −78° C., diisopropylethylamine (3.4 mL) was added and after 30 additional minutes, the reaction mixture was allowed to warm to room temperature over 1.5 hours before being concentrated down under reduced pressure. The reaction mixture residue was taken into a mixture of ethyl acetate and brine. The organic phase was dried over anhydrous magnesium sulfate, filtered and concentrated under reduced pressure to yield a residue that was purified by chromatography (SiO$_2$, heptane/EA) to afford 1-(6-chloro-3-methoxy-2H-indazol-2-yl)-propan-2-one as a solid (0.46 g, 55%).

Alternatively, [2-(tert-butyldimethylsilanyloxy)propyl]-(4-chloro-2-nitrobenzyl)amine described in part a, was prepared as follows:

e. To a suspension of 2-(tert-butyldimethylsilanyloxy)propylamine (9 equivalents) in THF was slowly added 4-chloro-2-nitrobenzyl chloride in THF under vigorous stirring. After overnight stirring at room temperature, the mixture was concentrated under reduced pressure to give a residue that was triturated in diethyl ether and filtered. The ether fractions were collected and concentrated under reduced pressure to yield a residue that was purified by chromatography (SiO$_2$, heptane/EA) to afford [2-(tert-butyldimethylsilanyloxy)propyl]-(4-chloro-2-nitrobenzyl)amine.

Example 106

N-[2-(6-Chloro-3-methoxy-2H-indazol-2-yl)-1-cyano-1-methylethyl]-4-trifluoromethylthiobenzamide (compound No 2.009)

Using a procedure similar to that described in Example 1, except using 2-amino-3-(6-chloro-3-methoxy-2H-indazol-2-yl)-2-methylpropionitrile (40 mg, described in Example 105) and 4-trifluoromethylthiobenzoyl chloride, the title compound was isolated as a white solid (65 mg, 91%). MS (ES): M/Z [M+H]=469. 1H NMR: (400 MHz, DMSO-d$_6$): 1.71 (s, 3H), 4.20 (s, 3H), 4.76 (d, 1H), 4.89 (d, 1H), 6.87 (dd, J=9.0, 1.7 Hz, 1H), 7.51 (s, 1H), 7.86-7.91 (m, 3H), 7.97 (d, 2H) and 9.01 (s, 1H). 19F NMR (376 MHz, DMSO-d$_6$): −41.9 (s, 3F).

Example 107

N-[2-(5-Chloro-3-methoxy-2H-indazol-2-yl)-1-cyano-1-methylethyl]-4-trifluoromethoxybenzamide (compound No 2.012)

Using a procedure similar to that described in Example 1, except using 2-amino-3-(5-chloro-3-methoxy-2H-indazol-2- yl)-2-methylpropionitrile (57 mg), the title compound was isolated as a white solid (84 mg, 86%). MS (ES): M/Z [M+H]=453. 1H NMR: (400 MHz, DMSO-$d_6$): 1.70 (s, 3H), 4.18 (s, 3H), 4.77 (d, 1H), 4.90 (d, 1H), 7.16 (dd, J=9.3, 1.6 Hz, 1H), 7.46 (d, J=9.2 Hz, 1H), 7.52 (d, J=8.3 Hz, 2H), 7.94 (d, J=0.9 Hz, 1H), 7.98 (d, J=8.7 Hz, 2H) and 8.92 (s, 1H). 19F NMR (376 MHz, DMSO-$d_6$): −57.1 (s, 3F).

2-Amino-3-(5-chloro-3-methoxy-2H-indazol-2-yl)-2-methylpropionitrile (114 mg, 73%) was prepared using a procedure similar to that described in Example 1, part b, except starting from 1-(5-chloro-3-methoxy-2H-indazol-2-yl)propan-2-one (140 mg). 1-(5-chloro-3-methoxy-2H-indazol-2-yl)propan-2-one was prepared using a procedure similar to that described in Example 105 part a to d except using 5-chloro-2-nitrobenzaldehyde (2 g) and sodium triacetoxyborohydride (3.4 g) in part a to yield [2-(tert-butyldimethylsilanyloxy)propyl]-(5-chloro-2-nitrobenzyl)amine (2.2 g, 56%).

Example 108

N-[2-(5-Chloro-3-methoxy-2H-indazol-2-yl)-1-cyano-1-methylethyl]-4-trifluoromethylthiobenzamide (compound No 2.013)

Using a procedure similar to that described in Example 1, except using 2-amino-3-(5-chloro-3-methoxy-2H-indazol-2-yl)-2-methylpropionitrile (57 mg, described in Example 107) and 4-trifluoromethylthiobenzoyl chloride, the title compound was isolated as a white solid (96 mg, 95%). MS (ES): M/Z [M+H]=469. 1H NMR: (400 MHz, DMSO-$d_6$): 1.70 (s, 3H), 4.19 (s, 3H), 4.77 (d, 1H), 4.90 (d, 1H), 7.16 (d, J=9.2 Hz, 1H), 7.46 (d, J=9.4 Hz, 1H), 7.87 (d, J=8.0 Hz, 2H), 7.92-8.01 (m, 3H) and 9.00 (s, 1H). 19F NMR (376 MHz, DMSO-$d_6$): −41.9 (s, 3F).

Example 109

N-[2-(5-Chloro-3-ethoxy-2H-indazol-2-yl)-1-cyano-1-methylethyl]-4-trifluoromethoxybenzamide (compound No 2.014)

Using a procedure similar to that described in Example 1, except using 2-amino-3-(5-chloro-3-ethoxy-2H-indazol-2-yl)-2-methylpropionitrile (52 mg), the title compound was isolated as a white solid (85 mg, 97%). MS (ES): M/Z [M+H]=467. 1H NMR: (400 MHz, DMSO-$d_6$): 1.27 (t, J=7.0 Hz, 3H), 1.71 (s, 3H), 4.52 (q, J=6.9 Hz, 2H), 4.78 (d, 1H), 4.92 (d, 1H), 7.16 (dd, J=9.3, 2.0 Hz, 1H), 7.47 (d, J=9.3 Hz, 1H), 7.52 (d, J=8.2 Hz, 2H), 7.87 (d, J=1.5 Hz, 1H), 7.98 (d, J=8.8 Hz, 2H) and 8.91 (s, 1H). 19F NMR (376 MHz, DMSO-$d_6$): −57.1 (s, 3F).

2-Amino-3-(5-chloro-3-ethoxy-2H-indazol-2-yl)-2-methylpropionitrile (104 mg, 72%) was prepared using a procedure similar to that described in Example 1, part b, except starting from 1-(5-chloro-3-ethoxy-2H-indazol-2-yl)propan-2-one (131 mg). 1-(5-chloro-3-ethoxy-2H-indazol-2-yl)propan-2-one was prepared using a procedure similar to that described in Example 105 part a to d except using 5-chloro-2-nitrobenzaldehyde (2 g) and sodium triacetoxyborohydride (3.4 g) in part a and using ethanol instead of methanol in part b.

Example 110

N-[2-(5-Chloro-3-ethoxy-2H-indazol-2-yl)-1-cyano-1-methylethyl]-4-trifluoromethylthiobenzamide (compound No 2.015)

Using a procedure similar to that described in Example 1, except using 2-amino-3-(5-chloro-3-ethoxy-2H-indazol-2-yl)-2-methylpropionitrile (52 mg, described in Example 109) and 4-trifluoromethylthiobenzoyl chloride, the title compound was isolated as a white solid (83 mg, 93%). MS (ES): M/Z [M+H]=483. 1H NMR: (400 MHz, DMSO-$d_6$): 1.26 (t, J=7.0 Hz, 3H), 1.71 (s, 3H), 4.52 (q, J=7.0 Hz, 2H), 4.78 (d, 1H), 4.93 (d, 1H), 7.16 (dd, J=9.3, 1.9 Hz, 1H), 7.47 (d, J=9.3 Hz, 1H), 7.85-7.89 (m, 3H), 7.96 (d, J=8.8 Hz, 2H) and 8.99 (s, 1H). 19F NMR (376 MHz, DMSO-$d_6$): −42.0 (s, 3F).

Example 111

N-[1-Cyano-2-(3-methoxy-2H-indazol-2-yl)-1-methylethyl]-4-trifluoromethoxybenzamide (compound No 2.016)

Using a procedure similar to that described in Example 1, except using 2-amino-3-(3-methoxy-2H-indazol-2-yl)-2-methylpropionitrile (52 mg), the title compound was isolated as a white solid (140 mg, 77%). MS (ES): M/Z [M+H]=419. 1H NMR: (400 MHz, DMSO-$d_6$): 1.72 (s, 3H), 4.19 (s, 3H), 4.77 (d, 1H), 4.90 (d, 1H), 6.88 (d, J=1.2 Hz, 1H), 7.19 (d, J=6.7 Hz, 1H), 7.41 (d, J=8.9 Hz, 1H), 7.53 (d, J=8.2 Hz, 2H), 7.82 (d, J=8.6 Hz, 1H), 8.00 (d, J=8.7 Hz, 2H) and 8.95 (s, 1H). 19F NMR (376 MHz, DMSO-$d_6$): −57.1 (s, 3F).

2-Amino-3-(3-methoxy-2H-indazol-2-yl)-2-methylpropionitrile (130 mg, 83%) was prepared using a procedure similar to that described in Example 1, part b, except starting from 1-(3-methoxy-2H-indazol-2-yl)propan-2-one (138 mg). 1-(3-methoxy-2H-indazol-2-yl)propan-2-one was prepared using a procedure similar to that described in Example 105 part a to d except starting from 2-nitrobenzaldehyde (2.5 g) in part a.

Example 112

N-{2-[6-Chloro-3-(2-methoxyethoxy)-2H-indazol-2-yl]-1-cyano-1-methylethyl}-4-trifluoromethoxybenzamide (compound No 2.017)

Using a procedure similar to that described in Example 1, except using 2-amino-3-[6-chloro-3-(2-methoxyethoxy)-2H-indazol-2-yl]-2-methylpropionitrile (60 mg), the title compound was isolated as a white solid (41 mg, 43%). MS (ES): M/Z [M+H]=497. 1H NMR: (400 MHz, DMSO-$d_6$): 1.70 (s, 3H), 3.27 (s, 3H), 3.61 (dd, J=5.2, 3.7 Hz, 2H), 4.58 (dd, J=4.9, 3.9 Hz, 2H), 4.79 (d, 1H), 4.92 (d, 1H), 6.90 (dd, J=9.0, 1.8 Hz, 1H), 7.53-7.55 (m, 3H), 7.82 (d, J=9.1 Hz, 1H), 7.98 (d, 2H) and 8.93 (s, 1H). 19F NMR (376 MHz, DMSO-$d_6$): −57.1 (s, 3F).

2-Amino-3-[6-chloro-3-(2-methoxyethoxy)-2H-indazol-2-yl]-2-methylpropionitrile (60 mg, 61%) was prepared using a procedure similar to that described in Example 1, part b, except starting from 1-[6-chloro-3-(2-methoxyethoxy)-2H-indazol-2-yl]propan-2-one (90 mg). 1-[6-Chloro-3-(2-methoxyethoxy)-2H-indazol-2-yl]propan-2-one was prepared using a procedure similar to that described in Example 105 part a to d except using 2-methoxyethanol instead of methanol in part b.

Example 113

N-{2-[6-Chloro-3-(2-dimethylaminoethoxy)-2H-indazol-2-yl]-1-cyano-1-methylethyl}-4-trifluoromethoxybenzamide (compound No 2.018)

Using a procedure similar to that described in Example 1, except using 2-amino-3-[6-chloro-3-(2-dimethylaminoethoxy)-2H-indazol-2-yl]-2-methylpropionitrile (60 mg), the title compound was isolated as a white solid (44 mg, 46%). MS (ES): M/Z [M+H]=510. 1H NMR: (400 MHz, CHLOROFORM-d): 1.90 (s, 3H), 2.43 (s, 6H), 2.85 (dd, J=5.8, 4.8 Hz, 1H), 2.95 (dd, J=6.9, 4.8 Hz, 1H), 4.52 (d, J=14.2 Hz, 1H), 4.69 (ddd, J=10.3, 5.7, 4.9 Hz, 1H), 4.80 (ddd, J=10.2, 6.9, 4.7 Hz, 1H), 4.90 (d, J=14.2 Hz, 1H), 6.92 (dd, J=9.1, 1.7 Hz, 1H), 7.32 (d, J=8.0 Hz, 2H), 7.47 (dd, J=1.6, 0.6 Hz, 1H), 7.64 (dd, J=9.0, 0.6 Hz, 1H) and 9.00 (s, 1H). 19F NMR (376 MHz, CHLOROFORM-d): −58.1 (s, 3F).

2-Amino-3-[6-chloro-3-(2-dimethylaminoethoxy)-2H-indazol-2-yl]-2-methylpropionitrile (127 mg, 78%) was prepared using a procedure similar to that described in Example 1, part b, except starting from 1-[6-chloro-3-(2-dimethylaminoethoxy)-2H-indazol-2-yl]propan-2-one (150 mg). 1-[6-Chloro-3-(2-dimethylaminoethoxy)-2H-indazol-2-yl]propan-2-one was prepared using a procedure similar to that described in Example 105 part a to d except using 2-dimethylaminoethanol instead of methanol in part b.

Example 114

N-[1-Cyano-2-(5,7-dichloro-3-methoxy-2H-indazol-2-yl)-1-methylethyl]-4-trifluoromethoxybenzamide (compound No 2.020)

Using a procedure similar to that described in Example 1, except using 2-amino-3-(5,7-dichloro-3-methoxy-2H-indazol-2-yl)-2-methylpropionitrile (196 mg), the title compound was isolated as a white solid (147 mg, 46%). MS (ES): M/Z [M+H]=487. 1H NMR: (400 MHz, CHLOROFORM-d): 1.96 (s, 3H), 4.42 (s, 3H), 4.53 (d, J=14.2 Hz, 1H), 4.88 (d, J=14.2 Hz, 1H), 7.31 (d, 2H), 7.35 (d, J=1.7 Hz, 1H), 7.68 (d, J=1.7 Hz, 1H), 8.01-8.10 (m, 2H) and 9.13 (s, 1H). 19F NMR (376 MHz, CHLOROFORM-d): −58.1 (s, 3F).

2-Amino-3-(5,7-dichloro-3-methoxy-2H-indazol-2-yl)-2-methylpropionitrile was prepared using a procedure similar to that described in Example 1, part b, except starting from 1-(5,7-dichloro-3-methoxy-2H-indazol-2-yl)propan-2-one. 1-(4,6-dichloro-3-methoxy-2H-indazol-2-yl)propan-2-one was prepared using a procedure similar to that described in Example 105 part a to d except using 3,5-dichloro-2-nitrobenzaldehyde (2.1 g) and decaborane (0.41 g) in part a to yield [2-(tert-butyldimethylsilanyloxy)propyl]-(3,5-dichloro-2-nitrobenzyl)amine (1.2 g, 32%). 3,5-Dichloro-2-nitrobenzaldehyde (2.2 g, 79%) was prepared by nitration of 3,5-dichlorobenzaldehyde (2.2 g) in a mixture of nitric acid (1.5 mL) and sulfuric acid (8 mL) at 0° C. for 30 minutes.

Example 115

N-[1-Cyano-2-(5,7-dichloro-3-methoxy-2H-indazol-2-yl)-1-methylethyl]-4-trifluoromethylthiobenzamide (compound No 2.019)

Using a procedure similar to that described in Example 1, except using 2-amino-3-(5,7-dichloro-3-methoxy-2H-indazol-2-yl)-2-methylpropionitrile (181 mg, described in Example 114) and 4-trifluoromethylthiobenzoyl chloride, the title compound was isolated as a white solid (161 mg, 51%). MS (ES): M/Z [M+H]=503. 1H NMR: (400 MHz, CHLOROFORM-d): 1.96 (s, 3H), 4.42 (s, 3H), 4.53 (d, J=14.2 Hz, 1H), 4.88 (d, J=14.2 Hz, 1H), 7.35 (d, J=1.7 Hz, 1H), 7.68 (d, J=1.7 Hz, 1H), 7.75 (d, J=8.2 Hz, 2H), 8.02-8.09 (m, 2H) and 9.21 (s, 1H). 19F NMR (376 MHz, CHLOROFORM-d): −42.4 (s, 3F).

Example 116

N-[1-Cyano-2-(4,6-dichloro-3-methoxy-2H-indazol-2-yl)-1-methylethyl]-4-trifluoromethoxybenzamide (compound No 2.021)

Using a procedure similar to that described in Example 1, except using 2-amino-3-(4,6-dichloro-3-methoxy-2H-indazol-2-yl)-2-methylpropionitrile (30 mg), the title compound was isolated as a white solid (45 mg, 92%). MS (ES): M/Z [M+H]=487. 1H NMR: (400 MHz, DMSO-$d_6$): 1.75 (s, 3H), 4.12 (s, 3H), 4.94 (s, 2H), 7.17 (d, J=1.3 Hz, 1H), 7.53 (d, J=8.2 Hz, 2H), 7.63 (d, J=1.2 Hz, 1H), 7.98 (d, J=8.7 Hz, 2H) and 8.95 (s, 1H). 19F NMR (376 MHz, DMSO-$d_6$): −57.1 (s, 3F).

2-Amino-3-(4,6-dichloro-3-methoxy-2H-indazol-2-yl)-2-methylpropionitrile (60 mg, 32%) was prepared using a procedure similar to that described in Example 1, part b, except starting from 1-(4,6-dichloro-3-methoxy-2H-indazol-2-yl)propan-2-one (170 mg). 1-(4,6-dichloro-3-methoxy-2H-indazol-2-yl)propan-2-one was prepared using a procedure similar to that described in Example 105 part a to d except using 2,4-dichloro-6-nitrobenzaldehyde (1 g) in part a to yield [2-(tert-butyldimethylsilanyloxy)propyl]-(2,4-dichloro-6-nitrobenzyl)amine (0.6 g, 37%). 2,4-Dichloro-6-nitrobenzaldehyde was prepared as follows:
  a. To a solution of 1,3-dichloro-5-nitrobenzene (7.7 g) and chloroform (4 mL) in a mixture of THF and DMF (1:1.5, 100 mL), was slowly added at −78° C. a one molar solution of sodium hexamethyldisilazane (NaHMDS) in THF (7.7 mL). After stirring for 30 minutes, the reaction was quenched at −78° C. with a methanolic solution of hydrochloric acid and let warm to room temperature. The reaction mixture was extracted with ethyl acetate. The organic phase was dried over anhydrous magnesium sulfate, filtered and concentrated under reduced pressure to yield a residue that contained 70% of 1,5-dichloro-2-dichloromethyl-3-nitrobenzene.

b. A mixture of 1,5-dichloro-2-dichloromethyl-3-nitrobenzene (5.8 g, 70% pure) and zinc dichloride in formic acid (85%) was heated under reflux for 14 hours. The reaction mixture was concentrated under reduced pressure to yield a residue that was poured into water and extracted with ethyl acetate. The organic phase was dried over anhydrous magnesium sulfate, filtered and concentrated under reduced pressure to yield a residue that was purified by chromatography ($SiO_2$, heptane/EA) to afford 2,4-dichloro-6-nitrobenzaldehyde as a solid (2.9 g, 87% pure). 1H NMR: (400 MHz, CHLOROFORM-d): 7.76 (d, J=1.9 Hz, 1H), 7.93 (d, J=1.9 Hz, 1H) and 10.32 (s, 1H).

Example 117

N-[1-Cyano-2-(4,6-dichloro-3-methoxy-2H-indazol-2-yl)-1-methylethyl]-4-trifluoromethylthiobenzamide (compound No 2.022)

Using a procedure similar to that described in Example 1, except using 2-amino-3-(4,6-dichloro-3-methoxy-2H-indazol-2-yl)-2-methylpropionitrile (30 mg, described in Example 116) and 4-trifluoromethylthiobenzoyl chloride, the title compound was isolated as a white solid (42 mg, 83%). MS (ES): M/Z [M+H]=503. 1H NMR: (400 MHz, DMSO-$d_6$): 1.75 (s, 3H), 4.12 (s, 3H), 4.94 (d, J=6.5 Hz, 2H), 7.17 (d, J=1.2 Hz, 1H), 7.62 (d, J=1.1 Hz, 1H), 7.86-7.91 (m, 2H), 7.93-7.99 (m, 2H) and 9.03 (s, 1H). 19F NMR (376 MHz, DMSO-$d_6$): −41.9 (s, 3F).

Example 118

N-[2-(6-Bromo-3-methoxy-2H-indazol-2-yl)-1-cyano-1-methylethyl]-4-trifluoromethoxybenzamide (compound No 2.023)

Using a procedure similar to that described in Example 1, except using 2-amino-3-(6-bromo-3-methoxy-2H-indazol-2-yl)-2-methylpropionitrile (50 mg), the title compound was isolated as a white solid (73 mg, 90%). MS (ES): M/Z [M+H]=497. 1H NMR: (400 MHz, DMSO-$d_6$): 1.71 (s, 3H), 4.19 (s, 3H), 4.76 (d, 1H), 4.88 (d, 1H), 6.97 (dd, J=9.0, 1.4 Hz, 1H), 7.53 (d, J=8.3 Hz, 2H), 7.68 (d, J=0.8 Hz, 1H), 7.83 (d, J=9.1 Hz, 1H), 7.98 (d, J=8.7 Hz, 2H) and 8.92 (s, 1H). 19F NMR (376 MHz, DMSO-$d_6$): −57.1 (s, 3F).

2-Amino-3-(6-bromo-3-methoxy-2H-indazol-2-yl)-2-methylpropionitrile was prepared using a procedure similar to that described in Example 1, part b, except starting from 1-(6-bromo-3-methoxy-2H-indazol-2-yl)propan-2-one. 1-(6-bromo-3-methoxy-2H-indazol-2-yl)propan-2-one was prepared using a procedure similar to that described in Example 105 part a to d except using 4-bromo-2-nitrobenzaldehyde (5.1 g) and decaborane (0.81 g) in part a to yield [2-(tert-butyldimethylsilanyloxy)propyl]-(4-bromo-2-nitrobenzyl)amine (3.4 g).

Example 119

N-[2-(6-Bromo-3-methoxy-2H-indazol-2-yl)-1-cyano-1-methylethyl]-4-trifluoromethylthiobenzamide (compound No 2.024)

Using a procedure similar to that described in Example 1, except using 2-amino-3-(6-bromo-3-methoxy-2H-indazol-2-yl)-2-methylpropionitrile (50 mg, described in Example 118) and 4-trifluoromethylthiobenzoyl chloride, the title compound was isolated as a white solid (80 mg, 96%). MS (ES): M/Z [M+H]=513. 1H NMR: (400 MHz, DMSO-$d_6$): 1.71 (s, 3H), 4.19 (s, 3H), 4.77 (d, 1H), 4.89 (d, 1H), 6.97 (dd, J=9.1, 1.5 Hz, 1H), 7.68 (d, J=0.9 Hz, 1H), 7.83 (d, J=9.1 Hz, 1H), 7.86-7.91 (m, 2H), 7.94-7.99 (m, 2H) and 9.00 (s, 1H). 19F NMR (376 MHz, DMSO-$d_6$): −41.9 (s, 3F).

Example 120

N-[1-Cyano-2-(3-methoxy-6-trifluoromethyl-2H-indazol-2-yl)-1-methylethyl]-4-trifluoromethoxybenzamide (compound No 2.025)

Using a procedure similar to that described in Example 1, except using 2-amino-3-(3-methoxy-6-trifluoromethyl-2H-indazol-2-yl)-2-methylpropionitrile (50 mg), the title compound was isolated as a white solid (62 mg, 77%). MS (ES): M/Z [M+H]=487. 1H NMR: (400 MHz, DMSO-$d_6$): 1.72 (s, 3H), 4.23 (s, 3H), 4.85 (d, 1H), 4.97 (d, 1H), 7.08 (dd, J=9.0, 1.1 Hz, 1H), 7.53 (d, J=8.2 Hz, 2H), 7.86 (s, 1H), 7.99 (d, J=8.8 Hz, 2H), 8.09 (d, J=9.0 Hz, 1H) and 8.92 (s, 1H). 19F NMR (376 MHz, DMSO-$d_6$): −61.8 (s, 3F) and −57.1 (s, 3F).

2-Amino-3-(3-methoxy-6-trifluoromethyl-2H-indazol-2-yl)-2-methylpropionitrile was prepared using a procedure similar to that described in Example 1, part b, except starting from 1-(3-methoxy-6-trifluoromethyl-2H-indazol-2-yl)propan-2-one. 1-(3-methoxy-6-trifluoromethyl-2H-indazol-2-yl)propan-2-one was prepared using a procedure similar to that described in Example 105 part a to d except using 2-nitro-4-(trifluoromethyl)benzaldehyde (1 g) in part a to yield [2-(tert-butyldimethylsilanyloxy)propyl]-[2-nitro-4-(trifluoromethyl)benzyl]amine (0.6 g, 33%).

Example 121

N N-[1-Cyano-2-(3-methoxy-6-trifluoromethyl-2H-indazol-2-yl)-1-methylethyl]-4-trifluoromethylthiobenzamide (compound No 2.026)

Using a procedure similar to that described in Example 1, except using 2-amino-3-(3-methoxy-6-trifluoromethyl-2H-indazol-2-yl)-2-methylpropionitrile (50 mg, described in Example 120) and 4-trifluoromethylthiobenzoyl chloride, the title compound was isolated as a white solid (66 mg, 78%). MS (ES): M/Z [M+H]=503. 1H NMR: (400 MHz, DMSO-$d_6$): 1.72 (s, 3H), 4.24 (s, 3H), 4.84 (d, J=13.8 Hz, 1H), 4.96 (d, J=13.9 Hz, 1H), 7.08 (dd, J=9.0, 1.4 Hz, 1H), 7.85 (s, 1H), 7.88 (d, J=8.2 Hz, 2H), 7.94-7.99 (m, 2H), 8.09 (d, J=9.0 Hz, 1H) and 8.99 (s, 1H). 19F NMR (376 MHz, DMSO-$d_6$): −42.0 (s, 3F) and −61.8 (s, 3F).

Example 122

N-[2-(6-Chloro-3-ethoxy-2H-indazol-2-yl)-1-cyano-1-methylethyl]-4-trifluoromethoxybenzamide (compound No 2.027)

Using a procedure similar to that described in Example 1, except using 2-amino-3-(6-chloro-3-ethoxy-2H-indazol-2-yl)-2-methylpropionitrile (113 mg), the title compound was isolated as a white solid (95 mg, 50%). MS (ES): M/Z [M+H]=467. 1H NMR: (400 MHz, CHLOROFORM-d): 1.58 (t, J=7.1 Hz, 3H), 1.91 (s, 3H), 4.50 (d, J=14.2 Hz, 1H), 4.63-4.81 (m, 2H), 4.83 (d, J=14.1 Hz, 1H), 6.92 (dd, J=9.1, 1.7 Hz, 1H), 7.34 (d, J=8.1 Hz, 2H), 7.46 (d, J=1.1 Hz, 1H), 7.62 (d, J=9.1 Hz, 1H), 7.89-8.02 (m, 2H) and 9.07 (s, 1H). 19F NMR (376 MHz, CHLOROFORM-d): −58.1 (s, 3F).

2-Amino-3-(6-chloro-3-ethoxy-2H-indazol-2-yl)-2-methylpropionitrile (221 mg, 95%) was prepared using a procedure similar to that described in Example 1, part b, except starting from 1-(6-chloro-3-ethoxy-2H-indazol-2-yl)propan-2-one (210 mg). 1-(6-chloro-3-ethoxy-2H-indazol-2-yl)propan-2-one was prepared using a procedure similar to that described in Example 105 part a to d except using 4-chloro-2-nitrobenzaldehyde (21.7 g) and decaborane (4.2 g) in part a and using ethanol instead of methanol in part b.

Example 123

N-[2-(6-Chloro-3-ethoxy-2H-indazol-2-yl)-1-cyano-1-methylethyl]-4-trifluoromethylthiobenzamide (compound No 2.028)

Using a procedure similar to that described in Example 1, except using 2-amino-3-(6-chloro-3-ethoxy-2H-indazol-2-yl)-2-methylpropionitrile (108 mg, described in Example 122) and 4-trifluoromethylthiobenzoyl chloride, the title compound was isolated as a white solid (96 mg, 51%). MS (ES): M/Z [M+H]=483. 1H NMR: (400 MHz, CHLOROFORM-d): 1.59 (t, J=7.0 Hz, 3H), 1.91 (s, 3H), 4.50 (d, J=14.2 Hz, 1H), 4.63-4.81 (m, 2H), 4.83 (d, J=14.2 Hz, 1H), 6.92 (dd, J=9.1, 1.7 Hz, 1H), 7.47 (d, J=1.2 Hz, 1H), 7.62 (d, J=9.0 Hz, 1H), 7.79 (d, J=8.3 Hz, 2H), 7.90-7.99 (m, 2H) and 9.15 (s, 1H). 19F NMR (376 MHz, CHLOROFORM-d): −42.3 (s, 3F).

Example 124

N-[2-(6-Chloro-3-propoxy-2H-indazol-2-yl)-1-cyano-1-methylethyl]-4-trifluoromethoxybenzamide (compound No 2.029)

Using a procedure similar to that described in Example 1, except using 2-amino-3-(6-chloro-3-propoxy-2H-indazol-2-yl)-2-methylpropionitrile (103 mg), the title compound was isolated as a white solid (104 mg, 54%). MS (ES): M/Z [M+H]=481. 1H NMR: (400 MHz, CHLOROFORM-d): 1.14 (t, J=7.4 Hz, 3H), 1.90 (s, 3H), 1.92-2.03 (m, 2H), 4.51 (d, J=14.1 Hz, 1H), 4.55-4.69 (m, 2H), 4.81 (d, J=14.1 Hz, 1H), 6.91 (dd, J=9.1, 1.7 Hz, 1H), 7.34 (dd, J=8.8, 0.8 Hz, 2H), 7.46 (dd, J=1.7, 0.6 Hz, 1H), 7.62 (dd, J=9.1, 0.6 Hz, 1H), 7.90-8.01 (m, 2H) and 9.10 (s, 1H). 19F NMR (376 MHz, CHLOROFORM-d): −58.1 (s, 3F).

2-Amino-3-(6-chloro-3-propoxy-2H-indazol-2-yl)-2-methylpropionitrile (207 mg, 92%) was prepared using a procedure similar to that described in Example 1, part b, except starting from 1-(6-chloro-3-propoxy-2H-indazol-2-yl)propan-2-one (205 mg). 1-(6-chloro-3-propoxy-2H-indazol-2-yl)propan-2-one was prepared using a procedure similar to that described in Example 105 part a to d except using 4-chloro-2-nitrobenzaldehyde (21.7 g) and decaborane (4.2 g) in part a and using n-propanol instead of methanol in part b.

Example 125

N-[2-(6-Chloro-3-propoxy-2H-indazol-2-yl)-1-cyano-1-methylethyl]-4-trifluoromethylthiobenzamide (compound No 2.030)

Using a procedure similar to that described in Example 1, except using 2-amino-3-(6-chloro-3-propoxy-2H-indazol-2-yl)-2-methylpropionitrile (104 mg, described in Example 124) and 4-trifluoromethylthiobenzoyl chloride, the title compound was isolated as a white solid (88 mg, 46%). MS (ES): M/Z [M+H]=497. 1H NMR: (400 MHz, CHLOROFORM-d): 1.14 (t, J=7.4 Hz, 3H), 1.90 (s, 3H), 1.92-2.04 (m, 2H), 4.51 (d, J=14.2 Hz, 1H), 4.56-4.70 (m, 2H), 4.82 (d, J=14.2 Hz, 1H), 6.92 (dd, J=9.1, 1.7 Hz, 1H), 7.47 (d, J=1.7 Hz, 1H), 7.62 (dd, J=9.1, 0.5 Hz, 1H), 7.79 (dd, J=8.3 Hz, 2H), 7.91-7.99 (m, 2H) and 9.17 (s, 1H). 19F NMR (376 MHz, CHLOROFORM-d): −42.3 (s, 3F).

Example 126

N-[2-(6-Chloro-3-butoxy-2H-indazol-2-yl)-1-cyano-1-methylethyl]-4-trifluoromethoxybenzamide (compound No 2.031)

Using a procedure similar to that described in Example 1, except using 2-amino-3-(6-chloro-3-butoxy-2H-indazol-2-yl)-2-methylpropionitrile (88 mg), the title compound was isolated as a white solid (60 mg, 43%). MS (ES): M/Z [M+H]=495. 1H NMR: (400 MHz, CHLOROFORM-d): 1.04 (t, J=7.4 Hz, 3H), 1.51-1.65 (m, 2H), 1.89 (s, 3H), 1.89-1.98 (m, 2H), 4.51 (d, J=14.2 Hz, 1H), 4.57-4.73 (m, 2H), 4.81 (d, J=14.2 Hz, 1H), 6.91 (dd, J=9.1, 1.7 Hz, 1H), 7.34 (d, J=8.0 Hz, 2H), 7.46 (d, J=1.1 Hz, 1H), 7.62 (dd, J=9.1, 0.5 Hz, 1H), 7.91-8.00 (m, 2H) and 9.09 (s, 1H). 19F NMR (376 MHz, CHLOROFORM-d): −58.1 (s, 3F).

2-Amino-3-(6-chloro-3-butoxy-2H-indazol-2-yl)-2-methylpropionitrile (88 mg) was prepared using a procedure similar to that described in Example 1, part b, except starting from 1-(6-chloro-3-butoxy-2H-indazol-2-yl)propan-2-one (79 mg). 1-(6-chloro-3-butoxy-2H-indazol-2-yl)propan-2-one was prepared using a procedure similar to that described in Example 105 part a to d except using 4-chloro-2-nitrobenzaldehyde (21.7 g) and decaborane (4.2 g) in part a and using n-butanol instead of methanol in part b.

Example 127

Methyl 2-[2-cyano-2-methyl-2-(4-trifluoromethoxybenzoylamino)ethyl]-3-methoxy-2H-indazole-6-carboxylate (compound No 2.032)

Using a procedure similar to that described in Example 1, except using methyl 2-(2-amino-2-cyano-2-methylethyl)-3-methoxy-2H-indazole-6-carboxylate (88 mg), the title compound was isolated as a white solid (126 mg, 86%). MS (ES): M/Z [M+H]=477. 1H NMR: (400 MHz, DMSO-$d_6$): 1.72 (s, 3H), 3.87 (s, 3H), 4.21 (s, 3H), 4.83 (d, 1H), 4.97 (d, 1H), 7.37 (d, J=8.9 Hz, 1H), 7.53 (d, J=8.3 Hz, 2H), 7.93-8.03 (m, 3H), 8.07 (s, 1H) and 8.92 (s, 1H). 19F NMR (376 MHz, DMSO-$d_6$): −57.1 (s, 3F).

Methyl 2-(2-amino-2-cyano-2-methylethyl)-3-methoxy-2H-indazole-6-carboxylate was prepared using a procedure similar to that described in Example 1, part b, except starting from methyl 3-methoxy-2-(2-oxo-propyl)-2H-indazole-6-carboxylate. 1 Methyl 3-methoxy-2-(2-oxo-propyl)-2H-indazole-6-carboxylate was prepared using a procedure similar to that described in Example 105 part a to d except using methyl 4-formyl-3-nitrobenzoate (2 g) in part a to yield methyl 4-{[2-(tert-butyldimethylsilanyloxy)propylamino]-methyl}-3-nitrobenzoate (2.83 g, 77%). In the basic cyclisation step in part b, desired methyl 2-[2-(tert-butyldimethylsilanyloxy)-propyl]-3-methoxy-2H-indazole-6-carboxylate (230 mg) was isolated along with 2-[2-(tert-butyldimethylsilanyloxy)propyl]-3-hydroxy-2H-indazole-6-carboxylic acid (781 mg).

Example 128

N-[1-Cyano-2-(3-methoxy-6-nitro-2H-indazol-2-yl)-1-methylethyl]-4-trifluoromethoxybenzamide (compound No 2.033)

Using a procedure similar to that described in Example 1, except using 2-amino-3-(3-methoxy-6-nitro-2H-indazol-2-yl)-2-methylpropionitrile (63 mg), the title compound was isolated as a white solid (84 mg, 79%). MS (ES): M/Z [M+H]=464. 1H NMR: (400 MHz, DMSO-$d_6$): 1.73 (s, 3H), 4.25 (s, 3H), 4.88 (d, 1H), 5.00 (d, 1H), 7.53 (d, J=8.3 Hz, 2H), 7.61 (dd, J=9.3, 1.9 Hz, 1H), 7.99 (d, J=8.7 Hz, 2H), 8.12 (d, J=9.3 Hz, 1H), 8.42 (d, J=1.6 Hz, 1H) and 8.93 (s, 1H). 19F NMR (376 MHz, DMSO-$d_6$): −57.1 (s, 3F).

2-Amino-3-(3-methoxy-6-nitro-2H-indazol-2-yl)-2-methylpropionitrile was prepared using a procedure similar to that described in Example 1, part b, except starting from 1-(3-methoxy-6-nitro-2H-indazol-2-yl)propan-2-one. 1-(3-Methoxy-6-nitro-2H-indazol-2-yl)propan-2-one was prepared using a procedure similar to that described in Example 105 part a to d except using 2,4-dinitrobenzaldehyde (2 g) in part a to yield [2-(tert-butyldimethylsilanyloxy)propyl]-(2,4-dinitrobenzyl)amine (2.6 g, 64%).

Example 129

N-[2-(6-Amino-3-methoxy-2H-indazol-2-yl)-1-cyano-1-methylethyl]-4-trifluoromethoxybenzamide (compound No 2.034)

A mixture of N-[1-cyano-2-(3-methoxy-6-nitro-2H-indazol-2-yl)-1-methylethyl]-4-trifluoromethoxybenzamide (30 mg) described in Example 128 and palladium on charcoal in methanol (2 mL) were stirred at room temperature under hydrogen for 2.5 hours. The reaction mixture was filtered through a plug of Celite® and concentrated under reduced pressure to yield a residue that was purified by chromatography (SiO$_2$, heptane/EA) to afford the title compound as a white solid (18 mg, 64%). MS (ES): M/Z [M+H]=434. 1H NMR: (400 MHz, CHLOROFORM-d): 1.88 (s, 3H), 4.38 (s, 3H), 4.41 (d, 1H), 4.72 (d, J=14.2 Hz, 1H), 6.48 (dd, J=9.0, 1.8 Hz, 1H), 6.53 (d, J=1.2 Hz, 1H), 7.31 (d, J=8.3 Hz, 2H), 7.55 (d, J=9.0 Hz, 1H), 7.98 (d, J=8.8 Hz, 2H) and 9.43 (s, 1H). 19F NMR (376 MHz, CHLOROFORM-d): −58.0 (s, 3F).

Example 130

N-[2-(6-Acetylamino-3-methoxy-2H-indazol-2-yl)-1-cyano-1-methylethyl]-4-trifluoromethoxybenzamide (compound No 2.035)

Using a procedure similar to that described in Example 1, except using N-[2-(6-amino-3-methoxy-2H-indazol-2-yl)-1-cyano-1-methylethyl]-4-trifluoromethoxybenzamide (23 mg, described in Example 129) and acetyl chloride, the title compound was isolated as a white solid (8 mg, 32%). MS (ES): M/Z [M+H]=476. 1H NMR: (400 MHz, DMSO-$d_6$): 1.71 (s, 3H), 2.05 (s, 3H), 4.16 (s, 3H), 4.71 (d, 1H), 4.82 (d, 1H), 6.88 (dd, J=9.2, 1.6 Hz, 1H), 7.52 (d, J=8.0 Hz, 2H), 7.74 (d, J=9.1 Hz, 1H), 7.86 (s, 1H), 7.99 (d, J=8.8 Hz, 2H), 8.95 (s, 1H) and 9.89 (s, 1H). 19F NMR (376 MHz, DMSO-$d_6$): −57.1 (s, 3F).

Example 131

Methyl 2-[2-cyano-2-methyl-2-(4-trifluoromethoxybenzoylamino)ethyl]-3-methoxy-2H-indazole-6-carboxamide (compound No 2.036)

A solution of methyl 2-[2-cyano-2-methyl-2-(4-trifluoromethoxybenzoylamino)ethyl]-3-methoxy-2H-indazole-6-carboxylate (50 mg, described in Example 127) in methanol (3 mL) was stirred with ammonium hydroxide (1.5 mL) at room temperature for 8 days. The reaction mixture was concentrated under reduced pressure to yield a residue that was purified by chromatography (SiO$_2$, heptane/EA) to afford the title compound as a white solid (3 mg). MS (ES): M/Z [M+H]=462. 1H NMR: (400 MHz, METHANOL-$d_4$): 1.81 (s, 3H), 4.32 (s, 3H), 4.82 (d, 1H), 5.08 (d, J=14.0 Hz, 1H), 7.38 (dd, J=9.0, 1.4 Hz, 1H), 7.42 (d, J=8.6 Hz, 2H), 7.90 (d, J=9.0 Hz, 1H), 7.97 (d, J=8.9 Hz, 2H) and 7.99 (s, 1H). 19F NMR (376 MHz, METHANOL-$d_4$): −59.8 (s, 3F).

Compounds of Examples 132 to 137 were prepared according to the following general reaction scheme:

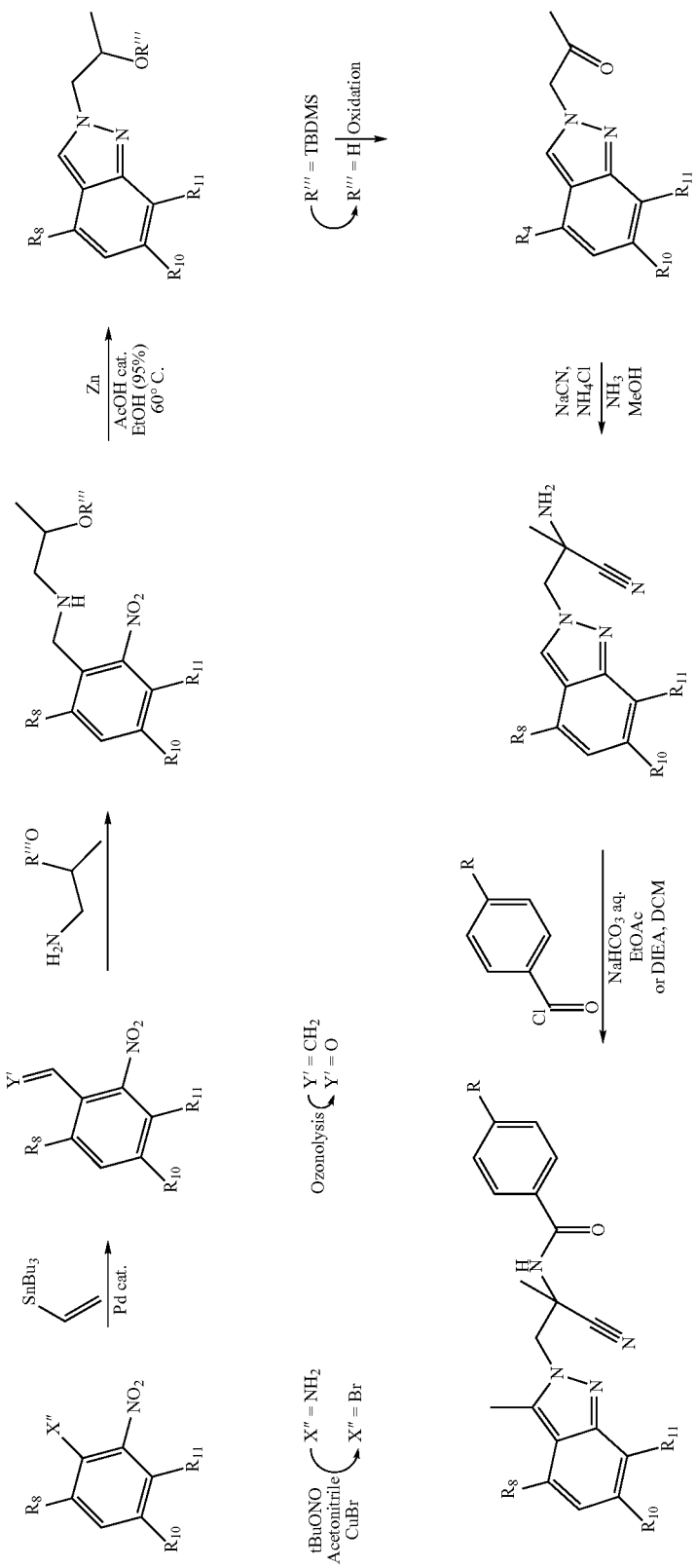

Final Product
V=C—R$_8$; W=C—H; X=C—R$_{10}$; Y=C—R$_{11}$;
Q=C—H; P=N;
R$_3$=R$_4$=H; a=1; R$_5$=CH$_3$; R$_6$=H;
Z=C(O); R$_7$=p-phenyl-R

Example 132

N-[2-(6-Chloro-2H-indazol-2-yl)-1-cyano-1-methylethyl]-4-trifluoromethoxybenzamide (compound No 2.037)

Using a procedure similar to that described in Example 1, except using 2-amino-3-(6-chloro-2H-indazol-2-yl)-2-methylpropionitrile (20 mg), the title compound was isolated as a white solid (34 mg, 93%). MS (ES): M/Z [M+H]=423. 1H NMR: (400 MHz, CHLOROFORM-d): 1.95 (s, 3H), 4.81 (d, 1H), 4.89 (d, 1H), 7.11 (dd, J=8.9, 1.7 Hz, 1H), 7.33 (d, J=8.4 Hz, 2H), 7.65 (d, J=8.9 Hz, 1H), 7.69 (s, 1H), 7.90 (d, J=8.7 Hz, 2H), 8.17 (s, 1H) and 8.49 (s, 1H). 19F NMR (376 MHz, CHLOROFORM-d): −58.1 (s, 3F).

2-Amino-3-(6-chloro-2H-indazol-2-yl)-2-methylpropionitrile (54 mg, 79%) was prepared using a procedure similar to that described in Example 1, part b, except starting from 1-(6-chloro-2H-indazol-2-yl)propan-2-one (68 mg). 1-(6-Chloro-2H-indazol-2-yl)propan-2-one was prepared using a procedure similar to that described in Example 105 part c and d except starting from 2-[2-(tert-butyldimethylsilanyloxy)propyl]-6-chloro-2H-indazole that was prepared as follows:

a. A mixture of [2-(tert-butyldimethylsilanyloxy)propyl]-(4-chloro-2-nitrobenzyl)amine (4.6 g, described in Example 105 part a), and zinc (2 g) in ethanol (95%, 20 mL) and one drop of acetic acid was heated to 60° C. for 24 hours. The reaction mixture was filtered through a plug of Celite® and concentrated under reduced pressure to yield a residue that was purified by chromatography (SiO$_2$, heptane/EA) to afford 2-[2-(tert-butyldimethylsilanyloxy)propyl]-6-chloro-2H-indazole as a white solid (0.9 g, 22%) along with recovered starting material (2.2 g, 48%).

Example 133

N-[2-(6-Chloro-2H-indazol-2-yl)-1-cyano-1-methylethyl]-4-trifluoromethylthiobenzamide (compound No 2.038)

Using a procedure similar to that described in Example 1, except using 2-amino-3-(6-chloro-2H-indazol-2-yl)-2-methylpropionitrile (20 mg, described in Example 132) and 4-trifluoromethylthiobenzoyl chloride, the title compound was isolated as a white solid (37 mg, 98%). MS (ES): M/Z [M+H]=439. 1H NMR: (400 MHz, CHLOROFORM-d): 1.95 (s, 3H), 4.81 (d, 1H), 4.89 (d, 1H), 7.12 (dd, J=9.0, 1.6 Hz, 1H), 7.65 (d, J=9.0, 1H), 7.69 (s, 1H), 7.78 (d, J=8.3 Hz, 2H), 7.89 (d, J=8.3 Hz, 2H), 8.18 (s, 1H) and 8.58 (s, 1H). 19F NMR (376 MHz, CHLOROFORM-d): −42.2 (s, 3F).

Example 134

N-[1-Cyano-2-(4,6-dichloro-2H-indazol-2-yl)-1-methylethyl]-4-trifluoromethoxybenzamide (compound No 2.040)

Using a procedure similar to that described in Example 1, except using 2-amino-3-(4,6-dichloro-2H-indazol-2-yl)-2-methylpropionitrile (20 mg), the title compound was isolated as a white solid (31 mg, 91%). MS (ES): M/Z [M+H]=457. 1H NMR: (400 MHz, CHLOROFORM-d): 1.96 (s, 3H), 4.82 (d, 1H), 4.92 (d, 1H), 7.15 (d, J=1.3 Hz, 1H), 7.34 (d, J=8.2 Hz, 2H), 7.60 (s, 1H), 7.89 (d, J=8.8 Hz, 2H) and 8.22 (s, 2H). 19F NMR (376 MHz, CHLOROFORM-d): −58.1 (s, 3F).

2-Amino-3-(4,6-dichloro-2H-indazol-2-yl)-2-methylpropionitrile (88 mg, 54%) was prepared using a procedure similar to that described in Example 1, part b, except starting from 1-(4,6-dichloro-2H-indazol-2-yl)propan-2-one (146 mg). 1-(4,6-Dichloro-2H-indazol-2-yl)propan-2-one was prepared using a procedure similar to that described in Example 105 part c and d except starting from 2-[2-(tert-butyldimethylsilanyloxy)propyl]-4,6-dichloro-2H-indazole that was prepared using a procedure similar to that described in Example 132 part a except starting from [2-(tert-butyldimethylsilanyloxy)propyl]-(2,4-dichloro-6-nitrobenzyl)amine described in Example 116.

Example 135

N-[1-Cyano-2-(4,6-dichloro-2H-indazol-2-yl)-1-methylethyl]-4-trifluoromethylthiobenzamide (compound No 2.041)

Using a procedure similar to that described in Example 1, except using 2-amino-3-(4,6-dichloro-2H-indazol-2-yl)-2-methylpropionitrile (20 mg, described in Example 134) and 4-trifluoromethylthiobenzoyl chloride, the title compound was isolated as a white solid (34 mg, 97%). MS (ES): M/Z [M+H]=473. 1H NMR: (400 MHz, CHLOROFORM-d): 1.96 (s, 3H), 4.82 (d, 1H), 4.93 (d, 1H), 7.15 (d, J=0.9 Hz, 1H), 7.60 (s, 1H), 7.79 (d, 2H), 7.88 (d, 2H), 8.22 (s, 1H) and 8.32 (s, 1H). 19F NMR (376 MHz, CHLOROFORM-d): −42.2 (s, 3F).

Example 136

N-[1-Cyano-1-methyl-2-(4,6,7-trichloro-2H-indazol-2-yl)ethyl]-4-trifluoromethoxybenzamide (compound No 2.048)

Using a procedure similar to that described in Example 1, except using 2-amino-2-methyl-3-(4,6,7-trichloro-2H-indazol-2-yl)propionitrile (60 mg), the title compound was isolated as a white solid (34 mg, 35%). Rf=0.65 (1:1 EA/heptane). 1H NMR: (400 MHz, DMSO-d$_6$): 1.70 (s, 3H), 5.12 (d, 1H), 5.24 (d, 1H), 7.47 (s, 1H), 7.52 (d, J=8.1 Hz, 2H), 7.97 (d, J=8.8 Hz, 2H), 8.72 (s, 1H) and 8.92 (s, 1H). 19F NMR (376 MHz, DMSO-d$_6$): −57.1 (s, 3F).

2-Amino-2-methyl-3-(4,6,7-trichloro-2H-indazol-2-yl)propionitrile (0.16 g, 60%) was prepared using a procedure similar to that described in Example 1, part b, except starting from 1-(4,6,7-trichloro-2H-indazol-2-yl)propan-2-one (0.25 g). 1-(4,6,7-Trichloro-2H-indazol-2-yl)propan-2-one was prepared using a procedure similar to that described in Example 105 part c and d except starting from 2-[2-(tert-butyldimethylsilanyloxy)propyl]-4,6,7-trichloro-2H-indazole (1.4 g, 69%) that was prepared using a procedure similar to that described in Example 132 part a except starting from [2-(tert-butyldimethylsilanyloxy)propyl]-(2-nitro-3,4,6-trichlorobenzyl)amine (2.2 g). [2-(tert-Butyldimethylsilanyloxy)propyl]-(2-nitro-3,4,6-trichlorobenzyl)amine (2.2 g, 44%) was prepared using a procedure similar to that described in Example 105 part a except starting from 2-nitro-3,4,6-trichlorobenzaldehyde (3 g) that was prepared as follows:

a. To a mixture of 2-nitro-3,4,6-trichloroaniline (57 g), described in Example 39 part a to c, and copper (II) bromide (105 g) in acetonitrile (1 L) was added tert-butyl nitrite (90%, 37 mL) and the mixture heated to 60° C. overnight. The reaction mixture was filtered a plug of Celite®, rinsed with ethyl acetate and the filtrates concentrated under reduced pressure to yield a residue that was purified by chromatography (SiO$_2$, heptane/EA) to afford 2-bromo-3-nitro-1,4,5-trichlorobenzene (53 g, 74%). Rf=0.8 (1:4 EA/heptane).

b. 2-Bromo-3-nitro-1,4,5-trichlorobenzene (53 g), tributylvinyltin (58 mL, 62 g) and [1,1'-bis(diphenylphosphino)ferrocene]dichloropalladium (II), complex with dichloromethane (1:1) (14 g) were heated in toluene (400 mL) at 100° C. for 24 hours. The mixture was concentrated under reduced pressure, taken up in ethyl acetate (1 L) and treated with a saturated solution of potassium fluoride (300 mL) overnight. The mixture was filtered through a plug of Celite®, the organic layer was separated and dried over sodium sulfate, filtered and concentrated under reduced pressure to give a residue that was purified by chromatography (SiO$_2$, heptane/EA) to afford 3-nitro-1,2,5-trichloro-4-vinylbenzene as an of white solid (34 g, 78%). Rf=0.75 (1:4 EA/heptane).

c. A solution of 3-nitro-1,4,5-trichloro-2-vinylbenzene (27 g) in a mixture of DCM and methanol (3:1, 300 mL) was treated with ozone gas for 2 hours at −78° C. The mixture was purged 10 minutes with oxygen and then quenched with dimethyl sulfide (2 mL) at −78° C. The mixture was allowed to warm to 0° C., treated with a 10% solution of sodium thiosulfate (200 mL) then diluted with more DCM. The organic layer was collected, dried over sodium sulfate, filtered and concentrated under reduced pressure to give a residue that was purified by chromatography (SiO$_2$, heptane/EA) to afford 2-nitro-3,4,6-trichlorobenzaldehyde as a white solid (20 g, 74%). Rf=0.5 (3:8 EA/heptane). 1H NMR: (400 MHz, DMSO-d$_6$): 8.44 (s, 1H) and 10.17 (s, 1H).

Example 137

N-[1-Cyano-1-methyl-2-(4,6,7-trichloro-2H-indazol-2-yl)ethyl]-4-trifluoromethylthiobenzamide (compound No 2.049)

Using a procedure similar to that described in Example 1, except using 2-amino-2-methyl-3-(4,6,7-trichloro-2H-indazol-2-yl)propionitrile (60 mg, described in Example 136) and 4-trifluoromethylthiobenzoyl chloride, the title compound was isolated as a white solid (40 mg, 40%). Rf=0.65 (1:1 EA/heptane). 1H NMR: (400 MHz, DMSO-d$_6$): 1.70 (s, 3H), 5.11 (d, 1H), 5.25 (d, 1H), 7.47 (s, 1H), 7.79-7.80 (m, 4H), 8.73 (s, 1H) and 9.00 (s, 1H). 19F NMR (376 MHz, DMSO-d$_6$): −42.0 (s, 3F).

Compounds of Examples 138 to 144 were prepared according to the following general reaction scheme:

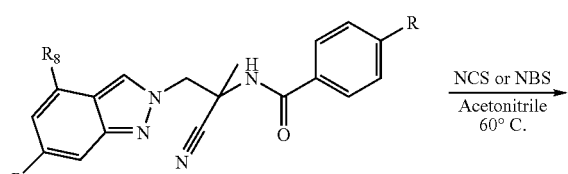

R = OCF$_3$ or SCF$_3$

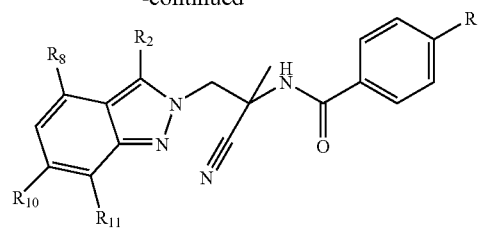

R$_2$ = Cl, Br or H
R$_{11}$ = Cl, Br or H
R = OCF$_3$ or SCF$_3$

Final Product
V=C—R$_8$; W=C—H; X=C—R$_{10}$; Y=C—R$_{11}$;
Q=C—R$_2$; P=N;
R$_3$=R$_4$=H; a=1; R$_5$=CH$_3$; R$_6$=H;
Z=C(O); R$_7$=p-phenyl-R Example 138

N-[1-Cyano-1-methyl-2-(3,6,7-trichloro-2H-indazol-2-yl)ethyl]-4-trifluoromethoxybenzamide (compound No 2.039)

A mixture of N-[2-(6-chloro-2H-indazol-2-yl)-1-cyano-1-methylethyl]-4-trifluoromethoxybenzamide (25 mg, described in Example 132), and N-chlorosuccinimide (50 mg) in acetonitrile (2 mL) was heated to 60° C. overnight. The mixture was concentrated under reduced pressure to yield a residue that was purified by chromatography (SiO$_2$, heptane/EA) to afford the title compound (22 mg, 75%) with 70% purity along with 30% of another isomer. MS (ES): M/Z [M+H]=491. 1H NMR: (400 MHz, CHLOROFORM-d): 1.96 (s, 3H), 4.81 (d, J=14.3 Hz, 1H), 5.06 (d, J=14.3 Hz, 1H), 7.25 (d, J=8.9 Hz, 1H), 7.32 (dd, J=8.1, 0.9 Hz, 2H), 7.51 (d, J=8.9 Hz, 1H), 8.05 (d, J=8.9 Hz, 2H) and 8.92 (s, 1H). 19F NMR (376 MHz, CHLOROFORM-d): −58.1 (s, 3F).

Example 139

N-[2-(3-Bromo-6-chloro-2H-indazol-2-yl)-1-cyano-1-methylethyl]-4-trifluoromethoxybenzamide (compound No 2.042)

A mixture of N-[2-(6-chloro-2H-indazol-2-yl)-1-cyano-1-methylethyl]-4-trifluoromethoxybenzamide (25 mg, described in Example 132), and N-bromosuccinimide (10 mg) in acetonitrile (1 mL) was heated to 60° C. for 3.5 hours. The mixture was cooled to room temperature, diluted with water and extracted with ethyl acetate. The organic layer was collected, dried over sodium sulfate, filtered and concentrated under reduced pressure to give a residue that was purified by chromatography (SiO$_2$, heptane/EA) to afford the title compound (12.5 mg, 42%). MS (ES): M/Z [M+H]=501. 1H NMR: (400 MHz, CHLOROFORM-d): 1.90 (s, 3H), 4.82 (d, J=14.3 Hz, 1H), 5.05 (d, J=14.3 Hz, 1H), 7.14 (dd, J=9.0, 1.6 Hz, 1H), 7.34 (d, J=8.2 Hz, 2H), 7.50 (d, J=8.9 Hz, 1H), 7.63 (d, J=0.9 Hz, 1H), 7.93 (d, J=8.8 Hz, 2H) and 8.71 (s, 1H). 19F NMR (376 MHz, CHLOROFORM-d): −58.1 (s, 3F).

Example 140

N-[2-(7-Bromo-6-chloro-2H-indazol-2-yl)-1-cyano-1-methylethyl]-4-trifluoromethoxybenzamide (compound No 2.043)

From the same reaction mixture described in Example 139 was also isolated the title compound (5 mg, 17%). MS (ES): M/Z [M+H]=501. 1H NMR: (400 MHz, CHLOROFORM-d): 1.99 (s, 3H), 4.87 (s, 2H), 7.22 (d, J=8.8 Hz, 1H), 7.31 (d, J=8.5 Hz, 2H), 7.63 (d, J=8.9 Hz, 1H), 8.04 (d, J=8.8 Hz, 2H), 8.31 (s, 1H) and 8.75 (s, 1H). 19F NMR (376 MHz, CHLOROFORM-d): −58.1 (s, 3F).

Example 141

N-[1-Cyano-2-(3,6-dichloro-2H-indazol-2-yl)-1-methylethyl]-4-trifluoromethoxybenzamide (compound No 2.044)

A mixture of N-[2-(6-chloro-2H-indazol-2-yl)-1-cyano-1-methylethyl]-4-trifluoromethoxybenzamide (50 mg, described in Example 132), and N-chlorosuccinimide (16 mg) in acetonitrile (1 mL) was heated to 60° C. for 3.5 hours. The mixture was cooled to room temperature, diluted with water and extracted with ethyl acetate. The organic layer was collected, dried over sodium sulfate, filtered and concentrated under reduced pressure to give a residue that was purified by chromatography ($SiO_2$, heptane/EA) to afford the title compound (46 mg, 85%). MS (ES): M/Z [M+H]=457. 1H NMR: (400 MHz, CHLOROFORM-d): 1.92 (s, 3H), 4.80 (d, J=14.3 Hz, 1H), 5.03 (d, J=14.3 Hz, 1H), 7.15 (dd, J=9.0, 1.4 Hz, 1H), 7.35 (d, J=8.5 Hz, 2H), 7.57 (d, J=9.0 Hz, 1H), 7.63 (s, 1H), 7.93 (d, J=8.7 Hz, 2H) and 8.65 (s, 1H). 19F NMR (376 MHz, CHLOROFORM-d): −58.1 (s, 3F).

Example 142

N-[1-Cyano-2-(6,7-dichloro-2H-indazol-2-yl)-1-methylethyl]-4-trifluoromethoxybenzamide (compound No 2.045)

From the same reaction mixture described in Example 141 was also isolated the title compound (6 mg, 11%). MS (ES): M/Z [M+H]=457. 1H NMR: (400 MHz, CHLOROFORM-d): 1.99 (s, 3H), 4.87 (s, 2H), 7.22 (d, J=8.8 Hz, 1H), 7.31 (d, J=8.2 Hz, 2H), 7.59 (d, J=8.9 Hz, 1H), 8.02 (d, J=8.8 Hz, 2H), 8.26 (s, 1H) and 8.81 (s, 1H). 19F NMR (376 MHz, CHLOROFORM-d): −58.1 (s, 3F).

Example 143

N-[1-Cyano-2-(3,7-dibromo-4,6-dichloro-2H-indazol-2-yl)-1-methylethyl]-4-trifluoromethoxybenzamide (compound No 2.046)

A mixture of N-[2-(4,6-dichloro-2H-indazol-2-yl)-1-cyano-1-methylethyl]-4-trifluoromethoxybenzamide, described in Example 134, and excess N-bromosuccinimide in acetonitrile was heated to 60° C. overnight. The mixture was cooled to room temperature, diluted with water and extracted with ethyl acetate. The organic layer was collected, dried over sodium sulfate, filtered and concentrated under reduced pressure to give a residue that was purified by chromatography ($SiO_2$, heptane/EA) to afford the title compound (13 mg). MS (ES): M/Z [M+H]=613. 1H NMR: (400 MHz, CHLOROFORM-d): 1.97 (s, 3H), 4.75 (br. s, 1H), 4.88 (d, J=14.3 Hz, 1H), 5.14 (d, J=14.3 Hz, 1H), 7.31 (d, J=8.3 Hz, 2H), 8.05 (d, J=8.8 Hz, 2H) and 8.65 (s, 1H). 19F NMR (376 MHz, CHLOROFORM-d): −58.1 (s, 3F).

Example 144

N-[2-(7-Bromo-6,7-dichloro-2H-indazol-2-yl)-1-cyano-1-methylethyl]-4-trifluoromethoxybenzamide (compound No 2.047)

From the same reaction mixture described in Example 143 was also isolated the title compound (18 mg). MS (ES): M/Z [M+Na]=557. 1H NMR: (400 MHz, CHLOROFORM-d): 2.00 (s, 3H), 4.84-4.93 (m, 2H), 7.25 (s, 1H), 7.31 (d, J=8.4 Hz, 2H), 8.02 (d, J=8.8 Hz, 2H), 8.35 (s, 1H) and 8.57 (s, 1H). 19F NMR (376 MHz, CHLOROFORM-d): −58.1 (s, 3F).

The compound of Example 145 was prepared according to the following general reaction scheme:

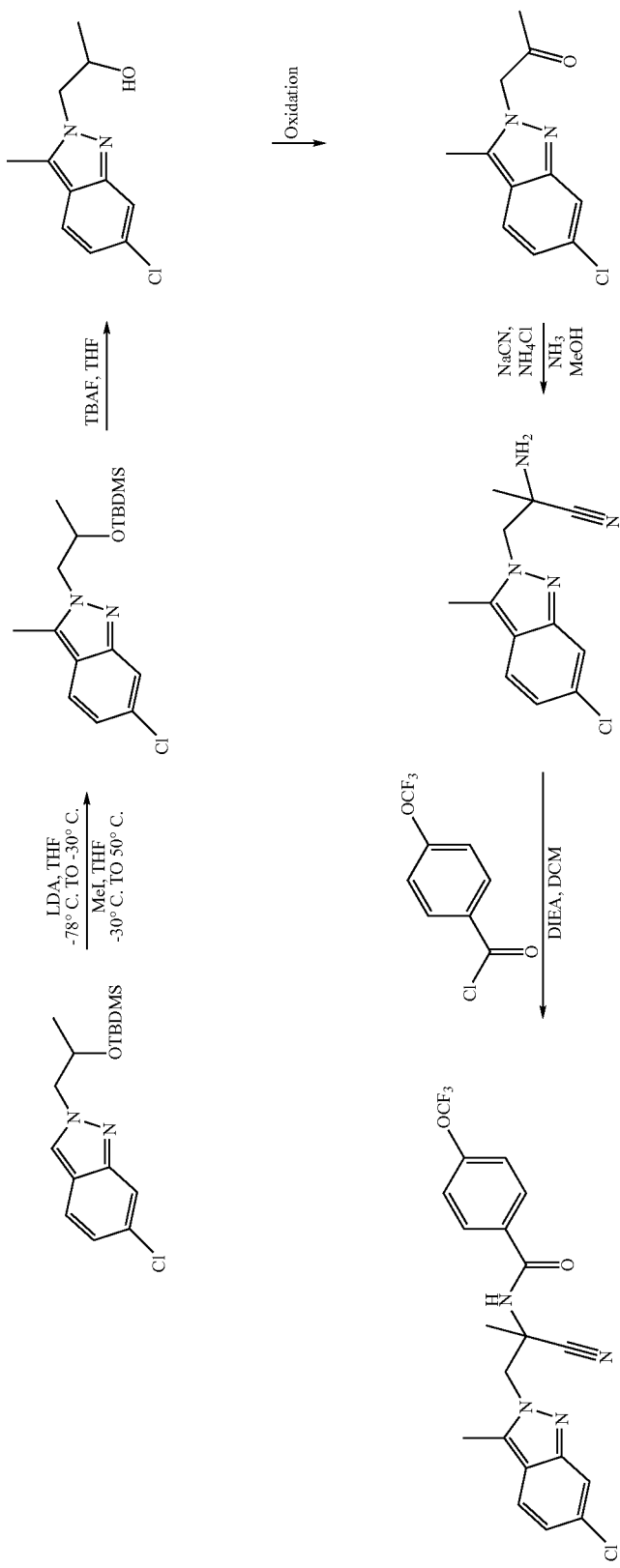

Example 145

N-[2-(6-Chloro-3-methyl-2H-indazol-2-yl)-1-cyano-1-methylethyl]-4-trifluoromethoxybenzamide (compound No 2.050)

Using a procedure similar to that described in Example 1, except using 2-amino-3-(6-chloro-3-methyl-2H-indazol-2-yl)-2-methylpropionitrile (33 mg), the title compound was isolated as a white solid (31 mg, 52%). 1H NMR: (400 MHz, CHLOROFORM-d): 1.98 (s, 3H), 2.79 (s, 3H), 4.69 (d, 1H), 4.83 (d, 1H), 7.05 (dd, J=8.9, 1.6 Hz, 1H), 7.34 (d, J=8.2 Hz, 2H), 7.55 (d, J=9.0 Hz, 1H), 7.60 (d, J=0.9 Hz, 1H), 7.96 (d, J=8.8 Hz, 2H) and 9.19 (s, 1H). 19F NMR (376 MHz, CHLOROFORM-d): −58.1 (s, 3F).

2-Amino-3-(6-chloro-3-methyl-2H-indazol-2-yl)-2-methylpropionitrile was prepared using a procedure similar to that described in Example 1, part b, except starting from 1-(6-chloro-3-methyl-2H-indazol-2-yl)propan-2-one. 1-(6-Chloro-3-methyl-2H-indazol-2-yl)propan-2-one was prepared using a procedure similar to that described in Example 105 part c and d except starting from 2-[2-(tert-butyldimethylsilanyloxy)propyl]-6-chloro-3-methyl-2H-indazole that was prepared as follows:

a. To a solution of diisopropylamine (0.31 mL) in THF (3 mL) was added a solution of n-butyl lithium (1.6 molar in hexanes, 1.26 ml) at −78° C. After stirring 30 minutes at −78° C., a solution of 2-[2-(tert-butyldimethylsilanyloxy)propyl]-6-chloro-2H-indazole (469 g), described in Example 132 part a, in THF (3 mL) was added and the mixture let warm to −30° C. over one hour. Methyl iodide (0.126 mL) was added at −30° C. and the mixture let warm to room temperature and then heated to 50° C. for 24 hours. The reaction mixture was quenched with water and extracted with ethyl acetate. The organic layer was collected, dried over magnesium sulfate, filtered and concentrated under reduced pressure to yield a residue that was purified by chromatography ($SiO_2$, heptane/EA) to afford a mixture (1.3:1, 408 mg) of desired 2-[2-(tert-butyldimethylsilanyloxy)propyl]-6-chloro-3-methyl-2H-indazole and starting material 2-[2-(tert-butyldimethylsilanyloxy)propyl]-6-chloro-2H-indazole.

Compounds of Examples 146 to 149 were prepared according to the following general reaction scheme:

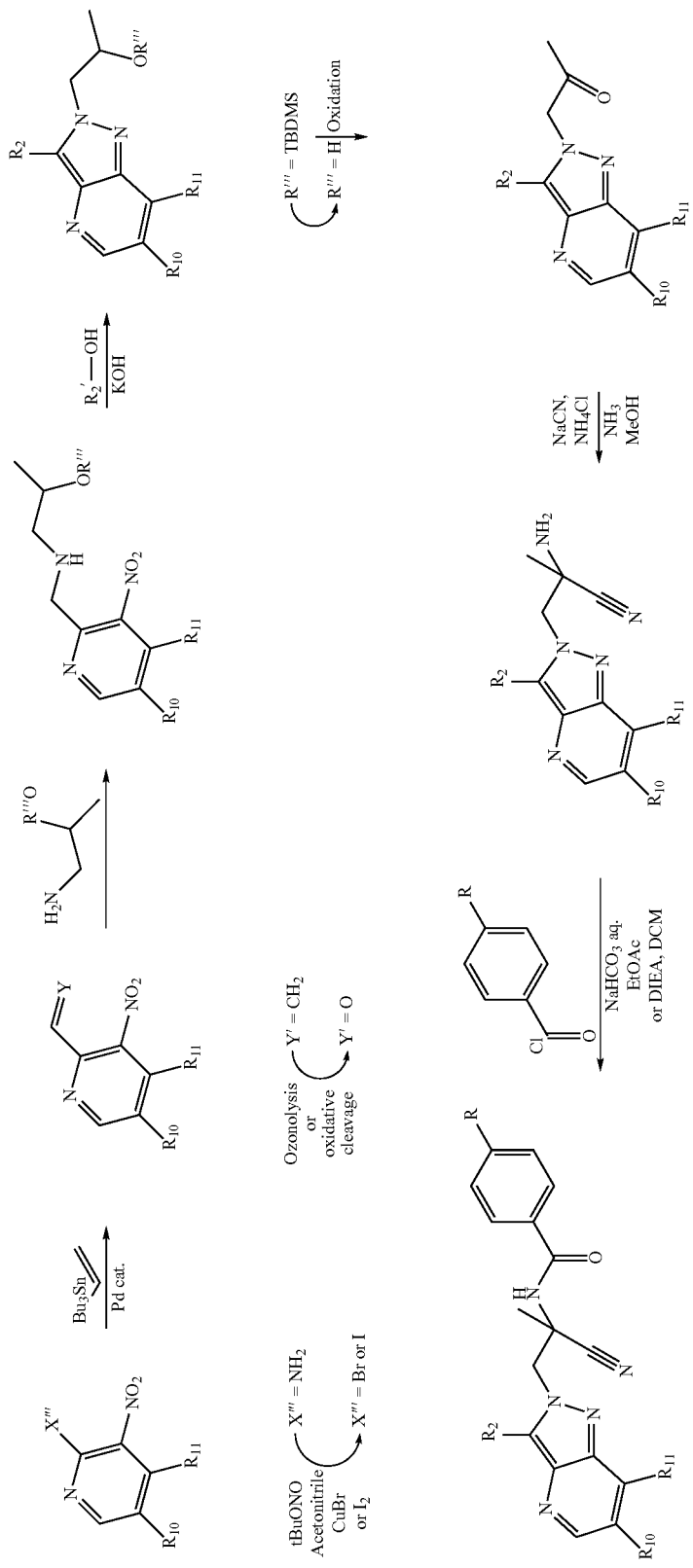

Final Product
V=N; W=C—H; X=C—R₁₀; Y=C—R₁₁;
Q=C—R₂; P=N;
R₃=R₄=H; a=1; R₅=CH₃; R₆=H;
Z=C(O); R₇=p-phenyl-R Example 146

N-[2-(6-Chloro-3-methoxy-2H-pyrazolo[4,3-b]pyridin-2-yl)-1-cyano-1-methylethyl]-4-trifluoromethoxybenzamide (compound No 3.001)

Using a procedure similar to that described in Example 1, except using 2-amino-3-(6-chloro-3-methoxy-2H-pyrazolo[4,3-b]pyridin-2-yl)-2-methylpropionitrile (15 mg), the title compound was isolated as a white solid (24 mg, 82%). MS (ES): M/Z [M+H]=454. 1H NMR: (400 MHz, CHLOROFORM-d): 1.91 (s, 3H), 4.52 (d, J=14.2 Hz, 1H), 4.66 (s, 3H), 4.85 (d, J=14.2 Hz, 1H), 7.33 (d, J=8.2 Hz, 2H), 7.77 (d, J=2.0 Hz, 1H), 7.94 (d, J=8.8 Hz, 2H), 8.31 (d, J=2.0 Hz, 1H) and 8.74 (s, 1H). 19F NMR (376 MHz, CHLOROFORM-d): −58.1 (s, 3F).

2-Amino-3-(6-chloro-3-methoxy-2H-pyrazolo[4,3-b]pyridin-2-yl)-2-methylpropionitrile (39 mg) was prepared quantitatively using a procedure similar to that described in Example 1, part b, except starting from 1-(6-chloro-3-methoxy-2H-pyrazolo[4,3-b]pyridin-2-yl)propan-2-one (32 mg). 1-(6-Chloro-3-methoxy-2H-pyrazolo[4,3-b]pyridin-2-yl)propan-2-one was prepared using a procedure similar to that described in Example 105 part a to d except using 5-chloro-3-nitropyridine-2-carboxaldehyde (1.2 g) and decaborane in part a to yield [2-(tert-butyldimethylsilanyloxy)propyl]-(5-chloro-3-nitropyridin-2-yl-methyl)amine (0.4 g, 17%). 5-Chloro-3-nitropyridine-2-carboxaldehyde was prepared using a procedure similar to that described in Example 136 part a to c except starting from 2-amino-5-chloro-3-nitropyridine in part a or using commercially available 2-bromo-5-chloro-3-nitropyridine in part b. Alternatively, oxidative cleavage using a 4% solution of osmium tetroxide in water (2 mL) and sodium periodate (1.2 g) was carried out in a mixture of THF and water (10:1, 20 mL) in part c instead of ozonolysis following a procedure similar to that described in Example 61 to afford 5-chloro-3-nitropyridine-2-carboxaldehyde (0.72 g, 72%) from 5-chloro-3-nitro-2-vinylpyridine (1 g).

Example 147

N-[2-(6-Chloro-3-methoxy-2H-pyrazolo[4,3-b]pyridin-2-yl)-1-cyano-1-methylethyl]-4-trifluoromethylthiobenzamide (compound No 3.002)

Using a procedure similar to that described in Example 1, 2-amino-3-(6-chloro-3-methoxy-2H-pyrazolo[4,3-b]pyridin-2-yl)-2-methylpropionitrile (15 mg, described in Example 146) and 4-trifluoromethylthiobenzoyl chloride, the title compound was isolated as a white solid (20 mg, 67%). MS (ES): M/Z [M+H]=470. 1H NMR: (400 MHz, CHLOROFORM-d): 1.92 (s, 3H), 4.53 (d, J=14.2 Hz, 1H), 4.67 (s, 3H), 4.86 (d, J=14.2 Hz, 1H), 7.77-7.82 (m, 3H), 7.93 (d, J=8.2 Hz, 2H), 8.31 (d, J=1.9 Hz, 1H) and 8.82 (s, 1H). 19F NMR (376 MHz, CHLOROFORM-d): −42.3 (s, 3F).

Example 148

N-[2-(6-Bromo-3-methoxy-7-methyl-2H-pyrazolo[4,3-b]pyridin-2-yl)-1-cyano-1-methylethyl]-4-trifluoromethoxybenzamide (compound No 3.007)

Using a procedure similar to that described in Example 1, except using 2-amino-3-(6-bromo-3-methoxy-7-methyl-2H-pyrazolo[4,3-b]pyridin-2-yl)-2-methylpropionitrile (20 mg), the title compound was isolated as a white solid (21 mg, 66%). 1H NMR: (400 MHz, CHLOROFORM-d): 1.93 (s, 3H), 2.57 (s, 3H), 4.51 (d, J=14.2 Hz, 1H), 4.66 (s, 3H), 4.85 (d, J=14.2 Hz, 1H), 7.31 (d, J=8.3 Hz, 2H), 7.97 (d, J=8.7 Hz, 2H), 8.39 (s, 1H) and 9.03 (s, 1H). 19F NMR (376 MHz, CHLOROFORM-d): −58.1 (s, 3F).

2-Amino-3-(6-bromo-3-methoxy-7-methyl-2H-pyrazolo[4,3-b]pyridin-2-yl)-2-methylpropionitrile (20 mg) was prepared using a procedure similar to that described in Example 1, part b, except starting from 1-(6-bromo-3-methoxy-7-methyl-2H-pyrazolo[4,3-b]pyridin-2-yl)propan-2-one (117 mg). 1-(6-Bromo-3-methoxy-7-methyl-2H-pyrazolo[4,3-b]pyridin-2-yl)propan-2-one was prepared using a procedure similar to that described in Example 105 part a to d except using 5-bromo-4-methyl-3-nitropyridine-2-carboxaldehyde (5.5 g) in part a to yield [2-(tert-butyldimethylsilanyloxy)propyl]-(5-bromo-4-methyl-3-nitropyridin-2-yl-methyl)amine (6 g, 67%). 5-Bromo-4-methyl-3-nitro-pyridine-2-carboxaldehyde was prepared using a procedure similar to that described in Example 136 part a to c except starting from 2-amino-5-bromo-4-methyl-3-nitropyridine (58.6 g) and using iodine (64 g) in part a instead of copper bromide to generate 5-bromo-2-iodo-4-methyl-3-nitropyridine (28.7 g, 33%). Oxidative cleavage using a 4% solution of osmium tetroxide in water (3 mL) and sodium periodate (23.1 g) was carried out in a mixture of THF and water (10:1, 330 mL) in part c instead of ozonolysis following a procedure similar to that described in Example 61 to afford 5-bromo-4-methyl-3-nitropyridine-2-carboxaldehyde (11.7 g, 59%) from 5-bromo-4-methyl-3-nitro-2-vinylpyridine (18.8 g). 2-Amino-5-bromo-4-methyl-3-nitropyridine (120.2 g, 85%) was prepared using a procedure similar to that described in Example 38 part a except starting from 2-amino-4-methyl-3-nitropyridine (101.5 g).

Example 149

N-[2-(6-Chloro-3-methoxy-7-methyl-2H-pyrazolo[4,3-b]pyridin-2-yl)-1-cyano-1-methylethyl]-4-trifluoromethoxybenzamide (compound No 3.008)

Using a procedure similar to that described in Example 1, except using 2-amino-3-(6-chloro-3-methoxy-7-methyl-2H-pyrazolo[4,3-b]pyridin-2-yl)-2-methylpropionitrile (26 mg), the title compound was isolated as a white solid (17 mg, 38%). 1H NMR: (400 MHz, CHLOROFORM-d): 1.93 (s, 3H), 2.56 (s, 3H), 4.51 (d, J=14.2 Hz, 1H), 4.66 (s, 3H), 4.86 (d, J=14.2 Hz, 1H), 7.31 (d, J=8.4 Hz, 2H), 7.98 (d, J=8.7 Hz, 2H), 8.28 (s, 1H) and 9.05 (s, 1H). 19F NMR (376 MHz, CHLOROFORM-d): −58.1 (s, 3F).

2-Amino-3-(6-chloro-3-methoxy-7-methyl-2H-pyrazolo[4,3-b]pyridin-2-yl)-2-methyl propionitrile (26 mg) was prepared using a procedure similar to that described in Example 1, part b, except starting from 1-(6-chloro-3-methoxy-7-methyl-2H-pyrazolo[4,3-b]pyridin-2-yl)propan-2-one (78 mg). 1-(6-Chloro-3-methoxy-7-methyl-2H-pyrazolo[4,3-b]pyridin-2-yl)propan-2-one was prepared using a procedure similar to that described in Example 105 part a to d except using 5-chloro-4-methyl-3-nitropyridine-2-carboxaldehyde (1.3 g) in part a to yield [2-(tert-butyldimethylsilanyloxy)propyl]-(5-chloro-4-methyl-3-nitropyridin-2-yl-methyl)amine (1.4 g, 57%). 5-Chloro-4-methyl-3-nitro-pyridine-2-carboxaldehyde was prepared using a procedure similar to that described in Example 136 part a to c except starting from 2-amino-5-chloro-4-methyl-3-nitropyridine (32 g) in part a to generate 2-bromo-5-chloro-4-methyl-3-nitropyridine (25.2 g, 59%). Oxidative cleavage using a 4% solution of osmium tetroxide in water (1.5 mL) and sodium periodate (2.5 g) was carried out in a mixture of THF and water (10:1, 60 mL) in part c instead of ozonolysis following a procedure similar to that described in Example 61 to afford 5-chloro-4-methyl-3-nitropyridine-2-carboxaldehyde (1.3 g, 56%) from 5-chloro-4-methyl-3-nitro-2-vinylpyridine (2.3 g). 2-Amino-5-chloro-4-methyl-3-nitropyridine (4.6 g, 75%) was prepared using a procedure similar to that described in Example 38 part a except starting from 2-amino-4-methyl-3-nitropyridine (5 g) and using N-chlorosuccinimide (5.8 g) instead of N-bromosuccinimide.

Compounds of Examples 150 to 152 were prepared according to the following general reaction scheme:

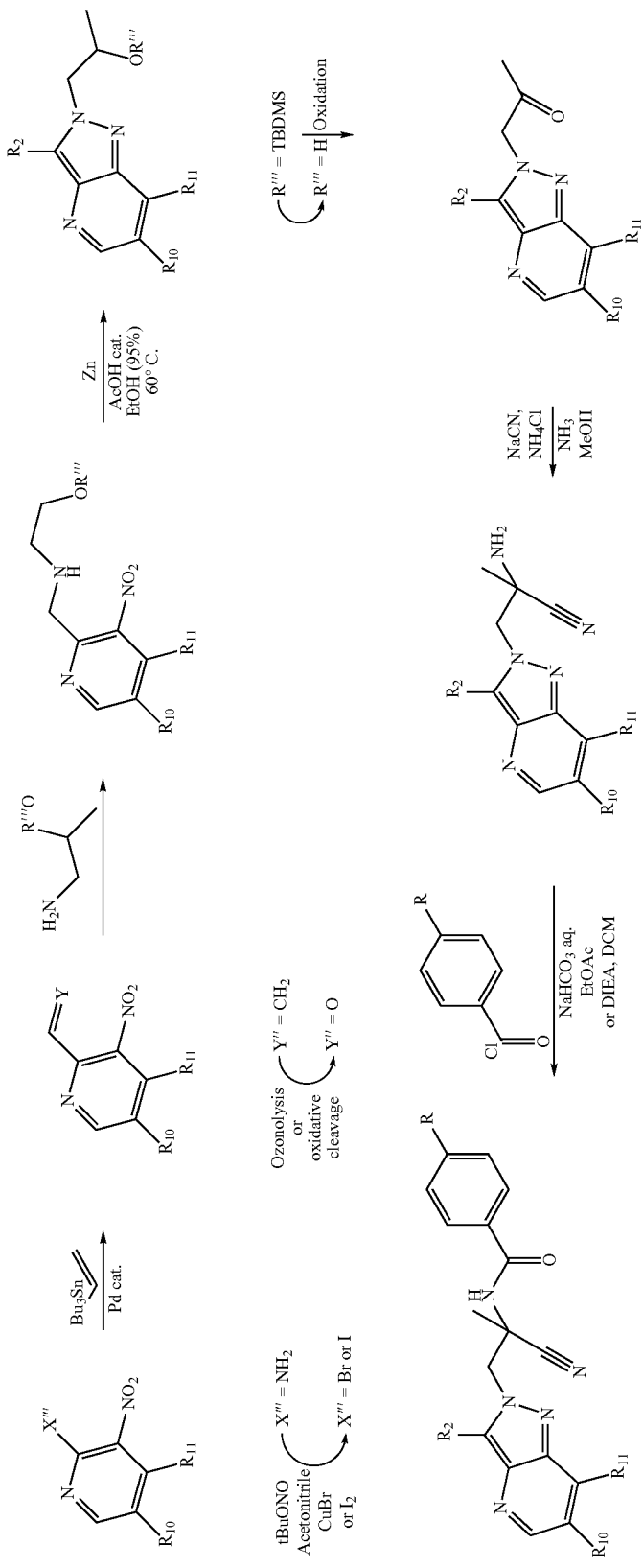

Final Product
V=N; W=C—H; X=C—R$_{10}$; Y=C—R$_{11}$;
Q=C—R$_2$; P=N;
R$_3$=R$_4$=H; a=1; R$_5$=CH$_3$; R$_6$=H;
Z=C(O); R$_7$=p-phenyl-R Example 150

N-[2-(6-Bromo-7-methyl-2H-pyrazolo[4,3-b]pyridin-2-yl)-1-cyano-1-methylethyl]-4-trifluoromethoxybenzamide (compound No 3.009)

Using a procedure adapted from that described in Example 1, using 2-amino-3-(6-bromo-7-methyl-2H-pyrazolo[4,3-b]pyridin-2-yl)-2-methylpropionitrile (27 mg), the title compound was isolated as a white solid (5 mg, 11%). MS (ES): M/Z [M+H]=482. 1H NMR: (400 MHz, CHLOROFORM-d): 1.97 (s, 3H), 2.68 (s, 3H), 4.82 (d, 1H), 4.98 (d, 1H), 7.32 (d, J=8.3 Hz, 2H), 7.93 (d, J=8.7 Hz, 2H), 8.38 (s, 1H), 8.41 (s, 1H) and 8.61 (s, 1H). 19F NMR (376 MHz, CHLOROFORM-d): −58.1 (s, 3F).

2-Amino-3-(6-bromo-7-methyl-2H-pyrazolo[4,3-b]pyridin-2-yl)-2-methylpropionitrile (33 mg) was prepared using a procedure similar to that described in Example 1, part b, except starting from 1-(6-bromo-7-methyl-2H-pyrazolo[4,3-b]pyridin-2-yl)propan-2-one (27 mg). 1-(6-Bromo-7-methyl-2H-pyrazolo[4,3-b]pyridin-2-yl)propan-2-one was prepared using a procedure similar to that described in Example 105 part c and d except starting from 2-[2-(tert-butyldimethylsilanyloxy)propyl]-6-bromo-7-methyl-2H-pyrazolo[4,3-b]pyridine. 2-[2-(tert-Butyldimethylsilanyloxy)propyl]-6-bromo-7-methyl-2H-pyrazolo[4,3-b]pyridine (0.15 g, 9%) was isolated along with 1-(6-bromo-7-methyl-2H-pyrazolo[4,3-b]pyridin-2-yl)propan-2-ol (0.14 g, 12%) using a procedure similar to that described in Example 132 part a except using [2-(tert-butyldimethylsilanyloxy)propyl]-(5-bromo-4-methyl-3-nitropyridin-2-yl-methyl)amine (1.9 g) described in Example 148.

Example 151

N-[2-(6-Bromo-7-methyl-2H-pyrazolo[4,3-b]pyridin-2-yl)-1-cyano-1-methylethyl]-4-trifluoromethylthiobenzamide (compound No 3.023)

Using a procedure adapted from that described in Example 1, using 2-amino-3-(6-bromo-7-methyl-2H-pyrazolo[4,3-b]pyridin-2-yl)-2-methylpropionitrile (56.7 mg, described in Example 150) and 4-trifluoromethylthiobenzoyl chloride, the title compound was isolated as a white solid (26 mg, 27%). MS (ES): M/Z [M+H]=498. 1H NMR: (400 MHz, CHLOROFORM-d): 1.97 (s, 3H), 2.67 (s, 3H), 4.82 (d, 1H), 4.97 (d, 1H), 7.77 (d, J=8.2 Hz, 2H), 7.92 (d, J=8.3 Hz, 2H), 8.38 (s, 1H), 8.54 (s, 1H) and 8.61 (s, 1H). 19F NMR (376 MHz, CHLOROFORM-d): −42.3 (s, 3F).

Example 152

N-[2-(6-Chloro-7-methyl-2H-pyrazolo[4,3-b]pyridin-2-yl)-1-cyano-1-methylethyl]-4-trifluoromethoxybenzamide (compound No 3.010)

Using a procedure similar to that described in Example 1, except using 2-amino-3-(6-chloro-7-methyl-2H-pyrazolo[4,3-b]pyridin-2-yl)-2-methylpropionitrile (32 mg), the title compound was isolated as a white solid (4 mg, 9%). 1H NMR: (400 MHz, CHLOROFORM-d): 1.97 (s, 3H), 2.67 (s, 3H), 4.83 (d, 1H), 4.97 (d, 1H), 7.32 (d, J=8.2 Hz, 2H), 7.93 (d, J=8.7 Hz, 2H), 8.39 (s, 1H), 8.44 (s, 1H) and 8.51 (s, 1H). 19F NMR (376 MHz, CHLOROFORM-d): −58.1 (s, 3F).

2-Amino-3-(6-chloro-7-methyl-2H-pyrazolo[4,3-b]pyridin-2-yl)-2-methylpropionitrile (33 mg) was prepared using a procedure similar to that described in Example 1, part b, except starting from 1-(6-chloro-7-methyl-2H-pyrazolo[4,3-b]pyridin-2-yl)propan-2-one (35 mg). 1-(6-Chloro-7-methyl-2H-pyrazolo[4,3-b]pyridin-2-yl)propan-2-one was prepared using a procedure similar to that described in Example 105 part c and d except starting from 2-[2-(tert-butyldimethylsilanyloxy)propyl]-6-chloro-7-methyl-2H-pyrazolo[4,3-b]pyridine. 2-[2-(tert-Butyldimethylsilanyloxy)propyl]-6-chloro-7-methyl-2H-pyrazolo[4,3-b]pyridine (0.13 g, 13%) was isolated along with 1-(6-chloro-7-methyl-2H-pyrazolo[4,3-b]pyridin-2-yl)propan-2-ol (0.13 mg, 21%) using a procedure similar to that described in Example 132 part a except using [2-(tert-butyldimethylsilanyloxy)propyl]-(5-chloro-4-methyl-3-nitropyridin-2-yl-methyl)amine (1.1 g) described in Example 149.

Compounds of Examples 153 to 154 were prepared according to the following general reaction scheme:

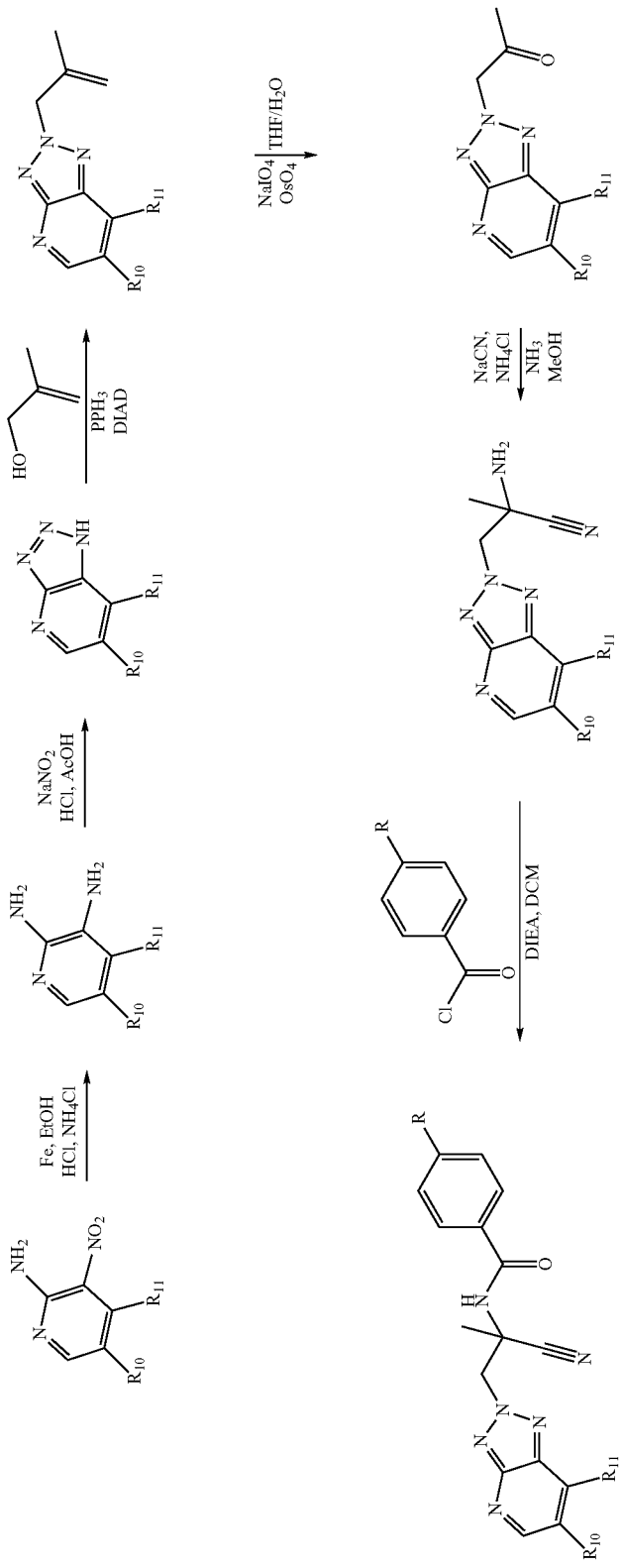

Final Product
V=N; W=C—H; X=C—$R_{10}$; Y=C—$R_{11}$;
Q=P=N;
$R_3$=$R_4$=H; a=1; $R_5$=$CH_3$; $R_6$=H;
Z=C(O); $R_7$=p-phenyl-R Example 153

N-[2-(6-Bromo-7-methyl-2H-[1,2,3]triazolo[4,5-b]pyridin-2-yl)-1-cyano-1-methylethyl]-4-trifluoromethoxybenzamide (compound No 3.003)

Using a procedure similar to that described in Example 1, except using 2-amino-3-(6-bromo-7-methyl-2H-[1,2,3]triazolo[4,5-b]pyridin-2-yl)-2-methylpropionitrile (60 mg), the title compound was isolated as a white solid (60 mg, 61%). Rf=0.4 (1:1 EA/heptane). MS (ES): M/Z [M−H]=481. 1H NMR: (400 MHz, DMSO-$d_6$): 1.76 (s, 3H), 2.56 (s, 3H), 5.41 (d, 1H), 5.54 (d, 1H), 7.52 (d, J=8.2 Hz, 2H), 7.92 (d, J=8.6 Hz, 2H) and 8.85 (s, 2H). 19F NMR (376 MHz, DMSO-$d_6$): −57.1 (s, 3F).

2-Amino-3-(6-bromo-7-methyl-2H-[1,2,3]triazolo[4,5-b]pyridin-2-yl)-2-methylpropionitrile (0.15 g, 55%) was prepared using a procedure similar to that described in Example 1, part b, except starting from 1-(6-bromo-7-methyl-2H-[1,2,3]triazolo[4,5-b]pyridin-2-yl)propan-2-one (0.25 g) that was prepared as follows:

a. To a mixture of 2-methyl-2-propen-1-ol (1.4 mL) and triphenylphosphine (3.7 g) in THF (80 mL) was added dropwise diisopropyl azodicarboxylate (DIAD, 2.7 mL). After stirring for 15 minutes, 6-bromo-7-methyl-2H-[1,2,3]triazolo[4,5-b]pyridine (2.3 g) was added and the reaction stirred for 3 hours at room temperature. The mixture was poured into water and extracted with ethyl acetate and washed with water. The organic layer was dried over sodium sulfate, filtered and concentrated under reduced pressure to give a residue that was purified by chromatography (SiO$_2$, heptane/EA) to afford 6-bromo-7-methyl-2-(2-methyl-allyl)-2H-[1,2,3]triazolo[4,5-b]pyridine. 6-Bromo-7-methyl-2H-[1,2,3]triazolo[4,5-b]pyridine (2.4 g, 74%) was prepared using a procedure similar to that described in Example 13 part a except starting from 5-bromo-4-methylpyridine-2,3-diamine (3.5 g, 80%) that was prepared using a procedure similar to that described in Example 38 part b except starting from 2-amino-5-bromo-4-methyl-3-nitropyridine (5 g) described in Example 148.

b. To a solution of 6-bromo-7-methyl-2-(2-methyl-allyl)-2H-[1,2,3]triazolo[4,5-b]pyridine (0.9 g) in a mixture of THF and water (8:1, 18 mL), was added sodium periodate (2 g) and a 4% osmium tetroxide solution in water (2 mL, 5 mole %). After stirring overnight at room temperature, the mixture was quenched with a 10% solution of sodium thiosulfate, extracted with ethyl acetate and washed with water. The organic layer was dried over sodium sulfate, filtered and concentrated under reduced pressure to give a residue that was purified by chromatography (SiO$_2$, heptane/EA) to afford 1-(6-bromo-7-methyl-2H-[1,2,3]triazolo[4,5-b]pyridin-2-yl)propan-2-one (0.3 g, 33%).

Example 154

N-[2-(6-Bromo-7-methyl-2H-[1,2,3]triazolo[4,5-b]pyridin-2-yl)-1-cyano-1-methylethyl]-4-trifluoromethylthiobenzamide (compound No 3.004)

Using a procedure similar to that described in Example 1, 2-amino-3-(6-bromo-7-methyl-2H-[1,2,3]triazolo[4,5-b]pyridin-2-yl)-2-methylpropionitrile (90 mg, described in Example 153) and 4-trifluoromethylthiobenzoyl chloride, the title compound was isolated as a white solid (65 mg, 43%). Rf=0.4 (1:1 EA/heptane). MS (ES): M/Z [M−H]=497. 1H NMR: (400 MHz, DMSO-$d_6$): 1.76 (s, 3H), 2.56 (s, 3H), 5.40 (d, 1H), 5.54 (d, 1H), 7.82-7.94 (m, 4H), 8.86 (s, 1H) and 8.93 (s, 1H). 19F NMR (376 MHz, DMSO-$d_6$): −42.0 (s, 3F).

Compounds of Examples 155 to 158 were prepared according to the following general reaction scheme:

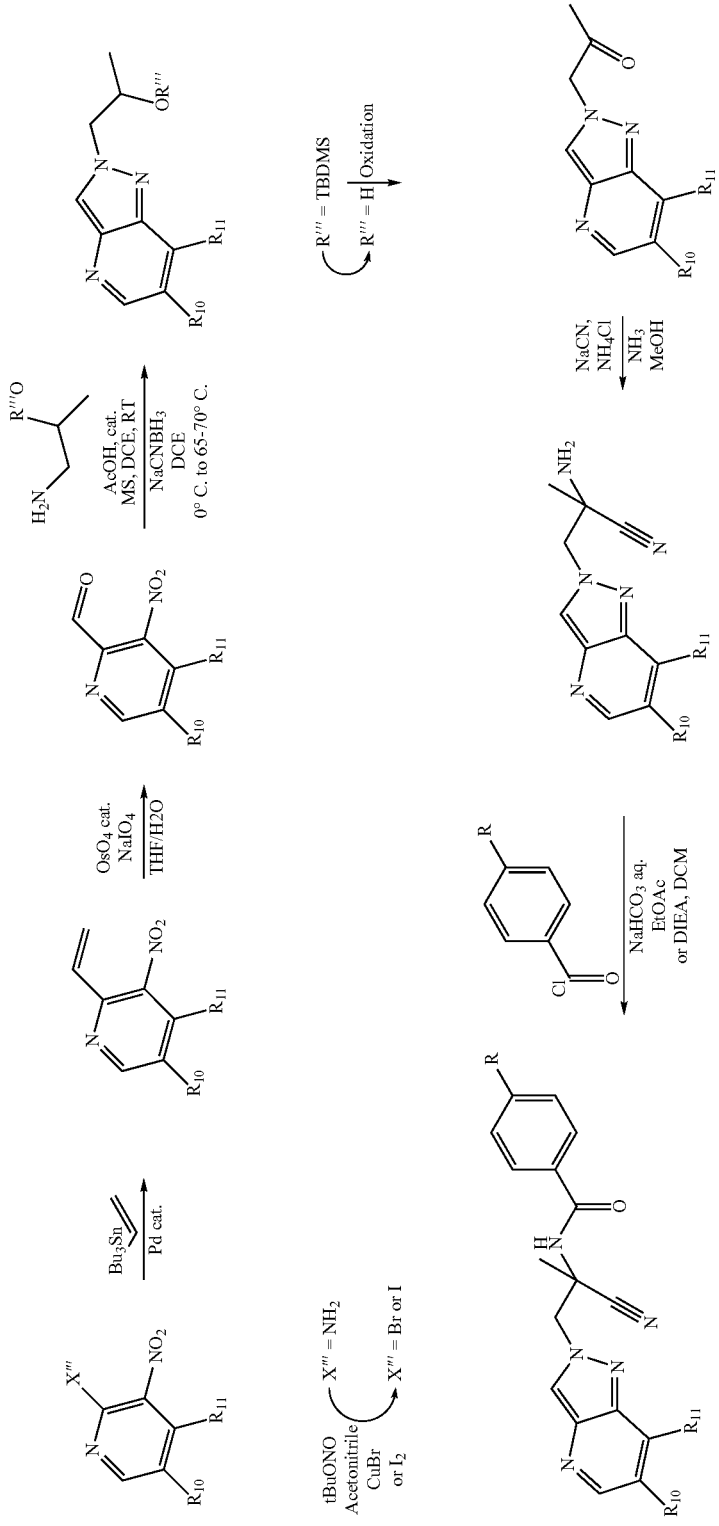

Final Product
V=N; W=C—H; X=C—R$_{10}$; Y=C—R$_{11}$;
Q=C—H; P=N;
R$_3$=R$_4$=H; a=1; R$_5$=CH$_3$; R$_6$=H;
Z=C(O); R$_7$=p-phenyl-R Example 155

N-[2-(6-Chloro-2H-pyrazolo[4,3-b]pyridin-2-yl)-1-cyano-1-methylethyl]-4-trifluoromethoxybenzamide (compound No 3.005)

Using a procedure similar to that described in Example 1, except using 2-amino-3-(6-chloro-2H-pyrazolo[4,3-b]pyridin-2-yl)-2-methylpropionitrile (1.1 g), the title compound was isolated as a white solid (1 g, 49%). MS (ES): M/Z [M+H]=424. 1H NMR: (400 MHz, CHLOROFORM-d): 1.95 (s, 3H), 4.86 (d, J=14.0 Hz, 1H), 5.02 (d, J=14.0 Hz, 1H), 7.33 (d, J=8.1 Hz, 2H), 7.88 (d, J=8.7 Hz, 2H), 8.02 (dd, J=2.1, 0.9 Hz, 1H), 8.03 (s, 1H), 8.42 (d, J=0.8 Hz, 1H) and 8.55 (d, J=2.1 Hz, 1H). 19F NMR (376 MHz, CHLOROFORM-d): −58.1 (s, 3F).

2-Amino-3-(6-chloro-2H-pyrazolo[4,3-b]pyridin-2-yl)-2-methylpropionitrile (1.1 g, 97%) was prepared using a procedure similar to that described in Example 1, part b, except starting from 1-(6-chloro-2H-pyrazolo[4,3-b]pyridin-2-yl)propan-2-one (1 g). 1-(6-Chloro-3-methoxy-2H-pyrazolo[4,3-b]pyridin-2-yl)propan-2-one was prepared using a procedure similar to that described in Example 105 part c and d except starting from 2-[2-(tert-butyldimethylsilanyloxy)propyl]-6-chloro-2H-pyrazolo[4,3-b]pyridine that was prepared as follows:

a. To a solution of 5-chloro-3-nitropyridine-2-carboxaldehyde (1 g), described in Example 146, in 1,2-dichloroethane (20 mL) was added 4 Å molecular sieves powder and 2-(tert-butyldimethylsilanyloxy)propylamine (1.22 g) described in Example 105 part a. After stirring overnight at room temperature, sodium cyanoborohydride (0.4 g) and acetic acid (0.33 mL) were added at 0° C. After stirring for one hour at 0° C., the reaction mixture was heated to 65° C. overnight. The reaction mixture was filtered through a plug of Celite® and concentrated under reduced pressure to yield a residue that was purified by chromatography (SiO$_2$, heptane/EA) to afford 2-[2-(tert-butyldimethylsilanyloxy)propyl]-6-chloro-2H-pyrazolo[4,3-b]pyridine (0.6 g, 37%). MS (ES): M/Z [M+H]=326. 1H NMR: (400 MHz, CHLOROFORM-d): −0.37 (s, 3H), −0.09 (s, 3H), 0.79 (s, 9H), 1.24 (d, J=6.1 Hz, 3H), 4.21-4.31 (m, 1H), 4.33-4.38 (m, 1H), 4.40-4.47 (m, 1H), 8.00 (dd, J=2.1, 0.9 Hz, 1H), 8.22 (d, J=0.7 Hz, 1H) and 8.48 (d, J=2.1 Hz, 1H).

Example 156

N-[2-(6-Chloro-2H-pyrazolo[4,3-b]pyridin-2-yl)-1-cyano-1-methylethyl]-4-trifluoromethylthiobenzamide (compound No 3.006)

Using a procedure similar to that described in Example 1, 2-amino-3-(6-chloro-2H-pyrazolo[4,3-b]pyridin-2-yl)-2-methylpropionitrile (35 mg, described in Example 155) and 4-trifluoromethylthiobenzoyl chloride, the title compound was isolated as a white solid (13 mg, 20%). MS (ES): M/Z [M+H]=440. 1H NMR: (400 MHz, CHLOROFORM-d): 1.96 (s, 3H), 4.86 (d, J=14.0 Hz, 1H), 5.01 (d, J=14.0 Hz, 1H), 7.71-7.83 (m, 2H), 7.83-7.92 (m, 2H), 8.02 (dd, J=2.1, 0.9 Hz, 1H), 8.12 (s, 1H), 8.43 (d, J=0.7 Hz, 1H) and 8.56 (d, J=2.1 Hz, 1H). 19F NMR (376 MHz, CHLOROFORM-d): −42.2 (s, 3F).

Example 157

N-[2-(6-Bromo-2H-pyrazolo[4,3-b]pyridin-2-yl)-1-cyano-1-methylethyl]-4-trifluoromethoxybenzamide (compound No 3.011)

Using a procedure similar to that described in Example 1, except using 2-amino-3-(6-bromo-2H-pyrazolo[4,3-b]pyridin-2-yl)-2-methylpropionitrile (156 mg), the title compound was isolated as a white solid (133 mg, 48%). MS (ES): M/Z [M+H]=468. 1H NMR: (400 MHz, CHLOROFORM-d): 1.93 (s, 3H), 4.84 (d, J=14.0 Hz, 1H), 5.00 (d, J=14.1 Hz, 1H), 7.31 (d, J=8.1 Hz, 2H), 7.82-7.90 (m, 2H), 7.99 (s, 1H), 8.20 (dd, J=1.9, 0.8 Hz, 1H), 8.39 (s, 1H) and 8.61 (d, J=2.0 Hz, 1H). 19F NMR (376 MHz, CHLOROFORM-d): −58.1 (s, 3F).

2-Amino-3-(6-bromo-2H-pyrazolo[4,3-b]pyridin-2-yl)-2-methylpropionitrile (416 mg, 80%) was prepared using a procedure similar to that described in Example 1, part b, except starting from 1-(6-bromo-2H-pyrazolo[4,3-b]pyridin-2-yl)propan-2-one (471 mg). 1-(6-Bromo-2H-pyrazolo[4,3-b]pyridin-2-yl)propan-2-one was prepared using a procedure similar to that described in Example 105 part c and d except starting from 2-[2-(tert-butyldimethylsilanyloxy)propyl]-6-bromo-2H-pyrazolo[4,3-b]pyridine (289 mg, 39%) that was prepared using a procedure similar to that described in Example 155 except starting from 5-bromo-3-nitropyridine-2-carboxaldehyde (462 mg). 5-Bromo-3-nitropyridine-2-carboxaldehyde was prepared using a procedure similar to that described in Example 136 part a to c except starting from 2-amino-5-bromo-3-nitropyridine (50 g) and using iodine (69.9 g) in part a instead of copper bromide to generate 5-bromo-2-iodo-3-nitropyridine as a yellow solid (27.4 g, 36%). Oxidative cleavage using a 4% solution of osmium tetroxide in water (4 mL) and sodium periodate (6.7 g) was carried out in a mixture of THF and water (10:1, 390 mL) in part c instead of ozonolysis following a procedure similar to that described in Example 61 to afford 5-bromo-3-nitropyridine-2-carboxaldehyde as a tan solid (3.8 g, 62%) from 5-bromo-3-nitro-2-vinylpyridine (6 g).

Example 158

N-[2-(6-Bromo-2H-pyrazolo[4,3-b]pyridin-2-yl)-1-cyano-1-methylethyl]-4-trifluoromethylthiobenzamide (compound No 3.012)

Using a procedure similar to that described in Example 1, 2-amino-3-(6-bromo-2H-pyrazolo[4,3-b]pyridin-2-yl)-2-methylpropionitrile (223 mg described in Example 157) and 4-trifluoromethylthiobenzoyl chloride, the title compound was isolated as a white solid (145 mg, 38%). MS (ES): M/Z [M+H]=484. 1H NMR: (400 MHz, CHLOROFORM-d): 1.95 (s, 3H), 4.86 (d, J=14.0 Hz, 1H), 5.01 (d, J=14.1 Hz, 1H), 7.78 (d, J=8.3 Hz, 2H), 7.84-7.90 (m, 2H), 8.11 (s, 1H), 8.22 (dd, J=2.0, 1.0 Hz, 1H), 8.42 (d, J=0.8 Hz, 1H) and 8.64 (d, J=2.0 Hz, 1H). 19F NMR (376 MHz, CHLOROFORM-d): −42.2 (s, 3F).

Compounds of Examples 159 to 160 were prepared according to the following general reaction scheme:

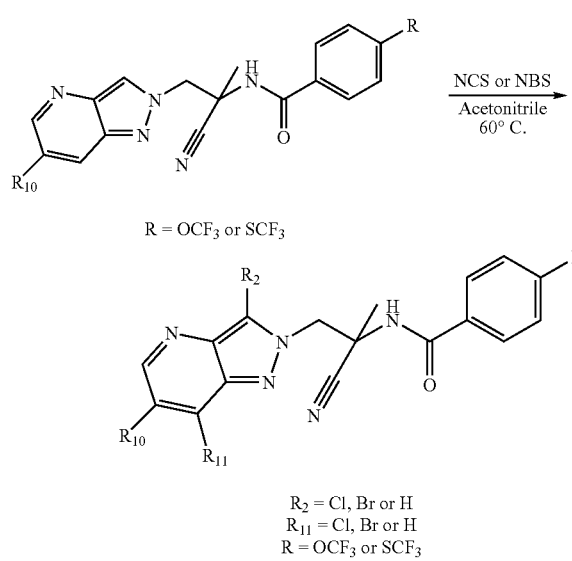

R = OCF₃ or SCF₃

R₂ = Cl, Br or H
R₁₁ = Cl, Br or H
R = OCF₃ or SCF₃

Final Product
V=N; W=C—H; X=C—R₁₀; Y=C—R₁₁;
Q=C—R₂; P=N;
R₃=R₄=H; a=1; R₅=CH₃; R₆=H;
Z=C(O); R₇=p-phenyl-R Example 159

N-[1-Cyano-2-(3,6-dichloro-2H-pyrazolo[4,3-b]pyridin-2-yl)-1-methylethyl]-4-trifluoromethoxybenzamide (compound No 3.017)

A mixture of N-[2-(6-Chloro-2H-pyrazolo[4,3-b]pyridin-2-yl)-1-cyano-1-methylethyl]-4-trifluoromethoxybenzamide (134 mg described in Example 155), and N-chlorosuccinimide (51 mg) in acetonitrile (3.5 mL) was heated to 60° C. overnight. The mixture was concentrated under reduced pressure to yield a residue that was purified by chromatography (SiO₂, heptane/EA) to afford the title compound as white solid (129 mg, 89%). MS (ES): M/Z [M+H]=458. 1H NMR: (400 MHz, DMSO-d₆): 1.78 (s, 3H), 5.10-5.20 (m, 2H), 7.53 (d, J=8.3 Hz, 2H), 7.97 (d, J=8.8 Hz, 2H), 8.43 (d, J=2.0 Hz, 1H), 8.59 (d, J=2.0 Hz, 1H) and 8.99 (s, 1H). 19F NMR (376 MHz, DMSO-d₆): −57.1 (s, 3F).

Example 160

N-[2-(3-Bromo-6-chloro-2H-pyrazolo[4,3-b]pyridin-2-yl)-1-cyano-1-methylethyl]-4-trifluoromethoxybenzamide (compound No 3.019)

A mixture of N-[2-(6-Chloro-2H-pyrazolo[4,3-b]pyridin-2-yl)-1-cyano-1-methylethyl]-4-trifluoromethoxybenzamide (134 mg described in Example 155) and N-bromosuccinimide (68 mg) in acetonitrile (3.5 mL) was heated to 60° C. overnight. The mixture was concentrated under reduced pressure to yield a residue that was purified by chromatography (SiO₂, heptane/EA) to afford the title compound as a white solid (125 mg, 80%). MS (ES): M/Z [M+H]=502. 1H NMR: (400 MHz, DMSO-d₆): 1.78 (s, 3H), 5.10-5.22 (m, 2H), 7.52 (d, J=8.2 Hz, 2H), 7.98 (d, J=8.7 Hz, 2H), 8.43 (d, J=2.0 Hz, 1H), 8.58 (d, J=1.9 Hz, 1H) and 9.00 (s, 1H). 19F NMR (376 MHz, DMSO-d₆): −57.1 (s, 3F).

TABLE 1

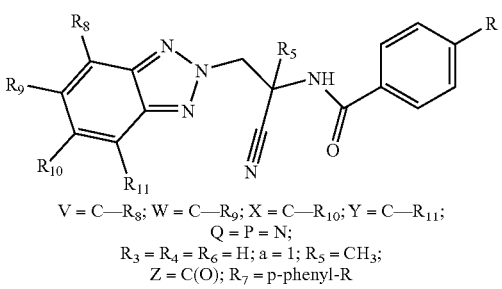

(Ic)

V = C—R₈; W = C—R₉; X = C—R₁₀; Y = C—R₁₁;
Q = P = N;
R₃ = R₄ = R₆ = H; a = 1; R₅ = CH₃;
Z = C(O); R₇ = p-phenyl-R

| Compound # | R | R₅ | R₈ | R₉ | R₁₀ | R₁₁ |
|---|---|---|---|---|---|---|
| 1.001 | OCF₃ | Me | H | Cl | H | H |
| 1.002 | CF₃ | Me | H | Cl | H | H |
| 1.003 | SCF₃ | Me | H | Cl | H | H |
| 1.004 | OCF₃ | Me | H | H | H | H |
| 1.005 | SCF₃ | Me | H | H | H | H |
| 1.006 | OCF₃ | Me | H | Me | H | H |
| 1.007 | SCF₃ | Me | H | Me | H | H |
| 1.008 | OCF₃ | Me | H | CF₃ | H | H |
| 1.009 | SCF₃ | Me | H | CF₃ | H | H |
| 1.010 | OCF₃ | Me | H | Cl | Cl | H |
| 1.011 | SCF₃ | Me | H | Cl | Cl | H |
| 1.012 | OCF₃ | Me | Cl | H | Cl | H |
| 1.013 | SCF₃ | Me | Cl | H | Cl | H |
| 1.014 | OCF₃ | Me | Cl | H | CF₃ | H |
| 1.015 | SCF₃ | Me | Cl | H | CF₃ | H |
| 1.016 | OCF₃ | Me | H | CN | H | H |
| 1.017 | SCF₃ | Me | H | CN | H | H |
| 1.018 | OCF₃ | Me | CF₃ | H | CF₃ | H |
| 1.019 | SCF₃ | Me | CF₃ | H | CF₃ | H |

TABLE 1-continued

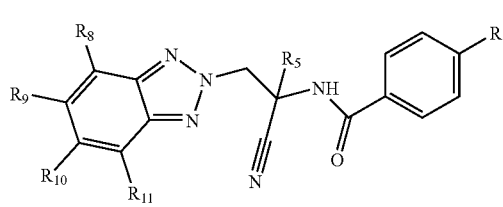

(Ic)

V = C—R$_8$; W = C—R$_9$; X = C—R$_{10}$; Y = C—R$_{11}$;
Q = P = N;
R$_3$ = R$_4$ = R$_6$ = H; a = 1; R$_5$ = CH$_3$;
Z = C(O); R$_7$ = p-phenyl-R

| Compound # | R | R$_5$ | R$_8$ | R$_9$ | R$_{10}$ | R$_{11}$ |
|---|---|---|---|---|---|---|
| 1.020 | OCF$_3$ | Me | H | Br | H | H |
| 1.021 | SCF$_3$ | Me | H | Br | H | H |
| 1.022 | SOCF$_3$ | Me | H | CN | H | H |
| 1.023 | SOCF$_3$ | Me | Cl | H | CF$_3$ | H |
| 1.024 | SOCF$_3$ | Me | Cl | H | Cl | H |
| 1.025 | SO$_2$CF$_3$ | Me | Cl | H | Cl | H |
| 1.026 | SO$_2$CF$_3$ | Me | H | CF$_3$ | H | H |
| 1.027 | SO$_2$CF$_3$ | Me | H | CN | H | H |
| 1.028 | SO$_2$CF$_3$ | Me | Cl | H | CF$_3$ | H |
| 1.029 | SO$_2$CF$_3$ | Me | H | H | H | H |
| 1.030 | SO$_2$CF$_3$ | Me | H | Me | H | H |
| 1.031 | SO$_2$CF$_3$ | Me | H | Cl | H | H |
| 1.032 | OPh | Me | H | Cl | H | H |
| 1.033 | OCF$_3$ | Me | Me | H | Cl | H |
| 1.034 | SCF$_3$ | Me | Me | H | Cl | H |
| 1.035 | OCF$_3$ | Me | H | OCF$_3$ | H | H |
| 1.036 | SCF$_3$ | Me | H | OCF$_3$ | H | H |
| 1.037 | OCF$_3$ | Me | CF$_3$ | H | Cl | H |
| 1.038 | SCF$_3$ | Me | CF$_3$ | H | Cl | H |
| 1.039 | OPh | Me | Me | H | Cl | H |
| 1.040 | OCF$_3$ | Me | H | Cl | Me | H |
| 1.041 | SCF$_3$ | Me | H | Cl | Me | H |
| 1.042 | OPh | Me | CF$_3$ | H | Cl | H |
| 1.043 | OCF$_3$ | Me | Cl | H | H | H |
| 1.044 | SCF$_3$ | Me | Cl | H | H | H |
| 1.045 | OPh | Me | Cl | H | H | H |
| 1.046 | Ph | Me | Cl | H | Cl | H |
| 1.047 | OCF$_3$ | Et | H | Cl | H | H |
| 1.048 | SCF$_3$ | Et | H | Cl | H | H |
| 1.049 | OCF$_3$ | CH$_2$CH(CH$_3$)$_2$ | H | Cl | H | H |
| 1.050 | SCF$_3$ | CH$_2$CH(CH$_3$)$_2$ | H | Cl | H | H |
| 1.051 | OCF$_3$ | t-Bu | H | Cl | H | H |
| 1.052 | SCF$_3$ | t-Bu | H | Cl | H | H |
| 1.053 | t-Bu | Me | Cl | H | Cl | H |
| 1.054 | OCF$_3$ | Me | CN | H | CF$_3$ | H |
| 1.055 | SCF$_3$ | Me | CN | H | CF$_3$ | H |
| 1.056 | OCF$_3$ | Me | CF$_3$ | H | CN | H |
| 1.057 | OCF$_3$ | Me | Br | Cl | H | H |
| 1.058 | OCF$_3$ | CH$_2$OH | H | Cl | H | H |
| 1.059 | SCF$_3$ | CH$_2$OH | H | Cl | H | H |
| 1.060 | OCF$_3$ | Me | Br | H | Cl | H |
| 1.061 | OCF$_3$ | CH$_2$SMe | H | Cl | H | H |
| 1.062 | OCF$_3$ | CH$_2$OMe | H | Cl | H | H |
| 1.063 | OCF$_3$ | CHOSO$_2$Me | H | Cl | H | H |
| 1.064 | OCF$_3$ | Me | Cl | Cl | H | Cl |
| 1.065 | SCF$_3$ | Me | Cl | Cl | H | Cl |
| 1.066 | SCF$_3$ | Me | CF$_3$ | H | CN | H |
| 1.067 | OCF$_3$ | Me | CN | H | Cl | H |
| 1.068 | OCF$_3$ | Me | p-Ph-CF$_3$ | H | Cl | H |
| 1.069 | CHFCF$_3$ | Me | Cl | H | Cl | H |
| 1.070 | OCF$_3$ | Me | Cl | H | OMe | H |
| 1.071 | SCF$_3$ | Me | Cl | H | OMe | H |
| 1.072 | OCF$_3$ | Me | H | OMe | H | H |
| 1.073 | SCF$_3$ | Me | H | OMe | H | H |
| 1.074 | OCF$_3$ | Me | CH$_2$NH$_2$ | H | Cl | H |
| 1.075 | OCF$_3$ | Me | Vinyl | H | Cl | H |
| 1.076 | SCF$_3$ | Me | Vinyl | H | Cl | H |
| 1.077 | OCF$_3$ | Me | CH(OH)CH$_2$OH | H | Cl | H |
| 1.078 | OCF$_3$ | Me | CH(F)CH$_2$F | H | Cl | H |
| 1.079 | OCF$_3$ | Me | Formyl | H | Cl | H |
| 1.080 | OCF$_3$ | Me | CH$_2$NMe | H | Cl | H |
| 1.081 | OCF$_3$ | Me | CH$_2$OH | H | Cl | H |
| 1.082 | OCF$_3$ | Me | CO$_2$H | H | Cl | H |

TABLE 1-continued

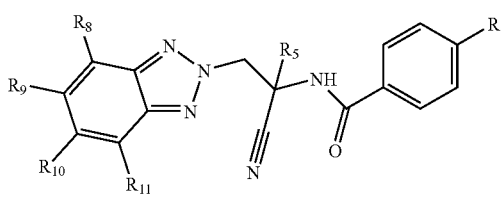

V = C—R$_8$; W = C—R$_9$; X = C—R$_{10}$; Y = C—R$_{11}$;
Q = P = N;
R$_3$ = R$_4$ = R$_6$ = H; a = 1; R$_5$ = CH$_3$;
Z = C(O); R$_7$ = p-phenyl-R

| Compound # | R | R$_5$ | R$_8$ | R$_9$ | R$_{10}$ | R$_{11}$ |
|---|---|---|---|---|---|---|
| 1.083 | OCF$_3$ | Me | Br | Cl | H | Br |
| 1.084 | OCF$_3$ | Me | CO$_2$Me | H | Cl | H |
| 1.085 | SCF$_3$ | Me | Br | Cl | H | Br |
| 1.086 | OCF$_3$ | Me | Br | Cl | H | Cl |
| 1.087 | SCF$_3$ | Me | Br | Cl | H | Cl |
| 1.088 | OCF$_3$ | Me | Br | Cl | Br | Cl |
| 1.089 | SCF$_3$ | Me | Br | Cl | Br | Cl |
| 1.090 | OCF$_3$ | Me | F | Cl | H | Cl |
| 1.091 | SCF$_3$ | Me | F | Cl | H | Cl |
| 1.092 | OCF$_3$ | Me | Me | Cl | H | Me |
| 1.093 | SCF$_3$ | Me | Me | Cl | H | Me |
| 1.094 | OCF$_3$ | Me | F | Br | H | Me |
| 1.095 | SCF$_3$ | Me | F | Br | H | Me |

Compounds of general formula (Ic) which are of particular interest are:

N-[2-(5-Chloro-2H-benzotriazol-2-yl)-1-cyano-1-methylethyl]-4-trifluoromethoxybenzamide (compound No 1.001)

N-[2-(5-Chloro-2H-benzotriazol-2-yl)-1-cyano-1-methylethyl]-4-trifluoromethylbenzamide (compound No 1.002)

N-[2-(5-Chloro-2H-benzotriazol-2-yl)-1-cyano-1-methylethyl]-4-trifluoromethylthiobenzamide (compound No 1.003)

N-[2-(2H-Benzotriazol-2-yl)-1-cyano-1-methylethyl]-4-trifluoromethoxybenzamide (compound No 1.004)

N-[2-(2H-Benzotriazol-2-yl)-1-cyano-1-methylethyl]-4-trifluoromethylthiobenzamide (compound No 1.005)

N-[1-Cyano-1-methyl-2-(5-methyl-2H-benzotriazol-2-yl)ethyl]-4-trifluoromethoxybenzamide (compound No 1.006)

N-[1-Cyano-1-methyl-2-(5-methyl-2H-benzotriazol-2-yl)ethyl]-4-trifluoromethylthiobenzamide (compound No 1.007)

N-[1-Cyano-1-methyl-2-(5-trifluoromethyl-2H-benzotriazol-2-yl)ethyl]-4-trifluoromethoxybenzamide (compound No 1.008)

N-[1-Cyano-1-methyl-2-(5-trifluoromethyl-2H-benzotriazol-2-yl)ethyl]-4-trifluoromethylthiobenzamide (compound No 1.009)

N-[1-Cyano-2-(5,6-dichloro-2H-benzotriazol-2-yl)-1-methylethyl]-4-trifluoromethoxybenzamide (compound No 1.010)

N-[1-Cyano-2-(5,6-dichloro-2H-benzotriazol-2-yl)-1-methylethyl]-4-trifluoromethylthiobenzamide (compound No 1.011)

N-[1-Cyano-2-(4,6-dichloro-2H-benzotriazol-2-yl)-1-methylethyl]-4-trifluoromethoxybenzamide (compound No 1.012)

N-[1-Cyano-2-(4,6-dichloro-2H-benzotriazol-2-yl)-1-methylethyl]-4-trifluoromethylthiobenzamide (compound No 1.013)

N-[2-(4-Chloro-6-trifluoromethyl-2H-benzotriazol-2-yl)-1-cyano-1-methylethyl]-4-trifluoromethoxybenzamide (compound No 1.014)

N-[2-(4-Chloro-6-trifluoromethyl-2H-benzotriazol-2-yl)-1-cyano-1-methylethyl]-4-trifluoromethylthiobenzamide (compound No 1.015)

N-[1-Cyano-2-(5-cyano-2H-benzotriazol-2-yl)-1-methylethyl]-4-trifluoromethoxybenzamide (compound No 1.016)

N-[1-Cyano-2-(5-cyano-2H-benzotriazol-2-yl)-1-methylethyl]-4-trifluoromethylthiobenzamide (compound No 1.017)

N-[2-(4,6-Bis(trifluoromethyl)-2H-benzotriazol-2-yl)-1-cyano-1-methylethyl]-4-trifluoromethoxybenzamide (compound No 1.018)

N-[2-(4,6-Bis(trifluoromethyl)-2H-benzotriazol-2-yl)-1-cyano-1-methylethyl]-4-trifluoromethylthiobenzamide (compound No 1.019)

N-[2-(5-Bromo-2H-benzotriazol-2-yl)-1-cyano-1-methylethyl]-4-trifluoromethoxybenzamide (compound No 1.020)

N-[2-(5-Bromo-2H-benzotriazol-2-yl)-1-cyano-1-methylethyl]-4-trifluoromethylthiobenzamide (compound No 1.021)

N-[1-Cyano-2-(5-cyano-2H-benzotriazol-2-yl)-1-methylethyl]-4-trifluoromethylsulfinylbenzamide (compound No 1.022)

N-[2-(4-Chloro-6-trifluoromethyl-2H-benzotriazol-2-yl)-1-cyano-1-methylethyl]-4-trifluoromethylsulfinylbenzamide (compound No 1.023)

N-[1-Cyano-2-(4,6-dichloro-2H-benzotriazol-2-yl)-1-methylethyl]-4-trifluoromethylsulfinylbenzamide (compound No 1.024)

N-[1-Cyano-2-(4,6-dichloro-2H-benzotriazol-2-yl)-1-methylethyl]-4-trifluoromethylsulfonylbenzamide (compound No 1.025)

N-[1-Cyano-1-methyl-2-(5-trifluoromethyl-2H-benzotriazol-2-yl)ethyl]-4-trifluoromethylsulfonylbenzamide (compound No 1.026)

N-[1-Cyano-1-methyl-2-(5-cyano-2H-benzotriazol-2-yl)-ethyl]-4-trifluoromethylsulfonylbenzamide (compound No 1.027)

N-[2-(4-Chloro-6-trifluoromethyl-2H-benzotriazol-2-yl)-1-cyano-1-methylethyl]-4-trifluoromethylsulfonylbenzamide (compound No 1.028)

N-[2-(2H-Benzotriazol-2-yl)-1-cyano-1-methylethyl]-4-trifluoromethylsulfonylbenzamide (compound No 1.029)

N-[1-Cyano-1-methyl-2-(5-methyl-2H-benzotriazol-2-yl)ethyl]-4-trifluoromethylsulfonylbenzamide (compound No 1.030)

N-[2-(5-Chloro-2H-benzotriazol-2-yl)-1-cyano-1-methylethyl]-4-trifluoromethylsulfonylbenzamide (compound No 1.031)

N-[2-(5-Chloro-2H-benzotriazol-2-yl)-1-cyano-1-methylethyl]-4-phenoxybenzamide (compound No 1.032)

N-[-2-(6-Chloro-4-methyl-2H-benzotriazol-2-yl)-1-cyano-1-methylethyl]-4-trifluoromethoxybenzamide (compound No 1.033)

N-[2-(6-Chloro-4-methyl-2H-benzotriazol-2-yl)-1-cyano-1-methylethyl]-4-trifluoromethylthiobenzamide (compound No 1.034)

N-[1-Cyano-1-methyl-2-(5-trifluoromethoxy-2H-benzotriazol-2-yl)ethyl]-4-trifluoromethoxybenzamide (compound No 1.035)

N-[1-Cyano-1-methyl-2-(5-trifluoromethoxy-2H-benzotriazol-2-yl)ethyl]-4-trifluoromethylthiobenzamide (compound No 1.036)

N-[2-(6-Chloro-4-trifluoromethyl-2H-benzotriazol-2-yl)-1-cyano-1-methylethyl]-4-trifluoromethoxybenzamide (compound No 1.037)

N-[2-(6-Chloro-4-trifluoromethyl-2H-benzotriazol-2-yl)-1-cyano-1-methylethyl]-4-trifluoromethylthiobenzamide (compound No 1.038)

N-[2-(6-Chloro-4-methyl-2H-benzotriazol-2-yl)-1-cyano-1-methylethyl]-4-phenoxybenzamide (compound No 1.039)

N-[2-(5-Chloro-6-methyl-2H-benzotriazol-2-yl)-1-cyano-1-methylethyl]-4-trifluoromethoxybenzamide (compound No 1.040)

N-[1-Cyano-1-methyl-2-(5-methyl-2H-benzotriazol-2-yl)ethyl]-4-trifluoromethylthiobenzamide (compound No 1.041)

N-[2-(6-Chloro-4-trifluoromethyl-2H-benzotriazol-2-yl)-1-cyano-1-methylethyl]-4-phenoxybenzamide (compound No 1.042)

N-[2-(4-Chloro-2H-benzotriazol-2-yl)-1-cyano-1-methylethyl]-4-trifluoromethoxybenzamide (compound No 1.043)

N-[2-(4-Chloro-2H-benzotriazol-2-yl)-1-cyano-1-methylethyl]-4-trifluoromethylthiobenzamide (compound No 1.044)

N-[2-(4-Chloro-2H-benzotriazol-2-yl)-1-cyano-1-methylethyl]-4-phenoxybenzamide (compound No 1.045)

N-[1-Cyano-2-(4,6-dichloro-2H-benzotriazol-2-yl)-1-methylethyl]biphenyl-4-carboxamide (compound No 1.046)

N-{1-[(5-Chloro-2H-benzotriazol-2-yl)methyl]-1-cyano-propyl}-4-trifluoromethoxybenzamide (compound No 1.047)

N-{1-[(5-Chloro-2H-benzotriazol-2-yl)methyl]-1-cyano-propyl}-4-trifluoromethylthiobenzamide (compound No 1.048)

N-{1-[(5-Chloro-2H-benzotriazol-2-yl)methyl]-1-cyano-3-methylbutyl}-4-trifluoromethoxybenzamide (compound No 1.049)

N-{1-[(5-Chloro-2H-benzotriazol-2-yl)methyl]-1-cyano-3-methylbutyl}-4-trifluoromethylthiobenzamide (compound No 1.050)

N-{1-[(5-Chloro-2H-benzotriazol-2-yl)methyl]-1-cyano-2,2-dimethylpropyl}-4-trifluoromethoxybenzamide (compound No 1.051)

N-{1-[(5-Chloro-2H-benzotriazol-2-yl)methyl]-1-cyano-2,2-dimethylpropyl}-4-trifluoromethylthiobenzamide (compound No 1.052)

N-[1-Cyano-2-(4,6-dichloro-2H-benzotriazol-2-yl)-1-methylethyl]-4-tert-butylbenzamide (compound No 1.053)

N-[1-Cyano-2-(4-cyano-6-trifluoromethyl-2H-benzotriazol-2-yl)-1-methylethyl]-4-trifluoromethoxybenzamide (compound No 1.054)

N-[1-Cyano-2-(4-cyano-6-trifluoromethyl-2H-benzotriazol-2-yl)-1-methylethyl]-4-trifluoromethylthiobenzamide (compound No 1.055)

N-[1-Cyano-2-(6-cyano-4-trifluoromethyl-2H-benzotriazol-2-yl)-1-methylethyl]-4-trifluoromethoxybenzamide (compound No 1.056)

N-[2-(4-Bromo-5-chloro-2H-benzotriazol-2-yl)-1-cyano-1-methylethyl]-4-trifluoromethoxybenzamide (compound No 1.057)

N-[2-(5-Chloro-2H-benzotriazol-2-yl)-1-cyano-1-(hydroxymethyl)ethyl]-4-trifluoromethoxybenzamide (compound No 1.058)

N-[2-(5-Chloro-2H-benzotriazol-2-yl)-1-cyano-1-(hydroxymethyl)ethyl]-4-trifluoromethylthiobenzamide (compound No 1.059)

N-[2-(4-Bromo-6-chloro-2H-benzotriazol-2-yl)-1-cyano-1-methylethyl]-4-trifluoromethoxybenzamide (compound No 1.060)

N-[2-(5-Chloro-2H-benzotriazol-2-yl)-1-cyano-1-(methylthiomethyl)ethyl]-4-trifluoromethoxybenzamide (compound No 1.061)

N-[2-(5-Chloro-2H-benzotriazol-2-yl)-1-cyano-1-(methoxymethyl)ethyl]-4-trifluoromethoxybenzamide (compound No 1.062)

N-[2-(5-Chloro-2H-benzotriazol-2-yl)-1-cyano-1-(methanesulfonylmethyl)ethyl]-4-trifluoromethoxybenzamide (compound No 1.063)

N-[1-Cyano-1-methyl-2-(4,5,7-trichloro-2H-benzotriazol-2-yl)-ethyl]-4-trifluoromethoxybenzamide (compound No 1.064)

N-[1-Cyano-1-methyl-2-(4,5,7-trichloro-2H-benzotriazol-2-yl)-ethyl]-4-trifluoromethylthiobenzamide (compound No 1.065)

N-[1-Cyano-2-(6-cyano-4-trifluoromethyl-2H-benzotriazol-2-yl)-1-methylethyl]-4-trifluoromethylthiobenzamide (compound No 1.066)

N-[2-(6-Chloro-4-cyano-2H-benzotriazol-2-yl)-1-cyano-1-methylethyl]-4-trifluoromethoxybenzamide (compound No 1.067)

N-{2-[6-Chloro-4-(4-trifluoromethylphenyl)-2H-benzotriazol-2-yl]-1-cyano-1-methylethyl}-4-trifluoromethoxybenzamide (compound No 1.068)

N-[1-Cyano-1-methyl-2-(4,5,7-trichloro-2H-benzotriazol-2-yl)-ethyl]-4-(1,2,2,2-tetrafluoroethyl)benzamide (compound No 1.069)

N-[2-(4-Chloro-6-methoxy-2H-benzotriazol-2-yl)-1-cyano-1-methylethyl]-4-trifluoromethoxybenzamide (compound No 1.070)

N-[2-(4-Chloro-6-methoxy-2H-benzotriazol-2-yl)-1-cyano-1-methylethyl]-4-trifluoromethylthiobenzamide (compound No 1.071)

N-[1-cyano-2-(5-methoxy-2H-benzotriazol-2-yl)-1-methylethyl]-4-trifluoromethoxybenzamide (compound No 1.072)

N-[1-cyano-2-(5-methoxy-2H-benzotriazol-2-yl)-1-methyl-ethyl]-4-trifluoromethylthiobenzamide (compound No 1.073)

N-[2-(4-Aminomethyl-6-chloro-2H-benzotriazol-2-yl)-1-cyano-1-methylethyl]-4-trifluoromethoxybenzamide (compound No 1.074)

N-[2-(6-Chloro-4-vinyl-2H-benzotriazol-2-yl)-1-cyano-1-methylethyl]-4-trifluoromethoxybenzamide (compound No 1.075)

N-[2-(6-Chloro-4-vinyl-2H-benzotriazol-2-yl)-1-cyano-1-methylethyl]-4-trifluoromethylthiobenzamide (compound No 1.076)

N-{2-[6-Chloro-4-(1,2-dihydroxyethyl)-2H-benzotriazol-2-yl]-1-cyano-1-methyl-ethyl}-4-trifluoromethoxybenzamide (compound No 1.077)

N-{2-[6-Chloro-4-(1,2-difluoroethyl)-2H-benzotriazol-2-yl]-1-cyano-1-methyl-ethyl}-4-trifluoromethoxybenzamide (compound No 1.078)

N-[2-(6-Chloro-4-formyl-2H-benzotriazol-2-yl)-1-cyano-1-methylethyl]-4-trifluoromethoxybenzamide (compound No 1.079)

N-[2-(6-Chloro-4-dimethylaminomethyl-2H-benzotriazol-2-yl)-1-cyano-1-methylethyl]-4-trifluoromethoxybenzamide (compound No 1.080)

N-[2-(6-Chloro-4-hydroxymethyl-2H-benzotriazol-2-yl)-1-cyano-1-methylethyl]-4-trifluoromethoxybenzamide (compound No 1.081)

6-Chloro-2-[2-cyano-2-({[4-(trifluoromethoxy)phenyl]carbonyl}amino)-propyl]-2H-benzotriazole-4-carboxylic acid (compound No 1.082)

Methyl 6-chloro-2-[2-cyano-2-({[4-(trifluoromethoxy)phenyl]carbonyl}-amino)propyl]-2H-benzotriazole-4-carboxylate (compound No 1.084)

N-[2-(5-Chloro-4,7-d bromo-2H-benzotriazol-2-yl)-1-cyano-1-methylethyl]-4-trifluoromethylthiobenzamide (compound No 1.085)

N-[2-(4-Bromo-5,7-dichloro-2H-benzotriazol-2-yl)-1-cyano-1-methylethyl]-4-trifluoromethoxybenzamide (compound No 1.086)

N-[2-(4-Bromo-5,7-dichloro-2H-benzotriazol-2-yl)-1-cyano-1-methylethyl]-4-trifluoromethylthiobenzamide (compound No 1.087)

N-[1-Cyano-2-(4,6-dibromo-5,7-dichloro-2H-benzotriazol-2-yl)-1-methylethyl]-4-trifluoromethoxybenzamide (compound No 1.088)

N-[1-Cyano-2-(4,6-dibromo-5,7-dichloro-2H-benzotriazol-2-yl)-1-methylethyl]-4-trifluoromethylthiobenzamide (compound No 1.089)

N-[1-Cyano-2-(5,7-dichloro-4-fluoro-2H-benzotriazol-2-yl)-1-methylethyl]-4-trifluoromethoxybenzamide (compound No 1.090)

N-[1-Cyano-2-(5,7-dichloro-4-fluoro-2H-benzotriazol-2-yl)-1-methylethyl]-4-trifluoromethylthiobenzamide (compound No 1.091)

N-[2-(5-Chloro-4,7-dimethyl-2H-benzotriazol-2-yl)-1-cyano-1-methylethyl]-4-trifluoromethoxybenzamide (compound No 1.092)

N-[2-(5-Chloro-4,7-dimethyl-2H-benzotriazol-2-yl)-1-cyano-1-methylethyl]-4-trifluoromethylthiobenzamide (compound No 1.093)

N-[2-(5-bromo-4-fluoro-7-methyl-2H-benzotriazol-2-yl)-1-cyano-1-methylethyl]-4-trifluoromethoxybenzamide (compound No 1.094)

N-[2-(5-bromo-4-fluoro-7-methyl-2H-benzotriazol-2-yl)-1-cyano-1-methylethyl]-4-trifluoromethylthiobenzamide (compound No 1.095)

The numbers 1.001 to 1.095 are assigned to the above compounds for identification and reference hereinafter.

TABLE 2

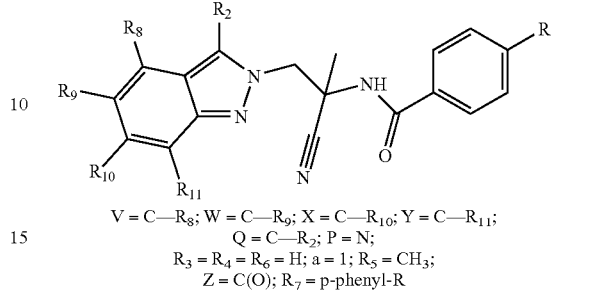

(Id)

$V = C-R_8;\ W = C-R_9;\ X = C-R_{10};\ Y = C-R_{11};$
$Q = C-R_2;\ P = N;$
$R_3 = R_4 = R_6 = H;\ a = 1;\ R_5 = CH_3;$
$Z = C(O);\ R_7 = \text{p-phenyl-R}$

| Compound # | R | $R_2$ | $R_8$ | $R_9$ | $R_{10}$ | $R_{11}$ |
|---|---|---|---|---|---|---|
| 2.001 | $OCF_3$ | H | H | $NO_2$ | H | H |
| 2.002 | $SCF_3$ | H | H | $NO_2$ | H | H |
| 2.003 | $OCF_3$ | H | H | Cl | H | Cl |
| 2.004 | OPh | H | H | Cl | H | Cl |
| 2.005 | $SCF_3$ | H | H | Cl | H | Cl |
| 2.006 | $OCF_3$ | H | H | Cl | H | Me |
| 2.007 | $SCF_3$ | H | H | Cl | H | Me |
| 2.008 | $OCF_3$ | OMe | H | H | Cl | H |
| 2.009 | $SCF_3$ | OMe | H | H | Cl | H |
| 2.010 | $OCF_3$ | Me | H | Cl | H | Cl |
| 2.011 | $SCF_3$ | Me | H | Cl | H | Cl |
| 2.012 | $OCF_3$ | OMe | H | Cl | H | H |
| 2.013 | $SCF_3$ | OMe | H | Cl | H | H |
| 2.014 | $OCF_3$ | OEt | H | Cl | H | H |
| 2.015 | $SCF_3$ | OEt | H | Cl | H | H |
| 2.016 | $OCF_3$ | OMe | H | H | H | H |
| 2.017 | $OCF_3$ | $O(CH_2)_2OMe$ | H | H | Cl | H |
| 2.018 | $OCF_3$ | $O(CH_2)_2NMe_2$ | H | H | Cl | H |
| 2.019 | $SCF_3$ | OMe | H | Cl | H | Cl |
| 2.020 | $OCF_3$ | OMe | H | Cl | H | Cl |
| 2.021 | $OCF_3$ | OMe | Cl | H | Cl | H |
| 2.022 | $SCF_3$ | OMe | Cl | H | Cl | H |
| 2.023 | $OCF_3$ | OMe | H | H | Br | H |
| 2.024 | $SCF_3$ | OMe | H | H | Br | H |
| 2.025 | $OCF_3$ | OMe | H | H | $CF_3$ | H |
| 2.026 | $SCF_3$ | OMe | H | H | $CF_3$ | H |
| 2.027 | $OCF_3$ | OEt | H | H | Cl | H |
| 2.028 | $SCF_3$ | OEt | H | H | Cl | H |
| 2.029 | $OCF_3$ | O-n-Pr | H | H | Cl | H |
| 2.030 | $SCF_3$ | O-n-Pr | H | H | Cl | H |
| 2.031 | $OCF_3$ | O-n-Bu | H | H | Cl | H |
| 2.032 | $OCF_3$ | OMe | H | H | $CO_2Me$ | H |
| 2.033 | $OCF_3$ | OMe | H | H | $NO_2$ | H |
| 2.034 | $OCF_3$ | OMe | H | H | $NH_2$ | H |
| 2.035 | $OCF_3$ | OMe | H | H | NHAc | H |
| 2.036 | $OCF_3$ | OMe | H | H | $CONH_2$ | H |
| 2.037 | $OCF_3$ | H | H | H | Cl | H |
| 2.038 | $SCF_3$ | H | H | H | Cl | H |
| 2.039 | $OCF_3$ | Cl | H | H | Cl | Cl |
| 2.040 | $OCF_3$ | H | Cl | H | Cl | H |
| 2.041 | $SCF_3$ | H | Cl | H | Cl | H |
| 2.042 | $OCF_3$ | Br | H | H | Cl | H |
| 2.043 | $OCF_3$ | H | H | H | Cl | Br |
| 2.044 | $OCF_3$ | Cl | H | H | Cl | H |
| 2.045 | $OCF_3$ | H | H | H | Cl | H |
| 2.046 | $OCF_3$ | Br | Cl | H | Cl | Br |
| 2.047 | $OCF_3$ | H | Cl | H | Cl | Br |
| 2.048 | $OCF_3$ | H | Cl | H | Cl | Cl |
| 2.049 | $SCF_3$ | H | Cl | H | Cl | Cl |
| 2.050 | $OCF_3$ | Me | H | H | Cl | H |

Compounds of general formula (Id) which are of particular interest are:

N-[1-Cyano-methyl-2-(5-nitro-2H-indazol-2-yl)ethyl]-4-trifluoromethoxybenzamide (compound No 2.001)

N-[1-Cyano-1-methyl-2-(5-nitro-2H-indazol-2-yl)ethyl]-4-trifluoromethylthiobenzamide (compound No 2.002)

N-[1-Cyano-2-(5,7-dichloro-2H-indazol-2-yl)-1-methylethyl]-4-trifluoromethoxybenzamide (compound No 2.003)

N-[1-Cyano-2-(5,7-dichloro-2H-indazol-2-yl)-1-methylethyl]-4-phenoxybenzamide (compound No 2.004)

N-[1-Cyano-2-(5,7-dichloro-2H-indazol-2-yl)-1-methylethyl]-4-trifluoromethylthiobenzamide (compound No 2.005)

N-[2-(5-Chloro-7-methyl-2H-indazol-2-yl)-1-cyano-1-methylethyl]-4-trifluoromethoxybenzamide (compound No 2.006)

N-[2-(5-Chloro-7-methyl-2H-indazol-2-yl)-1-cyano-1-methylethyl]-4-trifluoromethylthiobenzamide (compound No 2.007)

N-[2-(6-Chloro-3-methoxy-2H-indazol-2-yl)-1-cyano-1-methylethyl]-4-trifluoromethoxybenzamide (compound No 2.008)

N-[2-(6-Chloro-3-methoxy-2H-indazol-2-yl)-1-cyano-1-methylethyl]-4-trifluoromethylthiobenzamide (compound No 2.009)

N-[1-Cyano-2-(5,7-dichloro-3-methyl-2H-indazol-2-yl)-1-methylethyl]-4-trifluoromethoxybenzamide (compound No 2.010)

N-[2-(5,7-Dichloro-3-methyl-2H-indazol-2-yl)-1-cyano-1-methylethyl]-4-trifluoromethylthiobenzamide (compound No 2.011)

N-[2-(5-Chloro-3-methoxy-2H-indazol-2-yl)-1-cyano-1-methylethyl]-4-trifluoromethoxybenzamide (compound No 2.012)

N-[2-(5-Chloro-3-methoxy-2H-indazol-2-yl)-1-cyano-1-methylethyl]-4-trifluoromethylthiobenzamide (compound No 2.013)

N-[2-(5-Chloro-3-ethoxy-2H-indazol-2-yl)-1-cyano-1-methylethyl]-4-trifluoromethoxybenzamide (compound No 2.014)

N-[2-(5-Chloro-3-ethoxy-2H-indazol-2-yl)-1-cyano-1-methylethyl]-4-trifluoromethylthiobenzamide (compound No 2.015)

N-[1-Cyano-2-(3-methoxy-2H-indazol-2-yl)-1-methylethyl]-4-trifluoromethoxybenzamide (compound No 2.016)

N-{2-[6-Chloro-3-(2-methoxyethoxy)-2H-indazol-2-yl]-1-cyano-1-methylethyl}-4-trifluoromethoxybenzamide (compound No 2.017)

N-{2-[6-Chloro-3-(2-dimethylaminoethoxy)-2H-indazol-2-yl]-1-cyano-1-methylethyl}-4-trifluoromethoxybenzamide (compound No 2.018)

N-[1-Cyano-2-(5,7-dichloro-3-methoxy-2H-indazol-2-yl)-1-methylethyl]-4-trifluoromethylthiobenzamide (compound No 2.019)

N-[1-Cyano-2-(5,7-dichloro-3-methoxy-2H-indazol-2-yl)-1-methylethyl]-4-trifluoromethoxybenzamide (compound No 2.020)

N-[1-Cyano-2-(4,6-dichloro-3-methoxy-2H-indazol-2-yl)-1-methylethyl]-4-trifluoromethoxybenzamide (compound No 2.021)

N-[1-Cyano-2-(4,6-dichloro-3-methoxy-2H-indazol-2-yl)-1-methylethyl]-4-trifluoromethylthiobenzamide (compound No 2.022)

N-[2-(6-Bromo-3-methoxy-2H-indazol-2-yl)-1-cyano-1-methylethyl]-4-trifluoromethoxybenzamide (compound No 2.023)

N-[2-(6-Bromo-3-methoxy-2H-indazol-2-yl)-1-cyano-1-methylethyl]-4-trifluoromethylthiobenzamide (compound No 2.024)

N-[1-Cyano-2-(3-methoxy-6-trifluoromethyl-2H-indazol-2-yl)-1-methylethyl]-4-trifluoromethoxybenzamide (compound No 2.025)

N-[1-Cyano-2-(3-methoxy-6-trifluoromethyl-2H-indazol-2-yl)-1-methylethyl]-4-trifluoromethylthiobenzamide (compound No 2.026)

N-[2-(6-Chloro-3-ethoxy-2H-indazol-2-yl)-1-cyano-1-methylethyl]-4-trifluoromethoxybenzamide (compound No 2.027)

N-[2-(6-Chloro-3-ethoxy-2H-indazol-2-yl)-1-cyano-1-methylethyl]-4-trifluoromethylthiobenzamide (compound No 2.028)

N-[2-(6-Chloro-3-propoxy-2H-indazol-2-yl)-1-cyano-1-methylethyl]-4-trifluoromethoxybenzamide (compound No 2.029)

N-[2-(6-Chloro-3-propoxy-2H-indazol-2-yl)-1-cyano-1-methylethyl]-4-trifluoromethylthiobenzamide (compound No 2.030)

N-[2-(6-Chloro-3-butoxy-2H-indazol-2-yl)-1-cyano-1-methylethyl]-4-trifluoromethoxybenzamide (compound No 2.031)

Methyl 2-[2-cyano-2-methyl-2-(4-trifluoromethoxybenzoylamino)ethyl]-3-methoxy-2H-indazole-6-carboxylate (compound No 2.032)

N-[1-Cyano-2-(3-methoxy-6-nitro-2H-indazol-2-yl)-1-methylethyl]-4-trifluoromethoxybenzamide (compound No 2.033)

N-[2-(6-Amino-3-methoxy-2H-indazol-2-yl)-1-cyano-1-methylethyl]-4-trifluoromethoxybenzamide (compound No 2.034)

N-[2-(6-Acetylamino-3-methoxy-2H-indazol-2-yl)-1-cyano-1-methylethyl]-4-trifluoromethoxybenzamide (compound No 2.035)

Methyl 2-[2-cyano-2-methyl-2-(4-trifluoromethoxybenzoylamino)ethyl]-3-methoxy-2H-indazole-6-carboxamide (compound No 2.036)

N-[2-(6-Chloro-2H-indazol-2-yl)-1-cyano-1-methylethyl]-4-trifluoromethoxybenzamide (compound No 2.037)

N-[2-(6-Chloro-2H-indazol-2-yl)-1-cyano-1-methylethyl]-4-trifluoromethylthiobenzamide (compound No 2.038)

N-[1-Cyano-1-methyl-2-(3,6,7-trichloro-2H-indazol-2-yl)ethyl]-4-trifluoromethoxybenzamide (compound No 2.039)

N-[1-Cyano-2-(4,6-dichloro-2H-indazol-2-yl)-1-methylethyl]-4-trifluoromethoxybenzamide (compound No 2.040)

N-[1-Cyano-2-(4,6-dichloro-2H-indazol-2-yl)-1-methylethyl]-4-trifluoromethylthiobenzamide (compound No 2.041)

N-[2-(3-Bromo-6-chloro-2H-indazol-2-yl)-1-cyano-1-methylethyl]-4-trifluoromethoxybenzamide (compound No 2.042)

N-[2-(7-Bromo-6-chloro-2H-indazol-2-yl)-1-cyano-1-methylethyl]-4-trifluoromethoxybenzamide (compound No 2.043)

N-[1-Cyano-2-(3,6-dichloro-2H-indazol-2-yl)-1-methylethyl]-4-trifluoromethoxybenzamide (compound No 2.044)

N-[1-Cyano-2-(6,7-dichloro-2H-indazol-2-yl)-1-methylethyl]-4-trifluoromethoxybenzamide (compound No 2.045)

N-[1-Cyano-2-(3,7-dibromo-4,6-dichloro-2H-indazol-2-yl)-1-methylethyl]-4-trifluoromethoxybenzamide (compound No 2.046)

N-[2-(7-Bromo-6,7-dichloro-2H-indazol-2-yl)-1-cyano-1-methylethyl]-4-trifluoromethoxybenzamide (compound No 2.047)

N-[1-Cyano-1-methyl-2-(4,6,7-trichloro-2H-indazol-2-yl)ethyl]-4-trifluoromethoxybenzamide (compound No 2.048)

N-[1-Cyano-1-methyl-2-(4,6,7-trichloro-2H-indazol-2-yl)ethyl]-4-trifluoromethylthiobenzamide (compound No 2.049)

N-[2-(6-Chloro-3-methyl-2H-indazol-2-yl)-1-cyano-1-methylethyl]-4-trifluoromethoxybenzamide (compound No 2.050)

The numbers 2.001 to 2.050 are assigned to the above compounds for identification and reference hereinafter.

TABLE 3

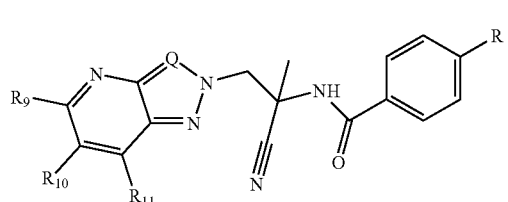

(Ie)

V = N; W = C—R$_9$; X = C—R$_{10}$; Y = C—R$_{11}$;
Q = C—R$_2$; P = N;
R$_3$ = R$_4$ = R$_6$ = H; a = 1; R$_5$ = CH$_3$;
Z = C(O); R$_7$ = p-phenyl-R

| Compound # | R | Q | R$_9$ | R$_{10}$ | R$_{11}$ |
|---|---|---|---|---|---|
| 3.001 | OCF$_3$ | C-OMe | H | Cl | H |
| 3.002 | SCF$_3$ | C-OMe | H | Cl | H |
| 3.003 | OCF$_3$ | N | H | Br | Me |
| 3.004 | SCF$_3$ | N | H | Br | Me |
| 3.005 | OCF$_3$ | C—H | H | Cl | H |
| 3.006 | SCF$_3$ | C—H | H | Cl | H |
| 3.007 | OCF$_3$ | C-OMe | H | Br | Me |
| 3.008 | OCF$_3$ | C-OMe | H | Cl | Me |
| 3.009 | OCF$_3$ | C—H | H | Br | Me |
| 3.010 | OCF$_3$ | C—H | H | Cl | Me |
| 3.011 | OCF$_3$ | C—H | H | Br | H |
| 3.012 | SCF$_3$ | C—H | H | Br | H |
| 3.013 | OCF$_3$ | C—H | H | Cl | Cl |
| 3.014 | SCF$_3$ | C—H | H | Cl | Cl |
| 3.015 | OCF$_3$ | C—H | H | Br | Cl |
| 3.016 | SCF$_3$ | C—H | H | Br | Cl |
| 3.017 | OCF$_3$ | C—Cl | H | Cl | H |
| 3.018 | SCF$_3$ | C—Cl | H | Cl | H |
| 3.019 | OCF$_3$ | C—Br | H | Cl | H |
| 3.020 | SCF$_3$ | C—Br | H | Cl | H |
| 3.021 | OCF$_3$ | C—H | H | Cl | Br |
| 3.022 | SCF$_3$ | C—H | H | Cl | Br |
| 3.023 | SCF$_3$ | C—H | H | Br | Me |

Compounds of general formula (Ie) which are of particular interest are:

N-[2-(6-Chloro-3-methoxy-2H-pyrazolo[4,3-b]pyridin-2-yl)-1-cyano-1-methylethyl]-4-trifluoromethoxybenzamide (compound No 3.001)

N-[2-(6-Chloro-3-methoxy-2H-pyrazolo[4,3-b]pyridin-2-yl)-1-cyano-1-methylethyl]-4-trifluoromethylthiobenzamide (compound No 3.002)

N-[2-(6-Bromo-7-methyl-2H-[1,2,3]triazolo[4,5-b]pyridin-2-yl)-1-cyano-1-methylethyl]-4-trifluoromethoxybenzamide (compound No 3.003)

N-[2-(6-Bromo-7-methyl-2H-[1,2,3]triazolo[4,5-b]pyridin-2-yl)-1-cyano-1-methylethyl]-4-trifluoromethylthiobenzamide (compound No 3.004)

N-[2-(6-Chloro-2H-pyrazolo[4,3-b]pyridin-2-yl)-1-cyano-1-methylethyl]-4-trifluoromethoxybenzamide (compound No 3.005)

N-[2-(6-Chloro-2H-pyrazolo[4,3-b]pyridin-2-yl)-1-cyano-1-methylethyl]-4-trifluoromethylthiobenzamide (compound No 3.006)

N-[2-(6-Bromo-3-methoxy-7-methyl-2H-pyrazolo[4,3-b]pyridin-2-yl)-1-cyano-1-methylethyl]-4-trifluoromethoxybenzamide (compound No 3.007)

N-[2-(6-Chloro-3-methoxy-7-methyl-2H-pyrazolo[4,3-b]pyridin-2-yl)-1-cyano-1-methylethyl]-4-trifluoromethoxybenzamide (compound No 3.008)

N-[2-(6-Bromo-7-methyl-2H-pyrazolo[4,3-b]pyridin-2-yl)-1-cyano-1-methylethyl]-4-trifluoromethoxybenzamide (compound No 3.009)

N-[2-(6-Chloro-7-methyl-2H-pyrazolo[4,3-b]pyridin-2-yl)-1-cyano-1-methylethyl]-4-trifluoromethoxybenzamide (compound No 3.010)

N-[2-(6-Bromo-2H-pyrazolo[4,3-b]pyridin-2-yl)-1-cyano-1-methylethyl]-4-trifluoromethoxybenzamide (compound No 3.011)

N-[2-(6-Bromo-2H-pyrazolo[4,3-b]pyridin-2-yl)-1-cyano-1-methylethyl]-4-trifluoromethylthiobenzamide (compound No 3.012)

N-[2-(6-Bromo-7-methyl-2H-pyrazolo[4,3-b]pyridin-2-yl)-1-cyano-1-methylethyl]-4-trifluoromethylthiobenzamide (compound No 3.023)

N-[1-Cyano-2-(3,6-dichloro-2H-pyrazolo[4,3-b]pyridin-2-yl)-1-methylethyl]-4-trifluoromethoxybenzamide (compound No 3.017)

N-[2-(3-Bromo-6-chloro-2H-pyrazolo[4,3-b]pyridin-2-yl)-1-cyano-1-methylethyl]-4-trifluoromethoxybenzamide (compound No 3.019)

The numbers 3.001 to 3.012, 3.017, 3019 and 3.023 are assigned to the above compounds for identification and reference hereinafter.

Method of Use Examples

Method A: Screening Method to Test Activity of Compounds Against *Haemonchus contortus*.

Twenty L1 *Haemonchus contortus* larvae were added to wells of a microtitre plate containing a nutrient medium and the test compound in DMSO. The microtitre plate was then held at 27° C. where the L1 larvae were allowed to develop. An analysis was conducted at 4 days to determine successful development to the L3 stage. Larvae exposed to DMSO and no test compound served as controls. Compounds numbers 1.002, 1.005, 1.006, 1.008, 1.009, 1.010, 1.011, 1.014, 1.017, 1.018, 1.025, 1.031, 1.045, 1.054, 1.055, 1.061, 1.076, 1.079, 1.081, 1.084, 2.004, 2.010, 2.020, 2.033, 3.003 and 3.004 gave at least 90% motility inhibition at a test concentration of 0.15 ppm at the 4 days assessment. Compounds numbers 1.003, 1.007, 1.011, 1.015, 1.032, 1.038, 1.042, 1.043, 1.047, 1.048, 1.056, 1.057, 1.060, 1.066, 1.067, 1.070, 1.071, 1.075, 1.078, 2.001, 2002, 2.003, 2.005, 2.006, 2.007, 2.013, 2.015, 2.016, 2.021, 3010 and 3.019 gave at least 90% motility inhibition at a test concentration of 0.04 ppm at the 4 days assessment. Compounds numbers 1.001, 1.012, 1.020, 1.021, 1.033, 1.034, 1.037, 1.039, 1.044, 1.085, 1.089, 1.091, 1.092, 1.093, 2.012, 2.014, 2.027, 2.028, 2.039, 3.005, 3.007, 3.008 and 3.017 gave at least 90% motility inhibition at a test concentration of 0.01 ppm at the 4 days assessment. Compounds numbers 1.064, 1.065, 1.069, 1.083, 1.086, 1.087, 1.088, 1.090, 1.094, 1.095, 2.008, 2.009, 2.023, 2.024, 2.025, 2.026, 2.037, 2.038, 2.040, 2.041, 2.042, 2.043, 2.044, 2.045, 2.046, 2.047, 2.048, 2.049, 2.050, 3.001, 3.002, 3.006, 3.009, 3.011, 3.012 and 3.023 gave at least 90% motility inhibition at a test concentration of 0.0025 ppm at the 4 days assessment.

Method B: Screening Method to Test Activity of Compounds Against *Haemonchus contortus* In Vivo in Mongolian Gerbil (*Meriones unguiculatus*).

Mongolian gerbils, at least five weeks old, were immunosuppressed and artificially infected with ca. 1000 ensheathed *Haemonchus contortus* third instar larvae. Six days after infection, the Mongolian gerbils were treated by oral gavage with the test compounds, dissolved in a mixture of 2 parts DMSO and 1 part polyethylene glycol (PEG400), at doses of 100 mg/kg and dissolved in pure polyethylene glycol (PEG400) at doses of 10 and 1 mg/kg. Jirds treated only with the placebo (2 parts DMSO and 1 part PEG400 or pure PEG400) served as controls. On day 9 (3 days after treatment) the jirds were euthanized and necropsied for recovery of parasites from the stomach. Efficacy was calculated as the average % reduction in the number of worms in each test group compared with the average number of worms from the control group. In this screen, a vast reduction in nematode infestation was achieved with compounds of formula (I), especially from table 1, 2 and 3. Compound numbers 1.001, 1.008, 1.012, 1.013 and 1.014 provided at least 95% reduction in nematode infestation in Mongolian gerbils treated by oral gavage with test article at a dose of 100 mg/kg. Compound numbers 1.012, 1.033, 1.064, 2.008, 2.037, 2.038, 2.040, 2.041, 3.001 provided at least 95% reduction in nematode infestation at a dose of 10 mg/kg. Compound numbers 1.094, 2.048, 3.001, 3.007 and 3.009, provided at least 95% reduction in nematode infestation at a dose of 1 mg/kg. Compound numbers 3.005, 3.006, 3.011, 3.012, 3.017 and 3.019, provided at least 95% reduction in nematode infestation at a dose of 0.5 mg/kg.

Method C: Screening Method to Test Activity of Compounds Against *Ctenocephalides felis*.

Three to five day old *Ctenocephalides felis* adults (50) were aspirated into a test cage. A separate glass cylinder closed on one end with a self-sealing flexible film was placed on top of the test cage in such a position that the fleas could pierce the film and feed on the contents of the glass cylinder. The test compound was dissolved in DMSO and added to bovine blood which was then placed in the glass cylinder. DMSO treated blood served as the control. The fleas were held at 20-22° C., 40-60% relative humidity while the treated blood was held at 37° C. and 40-60% relative humidity. The treated blood was changed daily for six days during which time eggs and fecal material were allowed to accumulate in the flea cage. On day 6, the contents of each cage were inspected and placed in a dish containing larval diet consisting of sand, ground cat food and dried cow blood. The dishes were held at 28° C. and 82% relative humidity 11 days. Pupae were then sieved, weighed and returned to the controlled conditions for an additional 5 days after which adult emergence was assessed. Pupal weights and adult emergence were then compared to the controls. Compounds numbers 1.012, 1.013, 1.020, 1.034, 1.064 and 3.005 gave at least 80% reduction in pupal weights at a test concentration of 100 ppm. Compounds numbers 2.048 gave at least 80% reduction in pupal weights at a test concentration of 25 ppm.

Method D: Screening Method to Test Activity of Compounds Against *Trichostrongylus colubriformis*.

Twenty L1 *Trichostrongylus colubriformis* larvae were added to wells of a microtitre plate containing a nutrient medium and the test compound in DMSO. The microtitre plate was then held at 27° C. where the L1 larvae were allowed to develop. An analysis was conducted at 4 days to determine successful development to the L3 stage. Larvae exposed to DMSO and no test compound served as controls. Compounds numbers 1.008, 1.014, 1.042, 1.047, 1.048, 1.073, 2.001, 2.003 and 2.020, gave at least 90% motility inhibition at a test concentration of 0.15 ppm at the 4 days assessment. Compounds numbers 1.001, 1.003, 1.007, 1.011, 1.037, 1.038, 1.043, 1.056, 1.066, 1.070, 1.071, 2.012 and 2.016, gave at least 90% motility inhibition at a test concentration of 0.04 ppm at the 4 days assessment. Compounds numbers 1.012, 1.020, 1.021, 1.033, 1.034, 1.039, 1.064, 1.065, 2.008, 2.009 and 3.005 gave at least 90% motility inhibition at a test concentration of 0.01 ppm at the 4 days assessment. Compounds numbers 1.094, 2.040, 2.048, 2.049, 3.006, 3.009, 3.011 and 3.012 gave at least 90% motility inhibition at a test concentration of 0.0025 ppm at the 4 days assessment.

Method E: Screening Method to Test Activity of Compounds Against *Haemonchus contortus, Ostertagia circumcincta, Trichostrongylus axei, Trichostrongylus colubriformis, Cooperia curticei* and *Nematodirus baffus* In Vivo in Sheep.

Sheep were challenged orally with infective $3^{rd}$ stage larvae (L3) of *Ostertagia circumcincta* (~3,000 infective L3 per animal) on Day −28, *Haemonchus contortus* (~2,000 infective L3 per animal) on Day −25, *Nematodirus battus* (~3,000 infective L3 per animal) and *Trichostrongylus axei* (~3,000 infective L3 per animal) on Day −23 and *Cooperia curticei* (~3,000 infective L3 per animal) and *Trichostrongylus colubriformis* (~3,000 infective L3 per species per animal) on Day −21. The inoculation schedule was designed so that nematodes were expected to be in the adult stage on Day 0. Test compounds were dissolved in a mixture of DMSO/Corn oil (1:1) at a concentration of 100 mg/mL. All treatments were administered orally once on Day 0. At sacrifice on Day 15 the abomasum, small intestine and large intestine (including cecum) were removed. Nematode counts were conducted on 10% (abomasal and small intestinal content, abomasal soak) or 20% aliquots (large intestinal content). All nematodes were speciated, or assigned to species based on location of recovery (adult females, fourth-stage larvae) for a total count per species. Efficacy was calculated as the % reduction in the mean number of worms in each test group compared with the mean number of worms recovered from the control group. In this screen, a significant reduction in nematode infestation was achieved with compounds of formula (I), especially from table 1, 2 and 3. Compound numbers 1.012 and 1.013 provided at least 90% reduction in nematode infestation at a dose of 30 mg/kg.

In addition, compound numbers 1.064, 1.094, 2.048, 3.005, 3.009 and 3.011 provided >90% efficacy against one or more species of the nematodes tested, at doses as low as 1 or 3 mg/kg. For example, compound 3.009 provided >95% efficacy against *Trichostrongylus* at a dose of 3 mg/kg and compound numbers 1.064, 1.094 and 2.048 provided >95% efficacy against *Haemonchus, Ostertagia,* and *Trichostrongylus* at a dose of 3 mg/kg, and compound numbers 3.005 and 3.011 were more than 95% effective against these parasites at doses as low as 1 mg/kg.

Method F: Screening Method to Test Activity of Compounds Against Microfilaria of *Dirofilaria immitis*.

Four hundred to six hundred microfilaria of *Dirofilaria immitis* were added to wells of a microtitre plate containing buffer and the test compound in DMSO. The microtitre plate was then held at 37° C. in an environment containing 5% $CO_2$. An assessment was conducted at 24 hours to determine survival of the microfilaria. Microfilaria exposed to DMSO and no test compound served as controls. Compounds numbers 1.003, 1.012, 1.013, 1.064, 1.086, 1.087, 1.090, 1.094, 2.043, 2.046, 2.047, 2.048, 2.049, 3.005, 3.006, 3.009, 3.011, 3.012, 3.017, 3.019 and 3.023 gave at least 90% motility inhibition at a test concentration of 50 ppm.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:
1. An aryloazol-2-yl-cyanoethylamine compound of the formula (I):

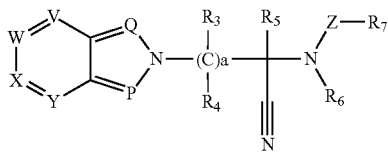

P is N;
Q is C—$R_2$ or N;
V is C—$R_8$ or N;
W is C—$R_9$;
X is C—$R_{10}$;
Y is C—$R_{11}$;
$R_2, R_8, R_9, R_{10}$ and $R_{11}$ each, independently of one another, is hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkylsulfinyl, haloalkylsulfinyl, alkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, $HO_2C$—, alkyl-$O_2C$—, unsubstituted or substituted aryl or unsubstituted or substituted phenoxy, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, and haloalkylsulfonyl;
$R_3, R_4$ and $R_5$ each, independently of one another, is hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independent of one another and are selected from the group consisting of halogen and alkyl; or unsubstituted or substituted phenyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino, and di(alkyl)amino; or
$R_4$ and $R_5$ together with the carbon to which they are attached form a cycloalkyl ring;
$R_6$ is hydrogen, alkyl, alkoxyalkyl, alkylcarbonyl, alkylthiocarbonyl or unsubstituted or substituted benzyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino, and di(alkyl)amino;
$R_7$ is hydrogen, alkyl, alkoxyalkyl, alkylcarbonyl, alkylthiocarbonyl or unsubstituted or substituted phenyl wherein the substituents may each be independent of one another and are selected from the group consisting of cyano, nitro, halogen, alkyl, haloalkyl, phenyl, phenoxy, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl alkylamino, and di(alkyl)amino; unsubstituted or substituted hetaryl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino, and di(alkyl)amino; or unsubstituted or substituted naphthyl or quinolyl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino, and di(alkyl)amino;
Z is a direct bond, C(O), C(S) or $S(O)_p$;
a is 1, 2 or 3;
p is 0, 1 or 2; and
salts thereof.
2. The aryloazol-2-yl-cyanoethylamine of claim 1, wherein
P is N;
Q is C—$R_2$ or N;
V is C—$R_8$ or N;
W is C—$R_9$ or N;
X is C—$R_{10}$ or N;
Y is C—$R_{11}$ or N;
$R_2, R_8, R_9, R_{10}$ and $R_{11}$ each, independently of one another, is hydrogen, amino, amido, cyano, nitro, halogen, $C_1$-$C_6$-alkyl, $C_2$-$C_6$-alkenyl, $C_2$-$C_6$-alkynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio arylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, $HO_2C$—, $C_1$-$C_6$-alkyl-$O_2C$—, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, and halo-$C_1$-$C_6$-alkylsulfonyl;
$R_3, R_4$ and $R_5$ each, independently of one another, is hydrogen, halogen, $C_1$-$C_6$-alkyl, hydroxy-$C_1$-$C_6$-alkyl, $C_1$-$C_6$-alkylthio-$C_1$-$C_6$-alkyl, halo-$C_1$-$C_6$-alkyl, $C_1$-$C_6$-alkoxy-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylsulfonyloxy-$C_1$-$C_6$-alkyl; unsubstituted or substituted $C_3$-$C_7$-cycloalkyl, wherein the substituents may each be independent of one another and are selected from the group consisting of halogen and $C_1$-$C_6$-alkyl; or unsubstituted or substituted phenyl, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, and di($C_1$-$C_6$-alkyl)amino; or $R_4$ and $R_5$ together with the carbon to which they are attached form a cycloalkyl ring;

$R_6$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or unsubstituted or substituted benzyl, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_1$-$C_6$-alkylamino, and di($C_1$-$C_6$-alkyl)amino;

$R_7$ is hydrogen, $C_1$-$C_6$-alkyl, $C_1$-$C_6$-alkoxy-$C_1$-$C_6$-alkyl, $C_1$-$C_6$-alkylcarbonyl, $C_1$-$C_6$-alkylthiocarbonyl or unsubstituted or substituted phenyl wherein the substituents may each be independent of one another and are selected from the group consisting of cyano, nitro, halogen, $C_1$-$C_6$-alkyl, halo-$C_1$-$C_6$-alkyl, phenyl, phenoxy, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl $C_1$-$C_6$-alkylamino, and di($C_1$-$C_6$-alkyl)amino; unsubstituted or substituted hetaryl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, and di($C_1$-$C_6$-alkyl)amino; or unsubstituted or substituted naphthyl or quinolyl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, and di($C_1$-$C_6$-alkyl)amino;

Z is a direct bond, C(O), C(S) or S(O)$_p$;

a is 1, 2 or 3;

p is 0, 1 or 2; and salts thereof.

3. The aryloazol-2-yl-cyanoethylamine of claim 2, wherein

P and Q are N;

V is C—$R_8$;

W is C—$R_9$;

X is C—$R_{10}$;

Y is C—$R_{11}$;

$R_8$, $R_9$, $R_{10}$ and $R_{11}$ each, independently of one another, is hydrogen, amino, amido, cyano, nitro, halogen, $C_1$-$C_6$-alkyl, $C_2$-$C_6$-alkenyl, $C_2$-$C_6$-alkynyl, $C_3$-$C_7$-cycloalkyl, hydroxy-$C_1$-$C_6$-alkyl, halo-$C_1$-$C_6$-alkyl, $C_1$-$C_6$-alkylthio, halo-$C_1$-$C_6$-alkylthio arylthio, $C_1$-$C_6$-alkoxy, phenoxy, $C_1$-$C_6$-alkoxy-$C_1$-$C_6$-alkoxy, $C_3$-$C_7$-cycloalkyloxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, di($C_1$-$C_6$-alkyl)amino, $C_1$-$C_6$-alkylcarboxylamino, $C_1$-$C_6$-alkylamino-$C_1$-$C_6$-alkoxy, di-$C_1$-$C_6$-alkylamino-$C_1$-$C_6$-alkoxy, $C_1$-$C_6$-alkylamino-$C_1$-$C_6$-alkyl, di-$C_1$-$C_6$-alkylamino-$C_1$-$C_6$-alkyl, amino-$C_1$-$C_6$-alkyl, formyl, HO$_2$C—, $C_1$-$C_6$-alkyl-O$_2$C—, unsubstituted or substituted aryl or unsubstituted or substituted phenoxy, whereby the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, and halo-$C_1$-$C_6$-alkylsulfonyl;

$R_3$, $R_4$ and $R_6$ are H;

$R_5$ is methyl;

$R_7$ is unsubstituted or substituted phenyl wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, and di($C_1$-$C_6$-alkyl)amino;

unsubstituted or substituted hetaryl, wherein the substituents may each be independent of one another and are selected from the group consisting of cyano, nitro, halogen, $C_1$-$C_6$-alkyl, halo-$C_1$-$C_6$-alkyl, $C_1$-$C_6$-alkylthio, halo-$C_1$-$C_6$-alkylthio, arylthio, $C_1$-$C_6$-alkoxy, halo-$C_1$-$C_6$-alkoxy, $C_1$-$C_6$-alkylcarbonyl, halo-$C_1$-$C_6$-alkylcarbonyl, $C_1$-$C_6$-alkylsulfinyl, halo-$C_1$-$C_6$-alkylsulfinyl, $C_1$-$C_6$-alkylsulfonyl, $C_1$-$C_6$-alkylamino, and di($C_1$-$C_6$-alkyl)amino;

Z is C(O); and a is 1; and salts thereof.

4. The aryloazol-2-yl-cyanoethylamine of claim 1, wherein

P and Q are N;

V is C—$R_8$;

W is C—$R_9$;

X is C—$R_{10}$;

Y is C—$R_{11}$;

$R_3$, $R_4$ and $R_6$ are hydrogen;

$R_5$ is hydrogen, $C_1$-$C_6$-alkyl, halo-$C_1$-$C_6$-alkyl, hydroxy-$C_1$-$C_6$-alkyl, $C_1$-$C_6$-alkylthio-$C_1$-$C_6$-alkyl, $C_1$-$C_6$-alkyloxy-$C_1$-$C_6$-alkyl, or $C_1$-$C_6$-alkylsulfonyloxy-$C_1$-$C_6$-alkyl;

$R_7$ is unsubstituted phenyl or phenyl substituted by one or more substituents selected from the group consisting of $C_1$-$C_6$-alkyl, halo-$C_1$-$C_6$-alkyl, phenyl, phenyloxy, $C_1$-$C_6$-alkoxy, halo-$C_1$-$C_6$-alkoxy, $C_1$-$C_6$-alkylthio, halo-$C_1$-$C_6$-alkylthio, halo-$C_1$-$C_6$-alkylsulfinyl and halo-$C_1$-$C_6$-alkylsulfonyl;

$R_8$, $R_9$, $R_{10}$ and $R_{11}$ each, independently of one another, is hydrogen, halogen, $C_1$-$C_6$-alkyl, halo-$C_1$-$C_6$-alkyl, cyano, $C_1$-$C_6$-alkoxy, halo-$C_1$-$C_6$-alkoxy, $C_2$-$C_6$-alkenyl, $C_1$-$C_6$-alkylamino, hydroxy-$C_1$-$C_6$-alkyl, formyl, $C_1$-$C_6$-alkylamino-$C_1$-$C_6$-alkyl, HO$_2$C—, $C_1$-$C_6$-alkyl-O$_2$C— or unsubstituted or substituted phenyl wherein the substituents are $C_1$-$C_6$-alkyl or halo-$C_1$-$C_6$-alkyl;

Z is C(O);

a is 1; and salts thereof.

5. The aryloazol-2-yl-cyanoethylamine of claim 1, wherein

P and Q are N;

V is C—$R_8$;

W is C—$R_9$;

X is C—$R_{10}$;

Y is C—$R_{11}$;

$R_3$, $R_4$ and $R_6$ are hydrogen;

$R_5$ is methyl, ethyl, butyl, CH$_2$OH, CH$_2$OCH$_3$, CH$_2$SCH$_3$, or CH$_2$OSO$_2$CH$_3$;

$R_7$ is a phenyl substituted with butyl, CF$_3$, phenyl, phenoxy, OCF$_3$, SCF$_3$, SOCF$_3$, or SO$_2$CF$_3$;

$R_8$, $R_9$, $R_{10}$ and $R_{11}$ each, independently of one another, is hydrogen, methyl, $CH_2NH_2$, $CH_2N(CH_3)_2$, vinyl, $CH_2OH$, $CH(OH)CH_2OH$, $CO_2H$, $CO_2CH_3$, Ph-$CF_3$, F, Cl, Br, $CF_3$, $OCF_3$ or CN;

Z is C(O);

a is 1; and salts thereof.

6. The aryloazol-2-yl-cyanoethylamine of claim 1, wherein

P is N;

Q is C—$R_2$;

V is C—$R_8$;

W is C—$R_9$;

X is C—$R_{10}$;

Y is C—$R_{11}$;

$R_2$ is hydrogen, Cl, methyl, methoxy, ethoxy, propoxy, butoxy, $O(CH_2)_2OCH_3$, or $O(CH_2)_2N(CH_3)_2$;

$R_3$, $R_4$ and $R_6$ are hydrogen;

$R_5$ is methyl;

$R_7$ is phenyl substituted by $OCF_3$, phenoxy, or $SCF_3$;

$R_8$, $R_9$, $R_{10}$ and $R_{11}$ each, independently of one another, is hydrogen, Cl, Br, $C_1$-$C_6$-alkyl, $CF_3$, nitro, amino, amido, $CO_2CH_3$, or $NHCOCH_3$;

Z is C(O);

a is 1; and salts thereof.

7. The aryloazol-2-yl-cyanoethylamine of claim 1, wherein

P is N;

Q is C—$R_2$ or N;

V is N;

W is C—$R_9$;

X is C—$R_{10}$;

Y is C—$R_{11}$;

$R_2$ is hydrogen, Cl, Br, or methoxy;

$R_3$, $R_4$ and $R_6$ are hydrogen;

$R_5$ is methyl;

$R_7$ is phenyl substituted by $OCF_3$ or $SCF_3$;

$R_9$, $R_{10}$ and $R_{11}$ each, independently of one another, is hydrogen, Cl, Br or methyl;

Z is C(O); and a is 1; and salts thereof.

8. A pesticidal composition comprising a compound of claim 1 and a pesticidally or veterinarily acceptable carrier.

9. The pesticidal composition of claim 8 which further comprises an additional pesticidal compound.

10. A method of making the compounds of formula (I) of claim 1 which comprises of:

(i) obtaining the carbonyl compounds of formula (IV) by treatment of a NH-aryl-azole of general formula (V) with compound of general formula (VI)

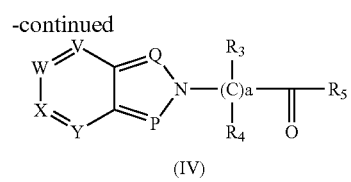

(VI)

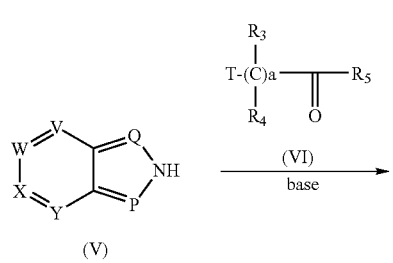

(V)

-continued

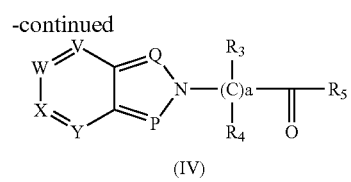

(IV)

wherein

P is N;

Q is C—$R_2$ or N;

V is C—$R_8$ or N;

W is C—$R_9$;

X is C—$R_{10}$;

Y is C—$R_{11}$;

$R_2$, $R_8$, $R_9$, $R_{10}$ and $R_{11}$ each, independently of one another, is hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkylsulfinyl, haloalkylsulfinyl, alkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, $HO_2C$—, alkyl-$O_2C$—, unsubstituted or substituted aryl or unsubstituted or substituted phenoxy, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl and haloalkylsulfonyl;

$R_3$, $R_4$ and $R_5$ each, independently of one another, is hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independent of one another and are selected from the group consisting of halogen and alkyl; unsubstituted or substituted phenyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino and di(alkyl)amino; or $R_4$ and $R_5$ together with the carbon to which they are attached form a cycloalkyl ring;

a is 1, 2 or 3; and T is a leaving group;

(ii) obtaining the α-amino nitrile derivatives of formula (II) by treatment of carbonyl compounds of general formula (IV) with a cyanide source with an amine of general formula $R_6$—$NH_2$ in the presence of an ammonium salt:

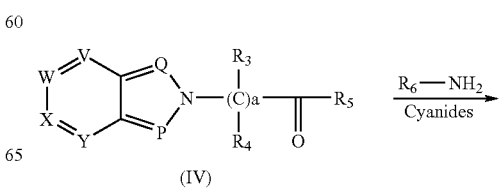

(IV)

-continued

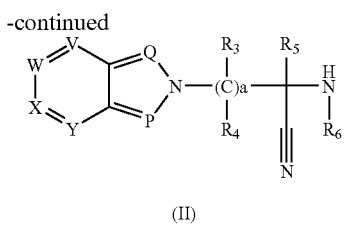

(II)

wherein, $R_3$, $R_4$, $R_5$, P, Q, V, W, X, Y, and a are as defined above; and $R_6$ is hydrogen, alkyl, alkoxyalkyl, alkylcarbonyl, alkylthiocarbonyl or unsubstituted or substituted benzyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino and di(alkyl)amino; and (iii) reacting compound (II) with compound (III) in the presence of a base in a solvent:

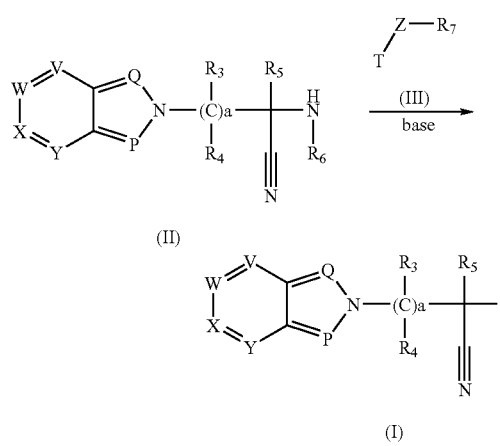

wherein $R_3$, $R_4$, $R_5$, $R_6$, P, Q, V, W, X, Y, and a are as defined above;

$R_7$ is hydrogen, alkyl, alkoxyalkyl, alkylcarbonyl, alkylthiocarbonyl or unsubstituted or substituted phenyl wherein the substituents may each be independent of one another and are selected from the group consisting of cyano, nitro, halogen, alkyl, haloalkyl, phenyl, phenoxy, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl alkylamino and di(alkyl)amino; unsubstituted or substituted hetaryl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino and di(alkyl)amino; or unsubstituted or substituted naphthyl or quinolyl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino and di(alkyl)amino;

Z is a direct bond, C(O), C(S) or $S(O)_p$;
p is 0, 1 or 2; and T is a leaving group.

11. A method of treating an endoparasitic infection in a mammal in need thereof which comprises administering an effective amount of the compound of claim 1 to the mammal.

12. The method of claim 11, wherein the endoparasitic infection is caused by a helminth selected from the group consisting of *Anaplocephala, Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria,* and combinations thereof.

13. The method of claim 12, wherein the helminth is *Haemonchus contortus, Ostertagia circumcincta, Trichostrongylus axei, Trichostrongylus colubriformis, Cooperia curticei, Nematodirus battus* and combinations thereof.

14. The method of claim 13, wherein the helminth is *Haemonchus contortus* and the compound is a compound of formula (I) wherein:
P is N;
Q is C—$R_2$ or N;
V is C—$R_8$ or N;
W is C—$R_9$;
X is C—$R_{10}$;
Y is C—$R_{11}$;
$R_2$ is hydrogen, Cl, Br, methyl or methoxy;
$R_3$, $R_4$ and $R_6$ are H;
$R_5$ is methyl;
$R_7$ is phenyl substituted with $OCF_3$, $SCF_3$ or $CHFCF_3$;
$R_8$ is H, Cl, Br, F or CN;
$R_9$ is H, Cl or Br;
$R_{10}$ is H, Cl, Br or $CF_3$;
$R_{11}$ is H, Cl, Br or methyl;
Z is C(O); and
a is 1.

15. The method of claim 13, wherein the helminth is *Haemonchus contortus* and the compound is a compound of formula (I) wherein:
P is N;
Q is C—$R_2$ or N;
V is N;
W is C—$R_9$;
X is C—$R_{10}$;
Y is C—$R_{11}$;
$R_2$ is hydrogen, Cl, Br or methoxy;
$R_3$, $R_4$ and $R_6$ are H;
$R_5$ is methyl;
$R_7$ is phenyl substituted with $OCF_3$ or $SCF_3$;
$R_9$ is H;
$R_{10}$ is Cl or Br;
$R_{11}$ is H;
Z is C(O); and
a is 1.

16. A method of treating an ectoparasitic infection in a mammal in need thereof which comprises administering an effective amount of the compound of claim 1 to the mammal.

17. The method of claim 16, wherein the ectoparasitic infection is caused by an ectoparasite selected from the group consisting of fleas, ticks, mites, mosquitoes, flies, lice, blowfly and combinations thereof.

18. The method of claim 17, wherein the ectoparasite are fleas.

19. A process of making the aryloazol-2-yl-cyanoethylamine compound of claim 1 which comprises:
(a)(i) reacting a compound of formula (V):

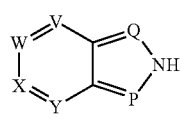

(V)

with a compound of formula (VI):

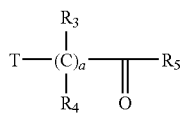

(VI)

to form the compound of formula (IV):

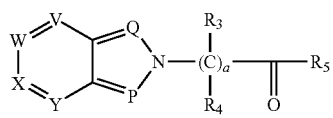

(IV)

wherein
P is N;
Q is C—$R_2$ or N;
V is C—$R_8$ or N;
W is C—$R_9$;
X is C—$R_{10}$;
Y is C—$R_{11}$;
$R_2, R_8, R_9, R_{10}$ and $R_{11}$ each, independently of one another, is hydrogen, amino, amido, cyano, nitro, halogen, alkyl, alkenyl, alkynyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkylsulfinyl, haloalkylsulfinyl, alkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, $HO_2C$—, alkyl-$O_2C$—, unsubstituted or substituted aryl or unsubstituted or substituted phenoxy, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl and haloalkylsulfonyl;

$R_3, R_4$ and $R_5$ each, independently of one another, is hydrogen, halogen, alkyl, hydroxyalkyl, alkylthioalkyl, haloalkyl, alkyloxyalkyl, alkylsulfinylalkyl, alkylsulfonylalkyl, alkylsulfonyloxyalkyl; unsubstituted or substituted cycloalkyl, wherein the substituents may each be independent of one another and are selected from the group consisting of halogen and alkyl; unsubstituted or substituted phenyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino and di(alkyl)amino; or $R_4$ and $R_5$ together with the carbon to which they are attached form a cycloalkyl ring;
T is a leaving group; and
a is 1, 2 or 3; or
(a)(ii) reacting a compound of formula (XIV):

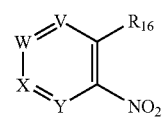

(XIV)

with a compound of formula (XV):

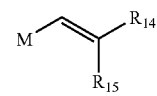

(XV)

to form the compound of formula (XIII)

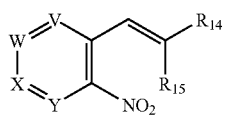

(XIII)

wherein V, W, X and Y are as defined above;
$R_{16}$ is halogen or trifluoromethanesulfonyl; and
$R_{14}$ and $R_{15}$ are independently $C_1$-$C_4$alkyl or $C_1$-$C_4$alkylcarbonyl; and
M is trialkyltin, a boronic acid or a boronate ester;
subjecting the compound of formula (XIII) to oxidative cleavage to form the compound of formula (X):

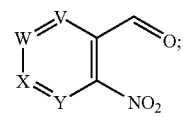

(X)

reacting the compound of formula (X) with a compound of formula (XI):

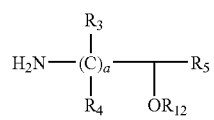

(XI)

wherein $R_3, R_4, R_5$ and a are as defined above, and $R_{12}$ is a hydroxy protecting group:
to form the compound of formula (IX):

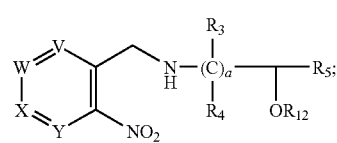

(IX)

subjecting the compound of formula (IX) to a heterocyclization step to form the compound of formula (VIII):

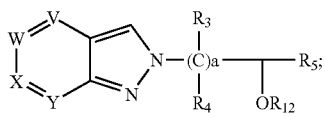

(VIII)

subjecting the compound of formula (VIII) to deprotection of the hydroxyl protecting group to form the compound of formula (VII):

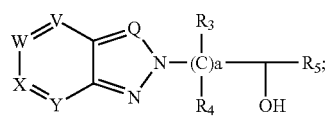

(VII)

where Q is CH; and
oxidizing the compound of formula (VII) to form the compound of formula (IV) where Q is CH;
(b) reacting the compound of formula (IV)

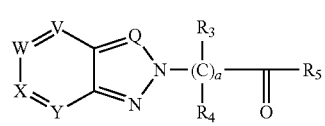

(IV)

with $R_6$-$NH_2$, where $R_6$ is hydrogen, alkyl, alkoxyalkyl, alkylcarbonyl, alkylthiocarbonyl or unsubstituted or substituted benzyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino and di(alkyl)amino, to form the compound of formula (II): and

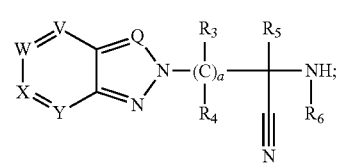

(II)

(c) reacting a compound of formula (II) with T-Z—$R_7$, wherein $R_7$ is hydrogen, alkyl, alkoxyalkyl, alkylcarbonyl, alkylthiocarbonyl or unsubstituted or substituted phenyl wherein the substituents may each be independent of one another and are selected from the group consisting of cyano, nitro, halogen, alkyl, haloalkyl, phenyl, phenoxy, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl alkylamino and di(alkyl)amino;
unsubstituted or substituted hetaryl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino and di(alkyl) amino; or
unsubstituted or substituted naphthyl or quinolyl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino and di(alkyl) amino;

Z is a direct bond, C(O), C(S) or $S(O)_p$; and T is a leaving group, in the presence of a base, to form the compound of claim 1,
wherein
P is N;
Q is C—$R_2$ or N;
V is C—$R_8$ or N;
W is C—$R_9$;
X is C—$R_{10}$;
Y is C—$R_{11}$;
$R_2$, $R_8$, $R_9$, $R_{10}$ and $R_{11}$ each, independently of one another, is hydrogen, amino, amido, cyano, nitro, halogen, alkyl, alkenyl, alkenyl, cycloalkyl, hydroxyalkyl, haloalkyl, alkylthio, haloalkylthio, arylthio, alkoxy, phenoxy, alkoxyalkoxy, cycloalkyloxy, haloalkoxy, alkylcarbonyl, haloalkylcarbonyl, alkylsulfinyl, haloalkylsulfinyl, alkylsulfonyl, alkylamino, di(alkyl)amino, alkylcarbonylamino, alkylaminoalkoxy, dialkylaminoalkoxy, alkylaminoalkyl, dialkylaminoalkyl, aminoalkyl, formyl, $HO_2C$—, alkyl-$O_2C$—, unsubstituted or substituted aryl or unsubstituted or substituted phenoxy, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl and haloalkylsulfonyl;
$R_3$, $R_4$ and $R_5$ each, independently of one another, is hydrogen, halogen, alkyl, hydroxyalkyl, alkylthioalkyl, haloalkyl, alkyloxyalkyl, alkylsulfonylalkyl, alkylsulfonylalkyl, alkylsulfonyloxyalkyl; unsubstituted or substituted cycloalkyl, wherein the substituents may each be independent of one another and are selected from the group consisting of halogen and alkyl; unsubstituted or substituted phenyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino and di(alkyl)amino; or
$R_4$ and $R_5$ together with the carbon to which they are attached form a cycloalkyl ring;
$R_6$ is hydrogen, alkyl, alkoxyalkyl, alkylcarbonyl, alkylthiocarbonyl or unsubstituted or substituted benzyl, whereby the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl, alkylamino and di(alkyl)amino;
$R_7$ is hydrogen, alkyl, alkoxyalkyl, alkylcarbonyl, alkylthiocarbonyl or unsubstituted or substituted phenyl wherein the substituents may each be independent of one another and are selected from the group consisting of cyano, nitro, halogen, alkyl, haloalkyl, phenyl, phenoxy, alkylthio, haloalkylthio, arylthio, alkoxy, haloalkoxy, alkylcarbonyl, haloalkylcarbonyl, alkylsulfinyl, haloalkylsulfinyl, alkylsulfonyl, haloalkylsulfonyl alkylamino and di(alkyl)amino; unsubstituted or substituted hetaryl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino and di(alkyl)amino; or unsubstituted or substituted naphthyl or quinolyl, wherein the substituents may each be independent of one another and are selected from the group consisting of cyano, nitro, halogen, alkyl, haloalkyl, alkylthio, haloalkylthio, arylthio, alkoxy, haloalkoxy, alkylcarbonyl, haloalkylcarbonyl, alkylsulfinyl, haloalkylsulfinyl, alkylsulfonyl, alkylamino and di(alkyl)amino;

Z is a direct bond, C(O), C(S) or S(O)$_p$;
a is 1, 2 or 3; and
p is 0, 1 or 2.

20. The compound of claim 1 wherein the compound has the formula (Ie)

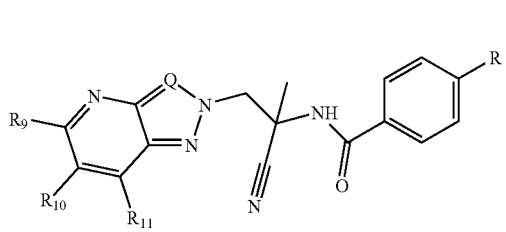

wherein:
R=SCF$_3$ or OCF$_3$;
Q=C—R$_2$;
R$_2$ is hydrogen, Br, F, Cl, methyl, methoxy, ethoxy or propoxy; and
R$_9$, R$_{10}$ and R$_{11}$ are each independently H, halogen or C$_1$-C$_6$-alkyl.

21. The compound of claim 20, wherein
R$_2$ is H, Br or methoxy; and
R$_9$, R$_{10}$ and R$_{11}$ are each independently H, Br or Cl.

22. The compound of claim 21, wherein
R$_2$ is H; and
R$_9$, R$_{10}$ and R$_{11}$ are each independently H, Br or Cl.

23. The compound of claim 22, wherein
R is OCF$_3$;
R$_2$ is H; and
R$_9$ and R$_{11}$ are H; and
R$_{10}$ is Br.

24. The compound of claim 1 wherein the compound has the formula (Id)

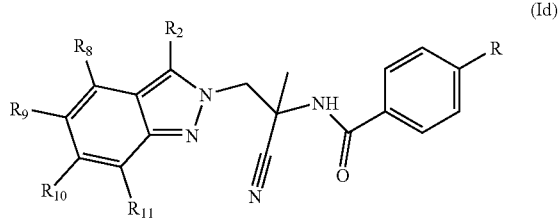

wherein:
R=SCF$_3$ or OCF$_3$;
R$_2$ is hydrogen, Br, F, Cl, methyl, methoxy, ethoxy, propoxy, butoxy, O(CH$_2$)$_2$OCH$_3$, or O(CH$_2$)$_2$N(CH$_3$)$_2$; and
R$_8$, R$_9$, R$_{10}$ and R$_{11}$ are each independently H, halogen, nitro, amino, amido, alkylcarbonylamino, HO$_2$C—, alkyl-O$_2$C—, C$_1$-C$_6$-haloalkyl or C$_1$-C$_6$-alkyl.

25. The compound of claim 24, wherein
R$_2$ is hydrogen, Br, Cl, methyl, methoxy or ethoxy; and
R$_8$, R$_9$, R$_{10}$ and R$_{11}$ are each independently H, Cl, Br, methyl, CF$_3$, or nitro.

26. The compound of claim 25, wherein
R$_2$ is hydrogen or methoxy; and
R$_8$, R$_9$, R$_{10}$ and R$_{11}$ are each independently H, Cl or Br.

27. The compound of claim 1, wherein the compound has the formula (Ic)

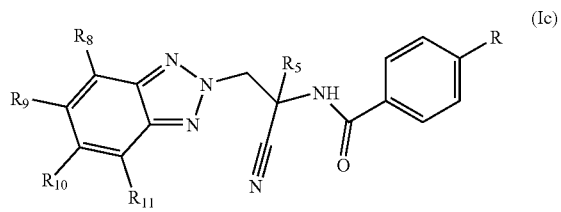

wherein:
R=SCF$_3$ or OCF$_3$;
R$_5$ is C$_1$-C$_6$-alkyl, hydroxyalkyl, alkylthioalkyl or alkylsulfonyloxyalkyl; and
R$_8$, R$_9$, R$_{10}$ and R$_{11}$ are each independently H, halogen, cyano, amino, aminoalkyl, alkylaminoalkyl, formyl, HO$_2$C—, alkyl-O$_2$C—, C$_1$-C$_6$-haloalkyl, C$_1$-C$_6$-alkyl, C$_1$-C$_6$-alkenyl, C$_1$-C$_6$-alkoxy or C$_1$-C$_6$-haloalkoxy.

28. The compound of claim 27, wherein:
R$_5$ is C$_1$-C$_6$-alkyl, or hydroxyalkyl; and
R$_8$, R$_9$, R$_{10}$ and R$_{11}$ are each independently H, halogen, HO$_2$C—, alkyl-O$_2$C—, C$_1$-C$_6$-haloalkyl, C$_1$-C$_6$-alkyl, C$_1$-C$_6$-alkoxy or C$_1$-C$_6$-haloalkoxy.

29. The compound of claim 28, wherein:
R$_5$ is methyl, or hydroxyalkyl; and
R$_8$, R$_9$, R$_{10}$ and R$_{11}$ are each independently H, methyl, CF$_3$, Cl, Br, F, methoxy or trifluoromethoxy.

30. The compound of claim 20, wherein:
R is OCF$_3$;
R$_2$ is methyl;
R$_9$ and R$_{11}$ are each H; and
R$_{10}$ is Br.

* * * * *